United States Patent [19]

Kempf et al.

[11] Patent Number: 5,616,714
[45] Date of Patent: Apr. 1, 1997

[54] RETROVIRAL PROTEASE INHIBITING COMPOUNDS

[75] Inventors: Dale J. Kempf, Libertyville; Daniel W. Norbeck, Lindenhurst; Lynn M. Codacovi, Antioch; Hing L. Sham, Gurnee; Steven J. Wittenberger, Mundelein, all of Ill.

[73] Assignee: Abbott Laboratories, Abbott Park, Ill.

[21] Appl. No.: 410,260

[22] Filed: Mar. 24, 1995

Related U.S. Application Data

[62] Division of Ser. No. 270,210, Aug. 23, 1994, abandoned, which is a division of Ser. No. 121,673, Sep. 14, 1993, Pat. No. 5,354,866, which is a continuation of Ser. No. 777,626, Oct. 23, 1991, abandoned, which is a continuation-in-part of Ser. No. 746,020, Aug. 15, 1991, abandoned, which is a continuation-in-part of Ser. No. 616,170, Nov. 20, 1990, abandoned, which is a continuation-in-part of Ser. No. 518,730, May 9, 1990, Pat. No. 5,142,056, which is a continuation-in-part of Ser. No. 456,124, Dec. 22, 1989, abandoned, which is a continuation-in-part of Ser. No. 405,604, Sep. 8, 1989, abandoned, which is a continuation-in-part of Ser. No. 355,945, May 23, 1989, abandoned.

[51] Int. Cl.$^6$ ............................................... C07D 417/00
[52] U.S. Cl. ...................................................... 546/269.7
[58] Field of Search ............................. 546/277; 514/342

[56] References Cited

U.S. PATENT DOCUMENTS

| 5,142,056 | 8/1992 | Kempf et al. ............................. 546/256 |
| 5,354,866 | 10/1994 | Kempf et al. ............................. 546/256 |

FOREIGN PATENT DOCUMENTS

| 393445 | 10/1990 | European Pat. Off. . |
| 402646 | 12/1990 | European Pat. Off. . |
| 428849 | 5/1991 | European Pat. Off. . |
| 441192 | 8/1991 | European Pat. Off. . |
| 3829594 | 3/1990 | Germany . |
| 4003575 | 8/1991 | Germany . |
| WO88/02374 | 4/1988 | WIPO . |

*Primary Examiner*—Jane Fan
*Attorney, Agent, or Firm*—Steven R. Crowley

[57] ABSTRACT

A retroviral protease inhibiting compound of the formula A—X—B is disclosed. Also disclosed are a composition and method for inhibiting a retroviral protease and for treating an HIV infection. Also disclosed are processes and intermediates useful for the preparation of the retroviral protease inhibitors.

10 Claims, No Drawings

RETROVIRAL PROTEASE INHIBITING COMPOUNDS

This invention was made with Government support under contract number AI27220 awarded by the National Institute of Allergy and Infectious Diseases. The Government has certain rights in this invention.

This is a division of U.S. patent application Ser. No. 08/270,210, filed Aug. 23, 1994, which is a division of U.S. Ser. No. 07/121,673, filed Sep. 14, 1993, now U.S. Pat. No. 5,354,866 which is a continuation of U.S. Ser. No. 07/777,626, filed Oct. 23, 1991, now abandoned which is a a continuation-in-part of U.S. patent application Ser. No. 07/746,020, filed Aug. 15, 1991, now abandoned which is a continuation-in-part of U.S. patent application Ser. No. 07/616,170, filed Nov. 20, 1990, now abandoned which is a continuation-in-part of U.S. patent application Ser. No. 518,730, filed May 9, 1990, now U.S. Pat. No. 5,142,056 which is a continuation-in-part of U.S. patent application Ser. No. 07/456,124, filed Dec. 22, 1989, now abandoned which is a continuation-in-part of U.S. patent application Ser. No. 07/405,604, filed Sep. 8, 1989, now abandoned which is a continuation-in-part of U.S. patent application Ser. No. 07/355,945, filed May 23, 1989, now abandoned.

TECHNICAL FIELD

The present invention relates to novel compounds and a composition and method for inhibiting retroviral proteases and in particular for inhibiting human immunodeficiency virus (HIV) protease, a composition and method for treating a retroviral infection and in particular an HIV infection, processes for making such compounds and synthetic intermediates employed in these processes.

BACKGROUND ART

Retroviruses are those viruses which utilize a ribonucleic acid (RNA) intermediate and a RNA-dependent deoxyribonucleic acid (DNA) polymerase, reverse transcriptase, during their life cycle. Retroviruses include, but are not limited to, the RNA viruses of the Retroviridae family, and also the DNA viruses of the Hepadnavirus and Caulimovirus families. Retroviruses cause a variety of disease states in man, animals and plants. Some of the more important retroviruses from a pathological standpoint include human immunodeficiency viruses (HIV-1 and HIV-2), which cause acquired immune deficiency syndrome (AIDS) in man, hepatitis B virus, which causes hepatitis and hepatic carcinomas in man, human T-cell lymphotrophic viruses I, II, IV and V, which cause human acute cell leukemia, and bovine and feline leukemia viruses which cause leukemia in domestic animals.

Proteases are enzymes which cleave proteins at specific peptide bonds. Many biological functions are controlled or mediated by proteases and their complementary protease inhibitors. For example, the protease renin cleaves the peptide angiotensinogen to produce the peptide angiotensin I. Angiotensin I is further cleaved by the protease angiotensin converting enzyme (ACE) to form the hypotensive peptide angiotensin II. Inhibitors of renin and ACE are known to reduce high blood pressure in vivo. An inhibitor of a retroviral protease should provide a therapeutic agent for diseases caused by the retrovirus.

The genomes of retroviruses encode a protease that is responsible for the proteolytic processing of one or more polyprotein precursors such as the pol and gag gene products. See Wellink, Arch. Virol. 98 1 (1988). Retroviral proteases most commonly process the gag precursor into core proteins, and also process the pol precursor into reverse transciptase and retroviral protease. In addition, retroviral proteases are sequence specific. See Pearl, Nature 328 482 (1987).

The correct processing of the precursor polyproteins by the retroviral protease is necessary for the assembly of infectious virions. It has been shown that in vitro mutagenesis that produces protease-defective virus leads to the production of immature core forms which lack infectivity. See Crawford, J. Virol. 53 899 (1985); Katoh, et al., Virology 145 280 (1985). Therefore, retroviral protease inhibition provides an attractive target for antiviral therapy. See Mitsuya, Nature 325 775 (1987).

Current treatments for vital diseases usually involve administration of compounds that inhibit vital DNA synthesis. Current treatments for AIDS (Dagani, Chem. Eng. News, Nov. 23, 1987 pp. 41–49) involve administration of compounds such as 2',3'-dideoxycytidine, 2',3'-dideoxyinosine, trisodium phosphonoformate, ammonium 21-tungsto-9-antimoniate, 1-beta-D-ribofuranosyl-1,2,4-triazole-3-carboxamide, 3'-azido-3'-deoxythymidine, and adriamycin that inhibit viral DNA synthesis; compounds such as AL-721 and polymannoacetate which may prevent HIV from penetrating the host cell; and compounds which treat the opportunistic infections caused by the immunosuppression resulting from HIV infection. None of the current AIDS treatments have proven to be totally effective in treating and/or reversing the disease. In addition, many of the compounds currently used to treat AIDS cause adverse side effects including low platelet count, renal toxicity and bone marrow cytopenia.

DISCLOSURE OF THE INVENTION

In accordance with the present invention, there are retroviral protease inhibiting compounds of the formula:

$$A—X—B \qquad (I)$$

or a pharmaceutically acceptable salt, prodrug or ester thereof.

X is

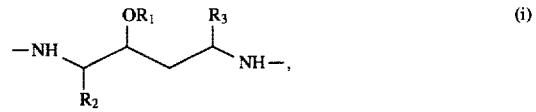   (i)

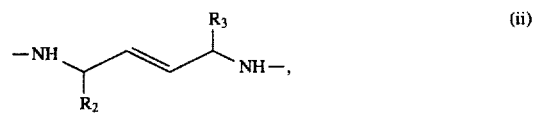   (ii)

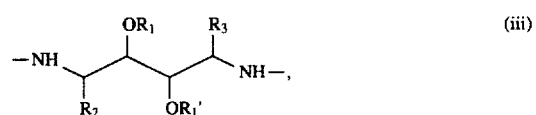   (iii)

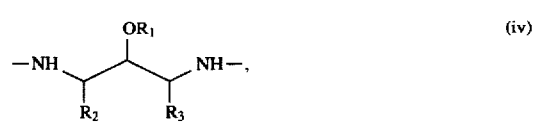   (iv)

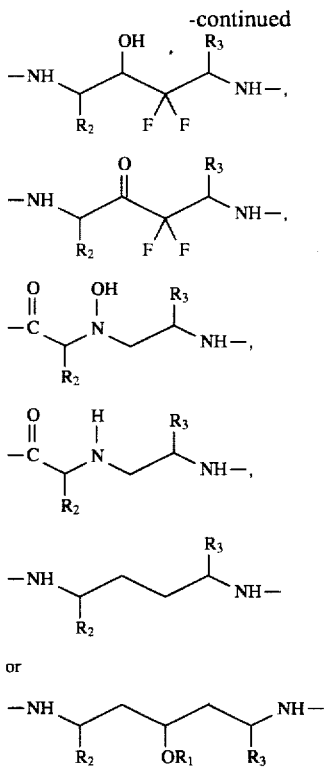

wherein $R_1$ and $R_1$. are independently selected from hydrogen, loweralkyl, alkoxyalkyl, thioalkoxyalkyl and alkoxyalkoxyalkyl or $R_1$ and $R_1$. and the oxygen atoms to which they are bonded taken together are —O—C(O)—O— or —O—C(S)—O— and $R_2$ and $R_3$ are independently —$((R_0)_d$—$R_5)$ wherein at each occurrence $R_0$ is independently selected from —(CH$_2$R$_4$)— and loweralkenylene wherein at each occurrence d is independently selected from 0 and 1, at each occurrence $R_4$ is independently selected from —S—, —O—, —NH—, —N (loweralkyl)—, —S(O)—, —S(O)$_2$—, and —CH$_2$— and at each occurrence $R_5$ and $R_{5*}$ are independently selected from (i) loweralkyl,
(ii) aryl,
(iii) thioalkoxyalkyl
(iv) (aryl)alkyl,
(v) cycloalkyl,
(vi) cycloalkylalkyl,
(vii) hydroxyalkyl,
(viii) alkoxyalkyl,
(ix) aryloxyalkyl,
(x) haloalkyl,
(xi) carboxyalkyl,
(xii) alkoxycarbonylalkyl,
(xiii) aminoalkyl,
(xiv) (N-protected)aminoalkyl,
(xv) alkylaminoalkyl,
(xvi) ((N-protected)(alkyl)amino)alkyl,
(xvii) dialkylaminoalkyl,
(xviii) guanidinoalkyl,
(xix) loweralkenyl,
(xx) heterocyclic,
(xxi) (heterocyclic)alkyl,
(xxii) hydrogen,
(xxiii) arylthioalkyl,
(xxiv) arylsulfonylalkyl,
(xxv) (heterocyclic)thioalkyl,
(xxvi) (heterocyclic)sulfonylalkyl,
(xxvii) (heterocyclic)oxyalkyl,
(xxviii) arylalkoxyalkyl,
(xxix) arylthioalkoxyalkyl,
(xxx) arylalkylsulfonylalkyl,
(xxxi) (heterocyclic)alkoxyalkyl,
(xxxii) (heterocyclic)thioalkoxyalkyl,
(xxxiii) (heterocyclic)alkylsulfonylalkyl,
(xxxiv) cycloalkyloxyalkyl,
(xxxv) cycloalkylthioalkyl,
(xxxvi) cycloalkylsulfonylalkyl,
(xxxvii) cycloalkylalkoxyalkyl,
xxxviii cycloalkylthioalkoxyalkyl,
(xxxix) cycloalkylalkylsulfonylalkyl,
(xl) aminocarbonyl,
(xli) alkylaminocarbonyl,
(xlii) dialkylaminocarbonyl,
(xliii) aroylalkyl,
(xliv) (heterocyclic)carbonylalkyl,
(xlv) polyhydroxyalkyl,
(xlvi) aminocarbonylalkyl,
(xlvii) alkylaminocarbonylalkyl and
(xlviii) dialkylaminocarbonylalkyl.

A and B are independently selected from (1) Z—W— wherein at each occurrence W is absent or represents a peptide chain containing 1–3 amino acids wherein and at each occurrence Z is $R_6$—$(C(R_{5*})(R_5))_e$—$(C(T))_f$— $(C(R_{5*})(R_5))_g$—$(U)_j$—$(C(R_{5*})(R_5))_j$—$C(T)f$— or $R_6$—$C(T)_{ff}$—$(U)_{ii}$—CH($R_{5a}$)—CH($R_{5b}$)—$(U)_{iii}$—$C(T)_{ff}$—.
At each occurrence $R_6$—$(C(R_{5*})(R_5))_e$—$(C(T))_f$— $(C(R_{5*})(R_5))_g$—$(U)_j$—$(C(R_{5*})(R_5))_j$—$C(T)_f$— or $R_6$—$C(T)_{ff}$—$(U)_{ii}$—CH($R_{5a}$)—CH($R_{5b}$)—$(U)_{ii}$—$C(T)_{ff}$— is bonded to the amino terminus of the peptide chain, at each occurrence T is independently selected from O and S, at each occurrence $R_5$ and $R_{5*}$ are independently defined as above or $R_5$, $R_{5*}$ and the carbon atom to which they are bonded or $R_{5a}$, $R_{5b}$ and the carbon atoms to which they are bonded taken together form a carbocyclic ring of from 3 to 8 carbon atoms which can be optionally substituted with a loweralkyl group or when e, g or j is 2 or more, $R_5$ and R5, on adjacent carbon atoms when taken together form a carbocyclic ring of from 3 to 8 carbon atoms which can be optionally substituted with a loweralkyl group, at each occurrence U is independently selected from O, S and —N($R_5$)— wherein $R_5$ is independently defined as above, at each occurrence e is independently selected from 0, 1, 2 and 3, at each occurrence f and ff are independently selected from 0 and 1, at each occurrence g is independently selected from 0, 1, 2 and 3, at each occurrence i, ii and iii are independently selected from 0 and 1, at each occurrence j is independently selected from 0, 1, 2 and 3, and at each occurrence $R_6$ is independently selected from (a) $R_7$—$(R_9)_k$— wherein at each occurrence $R_9$ is independently selected from N($R_7$), O and S and at each occurrence k is independently selected from 0 and 1,
(b) $(R_7)_2$N—O—,
(c) $R_7$S(O)$_2$N($R_5$)— and
(d) $R_{170}R_{171}$CH=CH— wherein at each occurrence $R_{171}$ is absent, O, S, NH or —N(alkyl)— and at each occurrence $R_{170}$ is aryl or heterocyclic and wherein at each occurrence $R_5$ is independently defined as above and at each occurrence $R_7$ is independently selected from:
(i) hydrogen,
(ii) loweralkyl,
(iii) cycloalkyl,
(iv) aryl,
(v) arylalkyl, (vi) (aryl)alkoxyalkyl,
(vii) aminoalkyl,
(viii) N-protected-aminoalkyl,
(ix) alkylaminoalkyl,
(x) (N-protected)(alkyl)aminoalkyl,
(xi) dialkylaminoalkyl,
(xii) carboxyalkoxyalkyl,
(xiii) (alkoxycarbonyl)alkoxyalkyl,
(xiv) carboxyalkyl,
(xv) alkoxycarbonylalkyl,
(xvi) (amino)carboxyalkyl,
(xvii) ((N-protected)amino)carboxyalkyl,
(xviii) (alkylamino)carboxyalkyl,
(xix) ((N-protected)alkylamino)carboxyalkyl,
(xx) (dialkylamino)carboxyalkyl,
(xxi) (amino)alkoxycarbonylalkyl,
(xxii) ((N-protected)amino)alkoxycarbonylalkyl,
(xxiii) (alkylamino)alkoxycarbonylalkyl,
(xxiv) ((N-protected)alkylamino)alkoxycarbonylalkyl,
(xxv) (dialkylamino)alkoxycarbonylalkyl,
(xxvi) aminocycloalkyl,
(xxvii) alkoxyalkyl,
(xxviii) (polyalkoxy)alkyl,
(xxix) heterocyclic,
(xxx) (heterocyclic)alkyl,
(xxxi) (hydroxyamino)alkyl,
(xxxii) (alkoxyamino)alkyl,
(xxxiii) N-protecting group,
(xxxiv) cycloalkylalkyl,
(xxxv) loweralkenyl,
(xxxvi) hydroxyalkyl,
(xxxvii) dihydroxyalkyl,
(xxxviii) (alkoxy)(alkyl)aminoalkyl,
(xxxix) alkylaminocycloalkyl,
(lx) dialkylaminocycloalkyl,
(lxi) polyhydroxyalkyl,
(lxii) aryloxyalkyl,
(lxiii) arylthioalkyl,
(lxiv) arylsulfonylalkyl,
(lxv) (heterocyclic)thioalkyl,
(lxvi) (heterocyclic)sulfonylalkyl,
(lxvii) (heterocyclic)oxyalkyl,
(lxviii) arylalkoxyalkyl,
(lxix) arylthioalkoxyalkyl,
(lXX) arylalkylsulfonylalkyl,
(lxxi) (heterocyclic)alkoxyalkyl,
(lxxii) (heterocyclic)thioalkoxyalkyl,
(lxXiii) (heterocyclic)alkylsulfonylalkyl,
(lxxiv) cycloalkyloxyalkyl,
(lxxv) cycloalkylthioalkyl,
(lxxvi) cycloalkylsulfonylalkyl,
(lxxvii) cycloalkylalkoxyalkyl,
(lxxviii) cycloalkylthioalkoxyalkyl,
(lxxix) cycloalkylalkylsufonylalkyl,
(lxxx) aroylalkyl,
(lxxxi) (heterocyclic)carbonylalkyl,
(lxxxii) (aryl)aminoalkyl,
(lxxxiii) (aryl)(alkyl)aminoalkyl,
(lxxxiv) (arylalkyl)aminoalkyl,
(lxxxv) (arylalkyl)(alkyl)aminoalkyl,
(lxxxvi) (heterocyclic)aminoalkyl,
(lxxxvii) (heterocyclic)(alkyl)aminoalkyl,
(lxxxviii ((heterocyclic)alkyl)aminoalkyl,
(lxxxix) ((heterocyclic)alkyl)alkylaminoalkyl
(xc) (alkoxyalkyl)aminoalkyl,
(xci) thioalkoxyalkyl,
(xcii) mercaptoalkyl,
(xciii) aminocarbonylalkyl,
(xciv) alkylaminocarbonylalkyl and
(xcv) dialkylaminocarbonylalkyl;

and (2) Z'—W'— wherein at each occurrence W' is absent or represents a peptide chain containing 1–3 amino acids and wherein at each occurrence Z' is $R_6$—$(C(R_{5*})(R_5))_e$—$(S(O))_m$—$(C(R_{5*})(R_5))_g$—$(U)_i$—$(C(R_{5*})(R_5))_j$—$C(T)i$— or $R_6$—$(S(O))_m$—$(U)_{ii}$—CH $(R_{5a})$—CH$(R_{5b})$—$(U)_{iii}$—$C(T)_i$ wherein $R_6$—$(C(R_{5*})(R_5))_e$—$(S(O))_m$—$(C(R_{5*})(R_5))_g$—$(U)_i$— $(C(R_{5*})$ $(R_5))_j$—$C(T)_i$— or $R_6$—$(S(O))_m$—$(U)_{ii}$—CH$(R_{5*})$—CH$(R_{5b})(U)_i$— $(U)_{iii}$—$C(T)_{ij}$— is bonded to the amino terminus of the peptide chain. At each occurrence T is independently selected from O and S, at each occurrence $R_5$ and $R_{5*}$ are independently defined as above or $R_5$, $R_{5*}$ and the carbon atom to which they are bonded or $R_{5a}$, $R_{5b}$ and the carbon atoms to which they are bonded taken together form a carbocyclic ring of from 3 to 8 carbon atoms which can be optionally substituted with a loweralkyl group or when e, g or j is 2 or more, $R_5$ and $R_{5*}$ on adjacent carbon atoms when taken together form a carbocyclic ring of from 3 to 8 carbon atoms which can be optionally substituted with a loweralkyl group, at each occurrence U is independently selected from O, S and —N($R_5$)— wherein $R_5$ is independently defined as above, at each occurrence e is independently selected from 0, 1, 2 and 3, at each occurrence m is independently selected from 1 and 2, at each occurrence g is independently selected from 0, 1, 2 and 3, at each occurrence i, ii and iii are independently selected from 0 and 1, at each occurrence j is independently selected from 0, 1, 2 and 3, and at each occurrence $R_6$ is independently defined as above.

Preferred compounds of the invention are compounds of the formula A—X—B wherein X is

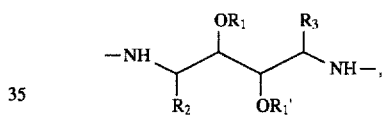

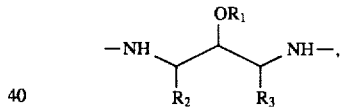

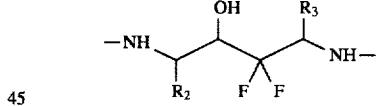

or

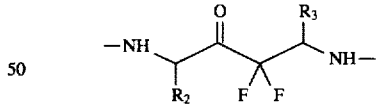

and wherein A is $R_6$—C(O)—NH—CH($R_5$)—C(O)— wherein $R_5$ and $R_6$ are defined as above and B is —C(O)— $R_6$ wherein $R_6$ is independently defined as above; or a pharmaceutically acceptable salt, prodrug or ester thereof.

Preferred compounds of the invention also are compounds of the formula I wherein X is

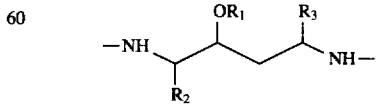

wherein $R_1$, $R_2$ and $R_3$ are defined as above.

More preferred compounds of the invention are compounds of the formula:

A—X—B
wherein X is

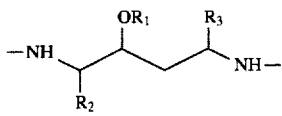

wherein $R_1$ is hydrogen, loweralkyl or alkoxyalkyl and $R_2$ and $R_3$ are independently $R_5$ wherein at each occurrence $R_5$ is independently defined as above.

A and B are independently selected from Z— wherein at each occurrence Z is $R_6$—$(CH(R_5))_e$—$(C(T))_f$—$(CH(R_5))_g$—$(U)_i$—$(CH(R_5))_j$—$C(T)_{f'}$—. At each occurrence T is independently selected from O and S, at each occurrence $R_5$ is independently defined as above, at each occurrence U is independently selected from O, S and —N ($R_5$)— wherein $R_5$ is independently defined as above, at each occurrence e is independently selected from 0, 1, 2 and 3, at each occurrence f is independently selected from 0 and 1, an each occurrence g is independently selected from 0, 1, 2 and 3, at each occurrence i is independently selected from 0 and 1, at each occurrence j is independently selected from 0, 1, 2 and 3, and at each occurrence Re is independently selected from $R_7$-$(R_9)_k$— wherein at each occurrence $R_9$ is independently selected from N($R_7$), O and S and at each occurrence k is independently selected from 0 and 1 and at each occurrence $R_7$ is independently defined as above.

Most preferred compounds of the invention are compounds of the formula:

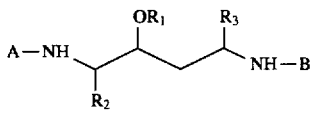

wherein $R_1$ is hydrogen, $R_2$ and $R_3$ are independently selected from (aryl)alkyl, A is $R_6$—C(O)—NH—CH($R_{5a}$)—C(O)— wherein $R_{5a}$ is loweralkyl and $R_6$ is $R_7$-$R_9$— wherein $R_7$ is heterocyclic or (heterocyclic)alkyl and $R_9$ is —N($R_{7a}$)—, S or O wherein $R_{7a}$ is hydrogen or loweralkyl and B is —C(O)—$R_6$, wherein $R_6$, is $R_7$-$R_9$— wherein $R_{7'}$ is heterocyclic or (heterocyclic)alkyl and $R_{9'}$ is —N($R_{7a'}$)—, S or O wherein $R_{7a'}$ is hydrogen or loweralkyl; or a pharmaceutically acceptable salt, prodrug or ester thereof.

Most preferred compounds of the invention also are compounds of the formula:

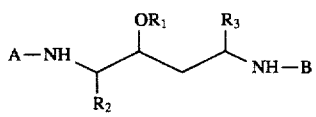

wherein $R_1$ is hydrogen, $R_2$ and $R_3$ are independently selected from (aryl)alkyl, A is —C(O)—$R_6$, wherein $R_6$ is $R_7$-$R_9$— wherein $R_7$ is heterocyclic or (heterocyclic) alkyl and $R_9$ is —N($R_{7a'}$)—, S or O wherein $R_{7a'}$ is hydrogen or loweralkyl and B is $R_6$—C(O)—NH—CH($R_{5a}$)—C(O)— wherein $R_{5a}$ is loweralkyl and $R_6$ is $R_7$-$R_9$— wherein $R_7$ is heterocyclic or (heterocyclic)alkyl and $R_9$ is —N($R_{7a}$)—, S or O wherein $R_{7a}$ is hydrogen or loweralkyl; or a pharmaceutically acceptable salt, prodrug or ester thereof.

Most preferred compounds of the invention also are compounds of the formula:

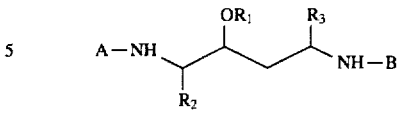

wherein $R_1$ is hydrogen, $R_2$ and $R_3$ are independently selected from (aryl)alkyl, and A and B are independently is —C(O)—$R_6$ wherein $R_6$ is $R_7$-$R_9$— wherein at each occurrence $R_7$ is independently selected from heterocyclic and (heterocyclic)alkyl and at each occurrence $R_9$ is independently selected from —N($R_{7a}$)—, S and O wherein $R_{7a}$ is hydrogen or loweralkyl; or a pharmaceutically acceptable salt, prodrug or ester thereof.

The term "a peptide chain of 1–3 amino acids" as used herein includes —(N($R_{10}$)—CH($R_5$)—C(O))$_n$— wherein at each occurrence $R_5$ is independently defined as above, at each occurrence n is independently selected from 1, 2 and 3, and at each occurrence $R_{10}$ is independently selected from hydrogen and loweralkyl, or $R_5$ and $R_{10}$ taken together is —(CH$_2$)$_p$— wherein p is 3–5.

The compounds of the invention comprise asymmetrically substituted centers. Such centers can be racemic or asymmetric. Racemic mixtures, mixtures of diastereomers, as well as single diastereomers of the compounds of the invention are included in the present invention. The terms "S" and "R" configuration are as defined by the IUPAC 1974 Recommendations for Section E, Fundamental Stereochemistry, Pure Appl. Chem. (1976) 45, 13–30.

The terms "Ile", "Val" and "Thr" as used herein refer to isoleucine, valine and threonine, respectively. In general, the amino acid abbreviations used herein follow the IUPAC-IUB Joint Commission on Biochemical Nomenclature for amino acids and peptides (Eur. J. Blochem. 1984, 158, 9–31).

The term "N-protecting group" or "N-protected" as used herein refers to those groups intended to protect the N-terminus of an amino acid or peptide or to protect an amino group against undersirable reactions during synthetic procedures. Commonly used N-protecting groups are disclosed in Greene, "Protective Groups In Organic Synthesis," (John Wiley & Sons, New York (1981)), which is hereby incorporated by reference. N-protecting groups comprise carbamates, amides, N-alkyl derivatives, amino acetal derivatives, N-benzyl derivatives, imine derivatives, enamine derivatives and N-heteroatom derivatives. Preferred N-protecting groups are formyl, acetyl, benzoyl, pivaloyl, t-butylacetyl, phenylsulfonyl, benzyl, t-butyloxycarbonyl (Boc), benzyloxycarbonyl (Cbz) and the like. N-protecting groups also refer to an L- or D-aminoacyl residue, which is derived from an L- or D- amino acid.

The term "O-protecting group" as used herein refers to a substituent which protects hydroxyl groups against undesirable reactions during synthetic procedures such as those O-protecting groups disclosed in Greene, "Protective Groups In Organic Synthesis," (John Wiley & Sons, New York (1981)). O-protecting groups comprise substituted methyl ethers, for example, methoxymethyl, benzyloxymethyl, 2-methoxyethoxymethyl, 2-(trimethylsilyl)ethoxymethyl, t-butyl, benzyl and triphenylmethyl; tetrahydropyranyl ethers; substituted ethyl ethers, for example, 2,2,2-trichloroethyl; silyl ethers, for example, trimethylsilyl, t-butyldimethylsilyl and t-butyldiphenylsilyl; and esters prepared by reacting the hydroxyl group with a carboxylic acid, for example, acetate, propionate, benzoate and the like.

The term "loweralkyl" as used herein refers to straight or branched chain alkyl radicals containing from 1 to 6 carbon atoms including, but not limited to, methyl, ethyl, n-propyl, iso-propyl, n-butyl, iso-butyl, sec-butyl, n-pentyl, 1-methylbutyl, 2,2-dimethylbutyl, 2-methylpentyl, 2, 2dimethylpropyl, n-hexyl and the like.

The term "alkylene" as used herein refers to a straight or branched chain carbon diradical containing from 1 to 6 carbon atoms including, but not limited to, —$CH_2$—, —$CH_2CH_2$—, —$CH(CH_3)CH_2$—, —$CH_2CH_2CH_2$— and the like.

The term "loweralkenyl" as used herein refers to a loweralkyl radical which contains at least one carbon-carbon double bond including, but not limited to, propenyl, butenyl and the like. Alkenyl groups can be unsubstituted or substituted with one or more substituents independently selected from loweralkyl, haloalkyl, cycloalkyl, aryl, heterocyclic, alkoxy, thioalkoxy, amino, alkylamino, dialkylamino, hydroxy, halo, mercapto, nitro, carboxaldehyde, carboxy, carboalkoxy and carboxamide.

The term "loweralkenylene" as used herein refers to a straight or branched chain carbon diradical containing from 2 to 6 carbon atoms which contains a carbon-carbon double bond including, but not limited to, —CH=CH—, —C($CH_3$)=CH—, —$CH_2$CH=CH—, —$CH_2$—CH=CH—$CH_2$— and the like.

The term "aryl" as used herein refers to a $C_6$ monocyclic aromatic ring system or a $C_9$ or $C_{10}$ bicyclic carbocyclic ring system having one or more aromatic rings including, but not limited to, phenyl, naphthyl, tetrahydronaphthyl, indanyl, indenyl and the like. Aryl groups can be unsubstituted or substituted with one, two or three substituents independently selected from loweralkyl, haloalkyl, alkoxy, thioalkoxy, alkoxycarbonyl, alkanoyl, hydroxy, halo, mercapto, nitro, amino, alkylamino, dialkylamino, carboxaldehyde, carboxy, carboxamide, arylalkyl, arylalkoxy, (heterocyclic)alkyl, (heterocyclic)alkoxy, aminoalkyl, aminoalkoxy, alkylaminoalkyl, alkylaminoalkoxy, dialkylaminoalkyl, dialkylaminoalkoxy, (alkoxyalkyl) aminoalkyl, (alkoxyalkyl) aminoalkoxy, di-(alkoxyalkyl) aminoalkyl, di-(alkoxyalkyl) aminoalkoxy, (alkoxyalkyl)(alkyl)aminoalkyl, (alkoxyalkyl)(alkyl)aminoalkoxy, hydroxyalkyl, hydroxyalkoxy, carboxyalkyl, carboxyalkoxy, alkoxyalkyl, thioalkoxyalkyl, polyalkoxyalkyl and dialkoxyalkyl. In addition, substituted aryl groups include tetrafluorophenyl and pentafluorophenyl.

The term "arylalkyl" as used herein refers to an aryl group appended to a loweralkyl radical including, but not limited to, benzyl, 4-hydroxybenzyl, 1-naphthylmethyl and the like.

The term "aminoalkyl" as used herein refers to —$NH_2$ appended to a loweralkyl radical.

The term "cyanoalkyl" as used herein refers to —CN appended to a loweralkyl radical.

The term "hydroxyalkyl" as used herein refers to —OH appended to a loweralkyl radical.

The term "dihydroxyalkyl" as used herein refers to a loweralkyl radical disubstituted with —OH groups.

The term "polyhydroxyalkyl" as used herein refers to a loweralkyl radical substituted with more than two —OH groups.

The term "mercaptoalkyl" as used herein refers to a loweralkyl radical to which is appended a mercapto (—SH) group.

The term "hydroxyaminoalkyl" as used herein refers to a hydroxyamino group (—NHOH) appended to a loweralkyl radical.

The term "alkoxyaminoalkyl" as used herein refers to —$NHR_{20}$ (wherein $R_{20}$ is an alkoxy group) appended to a loweralkyl radical.

The term "(alkoxy)(alkyl)aminoalkyl" as used herein refers to ($R_{21}$) ($R_{22}$)N— wherein $R_{21}$ is alkoxy and $R_{22}$ is loweralkyl appended to a loweralkyl radical.

The term "alkylamino" as used herein refers to a loweralkyl radical appended to an NH radical.

The term "hydroxyalkylamino" as used herein refers to a hydroxyalkyl group appended to an NH radical.

The term "dihydroxyalkylamino" as used herein refers to a dihydroxyalkyl group appended to an NH radical.

The term "(hydroxyamino)alkylamino" as used herein refers to —$NHR_{23}$ wherein $R_{23}$ is a hydroxyaminoalkyl group.

The term "(alkoxyamino)alkylamino" as used herein refers to —$NHR_{24}$ wherein $R_{24}$ is an alkoxyaminoalkyl group.

The term "((hydroxyamino)alkyl)(alkyl)amino" as used herein refers to —$NR_{25}R_{26}$ wherein $R_{25}$ is a hydroxyaminoalkyl group and $R_{26}$ is a loweralkyl group.

The term "((alkoxyamino)alkyl)(alkyl)amino" as used herein refers to —$NR_{27}R_{28}$ wherein $R_{27}$ is an alkoxyaminoalkyl group and $R_{28}$ is a loweralkyl group.

The term "(N-protected)aminoalkylamino" as used herein refers to an N-protected amino group which is appended to a loweralkyl group which in turn is appended to an —NH radical.

The term "cycloalkyl" as used herein refers to an aliphatic ring having 3 to 7 carbon atoms including, but not limited to, cyclopropyl, cyclopentyl, cyclohexyl and the like. Cycloalkyl groups can be unsubstituted or substituted with one, two or three substituents independently selected. from loweralkyl, haloalkyl, alkoxy, thioalkoxy, amino, alkylamino, dialkylamino, hydroxy, halo, mercapto, nitro, carboxaldehyde, carboxy, carboalkoxy and carboxamide.

The term "cycloalkylalkyl" as used herein refers to a cycloalkyl group appended to a loweralkyl radical, including but not limited to cyclohexylmethyl.

The term "alkylaminocycloalkyl" as used herein refers to an alkylamino group appended to a cycloalkyl radical.

The term "dialkylaminocycloalkyl" as used herein refers to a dialkylamino group appended to a cycloalkyl radical.

The terms "alkoxy" and "thioalkoxy" as used herein refer to $R_{29}O$— and $R_{29}S$—, respectively, wherein $R_{29}$ is a loweralkyl group or benzyl.

The term "haloalkoxy" as used herein refers to $R_{29}'O$— wherein $R_{29}'$ is a haloalkyl group The term "(hydroxyamino)alkoxy" as used herein refers to $R_{30}O$— wherein $R_{30}$ is a hydroxyaminoalkyl group.

The term "(alkoxyamino)alkoxy" as used herein refers to $R_{31}O$— wherein $R_{31}$ is an alkoxyaminoalkyl group.

The term "alkoxyalkyl" as used herein refers to an alkoxy group appended to a loweralkyl radical.

The term "thioalkoxyalkyl" as used herein refers to a thioalkoxy group appended to a loweralkyl radical.

The term "alkoxyalkoxyalkyl" as used herein refers to an alkoxy group appended to an alkoxy group which is in turn appended to a loweralkyl radical including, but not limited to, methoxyethoxymethyl and the like.

The term "guanidinoalkyl" as used herein refers to a guanidino group (—NHC(=NH)$NH_2$) appended to a loweralkyl radical.

The term "alkenyloxy" as used herein refers to $R_{32}O$— wherein $R_{32}$ is a loweralkenyl group.

The term "hydroxyalkoxy" as used herein refers to —OH appended to an alkoxy radical.

The term "dihydroxyalkoxy" as used herein refers to an alkoxy radical which is disubstituted with —OH groups.

The term "arylalkoxy" as used herein refers $R_{33}O$— wherein $R_{33}$ is a arylalkyl group as defined above.

The term "(heterocyclic)alkoxy" as used herein refers to $R_{34}O-$ wherein $R_{34}$ is a (heterocyclic) alkyl group.

The term "aryloxyalkyl" as used herein refers to a $R_{35}O-$ group appended to a loweralkyl radical, wherein $R_{35}$ is an aryl group.

The term "dialkylamino" as used herein refers to $-NR_{36}R_{37}$ wherein $R_{36}$ and $R_{37}$ are independently selected from loweralkyl groups.

The term "(hydroxyalkyl)(alkyl)amino" as used herein refers to $-NR_{38}R_{39}$ wherein $R_{38}$ is hydroxyalkyl and $R_{39}$ is loweralkyl.

The term "N-protected aminoalkyl" as used herein refers to $-NHR_{40}$ appended to a loweralkyl group, wherein $R_{40}$ is an N-protecting group.

The term "alkylaminoalkyl" as used herein refers to $NHR_{41}$ appended to a loweralkyl radical, wherein $R_{41}$ is a loweralkyl group.

The term "(N-protected)(alkyl)aminoalkyl" as used herein refers to $-NR_{42}R_{43}$, which is appended to a loweralkyl radical, wherein $R_{42}$ and $R_{43}$ are as defined above.

The term "dialkylaminoalkyl" as used herein refers to $-NR_{44}R_{45}$ which is appended to a loweralkyl radical wherein $R_{44}$ and $R_{45}$ are independently selected from loweralkyl.

The term "azidoalkyl" as used herein refers to a $-N_3$ group appended to a loweralkyl radical.

The term "carboxyalkyl" as used herein refers to a carboxylic acid group (—COOH) appended to a loweralkyl radical.

The term "alkoxycarbonylalkyl" as used herein refers to a $R_{46}C(O)-$ group appended to a loweralkyl radical, wherein $R_{46}$ is an alkoxy group.

The term "carboxyalkoxyalkyl" as used herein refers to a carboxylic acid group (—COOH) appended to an alkoxy group which is appended to a loweralkyl radical.

The term "alkoxycarbonylalkoxyalkyl" as used herein refers to an alkoxycarbonyl group ($R_{47}C(O)-$ wherein $R_{47}$ is an alkoxy group) appended to an alkoxy group which is appended to a loweralkyl radical.

The term "(amino)carboxyalkyl" as used herein refers to a loweralkyl radical to which is appended a carboxylic acid group (—COOH) and an amino group ($-NH_2$).

The term "((N-protected)amino)carboxyalkyl" as used herein refers to a loweralkyl radical to which is appended a carboxylic acid group (—COOH) and $-NHR_{48}$ wherein $R_{48}$ is an N-protecting group.

The term "(alkylamino)carboxyalkyl" as used herein refers to a loweralkyl radical to which is appended a carboxylic acid group (—COOH) and an alkylamino group.

The term "((N-protected)alkylamino)carboxyalkyl" as used herein refers to a loweralkyl radical to which is appended a carboxylic acid group (—COOH) and $-NR_{48}R_{49}$ wherein $R_{48}$ is as defined above and $R_{49}$ is a loweralkyl group.

The term "(dialkylamino)carboxyalkyl" as used herein refers to a loweralkyl radical to which is appended a carboxylic acid group (—COOH) and $-NR_{49}R_{49}$ wherein $R_{49}$ is as defined above.

The term "(amino)alkoxycarbonylalkyl" as used herein refers to a loweralkyl radical to which is appended an alkoxycarbonyl group as defined above and an amino group ($-NH_2$).

The term "((N-protected) amino) alkoxycarbonylalkyl" as used herein refers to a loweralkyl radical to which is appended an alkoxycarbonyl group as defined above and $-NHR_{50}$ wherein $R_{50}$ is an N-protecting group.

The term "(alkylamino)alkoxycarbonylalkyl" as used herein refers to a loweralkyl radical to which is appended an alkoxycarbonyl group as defined above and an alkylamino group as defined above.

The term "((N-protected) alkylamino) alkoxycarbonylalkyl" as used herein refers to a loweralkyl radical to which is appended an alkoxycarbonyl group as defined above and $-NR_{51}R_{52}$ wherein $R_{51}$ is an N-protecting group and $R_{52}$ is a loweralkyl group.

The term "(dialkylamino)alkoxycarbonylalkyl" as used herein refers to a loweralkyl radical to which is appended an alkoxycarbonyl group as defined above and $-NR_{53}R_{54}$ wherein $R_{53}$ and $R_{54}$ are independently selected from loweralkyl.

The term "carboxyalkylamino" as used herein refers to $-NHR_{55}$ wherein $R_{55}$ is a carboxyalkyl group.

The term "alkoxycarbonylalkylamino" as used herein refers to $-NHR_{56}$ wherein $R_{56}$ is an alkoxycarbonylakyl group.

The term "(amino)carboxyalkylamino" as used herein refers to $-NHR_{57}$ wherein $R_{57}$ is an (amino)carboxyalkyl group.

The term "((N-protected)amino)carboxyalkylamino" as used herein refers to $-NHR_{58}$ wherein $R_{58}$ is an [(N-protected)amino] carboxyalkyl group.

The term "(alkylamino)carboxyalkylamino" as used herein refers to $-NHR_{59}$ wherein $R_{59}$ is an (alkylamino)carboxyalkyl group.

The term "((N-protected)alkylamino)carboxyalkylamino" as used herein refers to $-NHR_{60}$ wherein: $R_{60}$ is an ((N-protected) alkylamino) carboxyalkyl group.

The term "(dialkylamino)carboxyalkylamino" as used herein refers to $-NHR_{61}$ wherein $R_{61}$ is a (dialkylamino) carboxyalkyl group.

The term "(amino)alkoxycarbonylalkylamino" as used herein refers to $-NHR_{62}$ wherein $R_{62}$ is an (amino) alkoxycarbonylalkyl group.

The term "((N-protected) amino) alkoxycarbonylalkylamino" as used herein refers to $-NHR_{63}$ wherein $R_{63}$ is an ((N-protected)amino)alkoxycarbonylalkyl group.

The term "(alkylamino)alkoxycarbonylalkylamino" as used herein refers to $-NHR_{64}$ wherein $R_{64}$ is an (alkylamino) alkoxycarbonylalkyl group.

The term "((N-protected) alkylamino) alkoxycarbonylalkylamino" as used herein refers to $-NHR_{65}$ wherein $R_{65}$ is an ((N-protected) alkylamino) alkoxycarbonylalkyl group.

The term "(dialkylamino)alkoxycarbonylalkylamino" as used herein refers to $-NHR_{66}$ wherein $R_{66}$ is a (dialkylamino) alkoxycarbonylalkyl group.

The term "aminocycloalkyl" as used herein refers to an $NH_2$ appended to a cycloalkyl radical.

The term "((alkoxy)alkoxy)alkyl" as used herein refers to an alkoxy group appended to an alkoxy group which is appended to a loweralkyl radical.

The term "polyalkoxyalkyl" as used herein refers to a polyalkoxy residue appended to a loweralkyl radical.

The term "polyalkoxy" as used herein refers to —OR wherein $R_{67}$ is a straight or branched chain containing 1-5, $C_{n'}-C_{n''}$ linkages wherein n' and n" are independently selected from 1 to 3, including but not limited to methoxyethoxymethoxy, methoxymethoxy and the like.

The term "(arylalkyl)amino" as used herein refers to $R_{68}NH-$ wherein $R_{68}$ is an arylalkyl group as defined above.

The term "(arylalkyl)(alkyl)amino" as used herein refers to $R_{69}R_{70}N-$ wherein $R_{69}$ is an arylalkyl group as defined above and $R_{70}$ is a loweralkyl group.

The term "(heterocyclic)alkylamino" as used herein refers to $R_{71}NH-$ wherein $R_{71}$ is a (heterocyclic)alkyl group.

The term "((heterocyclic)alkyl)(alkyl)amino" as used herein refers to $R_{72}R_{73}N-$ wherein $R_{72}$ is a (heterocyclic)alkyl group and $R_{73}$ is a loweralkyl group.

The term "dialkylaminoalkyl(alkyl)amino" as used herein refers to $-NR_{78}R_{79}$ wherein $R_{78}$ is a dialkylamino residue appended to a loweralkyl residue and $R_{79}$ is a loweralkyl residue.

The term "alkylaminoalkylamino" as used herein refers to $-NHR_{80}$ wherein $R_{80}$ is an alkylaminoalkyl group as previously defined.

The term "dialkylaminoalkylamino" as used herein refers to $-NHR_{81}$ wherein $R_{81}$ is a dialkylaminoalkyl group as previously defined.

The term "aminoalkylamino" as used herein refers to $-NHR_{82}$ wherein $R_{82}$ is an aminoalkyl residue.

The term "(dihydroxyalkyl)(alkyl)amino" as used herein refers to a loweralkyl group which is disubstituted with $-OH$ radicals, appended to an amino group, which amino group also has appended another loweralkyl group, including but not limited to N- (2,3-dihydroxypropyl) —N— (methyl) amine.

The term "di-(hydroxyalkyl)amino" as used herein refers to $-NR_{83}R_{84}$ wherein $R_{83}$ and $R_{84}$ are hydroxyalkyl residues.

The term "alkoxyalkyl(alkyl)amino" as used herein refers to $-NR_{85}R_{86}$ wherein $R_{85}$ is an alkoxyalkyl group and $R_{86}$ is a loweralkyl group.

The term "di-(alkoxyalkyl)amino" as used herein refers to $-NR_{87}R_{88}$ wherein $R_{87}$ and $R_{88}$ are alkoxyalkyl groups.

The term "di-(polyalkoxyalkyl)amino" as used herein refers to $-NR_{89}R_{90}$ wherein $R_{89}$ and $R_{90}$ are polyalkoxy residues appended to loweralkyl residues.

The term "((polyalkoxy)alkyl))(alkyl)amino" as used herein refers to $-NR_{91}R_{92}$ wherein $R_{91}$ is a polyalkoxy residue appended to a loweralkyl residue and $R_{92}$ is a loweralkyl residue.

The term "halo" or "halogen" as used herein refers to $-Cl$, $-Br$, $-I$ or $-F$.

The term "haloalkyl" as used herein refers to a loweralkyl radical in which one or more of the hydrogen atoms are replaced by halogen including, but not limited to, chloromethyl, trifluoromethyl, 1-chloro-2-fluoroethyl and the like.

The term "thioalkoxyalkyl" as used herein refers to a thioalkoxy group appended to a loweralkyl radical.

The term "alkylsulfonyl" as used herein refers to $R_{93}SO_2-$ wherein $R_{93}$ is loweralkyl group.

The term "arylthioalkyl" as used herein refers to $R_{94}-S-R_{95}-$ wherein $R_{94}$ is an aryl group and $R_{95}$ is an alkylene group.

The term "arylsulfonylalkyl" as used herein refers to $R_{96}-S(O)_2-R_{97}-$ wherein $R_{96}$ is any aryl group and R97 is an alkylene group.

The term "(heterocyclic)oxyalkyl" as used herein refers to $R_{98}-O-R_{99}-$ wherein $R_{98}$ is an aryl group and $R_{99}$ is an alkylene group.

The term "(heterocyclic)thioalkyl" as used herein refers to $R_{100}-S-R_{101}-$ wherein $R_{100}$ is an aryl group and R101 is an alkylene group.

The term "(heterocyclic)sulfonylalkyl" as used herein refers to $R_{102}-S(O)_2-R_{103}-$ wherein $R_{102}$ is an aryl group and $R_{103}$ is an alkylene group.

The "arylalkoxyalkyl" as used herein refers to $R_{104}-R_{105}-$ wherein $R_{104}$ is an arylalkyl group and $R_{105}$ is an alkylene group.

The "arylthioalkoxyalkyl" as used herein refers to $R_{106}-S-R_{107}-$ wherein $R_{106}$ is an arylalkyl group and $R_{107}$ is an alkylene group.

The "arylalkylsulfonylalkyl" as used herein refers to $R_{108}-S(O)_2-R_{109}-$ wherein $R_{108}$ is an arylalkyl group and $R_{109}$ is an alkylene group.

The term "(heterocyclic)alkoxyalkyl" as used herein refers to $R_{110}-O-R_{111}-$ wherein $R_{110}$ is a (heterocyclic)alkyl group and $R_{111}$ is an alkylene group.

The term "(heterocyclic)thioalkoxyalkyl" as used herein refers to $R_{112}-S-R_{113}-$ wherein $R_{112}$ is a (heterocyclic)alkyl group and $R_{113}$ is an alkylene group.

The term "(heterocyclic)alkylsulfonylalkyl" as used herein refers to $R_{114}-S(O)_2-R_{115}-$ wherein $R_{114}$ is a (heterocyclic)alkyl group and $R_{115}$ is an alkylene group.

The term "cycloalkyloxyalkyl" as used herein refers to $R_{116}-O-R_{117}-$ wherein $R_{116}$ is a cycloalkyl group and $R_{117}$ is an alkylene group.

The term "cycloalkylthioalkyl" as used herein refers to $R_{118}-S-R_{119}-$ wherein $R_{118}$ is a cycloalkyl group and $R_{119}$ is an alkylene group.

The term "cycloalkylsulfonylalkyl" as used herein refers to $R_{120}-S(O)_2-R_{121}-$ wherein $R_{120}$ is a cycloalkyl group and $R_{121}$ is an alkylene group.

The term "cycloalkylalkoxyalkyl" as used herein refers to $R_{122}-O-R_{123}-$ wherein $R_{122}$ is a cycloalkylalkyl group and $R_{123}$ is an alkylene group.

The term "cycloalkylthioalkoxyalkyl" as used herein refers to $R_{124}-S-R_{125}-$ wherein $R_{124}$ is a cycloalkylalkyl group and $R_{125}$ is an alkylene group.

The term "cycloalkylalkylsulfonylalkyl" as used herein refers to $R_{126}-S(O)_2-R_{127}-$ wherein $R_{126}$ is a cycloalkylalkyl group and $R_{127}$ is an alkylene group.

The term "alkanoyl" as used herein refers to $R_k-C(O)-$ wherein $R_k$ is a loweralkyl group.

The term "aminocarbonyl" as used herein refers to $-C(O)NH_2$.

The term "aminocarbonylalkyl" as used herein refers to an aminocarbonyl group appended to a loweralkyl radical.

The term "alkylaminocarbonyl" as used herein refers to $-C(O)NHR_{128}$ wherein $R_{128}$ is loweralkyl.

The term "alkylaminocarbonylalkyl" as used herein refers to an alkylaminocarbonyl group appended to a loweralkyl radical.

The term "dialkylaminocarbonyl" as used herein refers to $-C(O)NR_{129}R_{130}$ wherein $R_{129}$ and $R_{130}$ are independently selected from loweralkyl.

The term "dialkylaminocarbonylalkyl" as used herein refers to a dialkylaminocarbonyl group appended to a loweralkyl group.

The term "aroylalkyl" as used herein refers to $R_{131}-C(O)-R_{132}-$ wherein $R_{131}$ is an aryl group and $R_{132}$ is an alkylene group.

The term "(heterocyclic)carbonylalkyl" as used herein refers to $R_{133}-C(O)-R_{134}-$ wherein $R_{133}$ is a heterocyclic group and $R_{134}$ is an alkylene group.

The term "arylamino" as used herein refers to $R_{135}NH-$ wherein $R_{135}$ is an aryl group.

The term "(heterocyclic)amino" as used herein refers to $R_{136}NH-$ wherein $R_{136}$ is a heterocyclic group.

The term "aminoalkoxy" as used herein refers to an alkoxy radical to which is appended an amino ($-NH_2$) group.

The term "alkylaminoalkoxy" as used herein refers to an alkoxy radical to which is appended an alkylamino group.

The term "dialkylaminoalkoxy" as used herein refers to an alkoxy radical to which is appended a dialkylamino group.

The term "(alkoxyalkyl)aminoalkyl" refers to a loweralkyl radical to which is appended an (alkoxyalkyl)amino group.

The term "(alkoxyalkyl)aminoalkoxy" as used herein refers to an alkoxy radical to which is appended an (alkoxyalkyl) amino group.

The term "(alkoxyalkyl)(alkyl)aminoalkyl" refers to a loweralkyl radical to which is appended an (alkoxyalkyl)(alkyl)amino group.

The term "(alkoxyalkyl)(alkyl)aminoalkoxy" as used herein refers to an alkoxy radical to which is appended an (alkoxyalkyl)(alkyl)amino group.

The term "di-(alkoxyalkyl)aminoalkyl" refers to a loweralkyl radical to which is appended an di(alkoxyalkyl) amino group.

The term "d-(alkoxyalkyl)aminoalkoxy" as used herein refers to an alkoxy radical to which is appended an di(alkoxyalkyl)amino group.

The term "carboxyalkoxy" as used herein refers to an alkoxy radical to which is appended a carboxy (—COOH) group.

The term "aminocarbonylalkyl" as used herein refers to a loweralkyl radical to which is appended an aminocarbonyl ($NH_2C(O)$—) group.

The term "alkylaminocarbonylalkyl" as used herein refers to a loweralkyl radical to which is appended an alkylaminocarbonyl group.

The term "dialkylaminocarbonylalkyl" as used herein refers to a loweralkyl radical to which is appended an dialkylaminocarbonyl group.

At each occurrence, the term "heterocyclic ring" or "heterocyclic" as used herein independently refers to a 3- or 4-membered ring containing a heteroatom selected from oxygen, nitrogen and sulfur; or a 5- or 6-membered ring containing one, two or three heteroatoms independently selected from N, O and S. The 5-membered ring has 0–2 double bonds and the 6-membered ring has 0–3 double bonds. The nitrogen heteroatoms can be optionally quaternized or N-oxidized. The sulfur heteroatoms can be optionally S-oxidized. The term "heterocyclic" also includes bicyclic groups in which any of the above heterocyclic rings is fused to a benzene ring or a cyclohexane ring or another heterocyclic ring. Heterocyclics include: pyrrolyl, pyrrolinyl, pyrrolidinyl, pyrazolyl, pyrazolinyl, pyrazolidinyl, imidazolyl, imidazolinyl, imidazolidinyl, pyridyl, piperidinyl, pyrazinyl, piperazinyl, pyrimidinyl, pyridazinyl, oxazolyl, oxazolinyl, oxazolidinyl, isoxazolyl, isoxazolinyl, isoxazolidinyl, morpholinyl, thiazolyl, thiazolidinyl, isothiazolyl, isothiazolidinyl, indolyl, quinolinyl, tetrahydroquinolyl, isoquinolinyl, benzimidazolyl, benzothiazolyl, benzoxazolyl, benzofuranyl, furyl, dihydrofuranyl, tetrahydrofuranyl, pyranyl, dihydropyranyl, tetrahydropyranyl, dioxanyl, dioxolanyl, thienyl and benzothienyl.

Heterocyclics also include:

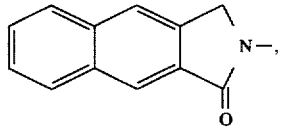

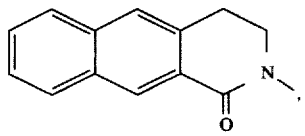

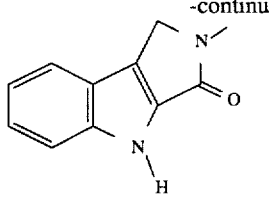

and

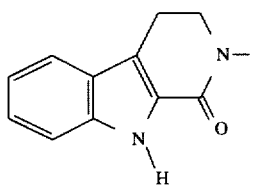

Heterocyclics can be unsubstituted or monosubstituted or disubstituted with substituents independently selected from hydroxy, halo, oxo(=O), alkylimino (R*N= wherein R* is a loweralkyl group), amino, (N-protected)amino, alkylamino, (N-protected)alkylamino, dialkylamino, alkoxy, polyalkoxy, haloalkyl, cycloalkyl, aryl, arylalkyl, —COOH, —$SO_3H$ and loweralkyl. In addition, nitrogen containing heterocycles can be N-protected.

The term "(heterocyclic)alkyl" as used herein refers to a heterocyclic group appended to a loweralkyl radical, including but not limited to imidazolylmethyl and thiazolylmethyl.

The term "heterocyclic carbonyloxy" as used herein refers to $R_{137}C(O)O$— wherein $R_{137}$ is a heterocyclic group.

The term "heterocyclic carbonylamino" as used herein refers to $R_{138}C(O)NH$— wherein $R_{138}$ is a heterocyclic group.

The term "(aryl)aminoalkyl" as used herein refers to a loweralkyl radical to which is appended $R_{300}NH$— wherein $R_{300}$ is an aryl group.

The term "(aryl)(alkyl)aminoalkyl" as used herein refers to a loweralkyl radical to which is appended $(R_{300})(R_{301})N$— wherein $R_{300}$ is an aryl group and $R_{301}$ is a loweralkyl group.

The term "(arylalkyl)aminoalkyl" as used herein refers to a loweralkyl radical to which is appended $R_{302}NH$— wherein $R_{302}$ is an arylalkyl group.

The term "(arylalkyl)(alkyl)aminoalkyl" as used herein refers to a loweralkyl radical to which is appended $(R_{303})(R_{304})N$— wherein $R_{303}$ is an arylalkyl group and $R_{304}$ is a loweralkyl group.

The term "(heterocyclic)aminoalkyl" as used herein refers to a loweralkyl radical to which is appended $R_{305}NH$— wherein $R_{305}$ is a heterocyclic group.

The term "(heterocyclic)(alkyl)aminoalkyl" as used herein refers to a loweralkyl radical to which is appended $(R_{306})(R_{307})N$— wherein $R_{306}$ is a heterocyclic group and $R_{307}$ is a loweralkyl group.

The term "((heterocyclic)alkyl)aminoalkyl" as used herein refers to a loweralkyl radical to which is appended $R_{308}NH$— wherein $R_{308}$ is a (heterocyclic)alkyl group.

The term "((heterocyclic)alkyl)(alkyl) aminoalkyl" as used herein refers to a loweralkyl radical to which is appended $(R_{309})(R_{310})N$— wherein $R_{309}$ is a (heterocyclic)alkylalkyl group and $R_{310}$ is a loweralkyl group.

The term "(alkoxyalkyl)aminoalkyl" as used herein refers to a loweralkyl radical to which is appended $R_{311}NH$— wherein $R_{311}$ is an alkoxyalkyl group.

When any variable (i.e., $R_1$, $R_2$, $R_3$, etc.) occurs more than one time in any substituent or in a compound of formula I, its definition on each occurrence is independent of its definition at every other occurrence. Also, combinations of substituents and/or variables are permissible only if such combinations result in stable compounds.

Preferred compounds of the invention are selected from the group consisting of:

(2S,3S,5S)-2-(N-(N-((2-Pyridinyl)methoxycarbonyl)valinyl)amino)-5-(N-((3-pyridinyl)methoxycarbonyl)amino)-1,6-diphenyl-3-hydroxyhexane;

(2S,3S,5S)-5-(N-(N-((N-Methyl-N-((2-pyridinyl)methyl)amino)carbonyl)valinyl)amino)-2-(N-((3-pyridinyl)-methoxycarbonyl)amino)-1,6-diphenyl-3 hydroxyhexane;

(2S,3S,5S)-2-(N-((3-Pyridinyl)-methoxycarbonyl)amino-5-(N-(N((N-Methyl-N-((6-methyl-2-pyridinyl)methyl)amino)carbonyl)valinyl)amino)-1,6-diphenyl-3-hydroxyhexane;

(2S,3S,5S)-2-(N-(N-((N-Methyl-N-((2-pyridinyl)methyl)amino)carbonyl)valinyl)amino)-5-(N-((3-pyridinyl)methoxycarbonyl)amino)-1,6-diphenyl-3-hydroxyhexane;

(2S,3S,5S)-5-(N-(N-((2-Pyridinyl)methoxycarbonyl)valinyl)amino)-2-(N-((3-pyridinyl)methoxycarbonyl)amino)-1,6-diphenyl-3-hydroxyhexane;

(2S,3S,5S)-5-(N-(N-((N-methyl-N-((2-pyridinyl)methyl)amino)carbonyl)isoleucinyl)amino)-2-(N-((3pyridinyl) methoxycarbonyl)amino)-1,6-diphenyl-3-hydroxyhexane.

(2S,3S,5S)-2,5-Di{N-(3-pyridylmethyl)oxy-carbonyl)amino}-3-hydroxy-1,6-diphenylhexane;

(2S,3S-5S)-2-(N-(N-((N-Methyl-N-((6-methyl-2-pyridinyl) methyl)amino)carbonyl)valinyl)amino)-5-(N-((3-pyridinyl)-methoxycarbonyl)amino)-1,6-diphenyl-3-hydroxyhexane; and (2S,3S,5S)-2-(N-[(pyridin-3-yl)methoxycarbonyl]amino)-5-(N-[(6-methylpyridin-2-yl)methoxycarbonylvalyllamino)-1,6-diphenyl-3-hydroxyhexane;

or a pharmaceutically acceptable salt, ester or prodrug thereof.

Compounds useful as intermediates for the preparation of the compound of formula I include the compound of the formula:

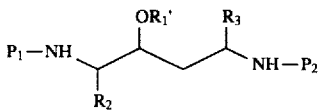

wherein $P_1$ and $P_2$ are independently selected from hydrogen and an N-protecting group; $R_1'$ is hydrogen, loweralkyl, alkoxyalkyl or an O-protecting group; and $R_2$ and $R_3$ are —$((R_0)_d$—$R_5)$ wherein at each occurrence $R_0$ is independently selected from —$(CH_2R_4)$— and loweralkenylene wherein at each occurrence d is independently selected from 0 and 1, at each occurrence $R_4$ is independently selected from —S—, —O—, —NH—, —N(loweralkyl)—, —S(O)—, —S(O)$_2$— and —CH$_2$— and at each occurrence $R_5$ is independently selected from (i) loweralkyl, (ii) aryl, (iii) thioalkoxyalkyl, (iv) (aryl)alkyl, (v) cycloalkyl, (vi) cycloalkylalkyl, (vii) hydroxyalkyl, (viii) alkoxyalkyl, (ix) aryloxyalkyl, (x) haloalkyl, (xi) caboxyalkyl, (xii) alkoxycarbonylalkyl, (xiii) aminoalkyl, (xiv) (N-protected) aminoalkyl, (xv) alkylaminoalkyl, (xvi) ((N-protected)(alkyl)amino)alkyl, (xvii) dialkylaminoalkyl, (xviii) guanidinoalkyl, (xix) loweralkenyl, (xx) heterocyclic, (xxi) (heterocyclic) alkyl, (xxii) hydrogen, (xxiii) arylthioalkyl, (xxiv) arylsulfonylalkyl, (xxv) (heterocyclic) thioalkyl, (xxvi) (heterocyclic)sulfonylalkyl, (xxvii) (heterocyclic)oxyalkyl, (xxviii) arylalkoxyalkyl, (xxix) arylthioalkoxyalkyl, (xxx) arylalkylsulfonylalkyl, (xxxi) (heterocyclic)alkoxyalkyl, (xxxii) (heterocyclic)thioalkoxyalkyl, (xxxiii) (heterocyclic)alkylsulfonylalkyl, (xxxiv) cycloalkyloxyalkyl, (xxxv) cycloalkylthioalkyl, (xxxvi) cycloalkylsulfonylalkyl, (xxxvii) cycloalkylalkoxyalkyl, (xxxviii) cycloalkylthioalkoxyalkyl, (xxxix) cycloalkylalkylsulfonylalkyl, (xl) aminocarbonyl, (xli) alkylaminocarbonyl, (xlii) dialkylaminocarbonyl, (xliii) aroylalkyl, (xliv) (heterocyclic)carbonylalkyl, (xlv) polyhydroxyalkyl, (xlvi) aminocarbonylalkyl, (xlvii) alkylaminocarbonylalkyl and (xlviii) dialkylaminocarbonylalkyl; or a salt or ester thereof.

The compounds of the invention can be prepared as shown in Schemes 1-5. The syntheses of carboxylic acids (A—OH and B—OH) and p-nitrophenyl esters (A—OPNP and B—OPNP) are described in the Examples. The process shown in Scheme 1 discloses the pinacol coupling of a protected aminoaldehyde (I) to give (II) and (III). Diols (II) and (III) are independently deoxygenated by initial reaction with α-acetoxyisobutyryl bromide and lithium bromide followed by reduction of the intermediate bromoacetate with tri-n-butyltin hydride to provide (IV) and (V), respectively. Basic hydrolysis of (IV) and (V) leads to (VI) and (VII), respectively.

The process described in Scheme 2 discloses the dimesylation and pyrolysis of (II) to provide (IX). Basic hydrolysis of (II) and (IX) provides (VIII) and (X), respectively. Treatment of (II) with α-acetoxyisobutyryl bromide in the absence of lithium bromide leads to (XI). Alternately, monomesylation of (II) to give (XIII) followed by pyrolysis in acetonitrile provides (XIV). Basic hydrolysis of either (XI) or (XIV) leads to (XII).

Another alternative process for converting (II) to the epimerized product (XII) is illustrated in Scheme 2A. Monoacetylation of (II) provides (XXX). Mesylation of (XXX), followed by heating provides (XI). Hydrolysis of (XI) gives (XII).

The process described in Scheme 3 discloses the aminolysis of (IV) to give the alcohol (XV). Mesylation of (XV) to give (XVI) followed by pyrolysis provides (E)-alkene (XVIII). Basic hydrolysis gives the diamine (XVIII).

The process described in Scheme 4 discloses the sequential addition of diisobutylaluminum hydride and vinylmagnesium bromide to (XIX) to give the mixture of allylic alcohols (XX). Mesylation of (XX) followed by displacement with RBMgBr/catalytic cuprous cyanide provides (E)-alkene (XXI). Epoxidation of (XXI) gives (XXII) which is opened with lithium azide to provide (XXIII). Reduction of the azido group in (XXIII) to give (XXIV) followed by acidic aleprotection of (XXIV) leads to aliamine (XXV).

The process described in Scheme 5 discloses the assemblage of HIV protease inhibitors from intermediate (XXVI), which represents structures (VI, (X'=—CH(OH)CH$_2$—)), (VII, (X'=—CH(OH)CH$_2$—)), (VIII, (X'=—CH(OH)CH(OH)—)), (X, (X'=—CH(OH)CH(OH)—)), (XII, (X'=—CH(OH)CH(OH)—)), (XVIII, (X'=—CH=CH—)), or (XXV, (X'=—CH(OH)—)). (X' can also be —CH$_2$CH$_2$—, —CH(OH)CF$_2$—, —C(O)CF$_2$— or —CH$_2$CH(OH)CH$_2$—).

The transformation of (XXVI) to (XXVII) can be achieved via an active ester such as a p-nitrophenyl ester of a carboxylic or sulfonic acid, or through direct coupling of the acid with (XXVI) in the presence of a coupling reagent. Alternately, protected α-aminoacids (W) can be coupled to (XXVI) to provide (XXVIII). Deprotection to give (XXIX), followed by coupling with Z—OH or activated derivatives thereof provides (XXVII). Alternatively, (XXVI) can be coupled with Z—W—OH or activated derivatives thereof to provide (XXVII).

Coupling reagents known in the art which can be used include, but are not limited to, dicyclohexylcarbodiimide (DCC), 3-ethyl-3'-(dimethylamino) propylcarbodiimide (EDC), bis(2-oxo-3-oxazolidinyl)-phosphinic chloride (BOP-Cl), diphenylphosphoryl azide (DPPA) and the like.

In addition to the use of the carboxylic acids or sulfonic acids for coupling with amines, acid halides and other activated esters are useful for-coupling with amines. Acid halide derivatives include the acid chloride. Activated ester derivatives include activated esters commonly used by those skilled in the art for activating carboxylic acid groups for coupling with an amine to form an amide bond or for coupling with an alcohol for forming an ester bond including, but not limited to, formic and acetic acid derived anhydrides, anhydrides derived from alkoxycarbonyl halides such as isobutyloxycarbonylchloride and the like, N-hydroxysuccinimide derived esters, N-hydroxyphthalimide derived esters, N-hydroxybenzotriazole derived esters, N-hydroxy-5-norbornene-2,3-dicarboxamide derived esters, 2,4,5-trichlorophenol derived esters and the like.

Scheme 6 illustrates the preparation of a particular substituent A which is N—(N'-2-pyridylmethyl-N'-methylaminocarbonyl)-L-valine (XXXV). 2-Picolinaldehyde (XXXI) is converted to 2-(N-methyl)aminomethylpyridine (XXXII) by treatment with methylamine, followed by hydrogenation. Reaction of (XXXII) with the methyl or benzyl ester of N-phenoxycarbonyl-L-valine ((XXXIII) provides (XXXIV). Hydrolysis (R=Me) or hydrogenation (R=benzyl) of (XXXIV) provides (XXXV).

Scheme 7 illustrates the preparation of the compounds of the invention wherein A and B are not identical. Starting with diamine (XXXVII) as a representative substituent X, monoacylation of the diamine with the p-nitrophenyl ester or p-nitrophenyl carbonate of A—OH provides a mixture of (XXXVIII) and (XXXIX). This mixture can be separated by silica gel chromatography. Acylation of (XXXVIII) with the p-nitrophenyl ester or p-nitrophenyl carbonate of B—OH provides (XL). Similarly, acylation of (XXXIX) with the p-nitrophenyl ester or p-nitrophenyl carbonate of B—OH provides (XLI).

Scheme 8 illustrates the preparation of compounds of the invention having substituent X derived from (XLIV) or (XLV). Reaction of aldehyde (XLII) with aminoester (XLIII) provides (XLIV). N-Oxidation of (XLIV) provides (XLV). Deprotection of (XLV) and coupling with the appropriate substituents A and B provides (XLVII). Alternatively, deprotection of (XLIV), followed by coupling with A and B and N-oxidation, provides (XLVII).

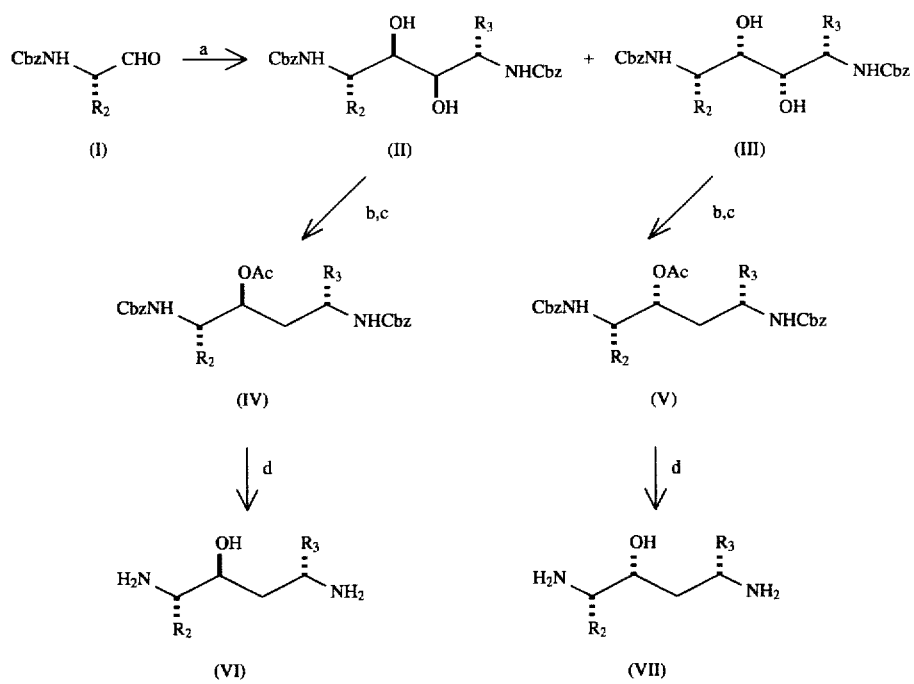

a, VCl$_3$.(THF)$_3$, Zn, CH$_2$Cl$_2$; b, LiBr, α-acetoxyisobutyryl bromide, CH$_3$CN; c, (n-Bu)$_3$SnH, AIBN, THF; d, Ba(OH)$_2$.8H$_2$O, H$_2$O, dioxane.

Scheme 2
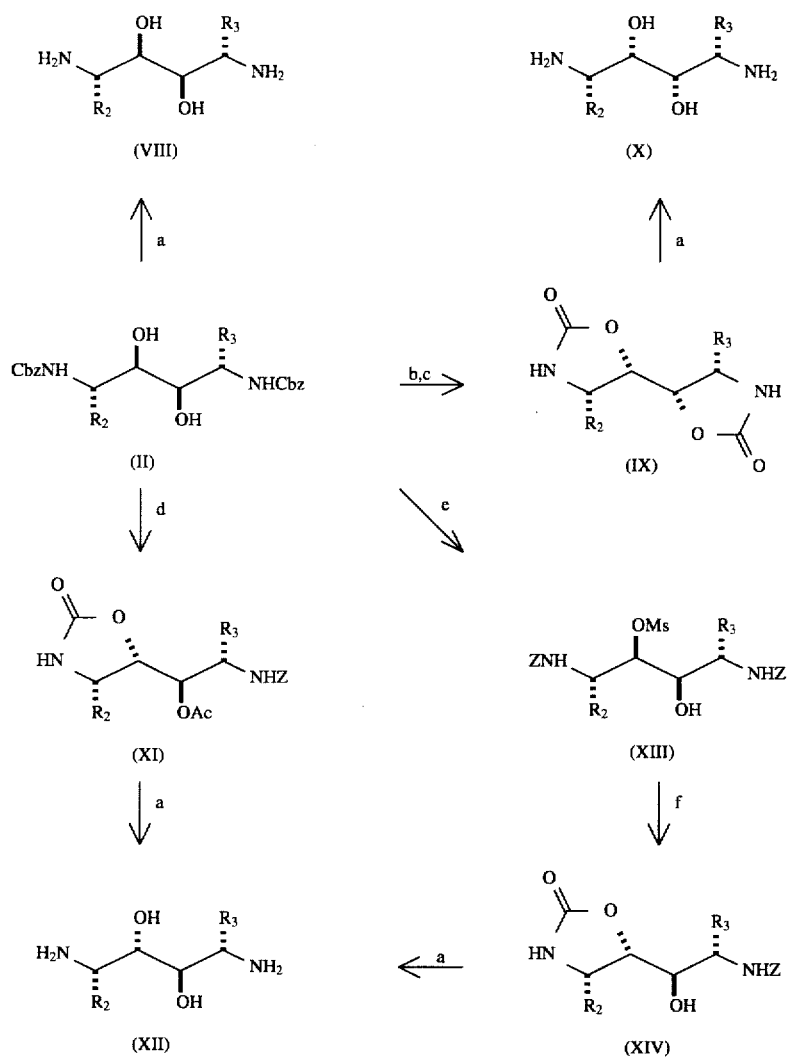
a, Ba(OH)$_2$·8H$_2$O, H$_2$O, dioxane; b, MsCl, Et$_3$N, DMAP, CH$_2$Cl$_2$; c, DMF, 120° C.; d, α-acetoxyisobutyryl bromide, CH$_3$CN; e, MsCl, Et$_3$N, DMAP, CH$_2$Cl$_2$; f, CH$_3$CN, reflux.
SCHEME 2A
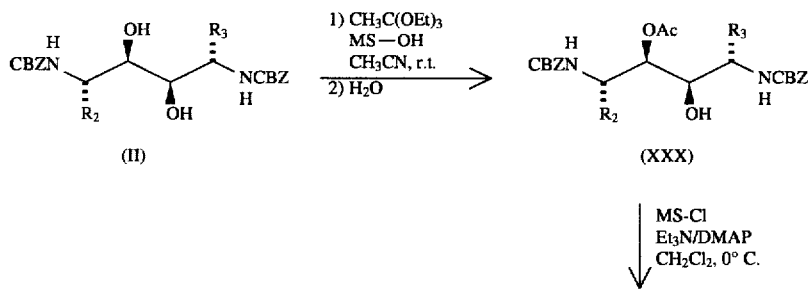

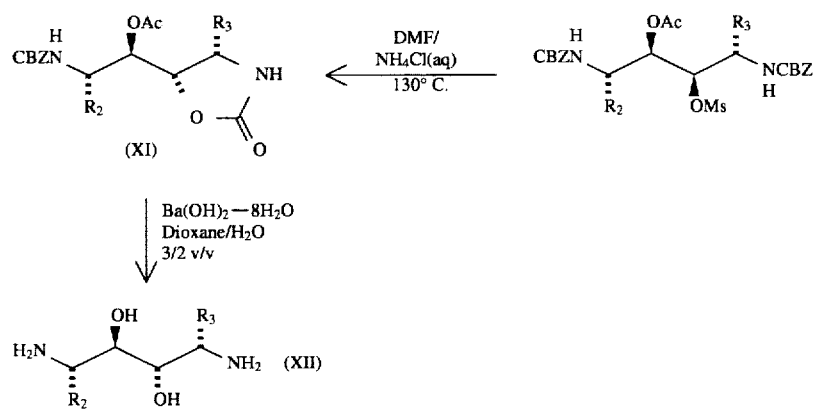
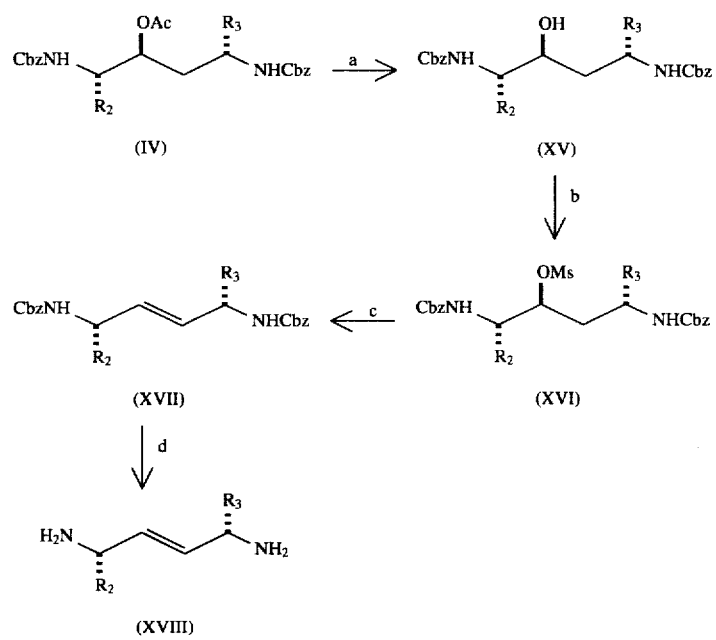
a, NH₄OH, H₂O, CH₃OH; b, MsCl, Et₃N, DMAP, CH₂Cl₂; c, DMF, reflux; d, Ba(OH)₂.8H₂O, H₂O, dioxane.
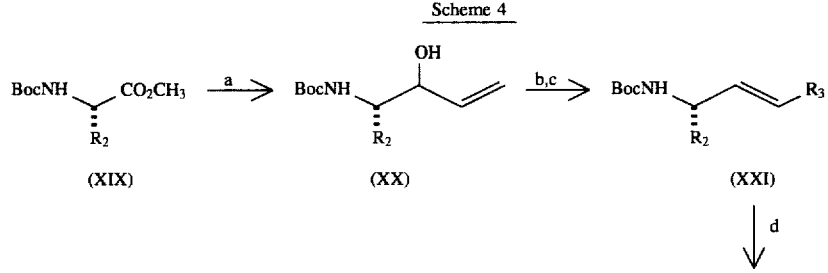

-continued
Scheme 4
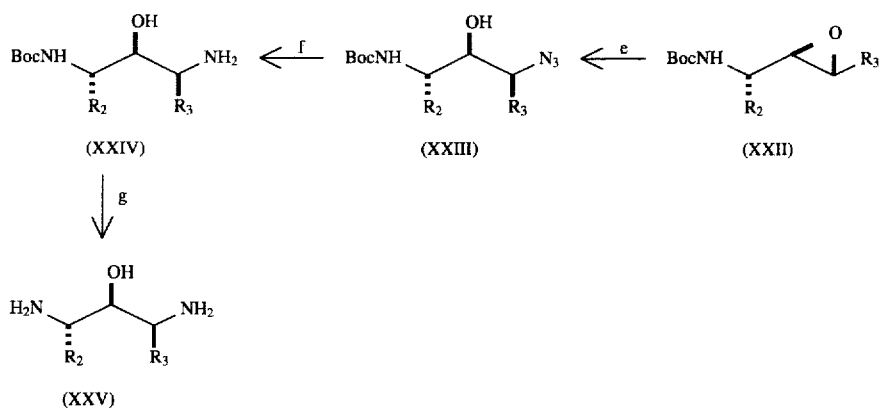
a, DIBAL, PhCH₃; vinylmagnesium bromide, THF; b, MsCl, EtN(i-Pr)₂, CH₂Cl₂; c, R₃MgBr, cat. CuCN, THF; d, MCPBA, CH₂Cl₂; e, LiN₃, NH₄Cl, DMF, H₂O; f, ammonium formate, Pd/C, CH₃OH; g, HCl, dioxane; NaOH.
Scheme 5
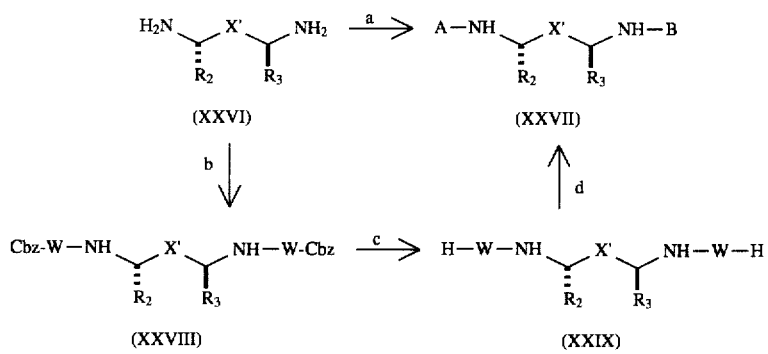
a, A—OPNP/B—OPNP or A—OH/B-OH + carbodiimide; b, Cbz—W—OPNP or Cbz—W—OH + carodiimide; c, H₂, Pd/C, CH₃OH; d, Z—OH or Z—OPNP.
SCHEME 6
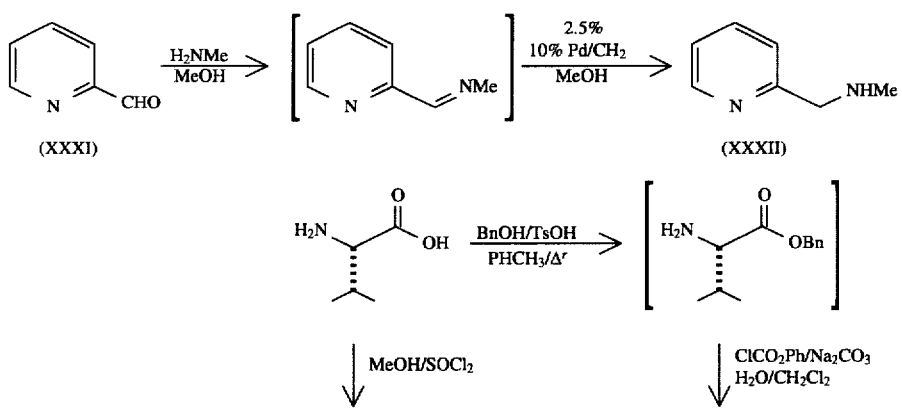

SCHEME 6 (-continued)
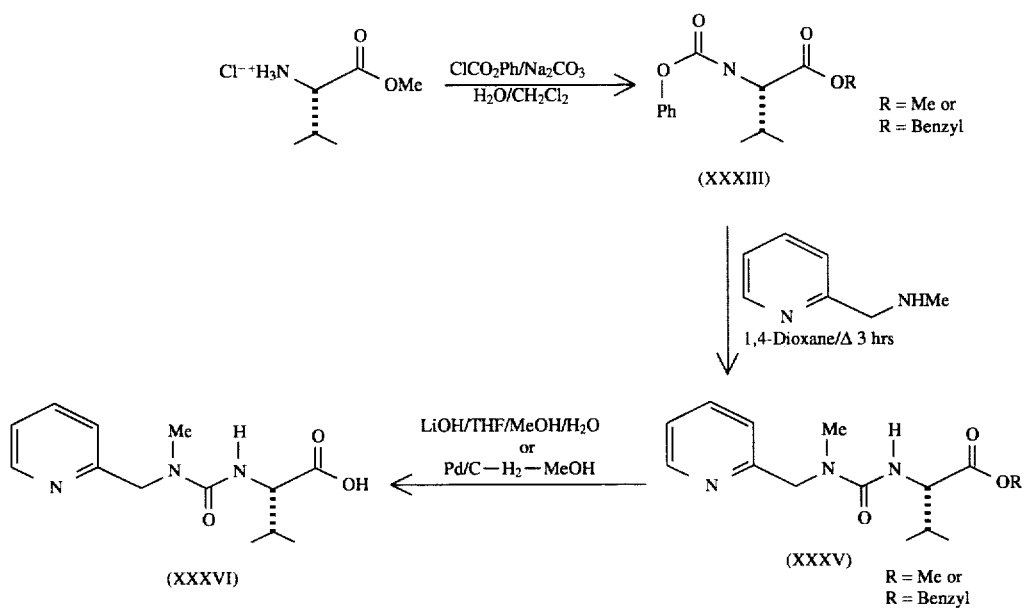
SCHEME 7
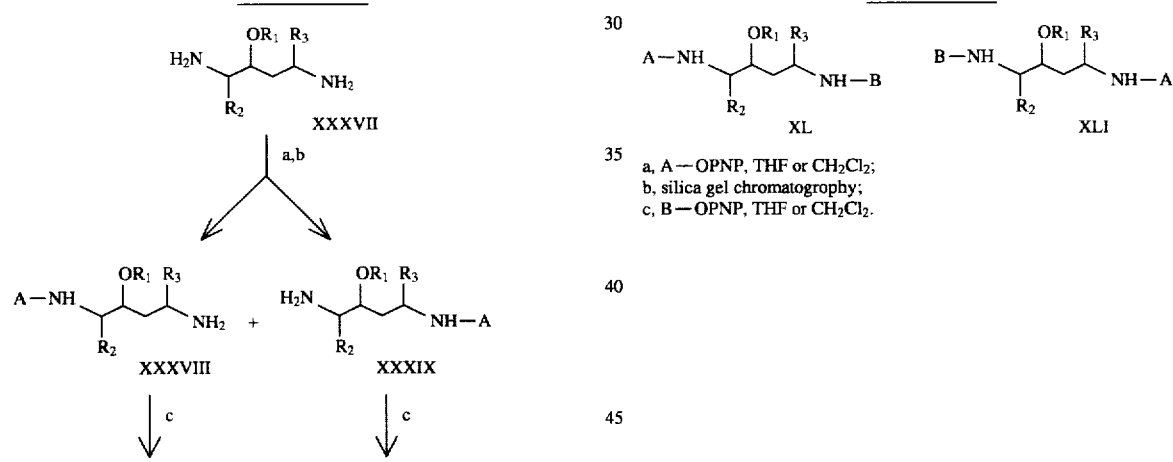
a, A—OPNP, THF or CH$_2$Cl$_2$;
b, silica gel chromatogrophy;
c, B—OPNP, THF or CH$_2$Cl$_2$.
SCHEME 8
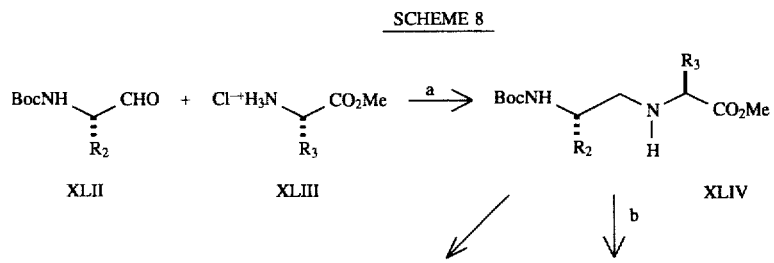

-continued
SCHEME 8

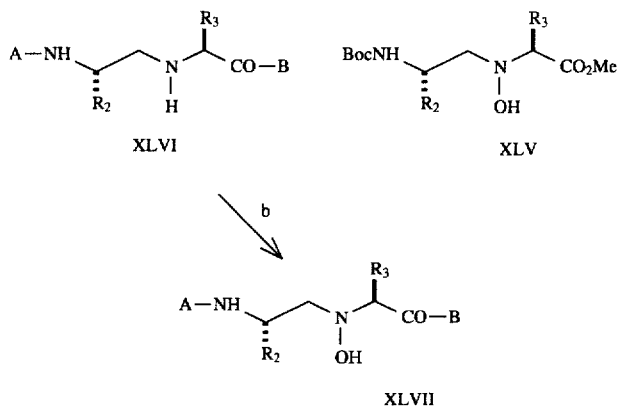

a, NaOAc, NaCNBH$_3$, i-PrOH; b, dimethyldioxirane, acetone.

The following examples will serve to further illustrate preparation of the novel compounds of the invention,

EXAMPLE 1

A. Cbz-L-phenylalaninal.

A solution of 24.5 ml of anhydrous dimethyl sulfoxide in 870 ml of anhydrous dichloromethane was cooled under N$_2$ atmosphere to −60° C. and treated over a period of 15 min with 131 ml of a 2M solution of oxalyl chloride in dichloromethane in order that the internal temperature remained below −50° C. After addition, the solution was stirred at −60° C. for 15 min and treated over a period of 20 min with a solution of 50 g (0.175 mol) of Cbz-L-phenylalaninol in 200 ml of dichloromethane. The resulting solution was stirred at −60° C. for 1 h, then treated over a period of 15 min with 97 ml of triethylamine in order that the internal temperature remained below −50° C. After addition the solution was stirred at −60° C. for 15 min, then, with the cooling bath in place, was treated rapidly (over a period of 1 rain) with a solution of 163 g of citric acid in 550 ml of water. The resulting slurry was stirred vigorously for 10 min, allowed to warm, diluted to 1 liter with water, and separated. The organic layer was washed with 700 ml of water followed by a mixture of 550 ml of water and 150 ml of saturated aqueous NaHCO$_3$, dried over MgSO$_4$, and concentrated in vacuo at 20° C. to give the crude desired compound as a light yellow solid.

B. (2S,3R,4R,5S)-2,5-Bis-(N-Cbz-amino)-3,4-dihydroxy-1,6-diphenylhexane and (2S,3S,4S,5S)-2,5-Bis-(N-Cbz-amino)-3,4-dihydroxy-1,6-diphenylhexane.

A suspension of 78.5 g of VCl$_3$·(tetrahydrofuran)$_3$ and 16 g of zinc dust in 400 ml of dry dichloromethane was stirred under N$_2$ atmosphere for 1 h at 25° C. A solution of 0.175 mol of Cbz-L-phenylalaninal in 200 ml of dichloromethane was then added in one portion, and the resulting mixture was stirred at ambient temperature under N$_2$ atmosphere for 16 h. The resulting mixture was added to 500 ml of 1M aqueous HCl, diluted with 500 ml of hot chloroform, and shaked vigorously for 2 min. The layers were separated, and the organic layer was washed with 1M aqueous HCl and separated. Filtration of the organic phase provided the crude desired product as a solid residue. The residue was slurried in 1.25 liters of acetone, treated with 5 ml of concentrated H$_2$SO$_4$, and stirred for 16 h at ambient temperature. The resulting mixture was filtered, and the residue (residue A) was washed with 50 ml of acetone. The combined filtrate was concentrated to a volume of 250 ml, diluted with 1000 ml of dichloromethane, washed three times with water and once with saturated brine, dried over MgSO$_4$, and concentrated to give a viscous oil. The oil was taken up in 1000 ml of 1M HCl in methanol (prepared from 71 ml of acetyl chloride and 1000 ml of methanol) and stirred at ambient temperature for 2 h. The resulting precipitate was filtered, washed with methanol, and air-dried on the filter to provide 26.7 g of the desired compound as a white solid. The filtrate was concentrated and filtered to give a second crop (8.3 g) of (2S,3R,4R,5S)-2,5-bis-(N-Cbz-amino)-3, 4-dihydroxy-1, 6-diphenylhexane. $^1$H NMR (d$_6$-DMSO) δ 2.59 (dd, J=13.5 Hz, 2H), 2.74 (dd, J=13, 9 Hz, 2H), 3.26 (br, 2H), 4.19 (m, 2H), 4.54 (m, 2H), 4.92 (m, 4H), 6.82 (d, J=9 Hz, 2H), 7.0–7.35 (m, 20H). Mass spectrum: (M+H)$^+$=569.

Residue A (above, 2.65 g) was suspended in 75 ml of tetrahydrofuran and 75 ml of 1M aqueous HCl and heated at reflux for 24 h. After concentration of the resulting solution in vacuo, the residue was taken up in 10% methanol in, chloroform, washed two times with water, dried over Na$_2$SO$_4$, and concentrated in vacuo to provide (2S,3S,4S, 5S)-2,5-bis-(N-Cbz-amino)-3,4-dihydroxy-1,6-diphenylhexane as a white solid. $^1$H NMR (d$_6$-DMSO) δ 2.64 im, 2H), 3.04 (m, 2H), 3.49 (m, 2H), 3.78 (m, 2H), 4.70 (d, J=7 Hz, 2H), 4 93 (AA', 4H), 7.1–7.4 (m, 20H). Mass spectrum: (M+H)$^+$=569.

C. (2S,3R,4S,5S)-3-Acetoxy-2,5-bis-(N-Cbz-amino)-3-bromo-1,6-diphenylhexane.

A suspension of 25 g (44 mmol) of (2S,3R,4R,5S)-2,5-bis-(N-Cbz-amino)-3,4-dihydroxy-1,6-diphenylhexane in 500 ml of 2:1 dichloromethane/hexane was treated with 23 g of α-acetoxyisobutyryl bromide. The resulting mixture was stirred at ambient temperature until the reaction clarified, washed with two 200 ml portions of saturated aqueous NaHCO$_3$, dried over MgSO$_4$, and concentrated in vacuo to give 30.8 g of the crude desired compound. A portion was purified by silica gel chromatography using 9:1 dichloromethane:ethyl acetate to provide the pure desired compound as a white solid. $^1$H NMR (CDCl$_3$) δ2.21 (s, 3H), 2.62 (dd, J=13, 11 Hz, 1H), 2.75 (d, J=7 Hz, 2H), 2.95 (br d, J=15 Hz, 1H), 4.03 (br t, J=10 Hz, 1 h), 4.40 (br d, J=10 Hz, 1H), 4.6–5.0 (m, 6 H), 5.12 (br d, J=13 Hz, 1H), 5.33 (br d, J=11 Hz, 1H), 7.0–7.4 (m, 10H). Mass spectrum: (M+NH$_4$)$^+$= 690, 692.

D. (2S,3S,5S)-3-Acetoxy-2,5-bis-(N-Cbz-amino)-1,6-diphenylhexane.

A solution of 30.8 g (44 mmol) of the crude resultant compound of Example 1C in 600 ml of tetrahydrofuran was treated with 17.8 ml (66 mmol) of tri-n-butyltin hydride and 1.45 g (8.8 mmol) of 2,2'-azobis- [2-methylpropionitrile]. The resulting solution was heated at reflux under $N_2$ atmosphere for 1.5 h. After being allowed to cool, the solution was concentrated in vacuo, and the residue was taken up into acetonitrile and washed with four portions of hexane. The acetonitrile layer was dried over $MgSO_4$, filtered, and concentrated in vacuo to provide 32 g of the crude desired compound. Mass spectrum: $(M+NH_4)^+=612$.

E. (2S,3S,5S)-2,5-Diamino-1,6-diphenyl-3-hydroxyhexane.

A suspension of 32 g of the crude resultant compound of Example 1D and 55.5 g (176 mmol) of barium hydroxide octahydrate in 400 ml of 1,4-dioxane and 400 ml of water was heated at reflux for 4 h. The resulting mixture was filtered, and the residue was rinsed with dioxane. The combined filtrates were concentrated to a volume of approximately 200 ml and extracted with four 400 ml portions of chloroform. The combined organic layers were dried over $Na_2SO_4$, filtered, and concentrated in vacuo. The residue was purified by silica gel chromatography using first 2% isopropylamine in chloroform and then 2% isopropylamine/2% methanol in chloroform to provide 10.1 g (81%) of the pure desired compound as a white solid. $^1$H NMR ($CDCl_3$) δ 1.54 (dt, J=14, 10 Hz, 1H), 1.67 (dt, J=14, 3 Hz, 1H), 2.50 (dd, J=13, 8 Hz, 1H), 2.58 (dd, J=13, 8 Hz, 1H), 2.8 (m, 2H), 2.91 (dd, J=13, 5 Hz, 1H), 3.10 (m, 1H), 3.72 (ddd, J=11, 3, 2 Hz, 1H), 7.1–7.4 (m, 10H). Mass spectrum: $(M+H)^+=285$.

EXAMPLE 2

A. α-Isocyanato-valine Methyl Ester.

A suspension of L-valine methyl ester hydrochloride (49 g, 0.29 mmol) in toluene (700 ml) was heated to 100° C. and phosgene gas was bubbled into the reaction mixture. After approximately 6 h, the mixture became homogeneous. The bubbling of phosgene was continued for 10 more min, then the solution was cooled with the bubbling of $N_2$ gas. The solvent was then evaporated and the residue chased with toluene two times. Evaporation of solvent gave 40.8 g (89%) of the crude desired compound.

B. N- ((2-Pyridinyl)methoxycarbonyl)-valine Methyl Ester.

A solution of 0.78 g (5.0 mmol) of the resultant compound of Example 2A and 0.55 ml (5.7 mmol) of pyridine-2-methanol in 30 mL of toluene was heated at reflux under $N_2$ atmosphere for 4 h. The solvent was removed in vacuo, and the residue was purified by silica gel chromatography using 2% methanol in chloroform to give 0.72 g (54%) of the desired compound as an oil. $^1$H NMR ($CDCl_3$) δ 0.91 (d, J=7 Hz, 3H), 0.98 (d, J=7 Hz, 3H), 2.19 (m, 1H), 3.75 (s, 3H), 4.32 (dd, J=9, 5 Hz, 1H), 5.24 (s, 2H), 5.39 (br d, 1H), 7.23 (ddd, J=8, 4, 1 Hz, 1H), 7.37 (d, J=8 Hz, 1H), 7.70 (td, J=8, 2 Hz, 1H), 8.60 (br d, 1H) . Mass spectrum: $(M+H)^+=267$.

C. N-((2-Pyridinyl)methoxycarbonyl)-valine.

Using the procedure of Example 3E but replacing the resultant compound of Example 3D with the resultant compound of Example 2B provided the desired compound.

D. N-((2-Pyridinyl)methoxycarbonyl)-Valine p-Nitrophenyl Ester.

Using the procedure of Example 3F but replacing the resultant compound of Example 3E with the resultant compound of Example 2C provided the desired compound.

E. (2S,3S,5S)-2,5-Bis-(N-(N-((2-pyridinyl)methoxycarbonyl)valinyl)-amino)-1,6-diphenyl-3-hydroxyhexane.

A solution of 0.13 g (0.46 mmol) of the resultant compound of Example 1E in 2 ml of dry dimethylformamide was treated with 0.5 g of the resultant compound of Example 2D. After being stirred at ambient temperature for 16 h, the solution was treated with saturated aqueous $NaHCO_3$, extracted with 5% methanol in chloroform, dried over $Na_2SO_4$, and concentrated in vacuo. The residue was purified by silica gel chromatography using a gradient of 2%–3%–5% methanol in chloroform to provide 161 mg (45%) of the pure desired compound, m.p. 220°–222° C. Mass spectrum: $(M+H)^+=753$.

Anal. Calcd for $C_{42}H_{52}N_6O_7 \cdot 0.5H_2O$: C, 66.21; H, 7.01; N, 11.03. Found: C, 65.92; H, 6.90; N, 10.80.

EXAMPLE 3

A. 2-(N-(t-Butyloxycarbonyl)aminomethyl)pyridine.

A solution of 21.2 g (97 mmol) of di-t-butyldicarbonate in 200 ml of dichloromethane was cooled to 0° C. and treated in portions with 10 ml (97 mmol) of 2-(aminomethyl)pyridine. After being allowed to warm to ambient temperature and stirred overnight, the resulting solution was diluted with 100 ml of dichloromethane, washed with three 100 ml portions of water, dried over $Na_2SO_4$, and concentrated in vacuo to provide 19.8 g (98%) of the desired compound ($R_f$ 0.28, 5% methanol in chloroform). $^1$H NMR ($CDCl_3$) δ 1.47 (s, 9H), 4.45 (d, J=6 Hz, 2H), 5.56 (br, 1H), 7.18 (m, 1H), 7.28 (d, J=8 Hz, 1H), 7.66 (td, J=7, 2 Hz, 1 H), 8.53 (m, 1H). Mass spectrum: $(M+H)^+=209$.

B. 2-((N-(t-Butyloxycarbonyl)-N-methylamino)methyl)pyridine.

A solution of 19.8 g (95 mmol) of the resultant compound of Example 3A in anhydrous tetrahydrofuran was cooled under $N_2$ atmosphere to 0° C. and treated with 4.95 g (124 mmol) of sodium hydride (60% dispersion in oil). The solution was stirred for 15 min, treated dropwise with 7.1 ml (114 mmol) of methyl iodide, stirred at ambient temperature for 2 h, and quenched cautiously with water. The resulting mixture was partitioned between ether and water, dried over $Na_2SO_4$, and concentrated in vacuo. Chromatography on silica gel provided 14.9 g (70%) of the desired compound as a colorless oil. $^1$H NMR ($CDCl_3$) δ 1.43, 1.49 (two s, 9H), 2.89, 2.94 (two S, 3H), 4.54, 4.57 (two S, 2H), 7.2 (m, 2H), 7.67 (td, J=8, 2 Hz, 1H), 8.55 (d, J=4 Hz, 1H). Mass spectrum: $(M+H)^+=223$.

C. 2-(N-Methylamino)methyl)pyridine Dihydrochloride.

The resultant compound of Example 3B (10 g) was treated with 200 ml of 6M aqueous HCl and heated at reflux for 10 min. After being allowed to cool, the solution was concentrated in vacuo. The residue was treated twice with 50 ml of dioxane and concentrated in vacuo to provide the crude desired compound as a light brown solid.

D. N-((N-Methyl-N- ((2-pyridinyl)methyl)amino)carbonyl)valine Methyl Ester.

A mixture of 1.61 g (7.2 mmol) of the resultant compound of Example 3C and 1.14 g (7.2 mmol) of the resultant compound of Example 2A in 40 ml of dichloromethane was treated with 2 ml (18 mmol) of 4-methylmorpholine. After being stirred for 2 h, the solution was partitioned between dichloromethane and water, dried over $Na_2SO_4$, and concentrated. Chromatography on silica gel using 2% methanol in chloroform provided 1.94 g (96%) of the desired compound ($R_f$ 0.32, 5% methanol in chloroform) as a colorless oil. $^1$H NMR (CDCl$_3$) δ 0.93 (d, J=7 Hz, 3H), 0.97 (d, J=7 Hz, 3H), 2.16 (m, 1H), 3.03 (s, 3H), 3.72 (s, 3H), 4.43 (dd, J=8, 5 Hz, 1H), 4.55 (s, 2 H), 6.15 (br, 1H), 7.22 (dd, J=8, 6 Hz, 1H), 7.28 (d, J=6 Hz, 1H), 7.69 (br t, 1H), 8.55 (d, J=5 Hz, 1H). Mass spectrum: (M+H)$^+$=280.

E. N-(ON-Methyl-N-((2-pyridinyl)-methyl]-amino)-carbonyl)-valine

A solution of 4.47 g (16 mmol) of the resultant compound of Example 3D in 65 ml of dioxane was treated with 65 ml of 0.5M aqueous lithium hydroxide. After being stirred at ambient temperature for 1 h, the resulting solution was concentrated in vacuo to a small volume (ca. 5 ml), neutralized to pH 5 with 1M aqueous HCl, and extracted with three 100 ml portions of ethyl acetate. The combined organic layers were dried over Na$_2$SO$_4$ and concentrated in vacuo to provide 3.61 g (85%) of the desired compound as an oil.

F. N-((N-Methyl-N-((2-pyridinyl)-methyl)-amino)-carbonyl)valine p-Nitropheyl Ester.

A solution of 3.61 g (13.6 mmol) of the resultant compound of Example 3E and 2.3 g (16 mmol) of p-nitrophenol in 60 ml of anhydrous tetrahydrofuran was treated with 3.09 g (15 mmol) of dicyclohexyl carbodiimide and stirred under N$_2$ atmosphere at ambient temperature for 4 h. The resulting mixture was filtered and the residue was rinsed with fresh tetrahydrofuran. The combined filtrates were concentrated in vacuo to provide the crude desired compound as a yellow oil.

G. (2S,3S,5S)-2,5Bis-(N-(N-((N-methyl-N-((2-pyridinyl) methyl)-amino)-carbonyl)valinyl)-amino)-1,6-diphenyl-3-hydroxyhexane.

A solution of 1.26 g (4.44 mmol) of the resultant compound of Example 1E in 20 ml of 1:1 tetrahydrofuran:dimethylformamide was treated with 11 mmol of the resultant compound of Example 3F. After being stirred at ambient temperature under N$_2$ atmosphere for 16 h, the resulting solution was diluted with 600 ml of ethyl acetate, washed with five 200 ml portions of aqueous NaHCO$_3$, dried over Na$_2$SO$_4$, and concentrated in vacuo. Purification of the residue on silica gel using first 2% methanol in chloroform then 5% methanol in chloroform provided 2.95 g (86%) of the pure desired compound as a white solid, m.p. 134°–137° C. Mass spectrum: (M+H)$^+$=779.

Anal. Calcd for C$_{44}$H$_{58}$N$_8$O$_5$·5H$_2$O: C, 65.57; H, 7.63; N, 13.90. Found: C, 65.74; H, 7.24; N, 13.83.

EXAMPLE 4

A. (2S,3R,4R,5S)-2,5-Diamino-3,4-dihydroxy-1,6-diphenylhexane.

Using the procedure of Example 1E with (2S,3R,4R,5S)-2,5-bis-(N-Cbz-amino)-3,4-dihydroxy-1,6-diphenylhexane provided the crude desired compound mixed with benzyl alcohol in 92% yield. Purification of a sample was achieved by silica gel chromatography using 2% isopropylamine in chloroform. $^1$H NMR (CDCl$_3$) δ2.71 (dd, J=13, 9 Hz, 2H), 2.92 (dd, J=13, 5 Hz, 2H), 3.03 (dd, J=9, 5 Hz, 2H), 3.68 (s, 2H), 7.15–7.35 (m, 10H). Mass spectrum: (M+H)$^+$=301.

B. (2S,3R,4R,5S)-2,5-Bis-(N-(Cbz-valinyl)amino)-3,4-dihydroxy-1,6-diphenylhexane.

A mixture of 2.5 g of the crude resultant compound of Example 4A and 6 g of Cbz-valine p-nitrophenyl ester in 80 ml of tetrahydrofuran was stirred at ambient temperature for 16 h. The resulting mixture was treated with 20 ml of 3M aqueous NaOH, stirred for 3 h, and concentrated in vacuo to a volume of 20 mi. The mixture was filtered, and the residue was washed sequentially with aqueous NaOH (until the residue was white), water, and diethyl ether. The residue was then taken up into 10% methanol in chloroform, dried over Na$_2$SO$_4$, and concentrated in vacuo to provide 2.77 g (75%) of the desired compound, m.p. 231°–232° C. Mass spectrum: (M+H)$^+$=767.

Anal. Calcd for C$_{44}$H$_{54}$N$_4$O$_8$·0.25H$_2$O: C, 68.51; H, 7.12; N, 7.26. Found: C, 68.48; H, 7.11; N, 7.12.

C. (2S,3R,4R,5S)-2,5-Bis-(N-(valinyl)amino)-3,4-dihydroxy-1,6-diphenylhexane.

A mixture of 2.21 g of the resultant compound of Example 4B and 0.55 g of 10% palladium-on carbon in 150 ml of methanol was shaken under 4 atmospheres of hydrogen for 4 h. The resulting mixture was filtered through Celite and concentrated in vacuo to provide the desired compound (R$_f$ 0.07, 10% methanol in chloroform) as a white solid, m.p. 205°–207° C. Mass spectrum: (M+H)$^+$=499.

Anal. Calcd for C$_{28}$H$_{42}$N$_4$O$_4$·0.75H$_2$O: C, 65.66; H, 8.56; N, 10.94. Found: C, 65.47; H, 7.93; N, 10.59.

D. trans-(2S,3R,4R,5S)-2,5-Bis-(N-(N-(trans-3-(3-pyridinyl)-2-propenoyl)valinyl)amino)-3,4-dihydroxy-1,6-diphenylhexane.

Using the procedure of Example 6I but replacing the resultant compound of Example 6H with the resultant compound of, Example 4C provided the desired compound, m.p. >260° C. Mass spectrum: (M+H)$^+$=761.

EXAMPLE 5

A. trans-Ethyl 3-(2-Pyridinyl)acrylate.

A solution of 0.43 g (10.7 mmol) of sodium hydride (60% oil dispersion) in anhydrous tetrahydrofuran was cooled under N$_2$ atmosphere to 0° C. and treated dropwise with 2.1 ml (10.5 mmol) of triethylphosphenoacetate. After being stirred for 10 min, the solution was treated with 1.0 ml of pyridine-2-carboxaldehyde, heated at reflux for 2 h, cooled, partitioned between ether and aqueous ammonium chloride, washed sequentially with water and saturated brine, dried over MgSO$_4$, and concentrated. Silica gel chromatography of the residue using 30% ethyl acetate in hexane provided 1.54 g (83%) of the desired compound as an oil. $^1$H NMR (CDCl$_3$) δ 1.34 (t, J=7 Hz, 3H), 4.28 (q, J=7 Hz, 2H), 6.92 (d, J=15 Hz, 1H), 7.27 (ddd, J=8, 5, 2 Hz, 1H), 7.43 (dr, J=8, 1 Hz, 1H), 7.69 (d, J=15 Hz, 1H), 7.71 (td, J =8, 2 Hz, 1H), 8.66 (dm, 1H).

B. trans-3-(2-Pyridinyl)acrylic Acid.

A solution of 13.6 g (82 mmol) of the resultant compound of Example 5A in 330 ml of 1,4-dioxane was treated with 330 ml of 0.5M aqueous lithium hydroxide. The resulting solution was stirred at ambient temperature for 2 h, neutralized with 165 ml of 1N aqueous HCl, concentrated in vacuo to a volume of 200 ml, and extracted with five 100 ml portions of chloroform. The combined organic layers were dried over Na$_2$SO$_4$ and concentrated in vacuo to give 11.3 g (94%) of the desired compound as a white solid.

C. (2S,3R,4R,5S)-2,5-Bis-(N-(N-(trans-3-(3-pyridinyl)-2-propenoyl))-valinyl)amino)-3,4-dihydroxy-1,6-diphenylhexane.

Using the procedure of Example 6I but replacing the resultant compound of Example 6H with the resultant compound of Example 4C and replacing trans-3-(3-pyridyl)acrylic acid with trans-3-(2-pyridyl)acrylic acid provided the desired compound, m. p. 285°–289° C. Mass spectrum: (M+H)$^+$=761.

Anal. Calcd for $C_{44}H_{52}N_6O_6 \cdot 0.75H_2O$: C, 68.24; H, 6.96; N, 10.85. Found: C, 68.04; H, 6.92; N, 10.87.

EXAMPLE 6

A. 4-(t-Butyloxycarbonylamino)-3-hydroxy-5-phenyl-1-pentene.

A solution of 10.25 g (36.7 mmol) of N-(tbutyloxycarbonyl)phenylalanine methyl ester in 60 ml of toluene was cooled to −78° C. under inert atmosphere and treated dropwise over a period of 45 min with 35 ml (52.5 mmol) of diisobutylaluminum hydride in toluene. The resulting solution was stirred for 5 min, treated with 200 ml (200 mmol) of vinylmagnesium bromide, and allowed to warm to 0° C. for 16 h. The solution was subsequently quenched cautiously with methanol, treated with-aqueous Rochelle salts, stirred for a few min, and filtered. The residue was digested several times with ethyl acetate and filtered; and the combined filtrates were washed with saturated brine, dried over $MgSO_4$, and concentrated. Silica gel chromatography using 20% ethyl acetate in hexane gave 5.46 g (54%) of the pure desired compound as a mixture of diastereomers.

B. 2-(t-Butyloxycarbonylamino)-1,5-diphenylpent-3-ene.

A solution of 15.1 g (54.5 mmol) of the resultant compound of Example 6A and 38 ml (220 mmol) of diisopropylethylamine in 450 ml of dry dichloromethane was cooled under $N_2$ atmosphere in an acetone/ice bath and treated dropwise with 8.5 ml (110 mmol) of methanesulfonyl chloride. The solution was stirred for 7 min after addition was complete, then was quenched with 400 ml of 10% citric acid. The bath was removed, and the mixture was extracted with 800 ml of ether. The organic layer was washed sequentially with 500 ml of water and 300 ml of saturated brine, dried over $MgSO_4$, and concentrated in vacuo to give the crude mesylate as an off-white solid. To a flame-dried 3-neck 1000 mL flask equipped with an internal low-temperature thermometer was added 1.45 g (16 mmol) of anhydrous cuprous cyanide. The flask was then charged with 500 ml of anhydrous tetrahydrofuran. The suspension was cooled under $N_2$ altmosphere in a dry ice/acetone bath. A solution of phenylmagnesium bromide (55 ml, 165 mmol) in ether (3M) was added via syringe. The bath was removed, and the resulting beige suspension was warmed with stirring by use of a water bath. As the internal temperature reached −5° C., the solid began to dissolve, and the solution began to turn darker. By the time the internal temperature reached −1° C., the solution was homogenous, and was immediately recooled by placement of the flask in a dry ice/acetone bath. As the internal temperature reached −65° C., addition of a solution of the above crude mesylate in 75 ml of tetrahydrofuran was added via cannula. The resulting solution was stirred at ca. −70° C. for 15 min. The bath was then removed, and the solution was immediately treated with 100 ml of saturated aqueous ammonium chloride followed by 300 ml of ether. As the mixture warmed, 100 ml of 1N $NH_4OH$ was added, and the mixture was stirred under air atmosphere for several hours while the aqueous layer turned dark blue. The mixture was then extracted with 500 ml of ether. The organic layer was washed with saturated brine and concentrated in vacuo without drying to give a yellow oil. The combined aqueous layers were extracted with 500 ml of additional ether, which was added to the above oil. The resulting solution was washed with saturated brine, dried over $MgSO_4$, and concentrated to a yellow oil. The oil was taken up in 100 ml of dichloromethane, treated with 50 g of silica gel, and concentrated in vacuo until the residue was a freely flowing solid. The solid was placed on top of a 60 mm column containing 300 g of silica gel and eluted sequentially with 1200 ml of hexane (to bring out biphenyl formed as a side product) followed by 5000 ml of 5% ethyl acetate in hexane. Combination of the pure fractions gave 11.95 g (65%) of the desired compound. $^1H$ NMR ($CDCl_3$, major isomer) δ 1.40 (s, 9 H), 2.7–2.9 (m, 2H), 3.32 (d, J=7 Hz, 2H), 4.4 (br, 2H), 5.43 (dd, J=15, 6 Hz, 1H), 5.64 (dr, J=15, 7 Hz, 1H), 7.0–7.3 (m, 10H).

C. 2-(t-Butyloxycarbonylamino)-1,5-diphenylpent-3-ene-3,4-oxide.

A solution of 11.71 g (34.75 mmol) of the resultant compound of Example 6B in 200 ml of dichloromethane was treated with 15 g (174 mmol) of solid sodium bicarbonate, cooled to 0° C. and treated with 24 g (69 mmol) of m-chloroperbenzoic acid (50%). The resulting suspension was sealed with a septum and stirred in a cold room (5° C.) for three days. The resulting mixture, which contained much precipitate, was decanted into a 1000 ml flask. The white residue was broken up and washed out with 400 ml of 10% sodium thiosulfate solution and 300 ml of ether. The two-phase mixture was stirred for 2 hours, and the layers were separated. The organic layer was washed sequentially with 200 ml portions of 2M NaOH, water, and saturated brine. The combined aqueous layers were extracted with 200 ml of ether, which was washed sequentially with 50 ml of water and 50 mL of aqueous brine, combined with the original organic phase, dried over $MgSO_4$, and concentrated in vacuo. The resulting oil was taken up in 100 ml of dichloromethane, treated with 50 g of silica gel, and concentrated in vacuo until the residue was a freely flowing solid. The solid was placed on top of a 60 mm column containing 300 g of silica gel and eluted sequentially with 1000 ml of 5% ethyl acetate in hexane followed by 3500 ml of 12% ethyl acetate in hexane. Concentration of the combined fractions gave 9.36 g (76%) of the desired compound (ca. 4:1 mixture of diastereomers) as an oil which solidified upon standing.

D. 4-Azido-2-(t-butyloxycarbonylamino)-1,5-diphenyl-3-hydroxypentane.

A solution of 9.12 g (25.84 mmol) of the resultant compound of Example 6C, 7.0 g (140 mmol) of lithium azide, and 1.73 g (32 mmol) of ammonium chloride in 75 ml of dimethylformamide and 7.5 ml of water was heated in an oil bath at 70° C. for 32 hours. After being allowed to cool, the resulting solution was treated with 1000 ml of 1:1 ether/hexane and 800 ml of water. The layers were separated, and the aqueous layer was extracted with 500 ml of additional 1:1 ether/hexane. The combined organic layers were washed sequentially with 400 ml of water and 200 ml of saturated brine, dried over $MgSO_4$, and concentrated in vacuo to a solid. The solid was taken up in 100 ml of dichloromethane, treated with 50 g of silica gel, and concentrated in vacuo until the residue was a freely flowing solid. The solid was placed on top of a 60 mm column containing 300 g of silica gel and eluted sequentially with 1000 ml of 10% ethyl acetate in hexane, 1000 ml of 15% ethyl acetate in hexane, and 2000 ml of 25% ethyl acetate in hexane. Concentration of the fractions gave 9.26 g (91%) of the desired compound as a ca. 4:1 mixture of diastereomers. $^1H$ NMR ($CDCl_3$, major isomer) δ 1.42 (s, 9H), 2.78 (m, 1H), 2.89 (m, 1H), 3.13 (m, 1H) 3.29 (m, 1H), 3.41 (m, 1H), 3.53 (m, 1H), 3.80 (m, 1H) 4.06 (m, 1H), 4.83 (m, 1H), 7.2–7.35 (m, 10H). Mass spectrum $(M+H)^+$=338.

E. 4-Amino-2-(t-butyloxycarbonylamino)-1,5-diphenyl-3-hydroxypentane.

A rapidly stirring suspension of 1.8 g of 10% palladium on carbon in 50 ml of methanol was treated under inert atmosphere with 10 g (0.16 mol) of solid ammonium formate. After 10 rain, a solution of 8.95 g (22.6 mmol) of the resultant compound of Example 6D in 80 ml of methanol was added. The resulting mixture was stirred for 2.5 h, filtered through Celite, and the catalyst was washed with 200 ml of 1:1 methanol: 1N ammonium hydroxide. The combined filtrates were concentrated in vacuo to a volume of 100 ml. The resulting mixture was treated with 1N NaOH and extracted with two portions of chloroform. The combined organic layers were dried over sodium sulfate and concentrated. The residue was chromatographed on 300 g of silica gel using the following eluents: 500 ml of 2% methanol in chloroform, 500 ml of 5% methanol in chloroform, 1500 ml of 10% methanol in chloroform, and 1000 ml of 2% isopropylamine/10% methanol in chloroform. Concentration of the appropriate fractions provided 5.85 g (70%) of (2S,3S,4S)-4-amino-2-(t-butyloxycarbonylamino)-1,5-diphenyl-3-hydroxypentane ($R_f$ 0.38, 2.5% methanol/2% isopropylamine in chloroform) as a white solid, m.p. 134°–135° C. $^1$H NMR (CDCl$_3$) δ 1.48 (s, 9H), 2.50 (dd, J=13, 10 Hz, 1H), 2.8–3.1 (m, 4H), 3.41 (br d, J=7 Hz, 1H), 4.11 (br q, J=8 Hz, 1H), 4.83 (br d, J=9 Hz, 1H), 7.15–7.35 (m, 10H) . Mass spectrum (M+H)$^+$=370.

Anal. Calcd. for $C_{22}H_{30}N_2O_3 \cdot 0.15H_2O$: C, 70.81; H, 8.18; N, 7.51. Found: C, 70.89; H, 8.15; N, 7.43.

Also isolated in the chromatography was 1.22 g (15%) of (2S,3R,4R)-4-amino-2-(t-butyloxycarbonylamino)-1,5-diphenyl-3-hydroxypentane.

F. (2S,4S)-2,4-Diamino-1,5-diphenyl-3-hydroxypentane.

The resultant compound of Example 6E (18 mg, 0.049 mmol) was treated with 1 ml of 4M HCl in dioxane, stirred for 0.5 h at ambient temperature, and concentrated in vacuo. The residue was partitioned between chloroform and aqueous NaHCO$_3$, dried over Na$_2$SO$_4$ and concentrated to provide the desired compound ($R_f$ 0.12, 10% methanol in chloroform) as a white solid, m.p. 106°–1070° C. $^1$H NMR (CDCl$_3$) δ 2.51 (dd, J=13, 10 Hz, 1H), 2.67 (dd, J=13, 9 Hz, 1H), 2.85–3.0 (m, 2 H), 3.19 (m, 1H) , 3.38 (m, 2H) , 7.15–7.35 (m, 10H). Mass spectrum: (M+H)$^+$=271.

G. (2S,4S) -2,4-Bis-(N-(Cbz-valinyl)-amino)-1,5-diphenyl-3-hydroxypentane.

A solution of 0.65 g (2.4 mmol) of the resultant compound of Example 6F, 2.68 g (7.2 mmol) of N-Cbz-valine p-nitrophenyl ester and 1.34 ml (9.6 mmol) of triethylamine in 6 ml of tetrahydrofuran was heated at reflux under N$_2$ atmosphere for 16 h. The resulting suspension was cooled, diluted with 30 ml of tetrahydrofuran, treated with 10 ml of 3M aqueous NaOH, and stirred at ambient temperature for 3 h. The mixture was diluted with 250 ml of chloroform, washed with four 100 ml portions of 0.5M aqueous NaOH, dried over MgSO$_4$, and concentrated in vacuo. Silica gel chromatography of the residue using 5% methanol in dichloromethane provided 1.70 g (96%) of the desired compound as a white solid, m.p. 198°–200° C. Mass spectrum (M+H)$^+$=737.

Anal. Calcd. for $C_{43}H_{52}N_4O_7 \cdot 0.5H_2O$: C, 69.24; H, 7.16; N, 7.51. Found: C, 69.40; H, 7.29; N, 7.47.

H. (2S,4S)-2,4-Bis-(N-(valinyl)-amino)-1,5-diphenyl-3-hydroxypentane.

A mixture of 1.65 g (2.24 mmol) of the resultant compound of Example 6G and 165 mg of 10% palladium on carbon in 80 ml of methanol was stirred rapidly under an H$_2$ atmosphere for 16 h. The resulting solution was filtered through Celite and concentrated in vacuo to provide 1.04 g (99%) of the desired compound as a white solid, m.p. 131°–132° C.

I. (2S,4S)-2,4-Bis-(N-(N-(trans-3-(3-pyridinyl)-2-propenoyl)-valinyl)amino)-1,5-diphenyl-3-hydroxypentane.

A mixture of 100 mg (0.213 mmol) of the resultant compound of Example 6H, 95.5 mg (0.64 mmol) of trans-3-(3pyridyl)acrylic acid, and 86.5 mg (0.64 mmol) of 1-hydroxybenzotriazole monohydrate in 2 ml of dry dimethylformamide was cooled under N$_2$ atmosphere to 0° C. and treated with 122.7 mg (0.64 mmol) of ethyl(dimethylaminopropyl)carbodiimide. The resulting solution was stirred at 0° C. for 0.5 h, then at ambient temperature for 16 h. The resulting mixture was concentrated in vacuo, and the residue was treated with saturated aqueous NaHCO$_3$ and extracted with five 10 ml portions of 10% methanol in dichloromethane. The combined organic layers were dried over Na2SO4 and concentrated. Silica gel chromatography of the residue using 10% methanol in dichloromethane provided 132 mg (85%) of the desired compound as a white solid, m.p. 271°–273° C. (dec). Mass spectrum: (M+H)$^+$=731.

EXAMPLE 7

(2S,4S)-2,4-Bis-(N-(N-(trans-3-(2-pyridinyl)-2-propenoyl)valinyl)amino)-1,5-diphenyl-3-hydroxypentane.

Using the procedure of Example 6I but replacing trans-3-(3-pyridyl)acrylic acid with the resultant compound of Example 5B provided, after silica gel chromatography using 10% methanol in dichloromethane, 155 mg (99%) of the desired compound, m.p. 257°–259° C. (dec). Mass spectrum: (M+H)$^+$=731.

EXAMPLE 8

A. trans-Ethyl 3-(4-Pyridyl)acrylate.

Using the procedure of Example 5A but replacing pyridine-2-carboxaldehyde with pyridine-4-carboxaldehyde provided the desired compound.

B. trans-3-(4-Pyridyl)acrylic Acid.

Using the procedure of Example 5B with the resultant compound of Example 8A provided the desired compound.

C. (2S,4S)-2,4-Bis-(N-(N-(trans-3-(4-pyridinyl)-2-propenoyl)valinyl)amino)-1,5-diphenyl-3-hydroxypentane.

Using the procedure of Example 6I but replacing trans-3-(3-pyridyl)acrylic acid with trans-3-(4-pyridyl)acrylic acid provided the desired compound, m.p. 250°–251° C. (dec) in 84% yield. Mass spectrum: (M +H)$^+$=731.

EXAMPLE 9

A. N-((4-Phenylpiperazin-1-yl)carbonyl)-valine Methyl Ester.

A solution of 2.016 g (12.8 mmol) of the resultant compound of Example 2A in 50 ml of dichloromethane was treated with 1.96 ml (12.6 mmol) of 1-phenylpiperazine. After being stirred at ambient temperature for 1 h, the solution was diluted with dichloromethane, washed with water, dried over Na$_2$SO$_4$, and concentrated in vacuo. Purification by silica gel chromatography using 25% ethyl acetate in chloroform provided the desired compound. $^1$H NMR (CDCl$_3$) δ 0.93 (d, J=7 Hz, 3H), 0.97 (d, J=7 Hz, 3H), 2.15 (m, 1H), 3.20 (dd, J=6, 5 Hz, 4H), 3, 58 (m, 4H), 3.74 (s, 3H), 4.48 (dd, J=8, 5 Hz, 1H), 5.00 (br d, J=8 Hz, 1H), 6.90 (t, J=7 Hz, 1H), 6.93 (d, J=7 Hz, 1H), 7.29 (m, 2H). Mass spectrum: (M+H)$^+$=320.

B. N-((4-Phenylpiperazin-1-yl)carbonyl)-valine.

Using the procedure of Example 3E with the resultant compound of Example 9A provided the desired compound as a foam.

C. N-((4-Phenylpiperazin-1-yl)carbonyl)-valine p-Nitrophenyl Ester.

Using the procedure of Example 3F with the resultant compound of Example 9B provided the crude desired compound.

D. (2S,3R,4R,5S)-2,5-Bis-(N-(N-((4-phenylpiperazin-1-yl)carbonyl)-valinyl)amino)-3,4-dihydroxy-1,6-diphenylhexane.

A solution of 0.2 g of the resultant compound of Example 9C in 1 ml of 1:1 tetrahydrofuran dimethyl-formamide was treated with 55 mg (0.11 mmol) of the resultant compound of Example 4A and stirred at ambient temperature for 16 h. The resulting solution was concentrated in vacuo, and the residue was purified by silica gel chromatography using first chloroform followed by 3% methanol in chloroform to provide 140 mg (87%) of the desired compound, m.p. 172°–173° C. Mass spectrum: $(M+H)^+=875$.

EXAMPLE 10

A. N-((4-Benzylpiperazin-1-yl)carbonyl)-valine Methyl Ester.

A solution of 1.2 g (7.64 mmol) of the resultant compound of Example 2A in 50 ml of dichloromethane was treated with 1.33 ml (7.64 mmol) of 1-benzylpiperazine. After being stirred at ambient temperature for 16 h, the solution was diluted with chloroform, washed with water, dried over $Na_2SO_4$, and concentrated in vacuo. Purification by silica gel chromatography using first 50% ethyl acetate in chloroform followed by 5% methanol in chloroform provided 1.72 g (68%) of the desired compound as an oil.

B. N-((4-Benzylpiperazin-1-yl)carbonyl)-valine.

Using the procedure of Example 3E with the resultant compound of Example 10A provided the desired compound as a foam.

C. N-((4-Benzylpiperazin-1-yl)carbonyl)-valine p-Nitrophenyl Ester.

Using the procedure of Example 3F with the resultant compound of Example 10B provided the crude desired compound.

D. (2S,3R,4R,5S)-2,5-Bis-(N-(N-((4-benzylpiperazin-1-yl)carbonyl)-valinyl)amino)-3,4-dihydroxy-1,6-diphenylhexane.

Using the procedure of Example 3G but replacing the resultant compound of Example 1E with the resultant compound of Example 4A and replacing the resultant compound of Example 3F with the resultant compound of Example 10C provided, after silica gel chromatography using first 3% then 5% methanol in chloroform, the desired compound, m.p. 178°–179° C. in 97% yield. Mass spectrum: $(M+H)^+=903$.

Anal. Calcd for $C_{52}H_{70}N_8O_6 \cdot 1.00H_2O$: C, 67.80; H, 7.88; N, 12.16. Found: C, 67.82; H, 7.78; N, 12.02.

EXAMPLE 11

A. (2S,3R,4R,5S)-2,5-Bis-(N-Cbz-amino)-3,4-bis-(mesyloxy)-1,6-diphenylhexane.

A slurry of 1.50 g (2.64 mmol) of (2S,3R,4R,5S)-2,5-bis-(N-Cbz-amino)-3,4-dihydroxy-1,6-diphenylhexane in 50 ml of anhydrous dichloromethane was cooled to 0° C. and treated sequentially with 0.43 ml of methanesulfonyl chloride, 64 mg of 4-dimethylaminopyridine and 1,1 ml of triethylamine. The resulting mixture was stirred for 15 h with the temperature being allowed to slowly climb to ambient temperature. After treatment with aqueous $NH_4Cl$, the separated organic layer was washed with aqueous $NaHCO_3$, dried over $MgSO_4$, and concentrated in vacuo to provide 1.70 g (90%) of the desired compound, m.p. 153°–155° C. $^1$H NMR (CDCl$_3$) δ 2.73 (m, 2 H), 2.92 (m, 2H), 3.09 (s, 6H), 4.61 (m, 2H), 4.83–5.06 (m, 8H), 7.12–7.37 (m, 20H).

B. (4S,5S,4'S,5'S)-4,4'-Dibenzyl-5,5'-bis-(oxazolidin-2-one).

A solution of 0.2 g of the resultant compound of Example 11A in 15 ml of dimethylformamide was heated at 120° C. under $N_2$ atmosphere for 18 h. After removal of the solvent, the residue was recrystallized from ethyl acetate/hexane to provide 46 mg of the desired compound.

C. (2S,3S,4S,5S)-2,5-Diamino-3,4-dihydroxy-1,6-diphenylhexane L

Using the procedure of Example 1E but replacing the resultant compound of Example 1D with either (2S,3S,4S,5S)-2,5-bis-(N-Cbz-amino)-3,4-dihydroxy-1,6-diphenylhexane or with the resultant compound of Example 11B provided the desired compound. $^1$H NMR (CDCl$_3$) δ 2.63 (dd, J=14, 11 Hz, 2H), 2.85 (dd, J=14, 4 HZ, 2H), 3.60 (dt, J=11, 4 HZ, 2H), 3.92 (d, J=3 HZ, 2H), 7.2–7.4 (m, 10H). Mass spectrum: $(M+H)^+=301$.

D. (2S,3S,4S,5S)-2,5-Bis-(N-(N-((4-phenylpiperazin-1-yl)carbonyl)-valinyl)amino)-3,4-dihydroxy-1,6-diphenylhexane.

A solution of 105 mg (0.35 mmol) of the resultant compound of Example 11C in 3 ml of dimethylformamide was treated with 0.5 g of the resultant compound of Example 9C. After being stirred at ambient temperature under $N_2$ atmosphere for 16 h, the resulting mixture was diluted with ethyl acetate and washed with five portions of 0.1M aqueous $K_2CO_3$. The solid product, which was not soluble in ethyl acetate, was collected by filtration, washed on the filter with water, digested on the filter two times with ether and filtered to provide the desired compound as a white solid, m.p. 165°–166° C.

EXAMPLE 12

(2S,3S,4S,5S)-2,5-Bis-(N-(N-((4-benzylpiperazin-1-yl)carbonyl)-valinyl)amino)-3,4-dihydroxy-1,6-diphenylhexane.

A solution of 80 mg (0.267 mmol) of the resultant compound of Example 11C in 3 ml of dimethylformamide was treated with 375 mg of the resultant compound of Example 10C. After being stirred at ambient temperature under $N_2$ atmosphere for 16 h, the resulting solution was diluted with 600 ml of ethyl acetate, washed with three portions of aqueous $NaHCO_3$ and one portion of saturated brine, dried over $Na_2SO_4$, and concentrated in vacuo. Purification of the residue on silica gel using first 3% methanol in chloroform then 5% methanol in chloroform provided 131 mg (54%) of the pure desired compound as a white solid, m.p. 171°–173° C. Mass spectrum: $(M+H)^+=903$.

Anal. Calcd for $C_{52}H_{70}N_8O_6 \cdot 1.00H_2O$: C, 67.80; H, 7.88; N, 12.16. Found: C, 68.08; H, 7.77; N, 11.91.

EXAMPLE 13

A. (4S,5S,1'R,2'S)-5-(1-Acetoxy-2-(N-Cbz-amino)-3-phenylpropyl)-4-benzyl-oxazolidin-2-one.

A suspension of 5.02 g (8.80 mmol) of (2S,3R,4R,5S)-2,5-bis-(N-Cbz-amino)-3,4-dihydroxy-1,6-diphenylhexane in 400 ml of acetonitrile was treated dropwise with 3 ml (20 mmol) of α-acetoxyisobutyryl bromide. The resulting solution was stirred under $N_2$ atmosphere at ambient-temperature for 2 h, filtered to remove traces of solid starting material, quenched cautiously with 100 ml of aqueous $NaHCO_3$, and concentrated in vacuo to a volume of 100 ml. The resulting mixture was extracted with two 100 ml portions of dichloromethane, dried over $Na_2SO_4$, and concentrated in vacuo. The residue was purified by silica gel chromatography using first 10% then 25% ethyl acetate in dichloromethane to provide 3.15 g (71%) of the desired compound as a white foam. $^1$H NMR (CDCl$_3$) δ 2.09 (s, 3H), 2.53 (br t, J=12 Hz, 1H), 2.72 (dd, J=13, 3 Hz, 1H), 2.83 (dd, J=14, 8 Hz, 1H), 2.95 (dd, J=14, 7 Hz, 1H), 3.95 (m, 1H), 4.45 (m, 1H), 4.8 (m, 2H), 5.0–5.1 (m, 3H), 5.29 (dd, J=9, 3 Hz, 1H), 7.0–7.4 (m, 10H) . Mass spectrum: $(M+NH_4)^+$=520.

B. (2S,3R,4R,5S)-2,5-Bis-(N-Cbz-amino)-1,6-diphenyl-2-hydroxy-3-mesyloxyhexane.

A slurry of 1.098 g (1.93 mmol) of (2S,3R,4R,5S)-2,5-bis-(N-Cbz-amino)-3,4-dihydroxy-1,6-diphenylhexane in 50 ml of anhydrous dichloromethane was treated sequentially with 0.313 ml of methanesulfonylchloride, 0.546 ml of triethylamine and 23 mg of 4-dimethylaminopyridine. After being stirred for 24 h at ambient temperature, the solution was washed sequentially with aqueous $NH_4Cl$ and aqueous $NaHCO_3$, dried over $MgSO_4$, and concentrated in vacuo. The residue was purified by silica gel chromatography using 5% ethyl acetate in dichloromethane to provide 560 mg (45%) of the desired compound, m.p. 68°–71° C. $^1$H NMR (CDCl$_3$) δ 2.7–3.0 (m, 4H), 3.17 (s, 3H), 3.69 (m, 1H), 3.92 (m, 1H), 4.19 (br s, 1H), 4.45 (m, 1H), 4.68 (m, 1H), 4.87–5.09 (m, 6 H) , 7.1–7.4 (m, 20H).

C. (4S,5S,1'R,2'S)-4-Benzyl-5-(2-N-Cbz-amino)-1-hydroxy-3-phenylpropyl)-oxazolidin-2 -one.

A solution of 320 mg (0.49 mmol) of the resultant compound of Example 13B in 15 ml of acetonitrile was heated at reflux under N2 atmosphere for 18 h. After being allowed to cool, the solvent was removed in vacuo and the residue was recrystallized from ethyl acetate/hexane to provide 89 mg (39%) of the desired compound.

D. (2S,3R,4S,5S)-2,5-Diamino-3,4-dihydroxy-1,6-diphenylhexane.

Using the procedure of Example 1E but replacing the resultant compound of Example 1D with either the resultant compound of Example 13A or the resultant compound of Example 13C provided the desired compound mixed with benzyl alcohol. Purification of a small portion by silica gel chromatography using 5% methanol/2% isopropylamine in chloroform provided the pure desired compound., m.p. 115°–119° C. $^1$H NMR (CDCl$_3$) δ 2.46 (dd, J=14, 9 Hz, 1H), 2.61 (dd, J=14, 11 Hz, 1H), 3.02 (td, J=9, 3 Hz, 1H), 3.19 (dd, J=14, 4 Hz, 1H), 3.35–3.4 (m, 2H), 3.51 (t, J=9 Hz, 1H), 3.76 (dd, J=9, 3 Hz, 1H), 7.2–7.4 (m, 10H).

E. (2S,3R,4S,5S)-2,5-Bis-(N-(N-((4-benzylpiperazin-1-yl)carbonyl)-valinyl)-amino)-3,4-dihydroxy-1,6-diphenylhexane.

Using the procedure of Example 3G but replacing the resultant compound of Example 1E with the resultant compound of Example 13D and replacing the resultant compound of Example 3F with the resultant compound of Example 10C provided the desired compound.

EXAMPLE 14

A. Thiazole-2-carboxaldehyde.

A solution of 5 g (60 mmol) of thiazole in 20 ml of anhydrous ether was cooled under $N_2$ atmosphere to −78° C. and treated over a period of 20 min with a solution of 26 ml of n-butyllithium (2.5M in hexane) diluted with 10 ml of ether. After addition, the solution was stirred for 30 min and treated with a solution of 6.0 ml (60 mmol) of N-formylmorpholine in 10 ml of anhydrous ether over a period of 10 min. The resulting solution was allowed to warm to ambient temperature over a period of 4 h, after which it was quenched at 0° C. with 4 N aqueous HCl. The mixture was diluted with 4N HCl, after which the aqueous layer was washed with ether, neutralized to pH 8 with aqueous NaOH and aqueous $NaHCO_3$, extracted with four 50 ml portions of ether, dried over $MgSO_4$, and concentrated in vacuo. The crude product thus obtained (5.02 g, 76%) as a brown solid was of sufficient purity for the next step.

B. trans-Methyl 3-(thiazol-2-yl)-2-propenoate.

Using the procedure of Example 5A but replacing triethylphosphonoacetate with trimethylphosphonoacetate and replacing pyridine-2-carboxaldehyde with the resultant compound of Example 14A provided, after silica gel chromatography using 4:1 hexane:ethyl acetate, a 40% yield of the desired compound as a yellow crystalline solid, m.p.75–75.5° C. $^1$H NMR (CDCl$_3$) δ 3.83 (s, 3H), 6.73 (d, J=15 Hz, 1H), 7.45 (d, J=3 Hz, 1H), 7.80 (d, J=15 Hz, 1H), 7.93 (d, J=3 Hz, 1H).

C. trans-3-(Thiazol-2-yl)-2-propenoic Acid.

A solution of 1.46 g (8.6 mmol) of the resultant compound of Example 14B in 10 ml of 1,4-dioxane and 5 ml of water was treated with 0.73 g (17 mmol) of lithium hydroxide monohydrate and stirred at ambient temperature for 16 h. The resulting solution was concentrated in vacuo to a volume of 5 ml and acidified to pH 2 with 4N HCl. The precipitate thus obtained was filtered and dried in vacuo to provide 1.2 g (90%) of the desired compound as an off-white solid, m.p. 185.5°–187° C. $^1$H NMR (d$_6$-DMSO) δ 6.67 (d, J=15 Hz, 1H), 7.70 (d, J=15 Hz, 1H), 7.95 (d, J=3 Hz, 1H), 8.01 (d, J=3 Hz, 1H), 12.81 (br s, 1H). Mass spectrum: $(M+H)^+$=156.

D. (2S,3R,4R,5S)-2,5-Bis-(N-(N-(trans-3-(thiazol-2-yl)-2-popenoyl)-(valinyl)-amino)-3,4-dihydroxy-1,6-diphenylhexane.

Using the procedure of Example 6I but replacing trans-3-(3-pyridyl)acrylic acid with the resultant compound of Example 14C and replacing the resultant compound of Example 6H with the resultant compound of Example 4C provided the desired compound, m.p. >260° C. Mass spectrum: $(M+H)^+$=773.

EXAMPLE 15

A. (2S,3S,4R,5S)-3-Acetoxy-2,5-bis-(N-Cbz-amino)-3-bromo-1,6-diphenylhexane.

Using the procedure of Example 1C but replacing (2S,3R,4R,5S)-2,5-bis-(N-Cbz-amino)-3,4-dihydroxy-1,6-diphenylhexane with (2S,3S,4S,5S)-2,5-bis-(N-Cbz-amino)-3,4-dihydroxy-1,6-diphenylhexane provided the desired compound in 11% yield along with (4S,5R,1'S,2'S)-5-(1-acetoxy-2-(N-Cbz-amino)-3-phenylpropyl)-4-benzyl-oxazolidin-2-one in 35% yield. (2S,3S,4R,5S)-3-Acetoxy- 2,5-bis-(N-Cbz-amino)-3-bromo-1,6-diphenylhexane: $^1$H NMR (CDCl$_3$) δ 2.05 (s, 3H), 2.57 (dd, J=13, 8 Hz, 1H), 2.74 (m, 2H), 2.92 (dd, J=14, 7 Hz, 1H), 3.82 (d, J=9 Hz, 1H), 4.32 (br q, 1H), 4.64 (m, 1H), 4.9–5.1 (m, 6H), 5.33 (br d, 1H), 7.0–7.4 (m, 20H) . Mass spectrum: (M+H)$^+$=673, 675.

B. (2S,3R,5S)-3-Acetoxy-2,5-bis-(N-Cbz-amino)-1,6-diphenylhexane.

Using the procedure of Example 1D but replacing the resultant compound of Example 1C with the resultant compound of Example 15A provided the desired compound. Mass spectrum: (M+NH$_4$)$^+$=612.

C. (2S,3R,5S)-2,5-Diamino-1,6-dipheny-3-hydroxyhexane.

Using the procedure of Example 1E but replacing the resultant compound of Example 1D with the resultant compound of Example 15B provided, after silica gel chromatography using first 2% isopropylamine in chloroform followed by 2% methanol and 2% isopropylamine in chloroform, the desired compound contaminated with Sn salts. $^1$H NMR (CDCl$_3$) δ 1.85 (m, 1H), 2.43 (dd, J=13, 10 Hz, 1H), 2.66 (dd, J=14, 9 Hz, 1H), 2.86 (dd, J=14, 4 Hz, 1H), 3.0–3.1 (m, 2H), 3.49 (m, 1H), 3.89 (m, 1H), 7.2–7.4 (m, 10H). Mass spectrum: (M+H)$^+$=285.

D. (2S,3R,5S)-2,5-Bis-(N-(N-((N-methyl-N-((2-pyridinyl)-methyl)-amino)-carbonyl)-valinyl)-amino)-1,6-diphenyl-3-hydroxyhexane.

Using the procedure of Example 3G but replacing the resultant compound of Example 1E with the resultant compound of Example 15C provided, after silica gel chromatography using 1.5% methanol in chloroform followed by 2% methanol in chloroform, the desired compound, m.p. 92°–96° C., in 65% yield. Mass spectrum: (M+H)$^+$=779.

EXAMPLE 16

A. α-Isocyanato-isoleucine Methyl Ester.

Using the procedure of Example 2A but replacing L-valine methyl ester hydrochloride with L-isoleucine methyl ester hydrochloride provided the desired compound as an oil.

B. N-((N-Methyl-N-((2-pyridinyl)methyl)amino)carbonyl)-isoleucine Methyl Ester.

Using the procedure of Example 3D but replacing the resultant compound of Example 2A with the resultant compound of Example 16A provided the desired compound. $^1$H NMR (CDCl$_3$) δ 0.92 (t, J=7 Hz, 3H), 0.94 (d, J=7 Hz, 3H), 1.21 (m, 1H), 1.46 (m, 1H), 1.90 (m, 1H), 3.02 (s, 3 H), 3.71 (s, 3H), 4.46 (dd, J=8, 5 Hz, 1H), 4.53 (s, 2H), 6.15 (br, 1H), 7.22 (dd, J=7, 5 Hz, 1H), 7.27 (d, J=7 Hz, 1H), 7.69 (td, J=7, 2 Hz, 1H), 8.55 (br d, 1H).

C. N-((N-Methyl-N-((2-pyridinyl)methyl)amino)carbonyl)-isoleucine p-Nitrophenyl Ester.

Using the procedures of Example 3E and Example 3F with the resultant compound of Example 16B provided the crude desired compound.

D. (2S,3S,5S)-2,5-Bis-(N-(N-((N-methyl-N-((2-pyridinyl)methyl)amino)carbonyl)isoleucinyl)amino)-1.6-diphenyl-3-hydroxyhexane.

Using the procedure of Example 3G but replacing the resultant compound of Example 3F with the resultant compound of Example 16C provided, after silica gel chromatography using 2% methanol in chloroform, the desired compound in 68% yield. The pure compound melted at 143°–145° C., resolidified, and melted again at 173°–174° C. Mass spectrum: (M+H)$^+$=807.

EXAMPLE 17

(2S,3S,5S)-2,5-Bis-(N-Cbz-amino)-1,6-diphenyl-3-hydroxyhexane.

A solution of 200 mg (0.34 mmol) of the resultant compound of Example 1D in 4 ml of methanol was treated with 2 ml of concentrated aqueous ammonium hydroxide. The resulting solution was stirred at ambient temperature for 6 h, and at 50° C. for 45 min. An additional 1 ml of concentrated aqueous ammonium hydroxide was added and heating was continued for 1 h. The resulting solution was diluted with 50 ml of dichloromethane, washed sequentially with water and saturated brine, dried over MgSO$_4$, and concentrated in vacuo. Silica gel chromatography of the residue using 25% ethyl acetate in hexane followed by 33% ethyl acetate in hexane provided 161 mg (84%) of the desired compound. $^1$H NMR (CDCl$_3$) δ 1.63 (m, 2H), 2.73 (m, 2H), 2.85 (m, 2H), 3.05 (br, 1H), 3.64 (m, 1H), 3.77 (br q, 1H), 3.93 (br q, 1H), 4.78 (br d, 1H), 5.05 (m, 4H), 7.0–7.4 (m, 20H). Mass spectrum: (M+H)$^+$=553.

Anal. Calcd for C$_{34}$H$_{36}$N$_2$O$_5$: C, 73.89; H, 6.57; N, 5.07. Found: C, 73.81; H, 6.61; N, 5.04.

EXAMPLE 18

A. trans-(2S,5S)-2,5-Bis-(N-(benzyloxycarbonyl)amino)-1,6-diphenyl-3-hexene.

A solution of 4.64 g of the resultant compound of Example 15A in 48 ml of acetic acid was treated with 1.33 g of zinc dust and stirred at ambient temperature for 3 days. The resulting solution was concentrated in vacuo, taken up in ethyl acetate, washed with saturated aqueous NaHCO$_3$, dried over MgSO$_4$, and concentrated in vacuo to provide 3.27 g (89%) of the desired compound.

B. trans-(2S,5S)-2,5-Diamino-1,6-diphenyl-3-hexene.

A solution of 3.27 g of the resultant compound of Example 18A in 75 ml of 30% HBr in acetic acid was allowed to stand at ambient temperature for 16 h. The resulting solution was concentrated in vacuo, and the residue was washed with hexane to remove benzyl bromide. The solid was then taken up in 1N NaOH, extracted with three 100 ml portions of dichloromethane, dried over Na$_2$SO$_4$, and concentrated. Silica gel chromatography using first 2% isopropylamine in chloroform, then 2% methanol/2% isopropylamine in chloroform provided 1.35 g (83%) of the desired compound.

C. trans-(2S,5S)-2,5-Bis-(N-(N-((N-methyl-N-((2-pyridinyl)methyl)amino)carbonyl)valinyl)amino)-1,6-diphenyl-3-hexene Using the procedure of Example 3G but replacing the resultant compound of Example 1E with the resultant compound of Example 18B provided, after silica gel chromatography using first 1.5% methanol in chloroform then 3% methanol in chloroform, 86 mg (75%) of the desired compound as a white solid. Mass spectrum: (M+H)$^+$=761.

EXAMPLE 19

A. trans-Ethyl 3-((Thiazol-2-yl)-amino)-2-propenoate.

A solution of 2.3 g of 2-aminothiazole and 1.55 ml of ethyl propiolate in 10 ml of dichloromethane and 5 ml of dimethylformamide was stirred at ambient temperature for 3 days. The resulting mixture was filtered, and the filtrate was concentrated in vacuo. The residue was chromatographed on silica gel using first 20% then 40% ethyl acetate in hexane to provide 1.54 g (51%) of the desired compound. $^1$H NMR (CDCl$_3$) δ 1.30 (t, J=7 Hz, 3H), 4.22 (q, J=7 Hz, 2H), 5.79 (d, J=15 Hz, 1H), 6.03 (d, J=5 Hz, 1H), 6.68 (d, J=5 Hz, 1H), 7.47 (br, 1H), 8.17 (d, J=15 Hz, 1H). Mass spectrum: (M+H)$^+$=199.

B. trans-3-((Thiazol-2-yl)-amino)-2-propenoic Acid.

Using the procedure of Example 3E but replacing the resultant compound of Example 3D with the resultant compound of Example 19A provided the desired compound in 70% yield. $^1$H, NMR (d$_6$-DMSO) δ 6.08 (d, J=15 Hz, 1H), 6.50 (d, J=5 Hz, 1H), 7.37 (d, J=5 Hz, 1H), 8.01 (d, J=15 Hz, 1H), 9.4 (br, 1H). Mass spectrum: (M+H)$^+$=171.

C. (2S,3R,4R,5S)-2,5-Bis-(N-(N (trans-3-((thiazol-2-yl)-amino)-2-propenoyl)-valinyl)amino)-3,4-dihydroxy-1,6-diphenylhexane.

Using the procedure of Example 6I but replacing the resultant compound of Example 6H with the resultant compound of Example 4C and replacing trans-3-(3-pyridyl)acrylic acid with the resultant compound of Example 19B provided the desired compound.

EXAMPLE 20

(2S,3S,5S)-3-Acetoxy-2,5-bis-(N-(N-((2-pyridinyl) methoxycarbonyl)-valinyl)-amino)-1,6-diphenylhexane.

A suspension of 59 mg (0.078 mmol) of the resultant compound of Example 2E in 1 ml of dichloromethane was treated sequentially with 0.017 ml (0.16 mmol) of 4-methylmorpholine, 0.007 ml (0.12 mmol) of acetic anhydride, and 5 mg of 4-dimethylaminopyridine. The resulting mixture was stirred at ambient temperature for 1 h, treated with 10 ml of aqueous NaHCO$_3$, stirred for 30 min, extracted with two 20 ml portions of dichloromethane, dried over Na$_2$SO$_4$, and concentrated in vacuo. Silica gel chromatography of the residue using 3% methanol in chloroform provided 51.6 mg (83%) of the desired compound.

EXAMPLE 21

(2S,3S,5S)-2,5-Bis-(N-Boc-amino)-1,6-diphenyl-3-hydroxyhexane.

A solution of 1.0 g (4.1 mmol) of the resultant compound of Example 1E and 1.98 g (9.1 mmol) of di-t-butyldicarbonate in 40 ml of dichloromethane was stirred at ambient temperature for 1 h. The solvent was removed in vacuo, and the residue was chromatographed on silica gel using 25% ethyl acetate in hexane followed by 33% ethyl acetate in hexane to provide 1.32 g (72%) of the desired compound. $^1$H NMR (CDCl$_3$) δ 1.39 (s, 18H), 1.62 (t, J=6 Hz, 2H), 2.74 (m, 2H), 2.85 (m, 2H), 3.65 (m, 2H), 3.86 (br q, 1H), 4.54 (br, 1H), 4.80 (br d, 1H), 7.05–7.3 (m, 10H) . Mass spectrum: (M+H)$^+$=485.

Anal. Calcd for C$_{28}$H$_{40}$N$_2$O$_5$: C, 69.39; H, 8.32; N, 5.78. Found: C, 69.21; H, 8.38; N, 5.73.

EXAMPLE 22

(2S,3S,5S)-2,5-Bis-(N-(t-butylacetyl)-amino-1,6-diphenyl-3-hydroxyhexane.

A solution of 150 mg (0.53 mmol) of the resultant compound of Example 1E and 0.18 ml (1.3 mmol) of triethylamine in 6 ml of dichloromethane was cooled under N$_2$ atmosphere to –40° C. and treated with 0.15 ml (1.1 mmol) of t-butylacetyl chloride. The resulting solution was stirred at –40° C. for 30 min, diluted with 50 ml of dichloromethane, washed sequentially with water and saturated brine, dried over MgSO$_4$, and concentrated in vacuo. Silica gel chromatography of residue using first 25% then 33% ethyl acetate in hexane provided 216 mg (85%) of the desired compound. $^1$H NMR (CDCl$_3$) δ 0.89 (s, 9H), 0.95 (s, 9H), 1.67 (m, 2H), 1.93 (s, 2H), 1.97 (s, 2H), 2.76 (AA', 2 H), 2.88 (d, J=7 Hz, 2H), 3.61 (br t, 1H), 3.97 (br q, 1H), 4.08 (m, 1H), 4.62 (br, 1H), 5.55 (br d, J=7 Hz, 1H), 5.77 (br d, J=9 Hz, 1H), 7.05–7.3 (m, 10H). Mass spectrum: (M+H)$^+$ =481 .

Anal. Calcd for C$_{30}$H$_{44}$N$_2$O$_3$: C, 74.96; H, 9.23; N, 5.83. Found: C, 74.41; H, 9.21; N, 5.73.

EXAMPLE 23

(2S,3S,5S)-2,5-Bis-(N-((4-pyridinyl)methoxycarbonyl)-amino)-1,6-diphenyl-3-hydroxyhexane A solution of 0.12 mmol of triphosgene in 2 ml of anhydrous tetrahydrofuran was cooled under N$_2$ atmosphere to –78° C. A solution of 0.36 mmol of pyridine-4-methanol and 0.36 mmol of 4-methylmorpholine in 1 ml of tetrahydrofuran was added dropwise. The resulting solution was stirred at –78° C. for 30 min, treated with a solution of 0.18 mmol of the resultant compound of Example 1E and 0.36 mmol of 4methylmorpholine in 1 ml of tetrahydrofuran, and stirred at –10° C. for 2 h. The solvent was then removed in vacuo, and the residue was chromatographed on silica gel to provide the desired compound.

EXAMPLE 24

A. 3-(N-(t-Butyloxycarbonyl)aminomethyl)pyridine.

Using the procedure of Example 3A but replacing 2(aminomethyl)pyridine with 3-(aminomethyl) pyridine provided the desired compound in 97% yield. $^1$H NMR (CDCl$_3$) δ 1.47 (s, 9H), 4.33 (br d, J=6. Hz, 2H), 4.95 (br, 1H), 7.27 (br t, J=6 Hz, 1H), 7.63 (br d, J=8 Hz, 1H), 8.52 (m, 2H).

B. 3-((N-(t-Butyloxycarbonyl)-N-methylamino)methyl)pyridine.

Using the procedure of Example 3B but replacing the resultant compound of Example 3A with the resultant compound of Example 24A provided the desired compound.

C. 3-(N-Methylamino)methyl)pyridine Dihydrochloride.

Using the procedure of Example 3C but replacing the resultant compound of Example 3B with the resultant compound of Example 24B provided the desired compound.

D. N-((N-Methyl-N-((3-pyridinyl)methyl)amino)carbonyl)valine Methyl Ester.

Using the procedure of Example 3D but replacing the resultant compound of Example 3C with the resultant compound of Example 24C provided the desired compound. $^1$H NMR (CDCl$_3$) δ 0.90 (d, J=7 Hz, 3H), 0.96 (d, J=7 Hz, 3H), 2.16 (pd, J=7, 5 Hz, 1H), 2.93 (s, 3H), 3.74 (s, 3H), 4.49 (dd, J=9, 5 Hz, 1H), 4.54 (s, 2H), 4.95 (br d, J=9 Hz, 1H), 7.28 (td, J=6, 1 Hz, 1H), 7.61 (ddd, J=7, 3, 2 Hz, 1H), 8.53 (m, 2H). Mass spectrum: (M+H)$^+$=280.

E. N-((N-Methyl-N-((3-pyridinyl)-methyl)-amino)-carbonyl)valine.

Using the procedure of Example 3E but replacing the resultant compound of Example 3D with the resultant compound of Example 24D provided the desired compound.

F. N-((N-Methyl-N-((3-pyridinyl)-methyl)-amino)-carbonyl)-valine p-Nitrophenyl Ester.

Using the procedure of Example 3F but replacing the resultant compound of Example 3E with the resultant compound of Example 24E provided the desired compound.

G. (2S,3S,5S)-2,5-Bis-(N-(N-((N-methyl-N((3-pyridinyl)methyl)amino)carbonyl)valinyl)amino)-1,6-diphenyl-3-hydroxyhexane.

Using the procedure of Example 3G but replacing the resultant compound of Example 3F with the resultant compound of Example 24F provided, after silica gel chromatography using first 2% methanol in chloroform, then 7% methanol in chloroform, and finally. 10% methanol in chloroform, the desired compound ($R_f$ 0.19, 10% methanol in chloroform) in 49% yield.

EXAMPLE 25

A. N-((2-Pyridinyl)methoxycarbonyl)-isoleucine Methyl Ester.

Using the procedure of Example 2B but replacing the resultant compound of Example 2A with the resultant compound of Example 16A provided the desired compound.

B. N-((2-Pyridinyl)methoxycarbonyl)-isoleucine.

Using the procedure of Example 3E but replacing the resultant compound of Example 3D with the resultant compound of Example 25A provided the desired compound.

C. N-((2-Pyridinyl)methoxycarbonyl)-isoleucine p-Nitrophenyl

Using the procedure of Example 3F but replacing the resultant compound of Example 3E with the resultant compound of Example 25B provided the desired compound.

D. (2S,3S,5S)-2,5-Bis-(N-(N-((2-pyridinyl)methoxycarbonyl)isoleucinyl)-amino)-1,6-diphenyl-3-hydroxyhexane.

Using the procedure of Example 1E but replacing the resultant compound of Example 1D with the resultant compound of Example 25C provided, after trituration of the residue with 4:1 ethyl acetate:hexane and filtration, the desired compound. Mass spectrum: (M+H)⁺=791.

Anal. Calcd for $C_{44}H_{56}N_6O_{7}·2H_2O$: C, 64.69; H, 7.40; N, 10.29. Found: C, 64.78; H, 6.90; N, 10.32.

EXAMPLE 26

(2S,3S,5S)-3-Acetoxy-2,5-bis-(N-(N-((N-methyl-N-((2-pyridinyl)-methyl)-amino)-carbonyl)-valinyl)-amino)-1,6-diphenylhexane.

Using the procedure of Example 20 but replacing the resultant compound of Example 2E with the resultant compound of Example 3G provided, after silica gel chromatography using 3% methanol in chloroform, the desired compound in 89% yield. Mass spectrum: (M+H)⁺=821.

EXAMPLE 27

(2S,3S,5S)-2,5-Bis-(N-Boc-amino)-1,6-dicyclohexyl-3-hydroxyhexane.

A mixture of 100 mg of the resultant compound of Example 21 and 100 mg of 5% rhodium on carbon in 3 ml of methanol was shaken under 4 atmospheres of $H_2$ for 1 day. The resulting mixture was filtered and concentrated in vacuo. Silica gel chromatography of the residue using 20% ethyl acetate in hexane provided 92 mg (90%) of the desired compound. ¹H NMR (CDCl₃) δ 0.75–1.90 (br envelope, 28 H), 1.44 (s, 18H), 3.30 (br, 1H), 3.63 (m, 2H), 3.72 (m, 1H), 4.41 (br, 1H), 4.66 (br d, 1H). Mass spectrum: (M+H)⁺=497.

Anal. Calcd for $C_{28}H_{50}N_2O_5·0.75H_2O$: C, 66.17; H, 10.21; N, 5.51. Found: C, 65.98; H, 10.42; N, 5.47.

EXAMPLE 28

A. Boc-(L)-(4-thiazolyl)-alaninal.

A solution of 5 g of Boc-(L)-(4-thiazolyl)alanine in 25 ml of anhydrous dimethylformamide was treated with 4.1 ml of ethanethiol and 60 mg of 4-dimethylaminopyridine. The resulting solution was cooled to 0° C., treated with 4.5 g of dicyclohexylcarbodiimide, and stirred at 0° C. for 20 min and at ambient temperature for 5 h. The mixture was filtered, concentrated, taken up in 5 ml of ethyl acetate, filtered, and concentrated in vacuo. Silica gel chromatography using 15% ethyl acetate in hexane provided 4.4 g (72%) of Boc-(L)-(4-thiazolyl)alanine ethanethiol ester. A portion of the above thioester (0.18 g) was combined with 0.25 g of 10% palladium on carbon in 3 ml of acetone. The mixture was treated with 0.3 ml of triethylsilane, stirred for 4 h, filtered through Celite, and concentrated in vacuo. Silica gel chromatography using first chloroform then 3% methanol in chloroform provided 0.1 g (68%) of the desired compound.

B. (2S,3R,4R,5S)-2,5-(Bis-(N-Boc-amino)-3,4-dihydroxy-1,6-di-(4-thiazolyl)-hexane.

Using the procedure of Example 1B, but replacing Cbz-L-phenylalaninal with the resultant compound of Example 28A and adding a neutralization step after addition of 1N aqueous HCl, provided, after extraction with chloroform, a crude mixture which was purified by silica gel chromatography to give the desired compound.

C. (2S,3S,5S)-2,5-Bis-(N-(N-((2-pyridinyl)methoxycarbonyl)-valinyl)-amino)-1,6-di-(4-thiazolyl)-3-hydroxyhexane.

Using sequentially the procedures of Examples 1C, 1D, 1E and 2E but replacing (2S,3R,4R,5S)-2,5-bis-(N-Cbz-amino)-3,4-dihydroxy-1,6-diphenylhexane with the resultant compound of Example 28B provided the desired compound.

EXAMPLE 29

A. (2S,3R,4R,5S)-2,5-Bis-(N-Cbz-amino)-1,6-di-(4-benzyloxyphenyl)-3,4-dihydroxy-hexane.

Using sequentially the procedures of Examples 1A and 1B but replacing Cbz-(L)-phenylalaninol with Cbz-(L)-O-benzyltyrosinol provided a crude mixture which was purified by silica gel chromatography to give the desired compound.

B. (2S,3S,5S)-2,5-Diamino-1,6-(4-hydroxyphenyl)-3-hydroxyhexane.

Using sequentially the procedures of Examples 1C, 1D and 17 but replacing (2S,3R,4R,5S)-2,5-bis-(N-Cbz-amino)-3,4-dihydroxy-1,6-diphenylhexane with the resultant compound of Example 29A provided a compound which was treated with methanol and 10% palladium on carbon, shaken under 4 atmospheres of $H_2$ for 4 h, filtered, and concentrated in vacuo to provide the desired compound.

C. (2S,3S,5S)-2,5-Bis-(N-(N-((2-pyridinyl)methoxycarbonyl)valinyl)-amino)-1,6-di-(4-hydroxyphenyl)-3-hydroxyhexane.

Using the procedure of Example 2E but replacing the resultant compound of Example 1E with the resultant compound of Example 29B provided the desired compound.

EXAMPLE 30

A. N-((2-Pyridinyl)methoxythionocarbonyl)-valine Methyl Ester.

A suspension of 1.0 g (5.96 mmol) of (L)-valine methyl ester in 10 ml of chloroform was cooled to -20° C and treated with a solution of 0.48 ml of thiophosgene in 5 ml of chloroform. The resulting solution was treated dropwise with 2.49 ml (17.9 mmol) of triethylamine, stirred at −20° C. for 15 min, then quenched with 10 ml of 0.1M HCl. The chloroform layer was separated, washed with four 5 ml portions of water, dried over $MgSO_4$, and concentrated in vacuo to provide 1.01 g of the α-isothiocyanato-(L)-valine methyl ester as an oil. The crude oil (1.01 g) was taken up in 10 ml of dichloromethane and added to a mixture of 0.81 g (4.15 mmol) of the resultant compound of Example 3C and 1.14 ml (10.4 mmol) of 4-methylmorpholine in 40 ml of dichloromethane. The resulting mixture was stirred at ambient temperature for 16 h, washed with three 15 ml portions of water, dried over $MgSO_4$, and concentrated in vacuo. Silica gel chromatography of the residue using 15% ethyl acetate in dichloromethane provided 1.23 g (100%) of the desired compound as an oil. $^1H$ NMR ($CDCl_3$) δ 1.02 (d, J=7 Hz, 3H), 1.06 (d, J=7 Hz, 3H), 2.33 (m, 1H), 3 40 (s, 3H), 3.74 (s, 3H), 4.83 (AA',2H), 5.10 (dd, J=8, 5 Hz, 1H), 7.27 (dd, J=8, 5 Hz, 1H), 7.33 (d, J=8 Hz, 1H), 7.73 (br t, J=8 Hz, 1H), 8.56 (dd, J=5, 1 Hz, 1H) . Mass spectrum: $(M+H)^+$= 296.

B. N-((2-Pyridinyl)methoxythionocarbonyl)-valine.

Using the procedure of Example 3E but replacing the resultant compound of Example 3D with the resultant compound of Example 30A provided the desired compound as a foam. $^1H$ NMR ($CDCl_3$) δ 1.04 (d, J=7 Hz, 3H), 1.08 (d, J=7 Hz, 3H), 2.41 (m, 1H), 3.41 (s, 3H), 4.80 (d, J=15 Hz, 1H), 4.94 (br d, J=15 Hz, 1H), 5.11 (dd, J=8, 5 Hz, 1H), 7.29 (ddd, J=8, 5, 1 Hz, 1H), 7.34 (d, J=8 Hz, 1H), 7.76 (td, J=8, 2 Hz, 1 H), 8.19 (br, 1H), 8.55 (ddd, J=5, 2, 1 Hz, 1H). Mass spectrum: $(M+H)^+$=282.

C. (2S,3S,5S)-2,5-Bis-(N-(N-((2-pyridinyl)methoxythionocarbonyl)-valinyl)-amino)-1,6-diphenyl-3-hydroxyhexane.

Using sequentially the procedures of Examples 3F and 3G but replacing the resultant compound of Example 3E with the resultant compound of Example 30B provided the desired compound.

EXAMPLE 31

A. (2S,3S,5S)-2,5-Bis-(N-(Cbz-threoninyl)amino)-1,6-diphenyl-3-hydroxyhexane.

Using the procedure of Example 6I but replacing the resultant compound of Example 6H with the resultant compound of Example 1E and replacing trans-3-(3-pyridyl)acrylic acid with Cbz-(L)-threonine provided, after silica gel chromatography, the desired compound.

EXAMPLE 32

(2S,3S,5S)-2,5-Bis-(N-(Cbz-valinyl)-amino)-1,6-diphenyl-3-hydroxyhexane.

Using the procedure of Example 6G but replacing the resultant compound of Example 6F with the resultant compound of Example 1E provided the desired compound.

EXAMPLE 33

(2S,3S,5S)-2,5-Bis-(N-(valinyl)-amino)-1,6-diphenyl-3-hydroxyhexane.

Using the procedure of Example 6H but replacing the resultant compound of Example 6G with the resultant compound of Example 32 provided the desired compound.

EXAMPLE 34

A. 3-(Thiazol-2-yl)-propanoic Acid.

According to procedure of Johes, et. al. (*J. Am. Chem. Soc.* 1950, 72, 4526), a solution of 0.5 g of the resultant compound of Example 14C and 0.15 g of sodium hydroxide in 4 ml of water was treated with 0.10 g of Raney nickel and shaken under 3 atmospheres of hydrogen for 16 h. The mixture was filtered, and the filtrate was neutralized with 4 N HCl, concentrated in vacuo, and acidified to pH 2 with 4N HCl. The resulting precipitate was filtered to give 0.17 g (34%) of the desired compound as a white solid.

B. (2S,3S,5S)-2,5-Bis-(N-(N-(3-(thiazol-2-yl)propanoyl)valinyl)amino)-1,6-diphenyl-3-hydroxyhexane.

Using the procedure of Example 6I but replacing the resultant compound of Example 6H with the resultant compound of Example 33 and replacing trans-3-(3-pyridyl)acrylic acid with the resultant compound of Example 34A provided the desired compound.

EXAMPLE 35

(2S,3S,5S)-2,5-Bis-(N-(N-((2-pyridinyl)methoxycarbonyl)valinyl)-amino)-1,6-diphenyl-3-(trifluoroacetoxy)exane.

Using the procedure of Example 20 but replacing acetic anhydride with trifluoroacetic anhydride and quenching the reaction with pH 6 buffer gave a two-layer mixture. The organic layer was diluted with dichloromethane, separated, dried over $Na_2SO_4$, and concentrated in vacuo to provide the desired compound.

$^1H$ NMR ($CDCl_3$) δ 0.69 (d, 3H), 0.72 (d, 3H), 0.81 (d, 3H), 0.85 (d, 3H), 1.63 (m, 1H), 1.94 (m, 1H), 2.08 (m, 2H), 2.66 (m, 2H), 2.81 (m, 2H), 3.81 (dd, 1H), 3.87 (dd, 1H), 4.53 (br, 1H), 5.01 (m, 2H), 5.22–5.28 (m, 6H), 5.92 (br, 1H), 6.04 (br d, 1H), 7.12–7.24 (m, 12H), 7.34 (br t, 2H), 7.72 (td, 2H), 8.60 (br d, 2H). Mass spectrum: $(M+H)^+$=849.

EXAMPLE 36

(2S,3S,5S)-2,5-Bis-(N-(N-((N-methyl-N-((2-pyridinyl)-methyl)-amino)-carbonyl)-valinyl)-amino)-1,6-diphenyl-3-(trifluoroacetoxy)-hexane.

Using the procedure of Example 20 but replacing acetic anhydride with trifluoroacetic anhydride, replacing the resultant compound of Example 2E with the resultant compound of Example 3G, and quenching the reaction with pH 6 buffer gave a two-layer mixture. The organic layer was diluted with dichloromethane, separated, dried over $Na_2SO_4$, and concentrated in vacuo to provide the desired compound.

EXAMPLE 37

A. ((3-Pyridinyl)methyl)-(4-nitrophenyl)carbonate,

A solution 20 g (0.1 mol) of (4-nitrophenyl)chloroformate in 150 ml of dichloromethane was cooled to 0° C. and treated sequentially with 8.0 ml (0.083 mol) of pyridine-3-methanol and 11 ml (0.1 mol) of 4-methylmorpholine. After addition, the solution was allowed to come to ambient temperature, stirred for 0.5 h, diluted with dichloromethane, washed sequentially with aqueous NaHCO₃ and water, dried over Na₂SO₄, and concentrated in vacuo. The residue was broken up, triturated with 3:1 hexane:ethyl acetate, and filtered. The resulting solid was dissolved in a minimum amount of boiling ethyl acetate/hexane, filtered hot to remove an insoluble dark oil, and allowed to cool. The desired crystalline product (18.65 g, 82%) was collected by filtration.

B. (2S,3S,5S)-5-Amino-2-(N-((3-pyridinyl)methoxycarbonyl)amino)-1,6-diphenyl-3-hydroxyhexane and (2S,3S,5S)-2-Amino-5-(N-((3-pyridinyl)methoxycarbonyl)-amino)-1,6-diphenyl-3-hydroxyhexane.

A solution of 1.5 g (5.28 mmol) of the resultant compound of Example 1E in 10 ml of tetrahydrofuran was treated dropwise over a 5 hour period with a solution of 1.6 g (5.8 mmol) of the resultant compound of Example 37A in 10 ml of tetrahydrofuran. After addition, the resulting solution was stirred at ambient temperature for 16 h and concentrated in vacuo. Silica gel chromatography using a gradient of 2–3.5% methanol in chloroform provided a mixture of the two desired compounds. Silica gel chromatography of the mixture using first 2% isopropylamine in dichloromethane followed by 2% isopropylamine/2% methanol in dichloromethane provided 0.38 g (16%) of (2S,3S,5S)-5-amino-2-(N-((3-pyridinyl)methoxycarbonyl)amino)-1,6-diphenyl-3-hydroxyhexane and 0.87 g (36%) of (2S,3S,5S)-2-amino-5-(N-((3-pyridinyl)methoxycarbonyl)amino)-1,6-diphenyl-3-hydroxyhexane.

C. (2S,3S,5S)-2-(N-(N-((N-Methyl-N-((2-pyridinyl)methyl)amino)carbonyl)valinyl)amino)-5,(N-((3-pyridinyl)methoxycarbonyl)amino)-1,6-diphenyl-3-hydroxyhexane.

A solution of 1.2 g (2.86 mmol) of (2S,3S,5S)-2-amino-5-(N-((3-pyridinyl)methoxycarbonyl)amino)-1,6-diphenyl-3-hydroxyhexane in 20 ml of tetrahydrofuran was treated with 1.55 g (4.01 mmol) of the resultant compound of Example 3F. The resulting solution was stirred at ambient temperature for 96 h, treated with aqueous NaHCO₃, extracted with chloroform, dried over Na₂SO₄, and concentrated in vacuo. The residued was purified by silica gel chromatography using first 2% then 4% methanol in chloroform to provide 1.75 g (92%) of the desired compound($R_f$ 0.28, 10% methanol in chloroform) as a white solid, m.p. 69°–71° C. Mass spectrum: $(M+1)^+$=667.

Anal. Calcd for $C_{38}H_{46}N_6O_5 \cdot 0.5H_2O$: C, 67.54; H, 7.01; N, 12.44. Found: C, 67.54; H, 6.83; N, 12.33.

EXAMPLE 38

(2S,3S,5S)-5-(N-(N-((N-Methyl-N-((2-pyridinyl)methyl)amino)carbonyl)valinyl)amino)-2-(N-((3-pyridinyl)methoxycarbonyl)amino)-1,6-diphenyl-3-hydroxyhexane, A solution of 0.95 g (2.27 mmol) of (2S,3S,5S)-5-amino-2-(N-((3-pyridinyl)methoxycarbonyl)amino)-1,6-diphenyl-3-hydroxyhexane in 15 ml of tetrahydrofuran was treated with 1.22 g (3.17 mmol) of the resultant compound of Example 3F. The resulting solution was stirred at ambient temperature for 24 h, treated with aqueous NaHCO₃, extracted with chloroform, dried over Na₂SO₄, and concentrated in vacuo. The residued was purified by silica gel chromatography using first 2% then 4% methanol in chloroform to provide 1.46 g (94%) of the desired compound ($R_f$ 0.26, 10% methanol in chloroform) as a white solid, m.p. 58°1∞61° C. Mass spectrum: $(M+1)^+$=667.

Anal. Calcd for $C_{38}H_{46}N_6O_5 \cdot 1.1H_2O$: C, 66.47; H, 7.08; N, 12.24. Found: C, 66.12; H, 6.68; N, 12.10.

EXAMPLE 39

(2S,3S,5S)-2-(N-(N-((2-Pyridinyl)methoxycarbonyl)valinyl)amino)-5-(N-((3-pyridinyl)methoxycarbonyl)amino)-1,6-diphenyl-3-hydroxyhexane.

Using the procedure of Example 37C but replacing the resultant compound of Example 3F with the resultant compound of Example 2D provided, after silica gel chromatography using a gradient of 2–5% methanol in chloroform, 104 mg (95%) of the desired compound ($R_f$ 0.30, 10% methanol in chloroform) as a white solid, m.p. 169°–171° C. Mass spectrum: $(M+1)^+$=654.

Anal. Calcd for $C_{37}H_{43}N_5O_6 \cdot 0.5H_2O$: C, 67.05; H, 6.69; N, 10.51. Found: C, 66.98; H, 6.53; N, 10.57.

EXAMPLE 40

(2S,3S,5S)-5-(N-(N-((2-Pyridinyl)methoxycarbonyl)valinyl)amino)-2-(N-((3-pyridinyl)methoxycarbonyl)amino)-1,6-diphenyl-3-hydroxyhexane.

Using the procedure of Example 38 but replacing the resultant compound of Example 3F with the resultant compound of Example 2D provided, after silica gel chromatography using a gradient of 2–5% methanol in chloroform, 102 mg (94%) of the desired compound ($R_f$ 0.30, 10% methanol in chloroform) as a white solid, m.p. 172°–174° C. Mass spectrum: $(M+1)^+$=654.

Anal. Calcd for $C_{37}H_{43}N_5O_6 \cdot 0.5H_2O$: C, 67.05; H, 6.69; N, 10.51. Found: C, 66.70; H, 6.41; N, 10.37.

EXAMPLE 41

A. 2-(((N-Methyl)amino)methyl)thiazole.

A mixture of 2.0 g (17.7 mmol) of the resultant compound of Example 14A, 4.78 g (71 mmol) of methylamine hydrochloride, 4.36 g (53 mmol) of sodium acetate and 1.67 g (27 mmol) of sodium cyanoborohydride in 50 ml of isopropyl alcohol was stirred at ambient temperature for 3 days. The resulting mixture was concentrated in vacuo, and the residue was taken up in ethyl acetate and extracted with saturated aqueous NaHCO₃. The aqueous layer was concentrated in vacuo to a small volume, saturated with NaCl, and extracted with 10% methanol in chloroform until no product remained in the aqueous layer by tlc. The combined organic layers were dried over Na₂SO₄ and concentrated in vacuo. Silica gel chromatography using first 5% then 10% methanol in chloroform provided 0.4 g (18%) of the desired compound.

B. N-((N-Methyl-N-((2-thiazolyl)methyl)amino)carbonyl)valine Methyl Ester.

A solution of 0.4 g (3.1 mmol) of the resultant compound of Example 41A and 3.1 mmol of the resultant compound of Example 2A in 10 ml of dichloromethane was stirred at ambient temperature for 1.5 h. The resulting solution was concentrated in vacuo, and the residue was purified by silica gel chromatography using first 1% then 2% methanol in chloroform to provide 0.57 g (64%) of the pure desired compound ($R_f$ 0.61, 10% methanol in chloroform).

C. N-((N-Methyl-N-((2-thiazolyl)methyl)amino)carbonyl)valine.

A solution of 0.57 g (2.0 mmol) of the resultant compound of Example 41B in 8 ml of dioxane was treated with 8 ml (4.0 mmol) of 0.5M aqueous lithium hydroxide. After being stirred at ambient temperature for 1 h, the resulting solution was neutralized with 1N aqueous HCl, concentrated in vacuo to a small volume, saturated with NaCl, and extracted with two 100 ml portions of ethyl acetate. The combined organic layers were dried over Na$_2$SO$_4$ and concentrated in vacuo to provide the desired compound.

D. N-((N-Methyl-N-((2-thiazolyl)methyl)amino)carbonyl)valine p-Nitrophenyl Ester.

A solution of 2.0 mmol of the resultant compound of Example 41C and 0.3 g (2.2 mmol) of 4-nitrophenol in 10 ml of tetrahydrofuran was treated with 0.43 g (2.2 mmol) of dicyclohexyl carbodiimide. After being stirred for 3 h at ambient temperature, the mixture was filtered and the residue was washed with 10 ml of fresh tetrahydrofuran. The combined filtrates were concentrated in vacuo to provide the crude desired compound (R$_f$ 0.11, 20% ethyl acetate in chloroform).

E. (2S,3S,5S)-2-(N-(N-((N-Methyl-N-((2-thiazolyl)methyl)amino)carbonyl)valinyl)amino)-5-(N-((3-pyridinyl)methoxycarbonyl)amino)-1,6-diphenyl-3-hydroxyhexane.

Using the procedure of Example 37C but replacing the resultant compound of Example 3F with the resultant compound of Example 41D provided the desired compound.

EXAMPLE 42

A. (1S,2S)-2-((3-Pyridinyl)methoxycarbonyl)amino-1-cyclohexanol.

A mixture of 21 mg (0.18 mmol) of (S,S)-2-aminocyclohexanol (Overman and Sugai, et. al., J. Org. Chem. 1985, 50, 4154), 60 mg (0.22 mmol) of the resultant compound of Example 37A 4 ml of tetrahydrofuran was heated at reflux for 1 h. The resulting mixture was concentrated in vacuo and purified by silica gel chromatography using 4% methanol in chloroform to provide 36 mg (79%) of the desired compound. $^1$H NMR (CDCl$_3$) δ 1.1–1.4 (m, 4H), 1.7 (m, 2H), 1.82 (br s, 1H), 2.02 (m, 2H), 3.25–3.45 (m, 2H), 4.98 (br, 1H), 5.12 (s, 2H), 7.29 (dd, J=7, 5 Hz, 1H), 7.70 (m, 1H), 8.55 (dd, J=5, 2 Hz, 1H), 8.60 (d, J=2 Hz, 1H). Mass spectrum: (M+H)$^+$=251.

B. (1'S,2'S)-(2-((3-Pyridinyl)methoxycarbonyl)amino-1-cyclohexyl)-4-nitrophenylcarbonate.

A solution of 31 mg (0.12 mmol) of the resultant compound of 42A in 5 ml of dichloromethane was treated with 35 mg (0.18 mmol) of 4-nitrophenyl chloroformate, stirred for 10 min, quenched with methanol and concentrated in vacuo. Silica gel chromatography using first 20% ethyl acetate in chloroform then 4% methanol in chloroform provided 48 mg (95%) of the desired compound. Mass spectrum: (M+H)$^+$=416.

C. (2S,3S,5S,1'S,2'S,1"S,2"S)-2,5-Bis-(N-(2-(N-((3-pyridinyl)methoxycarbonyl)amino-1-cyclohexyl)oxycarbonyl)amino)-1,6-diphenyl-3-hydroxyhexane.

A solution of 48 mg (0.11 mmol) of the resultant compound of Example 42B and 16 mg (0.06 mmol) of the resultant compound of Example 1E in 15 ml of tetrahydrofuran was heated at reflux for 4 h. The resulting solution was concentrated in vacuo and purified by silica gel chromatography using 4% methanol in chloroform to provide 31 mg (75%) of the desired compound (Rf 0.12, 10% methanol in chloroform) as a foam which solidified. Mass spectrum: (M+1)$^+$=837.

EXAMPLE 43

A. 4-(((N-Methyl)amino)methyl)thiazole.

Aqueous methylamine (100 ml, 40% by weight) was treated with 1.1 g (6.5 mmol) of 4-(chloromethyl)thiazole hydrochloride. The resulting solution was stirred at ambient temperature for 15 min, concentrated in vacuo, taken up in 5% methanol in chloroform, dried over Na$_2$SO$_4$, and concentrated in vacuo to provide 0.81 g (97%) of the crude desired compound.

B. N-((N-Methyl-N-((4-thiazolyl)methyl)amino)carbonyl)valine p-Nitrophenyl Ester.

Using sequentially the procedures of Examples 41B, 41C, and 41D, but replacing the resultant compound of Example 41A with the resultant compound of Example 43A provided the desired compound (R$_f$ 0.7, 20% ethyl acetate in chloroform).

C. (2S,3S,5S)-2-(N-(N-((N-Methyl-N-((4-thiazolyl)methyl)amino)carbonyl)valinyl)amino)-5-(N-((3-pyridinyl)methoxycarbonyl)amino)-1,6-diphenyl-3-hydroxyhexane.

Using the procedure of Example 37C but replacing the resultant compound of Example 3F with the resultant compound of Example 43B provided, after silica gel chromatography using a gradient of 2–3–5% methanol in chloroform, a 49% of the desired compound (R$_f$ 0.21, 10% methanol in chloroform) as a white solid. Mass spectrum: (M+1)$^+$=673. m.p. 71°–74° C.

Anal. Calcd for C$_{36}$H$_{44}$N$_6$O$_5$S·0.15CHCl$_3$: C, 62.87; H, 6.42; N, 12.17. Found: C, 62.63; H, 6.19; N, 12.02.

EXAMPLE 44

(2S,3S,5S)-5,(N-(N-((N-Methyl-N-((4-thiazolyl)methyl)amino)carbonyl)valinyl)amino)-2-(N-((3-pyridinyl)methoxycarbonyl)amino)-1,6-diphenyl-3-hydroxyhexane.

Using the procedure of Example 38 but replacing the resultant compound of Example 3F with the resultant compound of Example 43B provided, after silica gel chromatography using a gradient of 2–3–5% methanol in chloroform, a 43% of the desired compound (R$_f$ 0.23, 10% methanol in chloroform) as a white solid. Mass spectrum: (M+1)$^+$=673. m.p. 69°–73° C.

Anal. Calcd for C$_{36}$H$_{44}$N$_6$O$_5$S·0.2CHCl$_3$: C, 62.42; H, 6.37; N, 12.07. Found: C, 62.34; H, 6.11; N, 11.97.

EXAMPLE 45

A. 2-Amino-4-(((N-Methyl)amino)methyl)thiazole.

Using the procedure of Example 43A but replacing 4-(chloromethyl)thiazole hydrochloride with 2-amino-4-(chloromethyl)thiazole dihydrochloride provided the crude desired compound.

B. N-((N-Methyl-N-((2-amino-4-thiazolyl)methyl)amino)carbonyl)valine Methyl Ester.

A solution of 4.26 g (27 mmol) of the resultant compound of Example 2A in 100 ml of dichloromethane was added to 27 mmol of the crude resultant compound of Example 45A followed by 3 ml (54 mmol) of 4-methylmorpholine. The resulting mixture was stirred for 16 h at ambient temperature, washed with saturated aqueous sodium bicarbonate, dried over Na$_2$SO$_4$, and concentrated in vacuo to give the crude desired compound.

C. N-((N=Methyl-N-((2-((((t-butyl)oxy)carbonyl)amine)-4-thiazolyl)methyl)amine)carbonyl)valine Methyl Ester.

A solution of 1.0 g (3.33 mmol) of the crude resultant compound of Example 45B in 40 ml of dichloromethane was treated sequentially with 0.87 g (4 mmol) of di-t-butyldicarbonate and 10 mg of 4-dimethylaminopyridine. The resulting solution was stirred at ambient temperature for 3 days, washed with 10% citric acid, dried over Na$_2$SO$_4$, and concentrated in vacuo. Silica gel chromatography of the residue using first 30% then 40% ethyl acetate in chloroform provided 0.65 g (49%) of the desired compound ($R_f$ 0.58, 10% methanol in chloroform) as a foam. D. N-((N-Methyl-N-((2-((((t-butyl)oxy)carbonyl)amine)-4-thiazolyl)methyl)amine)carbonyl)valine Lithium Salt.

A solution of 0.62 g (1.55 mmol) of the resultant compound of Example 45C in 6.2 ml of dioxane was treated with 6.2 ml (3.1 mmol) of 0.5M aqueous lithium hydroxide. After being stirred for 2 h at ambient temperature, the resulting solution was concentrated in vacuo to give the crude desired compound.

E. (2S,3S,5S)-2-(N-(N-((N-Methyl-N-((2-((((t-butyl)oxy)carbonyl)amine)-4-thiazolyl)methyl)amine)carbonyl)valinyl)amine)-5-(N-((3-pyridinyl)methoxycarbonyl)amine)-1,6-diphenyl-3-hydroxyhexane.

To a solution of 70 mg (0.17 mmol) of (2S,3S,5S)-2-amine-5-(N-((3-pyridinyl)methoxycarbonyl)-amine)-1,6-diphenyl-3-hydroxyhexane, 0.20 mmol of the resultant compound of Example 45D, 34 mg (0.25 mmol) of 1-hydroxybenzotriazole monohydrate and 37 µL (0.34 mmol) of 4-methylmorpholine in 1 ml of tetrahydrofuran was added 48 mg (0.25 mmol) of ethyl-(3-dimethylaminopropyl)-carbodiimide. The resulting solution was stirred for 16 h at ambient temperature, diluted with chloroform, washed with saturated aqueous NaHCO3, dried over $Na_2SO_4$, and concentrated in vacuo. Silica gel chromatography using sequentially 1.5% and 3% methanol in chloroform provided 97.2 mg (72.5%) of the desired compound ($R_f$ 0.59, 10% methanol in chloroform) as a white solid, m.p. 95°–98° C. Mass spectrum: $(M+1)^+=788$.

EXAMPLE 46

(2S,3S,5S)-5-(N-(N-((N-Methyl-N-((2-((((t-butyl)oxy)carbonyl)amino)-4-thiazolyl)methyl)amino)carbonyl)valinyl)amino)-2-(N-((3-pyridinyl)methoxycarbonyl)amino)-1,6-diphenyl-3-hydroxyhexane.

Using the procedure of Example 45E but replacing (2S,3S,5S)-2-amino-5-(N-((3-pyridinyl)methoxycarbonyl)amino)-1,6-diphenyl-3-hydroxyhexane with (2S,3S,5S)-5-amino-2-(N-((3-pyridinyl)methoxycarbonyl)amino)-1,6-diphenyl-3-hydroxyhexane provided, after silica gel chromatography using a gradient of 1.5%–2%–3% methanol in chloroform, 96 mg (71.6%) of the desired compound ($R_f$ 0.60, 10% methanol in chloroform) as a white solid, m.p. 103°–105° C. Mass spectrum: $(M+1)^+=788$.

Anal. Calcd for $C_{41}H_{53}N_7O_7S \cdot 0.75H_2O$: C, 61.44; H, 6.85; N, 12.23. Found: C, 61.16; H, 6.64, N, 11.91.

EXAMPLE 47

A. (2S,3R,4S,5S)-5-Amino-2-(N-(N-((N-methyl-N-((2-pyridinyl) methyl)amino)carbonyl)valinyl)amino)-3,4-dihydroxy-1,6-diphenylhexane.

A solution of 0.40 g (0.133 mmol) of the resultant compound of Example 13D and 0.57 g (0.147 mmol) of the resultant compound of Example 3F in 10 ml of tetrahydrofuran was stirred at ambient temperature for 16 h. The resulting solution was diluted with 50 ml of chloroform, washed with several portions of 3N aqueous NaOH, dried over $Na_2SO_4$, and concentrated in vacuo. Silica gel chromatography of the residue using sequentially 3%, 5% and 10% methanol in chloroform provided 0.41 g (56%) of the desired compound ($R_f$ 0.15, 10% methanol in chloroform).

B. (2S,3R,4S,5S)-2-(N-(N-((N-Methyl-N-((2-pyridinyl) methyl)amino)carbonyl)valinyl)amino)-5-(N-((3-pyridinyl)methoxycarbonyl)amino)-3,4-dihydroxy-1,6-diphenylhexane.

A solution of 70 mg (0.13 mmol) of the resultant compound of Example 47A and 42 mg (0.15 mmol) of the resultant compound of Example 37A in 1 ml of tetrahydrofuran was stirred at ambient temperature for 16 h. The resulting solution was concentrated in vacuo, and the residue was purified by silica gel chromatography using a gradient of 2%–3.5% methanol in chloroform to provide 72 mg (83%) of the desired compound ($R_f$ 0.33, 10% methanol in chloroform) as a white solid, m.p. 86°–88° C. Mass spectrum: $(M+1)^+=683$.

Anal. Calcd for $C_{38}H_{46}N_6O_6 \cdot 19 \cdot 0.5H_2O$: C, 65.97; H, 6.85; N, 12.15. Found: C, 65.79; H, 6.53; N, 11.95.

EXAMPLE 48

A. (2S,3R,4S,5S)-5-Amino-2-(N-((3-pyridinyl)methoxycarbonyl)amino)-3,4-dihydroxy-1,6-diphenylhexane.

A solution of 250 mg (0.83 mmol) of the resultant compound of Example 13D and 251 mg (0.916 mmol) of the resultant compound of Example 37A in 20 ml of tetrahydrofuran was stirred at ambient temperature for 16 h. The resulting solution was concentrated in vacuo, and the residue was purified by silica gel chromatography using a gradient of 2%–3.5%–10% methanol in chloroform to provide 142 mg (57%) of the desired compound ($R_f$ 0.15, 10% methanol in chloroform).

B. (2S,3R,4S,5S)-5-(N-(N-((N-Methyl-N-((2-pyridinyl) methyl)amino)carbonyl)valinyl)amino)-2-(N-((3-pyridinyl) methoxycarbonyl)amino)-3,4-dihydroxy-1,6-diphenylhexane.

A solution of 70 mg (0.13 mmol) of the resultant compound of Example 48A in 1 ml of tetrahydrofuran was treated with 42 mg (0.15 mmol) of the resultant compound of Example 3F. The resulting solution was stirred at ambient temperature for 16 h and concentrated in vacuo. The residue was purified by silica gel chromatography using sequentially 2% and 3.5% methanol in chloroform to provide 66 mg (76%) of the desired compound ($R_f$ 0.33, 10% methanol in chloroform) as a white solid, m.p. 82°–83° C. Mass spectrum: $(M+1)^+=683$.

Anal. Calcd for $C_{38}H_{46}N_6O_6 \cdot 0.75H_2O$: C, 65.55; H, 6.88; N, 12.07. Found: C, 65.55; H, 6.49; N, 11.77.

EXAMPLE 49

A. (2S,3R,4S,5S)-5-Amino-2-(N-(N-((2-pyridinyl)methoxycarbonyl)valinyl)amino)-3,4-dihydroxy-1,6-diphenylhexane.

Using the procedure of Example 47A but replacing the resultant compound of Example 3F with the resultant compound of Example 2D provided, after silica gel chromatography using first 2% then 4% then 10% methanol in chloroform, 210 mg (24%) of the desired compound ($R_f$ 0.20, 10% methanol in chloroform).

D. (2S,3R,4S,5S)-2-(N-(N-(12-Pyridinyl)methoxycarbonyl)valinyl)amino)-5-(N-((3-pyridinyl)methoxycarbonyl)amino)-3,4-dihydroxy-1,6-diphenylhexane.

Using the procedure of Example 47B but replacing the resultant compound of Example 47A with the resultant compound of Example 49A provided, after silica gel chromatography using first 2% then 3.5% methanol in chloroform, 66 mg (75%) of the desired compound ($R_f$ 0.32, 10% methanol in chloroform) as a white solid, m.p.166°–168° C. Mass spectrum: $(M+1)^+=670$.

Anal. Calcd for $C_{37}H_{43}N_5O_7$: C, 66.35; H, 6.47; N, 10.46. Found: C, 66.25; H, 6.53; N, 10.28.

EXAMPLE 50

(2S,3R,4S,5S)-5-(N-(N-((2-Pyridinyl)methoxycarbonyl)valinyl)amino)-2- (N-((3-pyridinyl)methoxycarbonyl)amino)-3,4-dihydroxy-1,6-diphenylhexane.

Using the procedure of Example 48B but replacing the resultant compound of Example 3F with the resultant compound of Example 2D provided, after silica gel chromatography using first 2% then 4% then 10% methanol in chloroform, 61 mg (57%) of the desired compound ($R_f$ 0.32, 10% methanol in chloroform) as a white solid, m.p.184°–185° C. Mass spectrum: $(M+1)^+=670$.

Anal. Calcd for $C_{37}H_{43}N_5O_7 \cdot 0.5H_2O$: C, 65.47; H, 6.53; N, 10.32. Found: C, 65.23; H, 6.27; N, 10.25.

EXAMPLE 51

A. 1-Amino-2-methyl-2-propanol Hydrochloride.

A solution of 30 ml of borane-tetrahydrofuran (30 ml, 1M) was cooled under $N_2$ atmosphere to 0° C. and treated in a dropwise fashion with much gas evolution with 2 ml of acetone cyanohydrin. After addition, the resulting solution was heated at reflux for 4 h, allowed to cool, quenched cautiously (with gas evolution) with 100 ml of 1N aqueous HCl, and stirred for 1 h. The resulting mixture was washed four times with dichloromethane, then concentrated in vacuo to the desired compound an oil. The oil, when heated under high vacuum produced a white foam which was extremely hygroscopic.

D. 1-((3-Pyridinyl)methoxycarbonyl)amino-2-methyl-2-propanol.

Using the procedure of Example 42A but replacing trans-2-aminocyclohexanol hydrochloride with the resultant compound of 51A provided, after silica gel chromatography using first 4% then 7.5% methanol in chloroform, the desired compound. $^1$H NMR (CDCl$_3$) δ 1.22 (s, 6H), 3.20 (d, J=6 Hz, 2H), 5.13 (s, 2H), 5.18 (br, 1H), 7.30 (dd, J=7, 5 Hz, 1H), 7.71 (m, 1H), 8.58 (br d, J=5 Hz, 1H), 8.62 (br, 1H). Mass spectrum: $(M+H)^+=225$.

C. 1-((3-Pyridinyl)methoxycarbonyl)amino-2-methyl-2-propyl)-4-nitrophenyl carbonate.

Using the procedure of Example 42B but replacing the resultant compound of Example 42A with the resultant compound of Example 51B provided, after silica gel chromatography using first chloroform, then 3% methanol in chloform, the desired compound in 74% yield.

D. (2S,3S,5S)-2,5-Bis-(N-(N-(1-(3-pyridinyl)methoxycarbonyl)amino-2-methyl-2-propyl)oxycarbonyl)amino)-1,6-diphenyl-3- hydroxyhexane.

Using the procedure of Example 42C but replacing the resultant compound of Example 42B with the resultant compound of Example 51C provided, after silica gel chromatography using 5% methanol in chloroform, 80 mg the desired compound ($R_f$ 0.09, 5% methanol in chloroform). Mass spectrum: $(M+1)^+=785$.

EXAMPLE 52

A. N-((3-Pyridinyl)methoxycarbonyl)valine p-Nitrophenyl Ester.

Using the procedures of Examples 2B, 2C and 2D but replacing pyridine-2-methanol with pyridine-3-methanol provided the desired compound.

B. (2S,3S,5S)-5-(N-(N-((3-Pyridinyl)methoxycarbonyl)valinyl)amino)-2-(N-((3-pyridinyl)methoxycarbonyl)amino)-1,6-diphenyl-3-hydroxyhexane.

Using the procedure of Example 38 but replacing the resultant compound of Example 3F with the resultant compound of Example 52A provided, after silica gel chromatography using a gradient of 2–3.5% methanol in chloroform, 81 mg (87%) of the desired compound ($R_f$ 0.30, 10% methanol in chloroform) as a white solid. Mass spectrum: $(M+1)^+=654$.

EXAMPLE 53

(2S,3S,5S)-2-(N-(N-((3-Pyridinyl)methoxycarbonyl)valinyl)amino)-5-(N-((3-pyridinyl)methoxycarbonyl)amino)-1,6-diphenyl-3-hydroxyhexane.

Using the procedure of Example 37C but replacing the resultant compound of Example 3F with the resultant compound of Example 52A provided, after silica gel chromatography using a gradient of 2–3.5% methanol in chloroform, 76 mg (81%) of the desired compound ($R_f$ 0.30, 10% methanol in chloroform) as a white solid. Mass spectrum: $(M+1)^+=654$.

EXAMPLE 54

A. N-((2-Thiazolyl)methoxycarbonyl)valine p-Nitrophenyl Ester.

Using the procedures of Examples 2B, 2C and 2D but replacing pyridine-2-methanol with 2-(hydroxymethyl)-thiazole (Dondoni, et. al., *Synthesis*, 1987, 998; *Tetrahedron Lett.* 1983, 24, 2901) provided the desired compound.

B. (2S,3S,5S)-5-(N-(N-((2-Thiazolyl)methoxycarbonyl)valinyl)amino)-2-(N-((3-pyridinyl)methoxycarbonyl)amino)-1,6-diphenyl-3-hydroxyhexane.

Using the procedure of Example 38 but replacing the resultant compound of Example 3F with the resultant compound of Example 54A provided, after silica gel chromatography using a gradient of 2–3.5% methanol in chloroform, 69 mg (86%) of the desired compound ($R_f$ 0.36, 10% methanol in chloroform) as a white solid. Mass spectrum: $(M+1)^+=660$.

EXAMPLE 55

(2S,3S,5S)-2-(N-(N-((2-Thiazolyl)methoxycarbonyl)valinyl)amino)-5-(N-((3-pyridinyl)methoxycarbonyl)amino)-1,6-diphenyl-3-hydroxyhexane.

Using the procedure of Example 37C but replacing the resultant compound of Example 3F with the resultant compound of Example 54A provided, after silica gel chromatography using a gradient of 2–3.5% methanol in chloroform, a 90% of the desired compound ($R_f$ 0.36, 10% methanol in chloroform) as a white solid. Mass spectrum: $(M+1)^+=660$.

EXAMPLE 56

A. 4-(Chloromethyl)-2-methylthiazole.

A mixture of 7.13 g (56 mmol) of 1,3-dichloroacetone, 3.83 g (51 mmol) of thioacetamide and 4.73 g (56 mmol) of NaHCO$_3$ in 40 ml of dichloroethane was stirred at ambient temperature for four days. The resulting mixture was filtered and the filter cake was washed with fresh dichloroethane. The combined filtrates were added slowly to a precooled (0° C.) solution of 4.1 ml (56 mmol) of thionyl chloride in 30 ml of dichloroethane. The resulting mixture was heated at 70° C. for 40 min, cooled, and filtered. The residue was washed with a small amount of dichloromethane and dried under vacuum at 50° C. to provide 3.0 g of the crude desired compound.

B. 4-((N-Methyl)aminomethyl)-2-methylthiazole.

The resultant compound of 56A (1.0 g) was added slowly in portions to 100 ml of a rapidly stirred 40% aqueous solution of methylamine. After being stirred for 1 h, the solution was concentrated in vacuo, taken up in dichloromethane, dried over $Na_2SO_4$, and concentrated to provide the crude desired compound as a yellow oil.

C. N-((4-Nitrophenyloxy)carbonyl)valine Methyl Ester.

A solution of 1.36 g (6.8 mmol) of 4-(nitrophenyl) chloroformate in 50 ml of dichloromethane was cooled to 0° C. and treated sequentially with 1.03 g (6.1 mmol) of valine methyl ester hydrochloride and 1.42 ml (13 mmol) of 4-methylmorpholine. The resulting solution was stirred at ambient temperature for 1 h, diluted with dichloromethane, washed with aqueous $NaHCO_3$, dried over $Na_2SO_4$, and concentrated to give the crude desired compound.

D. N-((N-Methyl-N-((2-methyl-4-thiazolyl)methyl)amino)carbonyl)valine Methyl Ester.

A mixture of 5.4 mmol of the crude resultant compound of Example 56B and 6.1 mmol of the crude resultant compound of Example 56C was treated with 0.5 mmol of 4-dimethylpyridine in 40 ml of toluene and heated at reflux for 4 h. The resulting solution was concentrated in vacuo, taken up in dichloromethane, washed sequentially with aqueous $NaHCO_3$ and 10% citric acid, dried over $Na_2SO_4$, and concentrated in vacuo. Silica gel chromatography using first chloroform, then 2%, then 5% methanol in chloroform provided 1.1 g of the desired compound.

E. N-((N-Methyl-N-((2-methyl-4-thiazolyl)methyl)amino)carbonyl)valine p-Nitrophenyl Ester.

Using the procedures of Examples 41C and 41D but replacing the resultant compound of Example 41B with the resultant compound of Example 56D provided the desired compound.

F. (2S,3S,5S)-2-(N-(N-((N-Methyl-N-((2-methyl-4-thiazolyl)methyl)amino)carbonyl)valinyl)amino)-5-(N-((3-pyridinyl)methoxycarbonyl)amino)-1,6-diphenyl-3-hydroxyhexane.

Using the procedure of Example 37C but replacing the resultant compound of Example 3F with the resultant compound of Example 56E provided, after silica gel chromatography using a gradient of 1.5–3–5% methanol in chloroform, a 72% of the desired compound ($R_f$ 0.28, 10% methanol in chloroform) as a white solid. Mass spectrum: $(M+1)^+=687$. m.p. 66°–69° C.

EXAMPLE 57

A. (2S,3S,5S)-2-(N-(N-((N-Methyl-N-((2-((((t-butyl)oxy)carbonyl)amino)-4-thiazolyl)methyl)amino)carbonyl)valinyl)amino)-5-(N-(((t-butyl)oxy)carbonyl)amino)-1,6-diphenyl-3-hydroxyhexane Using the procedure of Example 45E but replacing (2S,3S,5S)-2-amino-5-(N-((3-pyridinyl)methoxy-carbonyl)amino)-1,6-diphenyl-3-hydroxyhexane with (2S,3S,5S)-2-amino-5-(N-(((t-butyl)oxy)carbonyl)amino)-1,6-diphenyl-3-hydroxyhexane provided 274 mg (93%) of the crude desired compound ($R_f$ 0.43, 10% methanol in chloroform).

B. (2S,3S,5S)-5-Amino-2-(N-(N-((N-methyl-N-((2-amino-4-thiazolyl)methyl)amino)carbonyl)valinyl)amino)-1,6-diphenyl-3-hydroxyhexane Using the procedure of Example 58B but replacing the resultant compound of Example 58A with the resultant compound of Example 57A provided the desired compound.

C. (2S,3S,5S)-2-(N-(N-((N-Methyl-N-((2-amino-4-thiazolyl)methyl)amino)carbonyl)valinyl)amino)-5-(N-pyridinyl)methoxy-carbonyl)amino)-1,6-diphenyl-3-hydroxyhexane Using the procedure of Example 47B but replacing the resultant compound of Example 47A with the resultant compound of Example 57B provided, after silica gel chromatography using a gradient of 2%–3%–3.5%–5%–7% methanol in chloroform, 42 mg (50%) of the desired compound ($R_f$ 0.22, 10% methanol in chloroform). Mass spectrum: $(M+1)^+=688$.

EXAMPLE 58

A. (2S,3S,5S)-5-(N-(N-((N-Methyl-N-((2-((((t-butyl)oxy)carbonyl)amino)-4-thiazolyl)methyl)amino)carbonyl)valinyl)amino)-2-(N-(((t-butyl)oxy)carbonyl)amino)-1,6-diphenyl-3-hydroxyhexane Using the procedure of Example 4 5E but replacing (2S,3S,5S)-2-amino-5-(N-((3-pyridinyl)methoxy-carbonyl)amino)-1,6-diphenyl-3-hydroxyhexane with (2S,3S,5S)-5-amino-2-(N-(((t-butyl)oxy)carbonyl)amino)-1,6-diphenyl-3-hydroxyhexane provided, after silica gel chromatography, 283 mg (96%) of the desired compound ($R_f$ 0.43, 10% methanol in chloroform).

B. (2S,3S,5S)-2-Amino-5-(N-(N-((N-methyl-N-((2-amino-4-thiazolyl)methyl)amino)carbonyl)valinyl)amino)-1,6-diphenyl-3-hydroxyhexane A solution of 283 mg of the resultant compound of Example 58A in 10 ml of dichloromethane was treated with 5 ml of trifluoroacetic acid and stirred overnight at ambient temperature. The resulting solution was concentrated in vacuo, partitioned between saturated aqueous $NaHCO_3$ and chloroform, dried over $Na_2SO_4$, and concentrated to provide the desired ($R_f$ 0.49, 2% isopropylamino/5% methanol in chloroform).

C. (2S,3S,5S)-5-(N-(N-((N-Methyl-N-((2-amino-4-thiazolyl)methyl)amino)carbonyl)valinyl)amino)-2-(N-((3-pyridinyl)methoxy-carbonyl)amino)-1,6-diphenyl-3-hydroxyhexane Using the procedure of Example 47B but replacing the resultant compound of Example 47A with the resultant compound of Example 58B provided, after silica gel chromatography using a gradient of 2%–3.5%–5% methanol in chloroform, 48 mg (58%) of the desired compound. Mass spectrum: $(M+1)^+=688$.

EXAMPLE 59

A. 2-(N-Ethylamino)methyl)pyridine

Using the procedure of Example 70A but replacing quinoline-2-carboxaldehyde with pyridine-2-carboxaldehyde and replacing methylamino with ethylamino provided the crude desired compound.

B. N-((N-Ethyl-N-((2-pyridinyl)methyl)amino)carbonyl)-valine p-Nitrophenyl Ester Using sequentially the procedures of Examples 41B, 41C, and 41D, but replacing the resultant compound of Example 41A with the resultant compound of Example 59A provided the desired compound.

C. (2S,3S,5S)-5-(N-(N-((N-Ethyl-N-((2-pyridinyl) methyl)amino)carbonyl)valinyl)amino)-2-(N-((3-pyridinyl)methoxy-carbonyl)amino)-1,6-diphenyl-3-hydroxyhexane Using the procedure of Example 38 but replacing the resultant compound of Example 3F with the resultant compound of Example 59B provided, after silica gel chromatography using a gradient of 2–5% methanol in chloroform, a 88% of the desired compound ($R_f$ 0.28, 10% methanol in chloroform) as a white solid. Mass spectrum: $(M+1)^+=861$.

EXAMPLE 60

(2S,3S,5S)-2-(N-(N-((N-Ethyl-N-((2-pyridinyl)methyl)amino)carbonyl)valinyl)amino)-5-(N-((3-pyridinyl)methoxy-carbonyl)amino)-1,6-diphenyl-3-hydroxyhexane Using the procedure of Example 37C but replacing the resultant compound of Example 3F with the resultant compound of Example 59B provided, after silica gel chromatography using a gradient of 2–5% methanol in chloroform, a 93% of the desired compound ($R_f$ 0.28, 10% methanol in chloroform) as a white solid. Mass spectrum: $(M+1)^+=861$

EXAMPLE 61

(2S,3R,4S,5S)-2-(N-(N-((N-methyl-N-((2-pyridinyl) methyl)amino)carbonyl)valinyl)amino)-5-(N-(((t-butyl)oxy)carbonyl)amino)-3,4-dihydroxy-1,6-diphenylhexane A solution of 110 mg (0.20 mmol) of the resultant compound of Example 47A in 1 ml of dichloromethane was treated with 53 mg (0.24 mmol) of di-t-butyldicarbonate. The resulting solution was stirred for 16 h at ambient temperature, concentrated in vacuo, and purified by silica gel chromatography using first 1.5% then 2% methanol in chloroform to provide 93 mg (72%) of the desired compound ($R_f$ 0.53, 10% methanol in chloroform) as a white solid, m.p. 105°–107° C. Mass spectrum: $(M+1)^+=648$.

Anal. Calcd for $C_{36}H_{49}N_5O_6 \cdot 0.25H_2O$: C, 66.29; H, 7.65; N, 10.74. Found: C, 66.11; H, 7.56; N, 10.64.

EXAMPLE 62

A. (2S,3R,4S,5S)-5-Amino-2-(N-(((t-butyl)oxy)carbonyl)amino)-3,4-dihydroxy-1,6-diphenylhexane A solution of 0.70 g (2.33 mmol) of the resultant compound of Example 13D and 0.61 g (2.8 mmol) of di-t-butyldicarbonate in 20 ml of dichloromethane was stirred at ambient temperature for 16 h. The resulting solution was concentrated in vacuo, and the residue was purified by silica gel chromatography using first 5% then 10% methanol in chloroform to provide 0.67 g (72%) of the desired compound ($R_f$ 0.32, 10% methanol in chloroform) as a white solid.

B. (2S,3R,4S,5S)-5-(N-(N-((N-Methyl-N-((2-pyridinyl)methyl)amino)carbonyl)valinyl)amino)-2-(N-(((t-butyl)oxy)carbonyl)amino)-3,4-dihydroxy-1,6-diphenylhexane Using the procedure of Example 48B but replacing the resultant compound of Example 48A with the resultant compound of Example 62A provided, after silica gel chromatography using first 1.5% then 2% methanol in chloroform, 103 mg (79%) of the desired compound ($R_f$ 0.55, 10% methanol in chloroform) as a white solid, m.p. 91°–93° C. Mass spectrum: $(M+1)^+=648$.

Anal. Calcd for $C_{36}H_{49}N_5O_6$: C, 66.75; H, 7.62; N, 10.81. Found: C, 66.58; H, 7.34; N, 10.64.

EXAMPLE 63

A. (2S,3S,5S)-5-Amino-2-(N-(((t-butyl)oxy)-carbonyl)amino)-1,6-diphenyl-3-hydroxyhexane and (2S,3S,5S)-2-Amino-5-(N-(((t-butyl)oxy)carbonyl)amino)-1,6-diphenyl-3-hydroxyhexane A solution of 1.5 g (5.3 mmol) of the resultant compound of Example 1E and 1.4 g (6.3 mmol) of di-t-butyldicarbonate in 50 ml of dichloromethane was stirred at ambient temperature for 16 h. The resulting solution was concentrated in vacuo, and the residue was purified by silica gel chromatography using first 5% then 10% methanol in chloroform to provide a mixture of the desired compounds. A second silica column using sequentially 0%, 0.5%, and 1% methanol in 2% isopropylamino/chloroform provided 0.65 g of (2S,3S,5S)-5-amino-2-(N-(((t-butyl)oxy)carbonyl)amino)-1,6-diphenyl-3-hydroxyhexane ($R_f$ 0.27) and 0.18 g of (2S,3S,5S)-2-amino-5-(N-(((t-butyl)oxy)carbonyl)amino)-1,6-diphenyl-3-hydroxyhexane ($R_f$ 0.23, 2% methanol/2% isopropylamino in chloroform) along with 0.15 g of a mixture or the two desired compounds.

B. (2S,3S,5S)-2-(N-(N-((N-Methyl-N-((2-pyridinyl) methyl)amino)carbonyl)valinyl)amino)-5-(N-(((t-butyl)oxy)carbonyl)amino)-1,6-diphenyl-3-hydroxyhexane Using the procedure of Example 37C but replacing (2S,3S,5S)-2-amino-5-(N-((3-pyridinyl)methoxy-carbonyl)amino)-1,6-diphenyl-3-hydroxyhexane with (2S,3S,5S)-2-amino-5-(N-(((t-butyl)oxy)carbonyl)amino)-1,6-diphenyl-3-hydroxyhexane provided, after silica gel chromatography using methanol in chloroform, 66 mg (92%) of the desired compound ($R_f$ 0.60, 10% methanol in chloroform) as a white solid, m.p. 84°–85° C. Mass spectrum: $(M+1)^+=632$.

Anal. Calcd for $C_{36}H_{49}N_5O_5 \cdot 0.5H_2O$: C, 67.48; H, 7.86; N, 10.93. Found: C, 67.40; H, 7.54; N, 10.90.

EXAMPLE 64

(2S,3S,5S)-5-(N-(N-((N-Methyl-N-((2-pyridinyl)methyl)amino)carbonyl)valinyl)amino)-2-(N-(((t-butyl)oxy)carbonyl)amino)-1,6-diphenyl-3-hydroxyhexane Using the procedure of Example 37C but replacing (2S,3S,5S)-2-amino-5-(N-((3-pyridinyl)methoxy-carbonyl)amino)-1,6-diphenyl-3-hydroxyhexane with (2S,3S,5S)-5-amino-2-(N-(((t-butyl)oxy)carbonyl)amino)-1,6-diphenyl-3-hydroxyhexane provided, after silica gel chromatography using 2% methanol in chloroform, 57 mg (80%) of the desired compound ($R_f$ 0.60, 10% methanol in chloroform). Mass spectrum: $(M+1)^+=632$.

EXAMPLE 65

(2S,3S,5S)-5-(N-(N-((N-Methyl-N-((2-methyl-4-thiazolyl)methyl)amino)carbonyl)valinyl)amino)-2-(N-((3-pyridinyl)methoxy-carbonyl)amino)-1,6-diphenyl-3-hydroxyhexane Using the procedure of Example 38 but replacing the resultant compound of Example 3F with the resultant compound of Example 56E provided, after silica gel chromatography using a gradient of 1-3-5% methanol in chloroform, a 82% of the desired compound ($R_f$ 0.30, 10% methanol in chloroform) as a white solid. Mass spectrum: $(M+1)^+=687$. m.p. 69°-72° C.

EXAMPLE 66

A. (2S,3R,4S,5S)-5-(N-(N-((N-Methyl-N-((2-((((t-butyl)oxy)carbonyl)amino)-4-thiazolyl)methyl)amino)carbonyl)valinyl)amino)-2-((((t-butyl)oxy)-carbonyl)amino)-3,4-dihydroxy-1,6-diphenylhexane Using the procedure of Example 45E but replacing (2S,3S,5S)-2-amino-5-(N-((3-pyridinyl)methoxy-carbonyl)amino)-1,6-diphenyl-3-hydroxyhexane with the resultant compound of Example 62A provided the desired compound ($R_f$ 0.68, 10% methanol in chloroform).

B. (2S,3R,4S,5S)-2-Amino-5-(N-(N-((N-methyl-N-((2-amino-4-thiazolyl)methyl)amino)carbonyl)valinyl)amino)-3,4-dihydroxy-1,6-diphenylhexane Using the procedure of Example 58B but replacing the resultant compound of Example 58A with the resultant compound of Example 66A provided the desired compound.

C. (2S,3R,4S,5S)-5-(N-(N-((N-Methyl-N-((2-amino-4-thiazolyl)methyl)amino)carbonyl)valinyl)amino)-2-((((t-butyl)oxy)carbonyl)amino)-3,4-dihydroxy-1,6-diphenylhexane Using the procedure of Example 61 but replacing the resultant compound of Example 47A with the resultant compound of Example 66B provided, after silica gel chromatography using first 2%, then 4%, then 6% methanol in chloroform, 61 mg (67%) of the desired compound ($R_f$ 0.35, 10% methanol in chloroform) as a white solid, m.p. 103°-107° C. Mass spectrum: $(M+1)^+=669$.

EXAMPLE 67

(2S,3S,5S)-5-(N-(((t-Butyl)oxy)carbonyl)amino)-2-(N-(N-((N-methyl-N-((2-amino-4-thiazolyl)methyl)amino)carbonyl)valinyl)amino)-1,6-diphenyl-3-hydroxyhexane A solution of 0.12 mmol of the resultant compound of Example 57B in 1 ml of dichloromethane was treated with 0.14 mmol of di-t-butyldicarbonate. After being stirred for three days at ambient temperature, the solution was concentrated in vacuo and purified by silica gel chromatography using a gradient of 2%-3.5%-5% methanol in chloroform to provide 48 mg (58%) of the desired compound ($R_f$ 0.22, 10% methanol in chloroform). Mass spectrum: $(M+1)^+=653$.

EXAMPLE 68

(2S,3S,5S)-2-(N-(((t-Butyl)oxy)carbonyl)amino)-5-(N-(N-((N-methyl-N-((2-amino-4-thiazolyl)methyl)amino)carbonyl)valinyl)amino)-1,6-diphenyl-3-hydroxyhexane Using the procedure of Example 67 but replacing the resultant compound of Example 57B with the resultant compound of Example 58B provided, after silica gel chromatography using first 2% then 3.5% methanol in chloroform, 42 mg (54%) of the desired compound.

EXAMPLE 69

A. 2-(((N-Methyl)amino)methyl)benzimidazole

Using the procedure of Example 43A but replacing 4-(chloromethyl)thiazole hydrochloride with 2-(chloromethyl)benzimidazole hydrochloride provided the crude desired compound in 30% yield after silica gel chromatography using 2% isopropylamino/5% methanol in chloroform.

B. N-((N-Methyl-N-((2-benzimidazolyl)methyl)amino)carbonyl)valine Methyl Ester

Using the procedure of Example 41B but replacing the resultant compound of Example 41A with the resultant compound of Example 69A provided, after silica gel chromatography using 4% methanol in chloroform, 1.74 g (87%) of the desired compound ($R_f$ 0.50, 4% methanol in chloroform).

C. N-((N-Methyl-N-((2-benzimidazolyl)methyl)amino)carbonyl)valine

Using the procedure of Example 41C but replacing the resultant compound of Example 41B with the resultant compound of Example 69B provided the desired compound.

D. N-((N-Methyl-N-((2-benzimidazolyl)methyl)amino)carbonyl)valine p-Nitrophenyl Ester Using the procedure of Example 41D but replacing the resultant compound of Example 41C with the resultant compound of Example 69C provided the desired compound.

E. (2S,3S,5S)-5-(N-(N-((N-Methyl-N-((2-benzimidazolyl)methyl)amino)carbonyl)valinyl)amino)-2-(N-((3-pyridinyl)methoxy-carbonyl)amino)-1,6-diphenyl-3-hydroxyhexane Using the procedure of Example 45E but replacing (2S,3S,5S)-2-amino-5-(N-((3-pyridinyl)methoxy-carbonyl)amino)-1,6-diphenyl-3-hydroxyhexane with (2S,3S,5S)-5-amino-2-(N-((3-pyridinyl)methoxy-carbonyl)amino)-1,6-diphenyl-3-hydroxyhexane and replacing the resultant compound of Example 45D with the resultant compound of Example 69C provided, after silica gel chromatography using first 2.5% then 4.5% methanol in chloroform, 74.2 mg (62%) of the desired compound ($R_f$ 0.30, 10% methanol in chloroform) as a white solid, m.p. 97°-100° C. Mass spectrum: $(M+1)^+=706$.

Anal. Calcd for $C_{40}H_{47}N_7O_5 \cdot 0.5H_2O$: C, 67.21; H, 6.77; N, 13.72. Found: C, 66.83; H, 6.70; N, 13.57.

EXAMPLE 70

A. 2-(N-Methylamino)methyl)quinoline

A mixture of 1.93 g of quinoline-2-carboxaldehyde and 0.19 g of 10 palladium on carbon in 15 ml of anhydrous methylamino and 45 ml of methanol was shaken under 4 atmospheres of hydrogen for 8 h. The resulting mixture was filtered through Celite and concentrated in vacuo to provide the crude desired compound.

B. N-((N-Methyl-N-((2-quinolinyl)methyl)amino)carbonyl)valine

Using sequentially the procedures of Examples 41B and 41C, but replacing the resultant compound of Example 41A with the resultant compound of Example 70A provided the desired compound.

C. (2S,3S,5S)-5-(N-(N-((N-Methyl-N-((2-quinolinyl)methyl)amino)carbonyl)valinyl)amino)-2-(N-((3-pyridinyl)methoxy-carbonyl)amino)-1,6-diphenyl-3-hydroxyhexane Using the procedure of Example 46 but replacing the resultant compound of Example 45D with the resultant compound of Example 70B provided, after silica gel chromatography using a gradient of 1–2.5% methanol in chloroform, 105 mg (60%) of the desired compound ($R_f$ 0.40, 10% methanol in chloroform) as a white solid. Mass spectrum: $(M+1)^+=717$.

EXAMPLE 71

(2S,3S,5S)-2-(N-((N-((N-Methyl-N-((2-quinolinyl)methyl)amino)carbonyl)valinyl)amino)-5-(N-((3-pyridinyl)methoxy-carbonyl)amino)-1,6-diphenyl-3-hydroxyhexane Using the procedure of Example 45E but replacing the resultant compound of Example 45D with the resultant compound of Example 70B provided, after silica gel chromatography using a gradient of 1–2.5% methanol in chloroform, 100 mg (60%) of the desired compound ($R_f$ 0.36, 10% methanol in chloroform) as a white solid. Mass spectrum: $(M+1)^+=717$.

EXAMPLE 72

A. 1-(N-Methylamino)methyl)isoquinoline

Using the procedure of Example 70A but replacing quinoline-2-carboxaldehyde with isoquinoline-1-carboxaldehyde (Minisci, et. al., J. Org. Chem., 1986, 51, 536) provided the crude desired compound.

B. N-((N-Methyl-N-((1-isoquinolinyl)methyl)amino)carbonyl)valine p-Nitrophenyl Ester Using sequentially the procedures of Examples 41B, 41C, and 41D, but replacing the resultant compound of Example 41A with the resultant compound of Example 72A provided the desired compound.

C. (2S,3S,5S)-5-(N-(N-((N-Methyl-N-((1-isoquinolinyl)methyl)amino)carbonyl)valinyl)amino)-2-(N-((3-pyridinyl)methoxy-carbonyl)amino)-1,6-diphenyl-3-hydroxyhexane Using the procedure of Example 38 but replacing the resultant compound of Example 3F with the resultant compound of Example 72C provided, after silica gel chromatography using a gradient of 2–3.5% methanol in chloroform, 98 mg (96%) of the desired compound ($R_f$ 0.41, 10% methanol in chloroform) as a white solid. Mass spectrum: $(M+1)^+=717$.

EXAMPLE 73

(2S,3S,5S)-2-(N-(N-((N-Methyl-N-((1-isoquinolinyl)methyl)amino)carbonyl)valinyl)amino)-5-(N-((3-pyridinyl)methoxy-carbonyl)amino)-1,6-diphenyl-3-hydroxyhexane Using the procedure of Example 37C but replacing the resultant compound of Example 3F with the resultant compound of Example 72C provided, after silica gel chromatography using a gradient of 2–3.5% methanol in chloroform, 69 mg (67%) of the desired compound ($R_f$ 0.41, 10% methanol in chloroform) as a white solid. Mass spectrum: $(M+1)^+=717$.

EXAMPLE 74

(2S,3S,5S)-2-(N-(N-((N-Methyl-N-((2-benzimidazolyl)methyl)amino)carbonyl)valinyl)amino)-5-(N-((3-pyridinyl)methoxy-carbonyl)amino)-1,6-diphenyl-3-hydroxyhexane Using the procedure of Example 45E but replacing the resultant compound of Example 45D with the resultant compound of Example 69C provided, after silica gel chromatography using first 2.5% then 4.5% methanol in chloroform, 74 mg (62%) of the desired compound ($R_f$ 0.27, 10% methanol in chloroform) as a off-white solid, m.p. 110°–114° C. Mass spectrum: $(M+1)^+=706$.

EXAMPLE 75

A. ((2-Thiazolyl)methyl)-(4-nitrophenyl)carbonate

A solution 2.3 g (11.5 mmol) of (4-nitrophenyl)chloroformate in 20 ml of dichloromethane was cooled to 0° C. and treated sequentially with a solution of 1.2 g (10.4 mmol) of 2-(hydroxymethyl)thiazole (Dondoni, et. al., *Synthesis*, 1987, 998; *Tetrahedron Lett.* 1983, 24, 2901) in 5 ml of dichloromethane and 1.7 ml (15.7 mmol) of 4-methylmorpholine. After addition, the solution was allowed to come to ambient temperature, stirred for 0.5 h, and concentrated in vacuo. Silica gel chromatography of the residue using first chloroform then 1% methanol in chloroform provided 1.15 g (39%) of the desired compound ($R_f$ 0.73, 10% methanol in chloroform).

B. (2S,3S,5S)-2,5-Bis-(N-((2-thiazolyl)methoxy-carbonyl)amino)-1,6-diphenyl-3-hydroxyhexane A solution of 130 mg (0.46 mmol) of the resultant compound of Example 75A and 60 mg (0.21 mmol) of the resultant compound of Example 1E in 0.5 ml of tetrahydrofuran was stirred at ambient temperature for 16 h. The resulting solution was concentrated in vacuo, and the residue was purified by silica gel chromatography using first 2% then 4% methanol in chloroform to provide 99 mg (83%) of the desired compound ($R_f$ 0.73, 10% methanol in chloroform) as a white solid, m.p. 66°–69° C. Mass spectrum: $(M+1)^+=567$.

Anal. Calcd for $C_{28}H_{36}N_4O_5S_2 \cdot 0.5H_2O$: C, 58.42; H, 5.43; N, 9.73. Found: C, 58.23; H, 5.20; N, 9.61.

EXAMPLE 76

(2S,3R,4R,5S)-2,5-Bis-(N-((3-pyridinyl)methoxy)carbonyl)amino)-3,4-dihydroxy-1,6-diphenylhexane Using the procedure of Example 75B but replacing the resultant compound of Example 75A with the resultant compound of Example 37A and replacing the resultant compound of Example 1E with the resultant compound of Example 4A provided, after silica gel chromatography using first 2% then 3.5% methanol in chloroform, 280 mg of the desired compound ($R_f$ 0.25, 10% methanol in chloroform) as a white solid, m.p. 191°–193° C. Mass spectrum: $(M+1)^+=$ 571.

Anal. Calcd for $C_{32}H_{34}N_4O_6$: C, 67.35; H, 6.01; N, 9.82. Found: C, 67.11; H, 6.01; N, 9.64.

EXAMPLE 77

(2S,3R,4S,5S)-2,5-Bis-(N-((3-pyridinyl)methoxycarbonyl)amino)-3,4-dihydroxy-1,6-diphenylhexane Using the procedure of Example 75B but replacing the resultant compound of Example 75A with the resultant compound of Example 37A and replacing the resultant compound of Example 1E with the resultant compound of Example 13D provided, after silica gel chromatography using first 2% then 3% methanol in chloroform, 110 mg of the desired compound ($R_f$ 0.42, 10% methanol in chloroform) as a white solid, m.p. 180°–186° C. Mass spectrum: $(M+1)^+=571$.

EXAMPLE 78

A. ((4-Thiazolyl) methyl)-4-nitrophenyl)carbonate

Using the procedure of Example 75A but replacing 2-(hydroxymethyl)thiazole with 4-(hydroxymethyl)thiazole (Kollonitsch, U.S. Pat. No. 3,299,083) provided, after silica gel chromatography using first chloroform then 1% methanol in chloroform, 380 mg (31%) of the desired compound ($R_f$ 0.70, 10% methanol in chloroform).

B. (2S,3S,5S)-2,5-Bis-(N-((4-thiazolyl)methoxycarbonyl)amino)-1,6-diphenyl-3-hydroxyhexane Using the procedure of Example 75B but replacing the resultant compound of Example 75A with the resultant compound of Example 78A provided, after silica gel chromatography using first 2% then 4% methanol in chloroform, 98.6 mg (83%) of the desired compound ($R_f$ 0.43, 10% methanol in chloroform) as a white solid, m.p. 64°–66° C. Mass spectrum: $(M+1)^+=567$.

Anal. Calcd for $C_{28}H_{36}N_4O_5S_2 \cdot 0.5H_2O$: C, 58.42; H, 5.43; N, 9.73. Found: C, 58.45; H, 5.24; N, 9.61.

EXAMPLE 79

A. ((2-Methyl-5-thiazolyl)methyl)-(4-nitrophenyl)carbonate

Using the procedure of Example 75A but replacing 2-(hydroxymethyl)thiazole with 2-methyl-5-(hydroxymethyl)thiazole (Mashraqui and Keehn, J. Am. Chem. Soc. 1982, 104, 4461) provided, after silica gel chromatography using 6% ethyl acetate in chloroform, 243 mg (65%) of the desired compound ($R_f$ 0.25, 10% methanol in chloroform).

B. (2S,3S,5S)-2,5-Bis-(N-((2-methyl-5-thiazolyl)methoxy-carbonyl)amino)-1,6-diphenyl-3-hydroxyhexane Using the procedure of Example 75B but replacing the resultant compound of Example 75A with the resultant compound of Example 79A provided, after silica gel chromatography using first 2% then 3% methanol in chloroform, 49 mg (29%) of the desired compound ($R_f$ 0.5, 10% methanol in chloroform). Mass spectrum: $(M+1)^+=595$.

EXAMPLE 80

A. 5-(Carbethoxy)thiazole

According to the procedure of Mashraqui and Keehn (J. Am. Chem. Soc. 1982, 104, 4461), ethyl α-chloro-α-formylacetate was condensed with thioformamide and vacuum distilled to provide 5.65 g (33%) of the desired compound.

B. 5-(Hydroxymethyl)thiazole

According to the procedure of Mashraqui and Keehn (J. Am. Chem. Soc. 1982, 104, 4461), 5-(carbethoxy)thiazole was reduced with lithium aluminum hydride to provide the crude desired compound in 44% yield.

C. ((5-Thiazolyl)methyl)-(4-nitrophenyl)carbonate

Using the procedure of Example 75A but replacing 2-(hydroxymethyl)thiazole with 5-(hydroxymethyl)thiazole and allowing the reaction to proceed at ambient temperature for 2 days provided, after silica gel chromatography using 6% ethyl acetate in chloroform, 1.1 g (71%) of the desired compound ($R_f$ 0.22, 6% ethyl acetate in chloroform). Mass spectrum: $(M+1)^+=281$.

D. (2S,3S,5S)-2,5-Bis-(N-((5-thiazolyl)methoxycarbonyl)amino)-1,6-diphenyl-3-hydroxyhexane Using the procedure of Example 75B but replacing the resultant compound of Example 75A with the resultant compound of Example 80C provided, after silica gel chromatography using first 2% then 3% methanol in chloroform, 145 mg (73%) of the desired compound ($R_f$ 0.56, 10% methanol in chloroform). Mass spectrum: $(M+1)^+=567$.

EXAMPLE 81

A. N-((4-Methylpiperazin-1-yl)carbonyl)valine Methyl Ester

Using the procedure of Example 41B but replacing the resultant compound of Example 41A with 1-methylpiperazine provided, after silica gel chromatography using first 5% then 7.5% methanol in chloroform, 1.40 g (100%) of the desired compound ($R_f$ 0.14, 5% methanol in chloroform). Mass spectrum: $(M+1)^+=258$.

B. N-((4-Methylpiperazin-1-yl)carbonyl)valine

Using the procedure of Example 41C but replacing the resultant compound of Example 41B with the resultant compound of Example 81A provided the desired compound.

C. (2S,3R,4S,5S)-5-(N-(N-((4-Methylpiperazin-1-yl)carbonyl)valinyl)amino)-2-(N-(((t-butyl)oxy)-carbonyl)amino)-3,4-dihydroxy-1,6-diphenylhexane To a solution of 70 mg (0.175 mmol) of the resultant compound of Example 62A, 0.21 mmol of the resultant compound of Example 81B, 35 mg (0.26 mmol) of 1-hydroxybenzotriazole monohydrate and 38 µL (0.35 mmol) of 4-methylmorpholine in 1 ml of tetrahydrofuran was added 50 mg (0.26 mmol) of ethyl-(3-dimethylaminopropyl)-carbodiimide. The resulting solution was stirred for 16 h at ambient temperature, diluted with 5% methanol in chloroform, washed with saturated aqueous $NaHCO_3$ and saturated brine, dried over $Na_2SO_4$, and concentrated in vacuo. Silica gel chromatography using sequentially 3%, 6% and 10% methanol in chloroform provided 82 mg (75%) of the desired compound ($R_f$ 0.18, 10% methanol in chloroform). Mass spectrum: $(M+H)^+=626$.

Anal. Calcd for $C_{34}H_{51}N_5O_6.0.5H_2O$: C, 64.33; H, 8.26; N, 11.03. Found: C, 64.05; H, 8.07; N, 11.07.

EXAMPLE 82

A. (2S,3S,4S,5S)-5-Amino-2-(N-(N-((2-pyridinyl)methoxy-carbonyl)valinyl)amino)-3,4-dihydroxy-1,6-diphenylhexane Using the procedure of Example 47A but replacing the resultant compound of Example 3F with the resultant compound of Example 2D and replacing the resultant compound of Example 13D with the resultant compound of Example 11C provided, after silica gel chromatography using first 5% then 10% methanol in chloroform, 340 mg (38%) of the desired compound ($R_f$ 0.20, 10% methanol in chloroform).

B. (2S,3S,4S,5S)-2-(N-(N-((2-Pyridinyl)methoxy-carbonyl)valinyl)amino)-5-(N-((3-pyridinyl)methoxy-carbonyl)amino)-3,4-dihydroxy-1,6-diphenylhexane Using the procedure of Example 47B but replacing the resultant compound of Example 47A with the resultant compound of Example 82A provided, after silica gel chromatography using first 2% then 4% methanol in chloroform, 86.7 mg (69%) of the desired compound as a white solid, m.p. 84°–85° C. Mass spectrum: $(M+1)^+=670$.

Anal. Calcd for $C_{37}H_{43}N_5O_6.1.0H_2O$: C, 64.61; H, 6.59; N, 10.18. Found: C, 64.46; H, 6.22; N, 10.04.

EXAMPLE 83

(2S,3S,4S,5S)-2,5-Bis-(N-((3-pyridinyl)methoxy-carbonyl)amino)-3,4-dihydroxy-1,6-diphenylhexane Using the procedure of Example 75B but replacing the resultant compound of Example 75A with the resultant compound of Example 37A and replacing the resultant compound of Example 1E with the resultant compound of Example 11C provided, after silica gel chromatography using first 2% then 5% methanol in chloroform, 98.6 mg (74%) of the desired compound ($R_f$ 0.45, 10% methanol in chloroform) as a white solid, m.p. 80°–82° C. Mass spectrum: $(M+1)^+=571$.

Anal. Calcd for $C_{32}H_{34}N_4O_6.0.5H_2O$: C, 66.31; H, 6.08; N, 9.67. Found: C, 66.09; H, 5.95; N, 9.53.

EXAMPLE 84

A. (2S,3R,4S,5S)-5-Amino-2-(N-(N-(((benzyl)oxy)carbonyl)valinyl)amino)-3,4-dihydroxy-1,6-diphenylhexane Using the procedure of Example 47A but replacing the resultant compound of Example 3F with Cbz-valine p-nitrophenyl ester provided the desired compound.

B. (2S,3R,4S,5S)-5-(N-(N-((4-Methylpiperazin-1-yl)carbonyl)valinyl)amino)-2-(N-(N-(((benzyl)oxy)carbonyl)valinyl)amino)-3,4-dihydroxy-1,6-diphenylhexane Using the procedure of Example 81C but replacing the resultant compound of Example 62A with the resultant compound of Example 84A provided, after silica gel chromatography using first 5% then 10% methanol in chloroform, 96.3 mg (71%) of the desired compound ($R_f$ 0.11, 10% methanol in chloroform) as a white solid, m.p. 216°–219° C. Mass spectrum: $(M+1)^+=759$.

Anal. Calcd for $C_{42}H_{58}N_6O_7.0.75H_2O$: C, 65.30; H, 7.76; N, 10.88. Found: C, 65.48; H, 7.49; N, 10.97.

EXAMPLE 85

(2S,3R,4R,5S)-2,5-Bis-(N-(N-((N-methyl-N-((4-thiazolyl)methyl)amino)carbonyl)valinyl)amino)-3,4-dihydroxy-1,6-diphenylhexane A solution of 75 mg (0.25 mmol) of the resultant compound of Example 43B and 0.75 mmol of the resultant compound of Example 4A in 1 ml of tetrahydrofuran was stirred at ambient temperature for 54 h. The resulting solution was concentrated in vacuo. Silica gel chromatography of the residue using first 2% then 5% methanol in chloroform, provided 182 mg (91%) of the desired compound ($R_f$ 0.33, 10% methanol in chloroform) as a white solid, m.p. 92°–94° C. Mass spectrum: $(M+1)^+=807$.

Anal. Calcd for $C_{40}H_{54}N_8O_6S_2.H_2O$: C, 58.23; H, 6.84; N, 13.58. Found: C, 57.87; H, 6.49; N, 13.40.

EXAMPLE 86

(2S,3S,4S,5S)-2,5-Bis-(N-(N-((N-methyl-N-((4-thiazolyl)methyl)amino)carbonyl)valinyl)amino)-3,4-dihydroxy-1,6-diphenylhexane Using the procedure of Example 3G but replacing the resultant compound of Example 1E with the resultant compound of Example 11C and replacing the resultant compound of Example 3F with the resultant compound of Example 43B provided, after silica gel chromatography using first 2% then 5% methanol in chloroform, 179 mg (89%) of the desired compound ($R_f$ 0.35, 10% methanol in chloroform) as a white solid, m.p. 94°–95° C. Mass spectrum: $(M+1)^+=807$.

Anal. Calcd for $C_{40}H_{54}N_8O_6S_2.0.5H_2O$: C, 58.87; H, 6.79; N, 13.73. Found: C, 58.69; H, 6.52; N, 13.66.

EXAMPLE 87

(2S,3R,4S,5S)-2,5-Bis-(N-(N-((N-methyl-N-((4-thiazolyl)methyl)amino)carbonyl)valinyl)amino)-3,4-dihydroxy-1,6-diphenylhexane Using the procedure of Example 85 but replacing the resultant compound of Example 4A with the resultant compound of Example 13D provided, after silica gel chromatography using first 2% then 5% methanol in chloroform, 169 mg (85%) of the desired compound ($R_f$ 0.31, 10% methanol in chloroform) as a white solid, m.p. 165°–167° C. Mass spectrum: $(M+1)^+=807$.

Anal. Calcd for $C_{40}H_{54}N_8O_6S_2 \cdot 0.5H_2O$: C, 58.87; H, 6.79; N, 13.73. Found: C, 58.61; H, 6.57; N, 13.57.

EXAMPLE 88

(2S,3S,5S)-2,5-Bis-(N-(N-((N-methyl-N-((4-thiazolyl)methyl)amino)carbonyl)valinyl)amino)-1,6-diphenyl-3-hydroxyhexane Using the procedure of Example 85 but replacing the resultant compound of Example 4A with the resultant compound of Example 1E provided, after silica gel chromatography using first 2% then 5% methanol in chloroform, 151 mg (77%) of the desired compound ($R_f$ 0.31, 10% methanol in chloroform) as a white solid, m.p. 154°–156° C. Mass spectrum: $(M+1)^+=791$.

Anal. Calcd for $C_{40}H_{54}N_8O_6S_2 \cdot 0.25H_2O$: C, 60.39; H, 6.90; N, 14.09. Found: 60.30; H, 6.74; N, 13.96.

EXAMPLE 89

A. (2S,3S,4S,5S)-5-Amino-2-(N-(N-((N-methyl-N-((2pyridinyl)methyl)amino)carbonyl)valinyl)amino)-3,4-dihydroxy-1,6-diphenylhexane Using the procedure of Example 47A but replacing the resultant compound of Example 13D with the resultant compound of Example 11C provided, after silica gel chromatography using first 5% then 10% methanol in chloroform, 282 mg (40%) of the desired compound ($R_f$ 0.14, 10% methanol in chloroform).

B. (2S,3S,4S,5S)-5-(N-(N-((N-Methyl-N-((4-thiazolyl)methyl)amino)carbonyl)valinyl)amino)-2-(N-(N-((N-methyl-N-((2-pyridinyl)methyl)amino)carbonyl)valinyl)amino)-3,4-dihydroxy-1,6-diphenylhexane Using the procedure of Example 38 but replacing the resultant compound of Example 3F with the resultant compound of Example 43B and replacing (2S,3S,5S)-5-amino-2-(N-((3-pyridinyl)methoxy-carbonyl)amino)-1,6-diphenyl-3-hydroxyhexane with the resultant compound of Example 89A provided, after silica gel chromatography using first 1.5% then 3% then 5% methanol in chloroform, 73 mg (83%) of the desired compound ($R_f$ 0.37, 10% methanol in chloroform) as a white solid, m.p. 84°–88° C. Mass spectrum: $(M+1)^+=801$.

Anal. Calcd for $C_{42}H_{56}N_8O_6S \cdot 0.5H_2O$: C, 62.28; H, 7.09; N, 13.83. Found: C, 62.03; H, 6.89; N, 13.64.

EXAMPLE 90

(2S,3S,4S,5S)-2-(N-(N-((N-Methyl-N-((2-pyridinyl)methyl)amino)carbonyl)valinyl)amino)-5-(N-(N-((N-methyl-N-((3-pyridinyl)methyl)amino)carbonyl)valinyl)amino)-3,4-dihydroxy-1,6-diphenylhexane Using the procedure of Example 38 but replacing the resultant compound of Example 3F with the resultant compound of Example 24F and replacing (2S,3S,5S)-5-amino-2-(N-((3-pyridinyl)methoxy-carbonyl)amino)-1,6-diphenyl-3-hydroxyhexane with the resultant compound of Example 89A provided, after silica gel chromatography sequentially 2%, 4% and 6% methanol in chloroform, 64 mg (73%) of the desired compound ($R_f$ 0.25, 10% methanol in chloroform) as a white solid, m.p. 92°–94° C. Mass spectrum: $(M+1)^+=795$.

EXAMPLE 91

(2S,3S,4S,5S)-2-(N-(N-((N-Methyl-N-((2-pyridinyl)methyl)amino)carbonyl)valinyl)amino)-5-(N-(N-((4-methyl-piperazin-1-yl)carbonyl)valinyl)amino)-3,4-dihydroxy-1,6-diphenylhexane Using the procedure of Example 81C but replacing the resultant compound of Example 62A with the resultant compound of Example 89A provided, after silica gel chromatography using sequentially 5% and 10% methanol in chloroform, 65 mg (62%) of the desired compound ($R_f$ 0.15, 10% methanol in chloroform). Mass spectrum: $(M+1)^+=773$.

EXAMPLE 92

(2S,3S,4S,5S)-2,5-Bis-(N-(N-((N-methyl-N-((2-((((t-butyl)oxy)carbonyl)amino)-4-thiazolyl)methyl)amino)carbonyl)valinyl)amino)-3,4-dihydroxy-1,6-diphenylhexane To a solution of 70 mg (0.23 mmol) of the resultant compound of Example 11C, 0.52 mmol of the resultant compound of Example 45D, 94 mg (0.69 mmol) of 1-hydroxybenzotriazole monohydrate and 50 μL (0.46 mmol) of 4-methylmorpholine in 1 ml of dimethylformamide was added 130 mg (0.69 mmol) of ethyl-(3-dimethylaminopropyl)-carbodiimide. The resulting solution was stirred for 16 h at ambient temperature, diluted with ethyl acetate, washed with saturated aqueous $NaHCO_3$, dried over $Na_2SO_4$, and concentrated in vacuo. Silica gel chromatography using sequentially 2% and 5% methanol in chloroform provided 210 mg (88%) of the desired compound ($R_f$ 0.57, 10% methanol in chloroform) as a white solid, m.p. 143°–145° C. Mass spectrum: $(M+1)^+=1037$.

EXAMPLE 93

(2S,3R,4S,5S)-2,5-Bis-(N-(N-((N-methyl-N-((2-((((t-butyl)oxy)carbonyl)amino)-4-thiazolyl)methyl)amino)carbonyl)valinyl)amino)-3,4-dihydroxy-1,6-diphenylhexane Using the procedure of Example 92 but replacing the resultant compound of Example 11C with the resultant compound of Example 13D provided, after silica gel chromatography using 2% methanol in chloroform, 188 mg (80%) of the desired compound ($R_f$ 0.5, 10% methanol in chloroform) as a white solid, m.p. 138°–140° C. Mass spectrum: $(M+1)^+=1037$.

EXAMPLE 94

(2S,3S,5S)-2,5-Bis-(N-(N-((N-methyl-N-((2-((((t-butyl)oxy)carbonyl)amino)-4-thiazolyl)methyl)amino)carbonyl)valinyl)amino)-1,6-diphenyl-3-hydroxyhexane Using the procedure of Example 92 but replacing the resultant compound of Example 11C with the resultant compound of Example 1E provided, after silica gel chromatography using 2% methanol in chloroform, 102 mg (43%) of the desired compound ($R_f$ 0.57, 10% methanol in chloroform) as a white solid, m.p. 115°–120° C. Mass spectrum: $(M+1)^+=1021$.

EXAMPLE 95

(2S,3S,4S,5S)-2,5-Bis-(N-(N-((N-methyl-N-((2-amino-4-thiazolyl)methyl)amino)carbonyl)valinyl)amino)-3,4-dihydroxy-1,6-diphenylhexane Using the procedure of Example 58B but replacing the resultant compound of Example 58A with the resultant compound of Example 92 provided, after silica gel chromatography using first 5% then 10% methanol in chloroform, 62 mg (43%) of the desired compound ($R_f$ 0.16, 10% methanol in chloroform) as an off-white solid, m.p. 122°–124° C. Mass spectrum: $(M+1)^+$=837.

Anal. Calcd for $C_{40}H_{56}N_{10}O_6S_2 \cdot 0.5CH_3OH \cdot 0.5CHCl_3$: C, 53.98; H, 6.41; H, 15.35. Found: C, 53.80; H, 6.36; N, 14.98.

EXAMPLE 96

(2S,3R,4S,5S)-2,5-Bis-(N-(N-((N-methyl-N-((2-amino-4-thiazolyl)methyl)amino)carbonyl)valinyl)amino)-3,4-dihydroxy-1,6-diphenylhexane Using the procedure of Example 58B but replacing the resultant compound of Example 58A with the resultant compound of Example 93 provided, after silica gel chromatography using first 5% then 10% methanol in chloroform followed by 2% isopropylamino/10% methanol in chloroform, 53 mg (38%) of the desired compound ($R_f$ 0.15, 10% methanol in chloroform) as a white solid, m.p. 130°–134° C. Mass spectrum: $(M+1)^+$=837.

Ana. Calcd for $C_{40}H_{56}N_{10}O_6S_2 \cdot 2.25H_2O$: C, 54.74; H, 6.95; N, 15.96. Found: C, 54.74; H, 6.56; N, 15.57.

EXAMPLE 97

(2S,3S,5S)-2,5-Bis-(N-(N-((N-methyl-N-((2-amino-4-thiazolyl)methyl)amino)carbonyl)valinyl)amino)-1,6-diphenyl-3-hydroxyhexane Using the procedure of Example 58B but replacing the resultant compound of Example 58A with the resultant compound of Example 94 provided, after silica gel chromatography using first 5% then 10% methanol in chloroform, 52 mg (72%) of the desired compound ($R_f$ 0.18, 10% methanol in chloroform) as a white solid, m.p. 110°–114° C. Mass spectrum: $(M+1)^+$=821.

Anal. Calcd for $C_{40}H_{56}N_{10}O_6S_2 \cdot 0.5CH_3OH \cdot 0.25CHCl_3$: C, 56.47; H, 6.75; N, 16.16. Found: C, 56.85; H, 6.47; N, 15.45.

EXAMPLE 98

(2S,3S,4S,5S)-2-(N-(N-((N-Methyl-N-((2-pyridinyl)methyl)amino)carbonyl)valinyl)amino)-5-(N-(N-((N-methyl-N-((2-thiazolyl)methyl)amino)carbonyl)valinyl)amino)-3,4-dihydroxy-1,6-diphenylhexane Using the procedure of Example 38 but replacing the resultant compound of Example 3F with the resultant compound of Example 41D and replacing (2S,3S,5S)-5-amino-2-(N-((3-pyridinyl)methoxy-carbonyl)amino)-1,6-diphenyl-3-hydroxyhexane with the resultant compound of Example 89A provided, after silica gel chromatography using first 2% then 5% methanol in chloroform, 68 mg (78%) of the desired compound ($R_f$ 0.34, 10% methanol in chloroform) as a white solid, m.p. 96°–97° C. Mass spectrum: $(M+1)^+$=801.

Anal. Calcd for $C_{42}H_{56}N_8O_6S \cdot 0.5H_2O$: C, 62.28; H, 7.09; N, 13.83. Found: C, 62.35; H, 6.98; N, 13.67.

EXAMPLE 99

A. (2S,3S,4S,5S)-2-Amino-5-(N-(N-((N-methyl-N-((4-thiazolyl)methyl)amino)carbonyl)valinyl)amino)-3,4-dihydroxy-1,6-diphenylhexane Using the procedure of Example 47A but replacing the resultant compound of Example 13D with the resultant compound of Example 11C and replacing the resultant compound of Example 3F with the resultant compound of Example 43B provided, after silica gel chromatography using first 2% then 10% methanol in chloroform, 113 mg (32%) of the desired compound ($R_f$ 0.21, 10% methanol-in chloroform). Mass spectrum: $(M+1)^+$=669.

B. (2S,3S,4S,5S)-2-(N-(N-((N-Methyl-N-((2-((((t-butyl)oxy)carbonyl)amino)-4-thiazolyl)methyl)amino)carbonyl)valinyl)amino)-5-(N-(N-((N-methyl-N-((4-thiazolyl)methyl)amino)carbonyl)valinyl)amino)-3,4-dihydroxy-1,6-diphenylhexane Using the procedure of Example 45E but replacing (2S,3S,5S)-2-amino-5-(N-((3-pyridinyl)methoxy-carbonyl)amino)-1,6-diphenyl-3-hydroxyhexane with the resultant compound of Example 99A provided the crude desired compound ($R_f$ 0.71, 10% methanol in chloroform).

C. (2S,3S,4S,5S)-2-(N-(N-((N-Methyl-N-((2-amino-4-thiazolyl)methyl)amino)carbonyl)valinyl)amino)-5-(N-(N-methyl-N-((4-thiazolyl)methyl)amino)carbonyl)valinyl)-amino)-3,4-dihydroxy-1,6-diphenylhexane Using the procedure of Example 58B but replacing the resultant compound of Example 58A with the resultant compound of Example 99B provided, after silica gel chromatography using sequentially 2%, 4% and 6% methanol in chloroform, 61 mg (58%) of the desired compound ($R_f$ 0.24, 10% methanol in chloroform) as a white solid, m.p. 118°–120° C. Mass spectrum: $(M+1)^+$=822.

Anal. Calcd for $C_{40}H_{55}N_9O_6S_2 \cdot 0.5CHCl_3$: C, 55.20; H, 6.29; N, 14.30. Found: C, 55.46; H, 5.91; N, 14.21.

EXAMPLE 100

(2S,3R,4R,5S)-2,5-Bis-(N-(N-((N-methyl-N-((2-benzimidazolyl)methyl)amino)carbonyl)valinyl)amino)-3,4-dihydroxy-1,6-diphenylhexane Using the procedure of Example 85 but replacing the resultant compound of Example 43B with the resultant compound of Example 69D provided, after silica gel chromatography using 10% methanol in chloroform, 78 mg (40%) of the desired compound ($R_f$ 0.18, 10% methanol in chloroform). Mass spectrum: $(M+1)^+$=873.

EXAMPLE 101

(2S,3S,4S,5S)-2,5-Bis-(N-(N-((N-methyl-N-((2-benzimidazolyl)methyl)amino)carbonyl)valinyl)amino)-3,4-dihydroxy-1,6-diphenylhexane Using the procedure of Example 85 but replacing the resultant compound of Example 43B with the resultant compound of Example 69D and replacing the resultant compound of Example 4A with the resultant compound of Example 11C provided, after silica gel chromatography using 10% methanol in chloroform, 100 mg (50%) of the desired compound ($R_f$ 0.15, 10% methanol in chloroform) as a white solid, m.p. 107°–109° C. Mass spectrum: $(M+1)^+$= 873.

EXAMPLE 102

(2S,3R,4S,5S)-2,5-Bis-(N-(N-((N-methyl-N-((2-benzimidazolyl)methyl)amino)carbonyl)valinyl)amino)-3,4-dihydroxy-1,6-diphenylhexane Using the procedure of Example 85 but replacing the resultant compound of Example 43B with the resultant compound of Example 69D and replacing the resultant compound of Example 4A with the resultant compound of Example 13D provided, after silica gel chromatography using 10% methanol in chloroform, 100 mg (50%) of the desired compound ($R_f$ 0.22, 10% methanol in chloroform) as a white solid, m.p. 145°–146° C. Mass spectrum: $(M+1)^+$= 873.

EXAMPLE 103

(2S,3S,5S)-2,5-Bis-(N-(N-((N-methyl-N-((2-benzimidazolyl)methyl)amino)carbonyl)valinyl)amino)-1,6-diphenyl-3-hydroxyhexane Using the procedure of Example 85 but replacing the resultant compound of Example 43B with the resultant compound of Example 69D and replacing the resultant compound of Example 4A with the resultant compound of Example 1E provided, after silica gel chromatography using 6% methanol in chloroform, 130 mg (61%) of the desired compound ($R_f$ 0.28, 10% methanol in chloroform) as a white solid, m.p. 150°–152° C. Mass spectrum: $(M+1)^+$=857.

EXAMPLE 104

(2S,3R,4S,5S)-2,5-Bis-(N-(N-((4-methyl-piperazin-1-yl)carbonyl)valinyl)amino)-3,4-dihydroxy-1,6-diphenylhexane Using the procedure of Example 92 but replacing the resultant compound of Example 11C with the resultant compound of Example 13D and replacing the resultant compound of Example 45D with the resultant compound of Example 81B provided, after silica gel chromatography using 10% methanol in chloroform followed by 2% isopropylamino/2% methanol in chloroform, 74 mg (42%) of the desired compound ($R_f$ 0.25, 2% isopropylamino/5% methanol in chloroform). Mass spectrum: $(M+1)^+$=751.

EXAMPLE 105

(2S,3S,4S,5S)-2-(N-(N-((N-Methyl-N-((4-thiazolyl)methyl)amino)carbonyl)valinyl)amino)-5-(N-(N-((4-methylpiperazin-1-yl)carbonyl)valinyl)amino)-3,4-dihydroxy-1,6-diphenylhexane Using the procedure of Example 81C but replacing the resultant compound of Example 62A with the resultant compound of Example 99A provided, after silica gel chromatography using sequentially 2%, 4% and 6% methanol in chloroform, 68 mg (69%) of the desired compound ($R_f$ 0.24, 10% methanol in chloroform). Mass spectrum: $(M+1)^+$=779.

EXAMPLE 106

(2S,3R,4S,5S)-2-(N-(N-((N-Methyl-N-((2-pyridinyl)methyl)amino)carbonyl)valinyl)amino)-5-(N-(N-((N-methyl-N-((2-thiazolyl)methyl)amino)carbonyl)valinyl)amino)-3,4-dihydroxy-1,6-diphenylhexane Using the procedure of Example 38 but replacing the resultant compound of Example 3F with the resultant compound of Example 41D and replacing (2S,3S,5S)-5-amino-2-(N-((3-pyridinyl)methoxy-carbonyl)amino)-1,6-diphenyl-3-hydroxyhexane with the resultant compound of Example 47A provided, after silica gel chromatography using sequentially 2%, 3.5% and 4% methanol in chloroform, 87 mg (85%) of the desired compound ($R_f$ 0.33, 10% methanol in chloroform) as a white solid, m.p. 174°–176° C. Mass spectrum: $(M+1)^+$=801.

Anal. Calcd for $C_{42}H_{56}N_8O_6S$: C, 62.98; H, 7.05; N, 13.99. Found: C, 62.59; H, 6.99; N, 13.83.

EXAMPLE 107

A. (2S,3S,4S,5S)-2-(N-(N-((N-Methyl-N-((2-((((t-butyl)oxy)carbonyl)amino)-4-thiazolyl)methyl)amino)carbonyl)valinyl)amino)-5-(N-(N-((N-methyl-N-(pyridinyl)methyl)amino)carbonyl)valinyl)amino)-3,4-dihydroxy-1,6-diphenylhexane Using the procedure of Example 45E but replacing (2S,3S,5S)-2-amino-5-(N-((3-pyridinyl)methoxy-carbonyl)amino)-1,6-diphenyl-3-hydroxyhexane with the resultant compound of Example 89A provided the desired compound ($R_f$ 0.65, 10% methanol in chloroform).

B. (2S,3S,4S,5S)-2-(N-(N-((N-Methyl-N-((2-amino-4-thiazolyl)methyl)amino)carbonyl)valinyl)amino)-5-(N-(N-methyl-N-((2-pyridinyl)methyl)amino)carbonyl)-valinyl)amino)-3,4-dihydroxy-1,6-diphenylhexane Using the procedure of Example 58B but replacing the resultant compound of Example 58A with the resultant compound of Example 107A provided, after silica gel chromatography using sequentially 3%, 5% and 7% methanol in chloroform, 53 mg (35%) of the desired compound ($R_f$ 0.21, 10% methanol in chloroform) as a white solid, m.p. 97°–99° C.

Anal. Calcd for $C_{42}H_{57}N_9O_6S.H_2O$: C, 60.48; H, 7.13; N, 15.11. Found: C, 60.25; H, 6.85; N, 14.84.

EXAMPLE 108

A. (2S,3S,4S,5S)-2-Amino-5-(N-(N-((N-methyl-N-((2-thiazolyl)methyl)amino)carbonyl)valinyl)amino)-3,4-dihydroxy-1,6-diphenylhexane Using the procedure of Example 47A but replacing the resultant compound of Example 13D with the resultant compound of Example 1!C and replacing the resultant compound of Example 3F with the resultant compound of Example 41D provided, after silica gel chromatography using first 5% then 10% methanol in chloroform, 248 mg (54%) of the desired compound ($R_f$ 0.20, 10% methanol in chloroform).

B. (2S,3S,4S,5S)-2-(N-(N-((N-Methyl-N-((2-((((t-butyl)oxy)carbonyl)amino)-4-thiazolyl)methyl)amino)carbonyl)valinyl)amino)-5-(N-(N-((N-methyl-N-((2-thiazolyl)methyl)-amino)carbonyl)valinyl)amino)-3,4-dihydroxy-1,6-diphenylhexane Using the procedure of Example 45E but replacing (2S,3S,5S)-2-amino-5-(N-((3-pyridinyl)methoxy-carbonyl)amino)-1,6-diphenyl-3-hydroxyhexane with the resultant compound of Example 108A provided the desired compound ($R_f$ 0.60, 10% methanol in chloroform).

C. (2S,3S,4S,5S)-2-(N-(N-((N-Methyl-N-((2-amino-4-thiazolyl)methyl)amino)carbonyl)valinyl)amino)-5-(N-(N-((N-methyl-N-((2-thiazolyl)methyl)amino)carbonyl)valinyl)-amino)-3,4-dihydroxy-1,6-diphenylhexane Using the procedure of Example 58B but replacing the resultant compound of Example 58A with the resultant compound of Example 108B provided, after silica gel chromatography using sequentially 3%, 5% and 7% methanol in chloroform, 69 mg (60%) of the desired compound ($R_f$ 0.18, 10% methanol in chloroform) as a white solid, m.p. 108°–111° C. Mass spectrum: $(M+1)^+=822$.

Anal. Calcd for $C_{40}H_{55}N_9O_6S_2 \cdot 1.5H_2O$: C, 56.58; H, 6.88; N, 14.85. Found: C, 56.66; H, 6.51; N, 14.62.

EXAMPLE 109

A. (2S,3R,4S,5S)-2-Amino-5-(N-(N-((N-methyl-N-((2-pyridinyl)methyl)amino)carbonyl)valinyl)amino)-3,4-dihydroxy-1,6-diphenylhexane Using the procedure of Example 58B but replacing the resultant compound of Example 58A with the resultant compound of Example 62B provided, after silica gel chromatography using first 5% then 10% methanol in chloroform, a 67% yield of the desired compound ($R_f$ 0.23, 10% methanol in chloroform).

B. (2S,3R,4S,5S)-2-(N-(N-(N-Methyl-N-((2-thiazolyl)methyl)amino)carbonyl)valinyl)amino)-5-(N-(N-((N-methyl-N-((2-pyridinyl)methyl)amino)carbonyl)valinyl)amino)-3,4-dihydroxy-1,6-diphenylhexane Using the procedure of Example 38 but replacing the resultant compound of Example 3F with the resultant compound of Example 41D and replacing (2S,3S,5S)-5-amino-2-(N-((3-pyridinyl)methoxy-carbonyl)amino)-1,6-diphenyl-3-hydroxyhexane with the resultant compound of Example 109A provided, after silica gel chromatography using sequentially 2%, 3.5% and 4% methanol in chloroform, 91 mg (79%) of the desired compound ($R_f$ 0.32, 10% methanol in chloroform) as a white solid, m.p. 173°–175° C. Mass spectrum: $(M+1)^+=801$.

Anal. Calcd for $C_{42}H_{56}N_8O_6S \cdot 0.5H_2O$: C, 62.28; H, 7.09; N, 13.83. Found: C, 62.23; H, 7.00; N, 13.45.

EXAMPLE 110

A. (2S,3R,4S,5S)-5-(N-(N-((N-Methyl-N-((2-((((t-butyl)oxy)carbonyl)amino)-4-thiazolyl)methyl)amino)carbonyl)valinyl)amino)-2-(N-(N-((N-methyl-N-((2-pyridinyl)methyl)amino)carbonyl)valinyl)amino)-3,4-dihydroxy-1,6-diphenylhexane Using the procedure of Example 45E but replacing (2S,3S,5S)-2-amino-5-(N-((3-pyridinyl)methoxy-carbonyl)amino)-1,6-diphenyl-3-hydroxyhexane with the resultant compound of Example 47A provided the desired compound ($R_f$ 0.63, 10% methanol in chloroform).

B. (2S,3R,4S,5S)-5-(N-(N-((N-Methyl-N-((2-amino-4-thiazolyl)methyl)amino)carbonyl)valinyl)amino)-2-(N-(N-((N-methyl-N-((2-pyridinyl)methyl)amino)carbonyl)-valinyl)amino)-3,4-dihydroxy-1,6-diphenylhexane Using the procedure of Example 58B but replacing the resultant compound of Example 58A with the resultant compound of Example 110A provided, after silica gel chromatography using sequentially 2%, 5% and 7% methanol in chloroform, 68 mg (57%) of the desired compound ($R_f$ 0.28, 10% methanol in chloroform).

EXAMPLE 111

A. N-((4-Morpholinyl)carbonyl)valine Methyl Ester

Using the procedure of Example 41B but replacing the resultant compound of Example 41A with morpholine provided a 91% yield of the desired compound. Mass spectrum: $(M+1)^+=245$.

B. N-((4-Morpholinyl)carbonyl)valine

Using the procedure of Example 41C but replacing the resultant compound of Example 41B with the resultant compound of Example 111A provided the desired compound in 98% yield.

C. N-((4-Morpholinyl)carbonyl)valine p-Nitrophenyl Ester

Using the procedure of Example 41D but replacing the resultant compound of Example 41C with the resultant compound of Example 111B provided the desired compound.

D. (2S,3S,4S,5S)-5-(N-(N-((4-Morpholinyl)carbonyl)valinyl)amino)-2-(N-(N-((2-pyridinyl)methoxycarbonyl)valinyl)amino)-3,4-dihydroxy-1,6-diphenylhexane Using the procedure of Example 45E but replacing the resultant compound of Example 45D with the resultant compound of Example 111B and replacing (2S,3S,5S)-2-amino-5-(N-((3-pyridinyl)methoxy-carbonyl)-amino)-1,6-diphenyl-3-hydroxyhexane with the resultant compound of Example 82A provided, after silica gel chromatography using sequentially 2% and 4% methanol in chloroform, 75 mg (68%) of the desired compound ($R_f$ 0.29, 10% methanol in chloroform). Mass spectrum: $(M+1)^+=747$.

Anal. Calcd for $C_{40}H_{54}N_6O_9 \cdot 1.5H_2O$: C, 62.08; H, 7.42; N, 10.86. Found: C, 62.20; H, 7.16; N, 11.11.

EXAMPLE 112

A. (2S,3S,4S,5S)-5-(N-(N-((N-Methyl-N-((2-((((t-butyl)oxy)carbonyl)amino)-4-thiazolyl)methyl)amino)carbonyl)valinyl)amino)-2-(N-(N-((2-pyridinyl)methoxy-carbonyl)valinyl)amino)-3,4-dihydroxy-1,6-diphenylhexane Using the procedure of Example 45E but replacing (2S,3S,5S)-2-amino-5-(N-((3-pyridinyl)methoxy-carbonyl)amino)-1,6-diphenyl-3-hydroxyhexane with the resultant compound of Example 82A provided the desired compound ($R_f$ 0.66, 10% methanol in chloroform).

B. (2S,3S,4S,5S)-5-(N-((N-Methyl-N-((2-amino-4-thiazolyl)methyl)amino)carbonyl)valinyl)amino)-2-(N-(N-((2-pyridinyl)methoxy-carbonyl)valinyl)amino)-3,4-dihydroxy-1,6-diphenylhexane Using the procedure of Example 58B but replacing the resultant compound of Example 58A with the resultant compound of Example 112A provided, after silica gel chromatography using sequentially 2%, 5% and 7% methanol in chloroform, 60 mg (50%) of the desired compound ($R_f$ 0.24, 10% methanol in chloroform) as a white solid, m.p. 188°–192° C. Mass spectrum: $(M+1)^+=803$.

Anal. Calcd for $C_{41}H_{54}N_8O_7S \cdot H_2O$: C, 59.98; H, 6.87; N, 13.65. Found: C, 60.27; H, 6.58; N, 13.48.

EXAMPLE 113

(2S,3S,5S)-2,5-Bis-(N-(N-((4-morpholinyl)carbonyl)valinyl)amino)-1,6-diphenyl-3-hydroxyhexane Using the procedure of Example 85 but replacing the resultant compound of Example 4A with the resultant compound of Example 1E and replacing the resultant compound of Example 43B with the resultant compound of Example 111C provided, after silica gel chromatography using 5% methanol in chloroform, 62 mg (58%) of the desired compound ($R_f$ 0.28, 10% methanol in chloroform) as a white solid, m.p. 198°–201° C. Mass spectrum: $(M+1)^+=709$.

EXAMPLE 114

A. (2S,3S,5S)-5-Amino-2-(N-(N-((N-methyl-N-((2-pyridinyl)methyl)amino)carbonyl)valinyl)amino)-1,6-diphenyl-3-hydroxyhexane Using the procedure of Example 58B but replacing the resultant compound of Example 58A with the resultant compound of Example 63B provided the desired compound ($R_f$ 0.28, 2% isopropylamino/2% methanol in chloroform).

B. (2S,3S,5S)-5-(N-(N-((N-Methyl-N-((2-thiazolyl)methyl)amino)carbonyl)valinyl)-2-(N-(N-((N-methyl-N-((2-pyridinyl)methyl)amino)carbonyl)valinyl)amino)-1,6-diphenyl-3-hydroxyhexane Using the procedure of Example 38 but replacing the resultant compound of Example 3F with the resultant compound of Example 41D and replacing (2S,3S,5S)-5-amino-2-(N-((3-pyridinyl)methoxy-carbonyl)amino)-1,6-diphenyl-3-hydroxyhexane with the resultant compound of Example 114A provided, after silica gel chromatography using first 2% then 4% methanol in chloroform, 75 mg (73%) of the desired compound ($R_f$ 0.34, 10% methanol in chloroform) as a white solid, m.p. 158°–160° C. Mass spectrum: $(M+1)^+=785$.

Anal. Calcd for $C_{42}H_{56}N_8O_5S$: C, 64.26; H, 7.19; N, 14.27. Found: C, 63.89; H, 7.14; N, 14.08.

EXAMPLE 115

A. (2S,3S,5S)-2-Amino-5-(N-(N-((N-methyl-N-((2-pyridinyl)methyl)amino)carbonyl)valinyl)amino)-1,6-diphenyl-3-hydroxyhexane Using the procedure of Example 58B but replacing the resultant compound of Example 58A with the resultant compound of Example 64 provided the desired compound ($R_f$ 0.20, 2% isopropylamino/2% methanol in chloroform).

B. (2S,3S,5S)-2-(N-(N-((N-Methyl-N-((2-thiazolyl)methyl)amino)carbonyl)valinyl)-5-(N-(N-((N-methyl-N-((2-pyridinyl)methyl)amino)carbonyl)valinyl)amino)-1,6-diphenyl-3-hydroxyhexane Using the procedure of Example 38 but replacing the resultant compound of Example 3F with the resultant compound of Example 41D and replacing (2S,3S,5S)-5-amino-2-(N-((3-pyridinyl)methoxy-carbonyl)amino)-1,6-diphenyl-3-hydroxyhexane with the resultant compound of Example 115A provided, after silica gel chromatography using first 2% then 4% methanol in chloroform, 81 mg (78%) of the desired compound ($R_f$ 0.33, 10% methanol in chloroform) as a white solid, m.p. 156°–158° C. Mass spectrum: $(M+1)^+=785$.

Anal. Calcd for $C_{42}H_{56}N_8O_5S$: C, 64.26; H, 7.19; 14.27. Found: C, 63.96; H, 6.99; N, 13.89.

EXAMPLE 116

A. Methyl 3-(1-Benzimidazolyl)propionate

A solution of 10.0 g (84 mmol) of benzimidazole, 22.7 ml (250 mmol) of methyl acrylate and 3 drops of DBU in 50 ml of tetrahydrofuran was heated at reflux for 2 days. The resulting solution was concentrated in vacuo, and the residue was purified by silica gel chromatography using 3% methanol in chloroform to provide 15.7 g (92%) of the desired compound ($R_f$ 0.58, 10% methanol in chloroform).

B. 3-(1-Benzimidazolyl)propionic Acid

Using the procedure of Example 41C but replacing the resultant compound of Example 41B with the resultant compound of Example 116A provided the desired compound.

C. (2S,3R,4R,5S)-2,5-Bis-(N-(N-(3-(1-benzimidazolyl)propanoyl)valinyl)amino)-3,4-dihydroxy-1,6-diphenylhexane Using the procedure of Example 92 but replacing the resultant compound of Example 45D with the resultant compound of Example 116B and replacing the resultant compound of Example 11C with the resultant compound of Example 4C provided, after silica gel chromatography using 10% methanol in chloroform, 216 mg (48%) of the desired compound ($R_f$ 0.20, 10% methanol in chloroform). Mass spectrum: $(M+1)^+=843$.

EXAMPLE 117

A. (2S,3R,4R,5S)-5-Amino-2-(N-(((t-butyl)oxy)carbonyl)amino)-3,4-dihydroxy-1,6-diphenylhexane Using the procedure of Example 62A but replacing the resultant compound of Example 13D with the resultant compound of Example 4A provided the desired compound ($R_f$ 0.58, 10% methanol in chloroform). Mass spectrum: $(M+1)^+=401$.

B. (2S,3R,4R,5S)-5-(N-(N-((N-Methyl-N-((2-pyridinyl)methyl)amino)carbonyl)valinyl)amino)-2-(N-(((t-butyl)oxy)carbonyl)amino)-3,4-dihydroxy-1,6-diphenylhexane Using the procedure of Example 48B but replacing the resultant compound of Example 48A with the resultant compound of Example 117A provided, after silica gel chro-

81 matography using first 1.5% then 2% methanol in chloroform, 101 mg (83%) of the desired compound ($R_f$ 0.50, 10% methanol in chloroform) as a white solid. Mass spectrum: $(M+1)^+=648$.

EXAMPLE 118

(2S,3S,4S,5S)-2,5-Bis-(N-(N-((N-methyl-N-((3-pyridinyl)methyl)amino)carbonyl)valinyl)amino)-3,4-dihydroxy-1,6-diphenylhexane Using the procedure of Example 85 but replacing the resultant compound of Example 4A with the resultant compound of Example 11C and replacing the resultant compound of Example 43B with the resultant compound of Example 24F provided, after silica gel chromatography using 2%, then 5%, then 10% methanol in chloroform, 460 mg (58%) of the desired compound ($R_f$ 0.17, 10% methanol in chloroform) as a white solid, m.p. 174°–175° C. Mass spectrum: $(M+1)^+=795$.

Anal. Calcd for $C_{44}H_{58}N_8O_6 \cdot H_2O$: C, 65.00; H, 7.44; N, 13.78. Found: C, 65.09; H, 7.29; N, 13.61.

EXAMPLE 119

(2S,3R,4R,5S)-2,5-Bis-(N-(N-((N-methyl-N-((3-pyridinyl)methyl)amino)carbonyl)valinyl)amino)-3,4-dihydroxy-1,6-diphenylhexane Using the procedure of Example 85 but replacing the resultant compound of Example 43B with the resultant compound of Example 24F provided, after silica gel chromatography using first 5%, then 7.5%, then 10% methanol in chloroform, 249 mg (96%) of the desired compound ($R_f$ 0.31, 10% methanol in chloroform) as a white solid, m.p. 95°–97° C. Mass spectrum: $(M+1)^+=795$.

Anal. Calcd for $C_{44}H_{58}N_8O_6 \cdot 1.5H_2O$: C, 64.29; H, 7.48; N, 13.63. Found: C, 64.30; H, 7.20; N, 13.56.

EXAMPLE 120

(2S,3S,4S,5S)-2,5-Bis-(N-(N-((N-methyl-N-((2-pyridinyl)methyl)amino)carbonyl)isoleucinyl)amino)-3,4-dihydroxy-1,6-diphenylhexane Using the procedure of Example 85 but replacing the resultant compound of Example 4A with the resultant compound of Example 11C and replacing the resultant compound of Example 43B with the resultant compound of Example 16C provided, after silica gel chromatography using first 2%, then 3%, then 5% methanol in chloroform, 160 mg (59%) of the desired compound ($R_f$ 0.38, 7.5% methanol in chloroform). Mass spectrum: $(M+1)^+823$.

Anal. Calcd for $C_{46}H_{62}N_8O_6 \cdot H_2O$: C, 65.69; H, 7.67; N, 13.32. Found: C, 65.61; H, 7.49; N, 13.06.

EXAMPLE 121

(2S,3R,4S,5S)-2,5-Bis-(N-(N-((N-methyl-N-((2-pyridinyl)methyl)amino)carbonyl)isoleucinyl)amino)-3,4-dihydroxy-1,6-diphenylhexane Using the procedure of Example 85 but replacing the resultant compound of Example 4A with the resultant compound of Example 13D and replacing the resultant compound of Example 43B with the resultant compound of Example 16C provided, after silica gel chromatography using first 1% then 3% methanol in chloroform, 565 mg

82

(67%) of the desired compound ($R_f$ 0.37, 7.5% methanol in chloroform). Mass spectrum: $(M+1)^+=823$.

Anal. Calcd for $C_{46}H_{62}N_8O_6 \cdot 0.25H_2O$: C, 66.76; H, 7.61; N, 13.54. Found: C, 66.56; H, 7.53; N, 13.45.

EXAMPLE 122

A. N-((N-Methyl-N-((2-pyridinyl)ethyl)amino)carbonyl)valine p-Nitrophenyl Ester

Using sequentially the procedures of Examples 41B, 41C, and 41D, but replacing the resultant compound of Example 41A with 2-((methylamino)ethyl)pyridine provided the desired compound.

B. (2S,3S,4S,5S)-2,5-Bis-(N-(N-((N-methyl-N-((2-pyridinyl)ethyl)amino)carbonyl)valinyl)amino)-3,4-dihydroxy-1,6-diphenylhexane Using the procedure of Example 85 but replacing the resultant compound of Example 4A with the resultant compound of Example 11C and replacing the resultant compound of Example 43B with the resultant compound of Example 122A provided, after silica gel chromatography using first 2% then 5% methanol in chloroform, 170 mg (62%) of the desired compound ($R_f$ 0.21, 7.5% methanol in chloroform) as a white solid, m.p. 109°–111° C. Mass spectrum: $(M+1)^+=823$.

Anal. Calcd for $C_{46}H_{62}N_8O_6 \cdot 0.5H_2O$: C, 66.40; H, 7.63; N, 13.47. Found: C, 66.17; H, 7.51; N, 13.41.

EXAMPLE 123

(2S,3R,4R,5S)-2,5-Bis-(N-(N-((N-methyl-N-((2-pyridinyl)ethyl)amino)carbonyl)valinyl)amino)-3,4-dihydroxy-1,6-diphenylhexane Using the procedure of Example 85 but replacing the resultant compound of Example 43B with the resultant compound of Example 122A provided, after silica gel chromatography using first 7.5% then 10% methanol in chloroform, 220 mg (78%) of the desired compound ($R_f$ 0.06, 7.5% methanol in chloroform). Mass spectrum: $(M+1)^+=823$.

Anal. Calcd for $C_{46}H_{62}N_8O_6 \cdot H_2O$: C, 65.69; H, 7.67; N, 13.32. Found: C, 65.64; H, 7.46; N, 13.26.

EXAMPLE 124

(2S,3R,4S,5S)-2,5-Bis-(N-(N-((N-methyl-N-((2-pyridinyl)ethyl)amino)carbonyl)valinyl)amino)-3,4-dihydroxy-1,6-diphenylhexane Using the procedure of Example 85 but replacing the resultant compound of Example 4A with the resultant compound of Example 13D and replacing the resultant compound of Example 4 3B with the resultant compound of Example 122A provided, after silica gel chromatography using first 5%, then 7.5%, then 10% methanol in chloroform, 186 mg (65%) of the desired compound ($R_f$ 0.23, 10% methanol in chloroform). Mass spectrum: $(M+1)^+=823$.

EXAMPLE 125

(2S,3R,4S,5S)-2,5-Bis-(N-(N-((N-methyl-N-((3-pyridinyl)methyl)amino)carbonyl)valinyl)amino)-3,4-dihydroxy-1,6-diphenylhexane Using the procedure of Example 85 but replacing the resultant compound of Example 4A with the resultant compound of Example 13D and replacing the resultant compound of Example 43B with the resultant compound of Example 24F provided, after silica gel chromatography using sequentially 2%, 7% and 10% methanol in chloroform, 189 mg (72%) of the desired compound ($R_f$ 0.20, 10% methanol in chloroform) as a off-white solid, m.p. 174°–176° C. Mass spectrum: $(M+1)^+=795$.

Anal. Calcd for $C_{44}H_{58}N_8O_6 \cdot H_2O$: C, 65.00; H, 7.44; N, 13.78. Found: C, 65.18; H, 7.19; N, 13.68.

EXAMPLE 126

(2S,3S,5S)-2,5-Bis-(N-(N-((N-methyl-N-((3-pyridinyl)methyl)amino)carbonyl)valinyl)amino)-1,6-diphenyl-3-hydroxyhexane Using the procedure of Example 85 but replacing the resultant compound of Example 4A with the resultant compound of Example 1E and replacing the resultant compound of Example 43B with the resultant compound of Example 24F provided, after silica gel chromatography using first 2%, then 7%, then 10% methanol in chloroform, 132 mg (81%) of the desired compound ($R_f$ 0.18, 10% methanol in chloroform) as a off-white solid, m.p. 193°–196° C. Mass spectrum: $(M+1)^+=779$.

Anal. Calcd for $C_{44}H_{58}N_8O_5 \cdot H_2O$: C, 66.31; H, 7.59; N, 14.06. Found: C, 66.22; H, 7.51; N, 13.59.

EXAMPLE 127

(2S,3R,4R,5S)-2,5-Bis-(N-(N-(3-(thiazol-2-yl)propanoyl)valinyl)amino)-3,4-dihydroxy-1,6-diphenylhexane Using the procedure of Example 92 but replacing the resultant compound of Example 45D with the resultant compound of Example 34A and replacing the resultant compound of Example 11C with the resultant compound of Example 4C provided the desired compound.

EXAMPLE 128

(2S,4S)-2,4-Bis-(N-(N-(3-(thiazol-2-yl)propanoyl)valinyl)amino)-1,5-diphenyl-3-hydroxypentane Using the procedure of Example 92 but replacing the resultant compound of Example 45D with the resultant compound of Example 34A and replacing the resultant compound of Example 11C with the resultant compound of Example 6H provided the desired compound.

EXAMPLE 129

(2S,3R,4R,5S)-2,5-Bis-(N-(N-((N-methyl-N-((2-thiazolyl)methyl)amino)carbonyl)valinyl)amino)-3,4-dihydroxy-1,6-diphenylhexane Using the procedure of Example 85 but replacing the resultant compound of Example 43B with the resultant compound of Example 41D provided, after silica gel chromatography using sequentially 1.5%, 2% and 5% methanol in chloroform, mg (87%) of the desired compound ($R_f$ 0.27, 10% methanol in chloroform) as a white solid, m.p. 146°–148° C. Mass spectrum: $(M+1)^+=807$.

Anal. Calcd for $C_{40}H_{54}N_8O_6S_2 \cdot 0.5H_2O$: C, 58.87; H, 6.79; N, 13.73. Found: C, 58.57; H, 6.60; N, 13.47.

EXAMPLE 130

(2S,3S,4S,5S)-2,5-Bis-(N-(N-((N-methyl-N-((2-thiazolyl)methyl)amino)carbonyl)valinyl)amino)-3,4-dihydroxy-1,6-diphenylhexane Using the procedure of Example 85 but replacing the resultant compound of Example 4A with the resultant compound of Example 11C and replacing the resultant compound of Example 43B with the resultant compound of Example 41D provided, after silica gel chromatography using sequentially 1.5%, 2% and 5% methanol in chloroform, 138 mg (85.7%) of the desired compound ($R_f$ 0.29, 10% methanol in chloroform) as a white solid, m.p. 176°–178° C. Mass spectrum: $(M+1)^+=807$.

Anal. Calcd for $C_{40}H_{54}N_8O_6S_2 \cdot 0.5H_2O$: C, 58.87; H, 6.79; N, 13.73. Found: C, 58.77; H, 6.59; N, 13.61.

EXAMPLE 131

(2S,3R,4S,5S)-2,5-Bis-(N-(N-((N-methyl-N-((2-thiazolyl)methyl)amino)carbonyl)valinyl)amino)-3,4-dihydroxy-1,6-diphenylhexane Using the procedure of Example 85 but replacing the resultant compound of Example 4A with the resultant compound of Example 13D and replacing the resultant compound of Example 43B with the resultant compound of Example 41D provided, after silica gel chromatography using sequentially 1.5%, 2% and 5% methanol in chloroform, 121.7 mg (75.4%) of the desired compound ($R_f$ 0.27, 10% methanol in chloroform) as a white solid, m.p. 198°–200° C. Mass spectrum: $(M+1)^+=807$.

Anal. Calcd for $C_{40}H_{54}N_8O_6S_2$: C, 59.53; H, 6.74; N, 13.88. Found: C, 59.67; H, 6.66; N, 13.80.

EXAMPLE 132

(2S,3S,5S)-2,5-Bis-(N-(N-((N-methyl-N-((2-thiazolyl)methyl)amino)carbonyl)valinyl)amino)-1,6-diphenyl-3-hydroxyhexane Using the procedure of Example 85 but replacing the resultant compound of Example 4A with the resultant compound of Example 1E and replacing the resultant compound of Example 43B with the resultant compound of Example 41D provided, after silica gel chromatography using sequentially 1.5%, 2% and 5% methanol in chloroform, 102 mg (64.6%) of the desired compound ($R_f$ 0.30, 10% methanol in chloroform) as a white solid, m.p. 195°–197° C. Mass spectrum: $(M+1)^+=791$.

Anal. Calcd for $C_{40}H_{54}N_8O_5S_2 \cdot 0.25H_2O$: C, 60.39; H, 6.90; N, 14.09. Found: 60.27; H, 6.79; N, 13.94.

EXAMPLE 133

A. (2S,3R,4R,5S)-5-Amino-2-(N-((3-pyridinyl)methoxy-carbonyl)amino)-3,4-dihydroxy-1,6-diphenylhexane Using the procedure of Example 48A but replacing the resultant compound of Example 13D with the resultant compound of Example 4A provided, after silica gel chromatography using sequentially 2%, 3.5%, 10% and 12% methanol in chloroform, 238 mg (41%) of the desired compound ($R_f$ 0.10, 10% methanol in chloroform). Mass spectrum: $(M+1)^+=436$.

B. (2S,3R,4R,5S)-2-(N-(N-((2-Pyridinyl)methoxycarbonyl)valinyl)amino)-5-(N-((3-pyridinyl)methoxy-carbonyl)amino)-3,4-dihydroxy-1,6-diphenylhexane Using the procedure of Example 38 but replacing the resultant compound of Example 3F with the resultant compound of Example 2D and replacing (2S,3S,5S)-5-amino-2-(N-((3-pyridinyl)methoxy-carbonyl)amino)-1,6-diphenyl-3-hydroxyhexane with the resultant compound of Example 133A provided, after silica gel chromatography using first 2% then 3.5% methanol in chloroform, 62.1 mg (58%) of the desired compound ($R_f$ 0.32, 10% methanol in chloroform) as a white solid, m.p. 189°–190° C. Mass spectrum: $(M+1)^+=770$.

Anal. Calcd for $C_{37}H_{43}N_5O_7 \cdot 0.25H_2O$: C, 65.91; H, 6.50; N, 10.39. Found: C, 65.91; H, 6.28; N, 10.36.

EXAMPLE 134

(2S,3S,4S,5S)-5-(N-(N-((N-Methyl-N-((2-pyridinyl)methyl)amino)carbonyl)valinyl)amino)-2-(N-((3-pyridinyl)methoxy-carbonyl)amino)-3,4-dihydroxy-1,6-diphenylhexane Using the procedure of Example 47B but replacing the resultant compound of Example 47A with the resultant compound of Example 89A provided, after silica gel chromatography using first 2% then 3.5% methanol in chloroform, 74 mg (85%) of the desired compound ($R_f$ 0.42, 10% methanol in chloroform) as a white solid, m.p. 84°–85° C. Mass spectrum: $(M+1)^+=683$.

Anal. Calcd for $C_{38}H_{46}N_6O_6 \cdot 0.5H_2O$: C, 65.97; H, 6.85; N, 12.15. Found: C, 65.61; H, 6.73; N, 11.70.

EXAMPLE 135

A. (2S,3S,5S)-2-Amino-5-(N-((5-thiazolyl)methoxycarbonyl)amino)-1,6-diphenyl-3-hydroxyhexane and (2S,3S,5S)-5-Amino-2-(N-((5-thiazolyl)methoxycarbonyl)amino)-1,6-diphenyl-3-hydroxyhexane Using the procedure of Example 37B but replacing the resultant compound of Example 37A with the resultant compound of Example 80C provided, after silica gel chromatography using first 2% then 5% methanol in chloroform provided a mixture of the two desired compounds. Silica gel chromatography of the mixture using first 2% isopropylamino in chloroform followed by 2% isopropylamino/1% methanol in chloroform and finally 2% isopropylamino/2% methanol in chloroform provided 111 mg (16%) of (2S,3S,5S)-2-amino-5-(N-((5-thiazolyl)-methoxy-carbonyl)amino)-1,6-diphenyl-3-hydroxyhexane and 185 mg (28%) of (2S,3S,5S)-2-amino-5-(N-((5-thiazolyl)-methoxy-carbonyl)amino)-1,6-diphenyl-3-hydroxyhexane. Mass spectrum for each compound: $(M+1)^+=426$.

B. (2S,3S,5S)-2-(N-(N-((2-Pyridinyl)methoxy-carbonyl)valinyl)amino)-5-(N-((5-thiazolyl)methoxycarbonyl)amino)-1,6-diphenyl-3-hydroxyhexane Using the procedure of Example 37C but replacing (2S,3S,5S)-2-amino-5-(N-((3-pyridinyl)methoxy-carbonyl)amino)-1,6-diphenyl-3-hydroxyhexane with (2S,3S,5S)-2-amino-5-(N-((5-thiazolyl)methoxy-carbonyl)amino)-1,6-diphenyl-3-hydroxyhexane and replacing the resultant compound of Example 3F with the resultant compound of Example 2D provided, after silica gel chromatography using a gradient of 1%–3%–5% methanol in chloroform, 56 mg (72%) of the desired compound ($R_f$ 0.50, 10% methanol in chloroform) as a white solid, m.p. 176°–177° C. Mass spectrum: $(M+1)^+=660$.

Anal. Calcd for $C_{35}H_{41}N_5O_6S \cdot 1.5H_2O$: C, 61.21; H, 6.46; N, 10.20. Found: C, 61.08; H, 6.00; N, 10.39.

EXAMPLE 136

(2S,3S,5S)-5-(N-(N-((2-Pyridinyl)methoxy-carbonyl)valinyl)amino)-2-(N-((5-thiazolyl)methoxy-carbonyl)amino)-1,6-diphenyl-3-hydroxyhexane Using the procedure of Example 37C but replacing (2S,3S,5S)-2-amino-5-(N-((3-pyridinyl)methoxy-carbonyl)amino)-1,6-diphenyl-3-hydroxyhexane with (2S,3S,5S)-5-amino-2-(N-((5-thiazolyl)methoxy-carbonyl)amino)-1,6-diphenyl-3-hydroxyhexane and replacing the resultant compound of Example 3F with the resultant compound of Example 2D provided, after silica gel chromatography using a gradient of 1%–3%–5% methanol in chloroform, 48 mg (62%) of the desired compound ($R_f$ 0.47, 10% methanol in chloroform) as a white solid, m.p. 166°–168° C. Mass spectrum: $(M+1)^+=660$.

EXAMPLE 137

(2S,3S,5S)-2-(N-(N-((N-Methyl-N-((2-pyridinyl)methyl)amino)carbonyl)isoleucinyl)amino)-5-(N-((5-thiazolyl)methoxy-carbonyl)amino)-1,6-diphenyl-3-hydroxyhexane Using the procedure of Example 37C but replacing (2S,3S,5S)-2-amino-5-(N-((3-pyridinyl)methoxy-carbonyl)amino)-1,6-diphenyl-3-hydroxyhexane with (2S,3S,5S)-2-amino-5-(N-((5-thiazolyl)methoxy-carbonyl)amino)-1,6-diphenyl-3-hydroxyhexane and replacing the resultant compound of Example 3F with the resultant compound of Example 16C provided, after silica gel chromatography using first 2% then 5% methanol in chloroform, 51 mg (62%) of the desired compound ($R_f$ 0.43, 10% methanol in chloroform) as a white solid, m.p. 66°–69° C. Mass spectrum: $(M+1)^+=687$.

EXAMPLE 138

(2S,3S,5S)-5-(N-(N-((N-Methyl-N-((2-pyridinyl)methyl)amino)carbonyl)isoleucinyl)amino)-2-(N-((5-thiazolyl)methoxy-carbonyl)amino)-1,6-diphenyl-3-hydroxyhexane Using the procedure of Example 37C but replacing (2S,3S,5S)-2-amino-5-(N-((3-pyridinyl)methoxy-carbonyl)amino)-1,6-diphenyl-3-hydroxyhexane with (2S,3S,5S)-5-amino-2-(N-((5-thiazolyl)methoxy-carbonyl)amino)-1,6- diphenyl-3-hydroxyhexane and replacing the resultant compound of Example 3F with the resultant compound of Example 16C provided, after silica gel chromatography using a gradient of 2%–5% methanol in chloroform, 51 mg (62%) of the desired compound ($R_f$ 0.47, 10% methanol in chloroform) as a white solid, m.p. 64°–67° C. Mass spectrum: $(M+1)^+=687$.

EXAMPLE 139

(2S,3S,5S)-2-(N-(N-((N-Methyl-N-((2-amino-4-thiazolyl)methyl)amino)carbonyl)valinyl)amino)-5-(N-((5-thiazolyl)methoxy-carbonyl)amino)-1,6-diphenyl-3-hydroxyhexane Using the procedure of Example 47B but replacing the resultant compound of Example 47A with the resultant compound of Example 57B and replacing the resultant compound of Example 37A with the resultant compound of Example 80C provided, after silica gel chromatography using a gradient of 2%–3%–5% methanol in chloroform, 46 mg (55%) of the desired compound ($R_f$ 0.24, 10% methanol in chloroform). Mass spectrum: $(M+1)^+=694$.

EXAMPLE 140

(2S,4S)-2,4-Bis-(N-(N-(Boc-glycinyl)valinyl)amino)-1,5-diphenyl-3-hydroxypentane A solution of 100 mg (0.21 mmol) of the resultant compound of Example 6H and 79.0 mg (0.94 mmol) of sodium bicarbonate in 2 ml of tetrahydrofuran and 2 ml of water was treated with a solution of 116.2 mg (0.43 mmol) of N-t-Boc-glycine N-hydroxysuccinimide ester in 2 ml of tetrahydrofuran. After being stirred at ambient temperature for 2 h, the solution was diluted with dichloromethane, washed with water, dried over MgSO$_4$, and concentrated in vacuo. Silica gel chromatography of the residue using 10% methanol in dichloromethane provided 129.6 mg (78%) of the desired compound as a white solid. $^1$H NMR (DMSO-d6) δ 0.69–0.82 (m, 12H), 1.37 (s, 18H), 1.73 (m, 1H), 1.94 (m, 1H), 2.45–2.62 (m, 2H), 2.73 (br d, 2H), 2.97 (dd, 1H), 3.53 (m, 4H), 3.86 (m, 1H), 4.02 (m, 2H), 4.22 (m, 1H), 5.29 (br d, 1H), 7.02–7.32 (m, 13H), 7.46–7.59 (m, 3H). Mass spectrum: $(M+H)^+=783$.

EXAMPLE 141

(2S,4S)-2,4-Bis-(N-(N-(glycinyl)valinyl)amino)-1,5-diphenyl-3-hydroxypentane

Using the procedure of Example 6F but replacing the resultant compound of Example 6E with the resultant compound of Example 140 provided, after silica gel chromatography using 10% methanol in dichloromethane, 48.7 mg (91%) of the desired compound as a white solid. $^1$H NMR (DMSO-d6) δ 0.70–0.83 (four d, 12H), 1.78 (m, 1H), 1.96 (m, 1H), 2.62 (m, 2H), 2.74 (br d, 2H), 2.97 (m, 1H), 3.46–3.87 (m, 5H), 4.02 (m, 2H), 4.21 (m, 1H), 5.33 (br d, 1H), 7.08–7.26 (m, 10H), 7.57 (br d, 2H), 7.67 (br d, 1H), 7.86 (br d, 1H). Mass spectrum: $(M+H)^+=583$.

EXAMPLE 142

(2S,4S)-2,4-Bis-(N-(N-((4-pyridinylthio)acetyl)valinyl)amino)-1,5-diphenyl-3-hydroxypentane A. (2S,4S)-2,4-Bis-(N-(N-(bromoacetyl)valinyl)amino)-1,5-diphenyl-3-hydroxypentane A solution of 100 mg (0.21 mmol) of the resultant compound of Example 6H and 34.5 µl (0.43 mmol) of pyridine in 10 ml of dichloromethane was treated with 37.2 µl (0.43 mmol) of bromoacetyl bromide at 0° C. After being stirred at 0° C. for 1 h, the solution was diluted with dichloromethane, washed with water, dried over MgSO$_4$, and concentrated in vacuo. Silica gel chromatography of the residue using 10% methanol in dichloromethane provided 108.3 mg (71%) of the desired compound as a white solid. Mass spectrum: $(M+H)^+=709$.

B. (2S,4S)-2,4-Bis-(N-(N-((4-pyridinylthio)acetyl)valinyl)amino)-1,5-diphenyl-3-hydroxypentane A solution of 50.0 mg (0.070 mmol) of the resultant compound of Example 142A and 18.4 µl (0.14 mmol) of triethylamino in 2 ml of dimethylformamide was treated with 15.6 mg (0.14 mmol) of 4-mercaptopyridine. After being stirred at ambient temperature for 2 h, the solution was diluted with dichloromethane, washed with water, dried over MgSO$_4$, and concentrated in vacuo. Silica gel chromatography of the residue using 10% methanol in dichloromethane provided 57.2 mg (73%) of the desired compound as a pale yellow solid. $^1$H NMR (CDCl$_3$) δ 0.72 (t, 6H), 0.79 (t, 6H), 1.74 (m, 1H), 1.93 (m, 1H), 2.56 (m, 2H), 2.76 (br d, 2H), 2.93 (m, 1H), 3.70–3.95 (m, 5H), 4.03 (m, 2H), 4.23 (dd, 1H), 5.32 (d, 1H), 7.04–7.25 (m, 10H), 7.31 (m, 4H), 7.54 (br d, 1H), 7.62 (br d, 1H), 8.02 (br d, 1H), 8.18 (br d, 1H), 8.34 (m, 4H). Mass spectrum: $(M+H)^+=771$.

EXAMPLE 143

(2S,4S)-2,4-Bis-(N-(N-((2-pyridinylthio)acetyl)valinyl)amino)-1,5-diphenyl-3-hydroxypentane Using the procedure of Example 142B but replacing 4-mercaptopyridine with 2-mercaptopyridine provided 32.3 mg (85%) of the desired compound as a white solid. $^1$H NMR (DMSO-d6) δ 0.62 (d, 3H), 0.68 (two d, 6H), 0.76 (d, 3H), 1.73 (m, 1H), 1.92 (m, 1H), 2.58 (dd, 2H), 2.70 (br d, 2H), 2.96 (dd, 1H), 3.73–3.96 (m, 5H), 4.01 (m, 2H), 4.18 (dd, 1H), 5.29 (d, 1H), 7.04–7.23 (m, 12H), 7.36 (dd, 2H), 7.49 (br d, 1H), 7.56 (br d, 1H), 7.64 (td, 2H), 7.83 (br d, 1H), 8.00 (br d, 1H), 8.38 (tt, 2H). Mass spectrum: $(M+H)^+=771$.

EXAMPLE 144

(2S,4S)-2,4-Bis-(N-(N-(N-(acetyl)glycinyl)valinyl)amino)-1,5-diphenyl-3-hydroxypentane A solution of 200 mg (0.34 mmol) of the resultant compound of Example 141 and 98.4 µl (0.75 mmol) of triethylamino in 4 ml of dimethylformamide was treated with 68.0 µl (0.72 mmol) of acetic anhydride. After being stirred at ambient temperature for 2 h, the solution was diluted with water and extracted with four 10 ml portions of 10% methanol in dichloromethane. The combined organic layers were dried over MgSO$_4$, and concentrated in vacuo. Silica gel chromatography of the residue using 10% methanol in dichloromethane provided 164.1 mg (72%) of the desired compound as a white solid. $^1$H NMR (DMSO-d6) δ 0.69–0.81 (four d, 12H), 1.76 (m, 1H), 1.84 (two s, 6H), 1.92 (m, 1H), 2.60 (dd, 2H), 2.74 (br d, 2H), 2.97 (dd, 1H), 3.67 (d, 2H), 3.72 (d, 2H), 3.85 (m, 1H), 4.02 (m, 2H), 4.17 (dd, 1H), 5.24 (d, 1H), 7.07–7.26 (m, 10H), 7.46(br d, 1H), 7.53 (br d, 1H), 7.56 (br d, 1H), 7.72(br d, 1H), 8.07 (br t, 1H), 8.12 (br t, 1H). Mass spectrum: $(M+H)^+$=667.

EXAMPLE 145

(2S,4S)-2,4-Bis-(N-(N-(N-((2-pyridinyl)methoxy-carbonyl)glycinyl)valinyl)amino)-1,5-diphenyl-3-hydroxypentane

A. N-((2-pyridinyl)methoxy-carbonyl)glycine Methyl Ester

Using the procedure of Example 2B but replacing the resultant compound of Example 2A with isocyanato-glycine methyl ester provided the desired compound.

B. N-((2-pyridinyl)methoxy-carbonyl)glycine

Using the procedure of Example 3E but replacing the resultant compound of Example 3D with the resultant compound of Example 145A provided the desired compound.

C. (2S,4S)-2,4-Bis-(N-(N-(N-((2-pyridinyl)methoxy-carbonyl)glycinyl)valinyl)amino)-1,5-diphenyl-3-hydroxypentane Using the procedure of Example 6I but replacing trans-3-(pyridinyl)acrylic acid with the resultant compound of Example 142B provided 289.6 mg (80%) of the desired compound as a white solid. $^1$H NMR (DMSO-d6) δ 0.63–0.75 (four d, 12H), 1.66 (m, 1H), 1.84 (m, 1H), 2.49 (m, 2H), 2.64 (m, 2H), 2.90 (m, 1H), 3.55 (m, 2H), 3.59 (d, 2H), 3.78 (m, 1H), 3.94 (m, 2H), 4.14 (dd, 1H), 5.00 (s, 4H), 5.19 (d, 1H), 6.98–7.23 (m, 12H), 7.29 (d, 2H), 7.42 (br d, 2H), 7.51 (m, 3H), 7.58 (d, 1H), 7.73 (br t, 1H), 8.44 (d, 2H). Mass spectrum: $(M+H)^+$=853.

EXAMPLE 146

(2S,4S)-2,4-Bis-(N-(N-(N-(3-(Cbz-amino)-3-methylbutyryl)glycinyl)valinyl)amino)-1,5-diphenyl-3-hydroxypentane Using the procedure of Example 6I but replacing trans-3-(pyridinyl)acrylic acid with N-(3-(Cbz-amino)-3-methylbutyryl)glycine provided 261.2 mg (86%) of the desired compound as a white solid. $^1$H NMR (CDCl$_3$) δ 0.66 (d, 3H), 0.69 (d, 3H), 0.75 (d, 3H), 0.77 (d, 3H), 1.34–1.42 (four s, 12H), 1.72 (m, 1H), 1.96 (m, 1H), 2.46–2.65 (m, 4H), 2.81 (m, 1H), 3.04–3.12 (m, 2H), 3.27 (dd, 1H), 3.47 (d, 2H), 3.55–3.69 (m, 4H), 3.89 (m, 2H), 4.37 (m, 1H), 4.69 (d, 1H), 5.03 (s, 4H), 5.35 (br, 1H), 5.73 (br, 1H), 6.48 (br d, 1H), 6.55 (br d, 1H), 6.70 (br, 1H), 6.84 (br d, 1H), 7.02 (br d, 2H), 7.10–7.38 (m, 20H). Mass spectrum: $(M+H)^+$=1049.

EXAMPLE 147

(2S,4S)-2,4-Bis-(N-(N-(N-(methoxy-carbonyl)glycinyl)valinyl)amino)-1,5-diphenyl-3-hydroxypentane Using the procedure of Example 144 but replacing acetic anhydride with methyl chloroformate provided 77.0 mg (43%) of the desired compound as a white solid. Mass spectrum: $(M+H)^+$=699.

EXAMPLE 148

(2S,4S)-2,4-Bis-(N-(N-(N-(3-amino-3-methylbutyryl)glycinyl)valinyl)amino)-1,5-diphenyl-3-hydroxypentane Using the procedure of Example 6H but replacing the resultant compound of Example 6G with the resultant compound of Example 146 provided 127.0 mg (95%) of the desired compound as a white solid. $^1$H NMR (CDCl$_3$) δ 0.73 (t, 6H), 0.87 (d, 6H), 1.23 (s, 6H), 1.24 (s, 3H), 1.26 (s, 3H), 1.61 (br s, 5H), 1.96 (m, 1H), 2.17–2.31 (m, 4H), 2.89 (m, 1H), 3.07 (m, 2H), 3.27 (m, 1H), 3.53 (m, 1H), 3.58 (m, 1H), 3.70–3.77 (m, 6H), 4.04–4.18 (m, 2H), 6.56 (br d, 1H), 6.94 (br d, 1H), 7.14–7.26 (m, 10H), 7.46 (br d, 1H), 7.83 (br d, 1H), 8.34 (m, 2H). Mass spectrum: $(M+H)^+$=781.

EXAMPLE 149

(2S,4S)-2,4-Bis-(N-(N-(N-(3-pyridinyl)glycinyl)valinyl)amino)-1,5-diphenyl-3-hydroxypentane Using the procedure of Example 6I but replacing trans-3-(pyridinyl)acrylic acid with N-(3-pyridinyl)glycine provided 94.2 mg (80%) of the desired compound as a pale yellow solid. $^1$H NMR (DMSO-d6) δ 0.63 (d, 3H), 0.70 (d, 6H), 0.77 (d, 3H), 1.73 (m, 1H), 1.92 (m, 1H), 2.56 (m, 2H), 2.71 (d, 2H), 2.97 (dd, 1H), 3.55–3.87 (m, 5H), 4.03 (m, 2H), 4.24 (dd, 1H), 5.36 (d, 1H), 6.22 (two d, 2H), 6.86 (m, 2H), 7.04–7.23 (m, 12H), 7.52–7.59 (m, 3H), 7.74 (br d, 1H), 7.78 (m, 2H), 7.96 (m, 2H). Mass spectrum: $(M+H)^+$=737.

EXAMPLE 150

(2S,4S)-2,4-Bis-(N-(N-(N-(2-pyridinyl)glycinyl)valinyl)amino)-1,5-diphenyl-3-hydroxypentane Using the procedure of Example 6I but replacing trans-3-(pyridinyl)acrylic acid with N-(2-pyridinyl) glycine provided 119.9 mg (76%) of the desired compound as a pale yellow solid. $^1$H NMR (DMSO-d6) δ 0.58 (d, 3H), 0.65 (d, 3H), 0.69 (d, 3H), 0.76 (d, 3H), 1.73 (m, 1H ), 1.92 (m, 1H), 2.57 (dd, 2H), 2.70 (dd, 2H), 2.96 (dd, 1H), 3.78–3.85 (m, 5H), 4.00 (m, 2H), 4.22 (dd, 1H), 5.29 (d, 1H), 6.49–6.58 (m, 4H), 6.78 (m, 2H), 7.04–7.23 (m, 10H), 7.32–7.41 (m, 3H), 7.48 (br d, 1H), 7.53 (br d, 2H), 7.94 (m, 2H). Mass spectrum: $(M+H)^+$=737.

EXAMPLE 151

(2S,4S)-2,4-Bis-(N-(N-(N-(3,3-dimethylbutyl)glycinyl)valinyl)amino)-1,5-diphenyl-3-hydroxypentane A solution of 200.0 mg (0.28 mmol) of the resultant compound of Example 142A in 5 ml of dimethylformamide was treated with 152 μl (1.13 mmol) of 3,3-dimethylbutylamino. After being stirred at ambient temperature for 2 h, the solution was diluted with chloroform, washed with water, dried over MgSO$_4$, and concentrated in vacuo. Silica gel chromatography of the residue using 10% methanol in dichloromethane provided 155.5 mg (74%) of the desired compound as a white solid. $^1$H NMR (DMSO-d6) δ 0.71–0.83 (four d, 12H), 0.85 (s, 18H), 1.33 (m, 4H), 1.78 (m, 1H), 1.98 (m, 1H), 2.43 (m, 4H), 2.58 (m, 2H), 2.73 (m, 2H), 2.96–3.12 (m, 5H), 3.86 (m, 1H), 4.04 (m, 2H), 4.27 (dd, 1H), 5.33 (d, 1H), 7.06–7.24 (m, 10H), 7.58 (br d, 2H), 7.64 (br d, 1H), 7.81 (br d, 1H). Mass spectrum: $(M+H)^+$=751.

EXAMPLE 152

(2S,4S)-2,4-Bis-(N-(N-(2-methoxyethyl)glycinyl)valinyl)amino)-1,5-diphenyl-3-hydroxypentane Using the procedure of Example 151 but replacing 3,3-dimethylbutylamino with 2-methoxyethylamino provided 150.5 mg (77%) of the desired compound as a white solid. $^1$H NMR (CDCl$_3$) δ 0.76 (d, 3H), 0.79 (d, 3H), 0.90 (d, 3H), 0.93 (d, 3H), 2.03 (m, 1H), 2.26 (m, 1H), 2.57–2.78 (m, 4H), 2.88–3.38 (m, 10H), 3.33 (s, 3H), 3.36 (s, 3H), 3.47 (t, 2H), 3.57 (m, 2H), 3.78 (dd, 1H), 3.84 (t, 1H), 4.11 (t, 1H), 6.76 (br d, 1H), 7.14–7.28 (m, 12H), 7.42 (br d, 1H), 7.72 (br d, 1H), 7.77 (br d, 1H). Mass spectrum: (M+H)$^+$=699.

EXAMPLE 153

(2S,4S)-2,4-Bis-(N-(N-(Cbz-alaninyl)valinyl)amino)-1,5-diphenyl-3-hydroxypentane Using the procedure of Example 6I but replacing trans-3-(pyridinyl)acrylic acid with Cbz-D-alanine provided 171.1 mg (91%) of the desired compound as a white solid. Mass spectrum: (M+H)$^+$=879.

EXAMPLE 154

(2S,3R,4S)-2,4-Bis-(N-(N-((2-pyridinyl)methoxycarbonyl)valinyl)amino)-5-(3,5-dimethylphenyl)-3-hydroxy-1-phenylpentane

A. (2S,3R,4R)-2-(Cbz-amino)-3,4-dihydroxy-5-(3,5-dimethylphenyl)-1-phenylpentane A suspension of 235 mg (3.6 mmol) of zinc dust and 2.24 g (6.0 mmol) of VCl$_3$.(tetrahydrofuran)$_3$ in 20 ml of dry dichloromethane was stirred under N$_2$ atmosphere for 1 h at 25° C. Then 490 mg (3.3 mmol) of 3,5-dimethylphenylacetaldehyde was added to it in one portion and a solution of 850 mg (3.0 mmol) of the resultant compound of Example 1A in 20 ml of dichloromethane was added dropwise over a period of 40 min. After being stirred at ambient temperature under N$_2$ atmosphere for 6 h, the resulting mixture was added to 50 ml of 1M aqueous HCl and shaken vigorously for 1 min. The organic layer was washed with 1M aqueous HCl, separated, dried over MgSO$_4$, and concentrated in vacuo. Silica gel chromatography of the residue using 20% ethyl acetate in hexane provided 666.0 mg (51%) of the desired compound as a white solid. Mass spectrum: (M+H)$^+$=434.

B. (2S,3R,4S)-3-Acetoxy-4-bromo-2-(Cbz-amino)-5-(3,5-dimethylphenyl)-1-phenylpentane Using the procedure of Example 1C but replacing (2S,3R,4S,5S)-2,5-bis-(N-Cbz-amino)-3,4-dihydroxy-1,6-diphenylhexane with the resultant compound of Example 154A provided, after silica gel chromatography using 25% ethyl acetate in hexane, 506.2 mg (62%) of the desired compound as a colorless oil. Mass spectrum: (M+NH4)$^+$= 555.

C. (2S)-2-(Cbz-amino)-5-(3,5-dimethylphenyl)-1-phenylpent-3-ene-3,4-oxide

A solution of 480 mg (0.89 mmol) of the resultant compound of Example 154B and 72 mg (1.33 mmol) of sodium methoxide in 25 ml of tetrahydrofuran was stirred at ambient temperature for 2 h. The solution was diluted with dichloromethane, washed with water, dried over MgSO$_4$, and concentrated in vacuo. Silica gel chromatography of the residue using 25% ethyl acetate in hexane provided 328.1 mg (89%) of the desired compound as a oil which solidified upon standing. Mass spectrum: (M+H)$^+$=416.

D. (2S,3R,4S)-4-Azido-2-(Cbz-amino)-5-(3,5-dimethyl-phenyl)-3-hydroxy-1-phenylpentane Using the procedure of Example 6D but replacing the resultant compound of Example 6C with the resultant compound of Example 154C provided 285.7 mg (86%) of the desired compound as a white solid. Mass spectrum: (M+NH$_4$)$^+$=476.

E. (2S-3R-4S)-2,4-Diamino-5-(3,5-dimethylphenyl)-3-hydroxy-1-phenylpentane

Using the procedure of Example 6E but replacing the resultant compound of Example 6D with the resultant compound of Example 154D provided 109.1 mg (84%) of the desired compound as a white solid. Mass spectrum: (M+H)$^+$=299.

F. (2S,4S)-2,4-Bis-(N-(N-((2-pyridinyl)methoxycarbonyl)valinyl)amino)-5-(3,5-dimethylphenyl)-3-hydroxy-1-phenylpentane Using the procedure of Example 6G but replacing the resultant compound of Example 6F with the resultant compound of Example 154E and replacing N-Cbz-valine p-nitrophenyl ester with the resultant compound of Example 2D provided 142.7 mg (69%) of the desired compound as a white solid. $^1$H NMR (CDCl$_3$) δ 0.67 (d, 3H), 0.79 (d, 3H), 0.88 (d, 3H), 0.92 (d, 3H), 2.04 (m, 1H), 2.22 (s, 6H), 2.31 (m, 1H), 2.83 (m, 1H), 3.07 (m, 3H), 3.62 (m, 2H), 3.78 (br t, 1H), 3.96 (m, 1H), 4.10 (dd, 1H), 5.02–5.17 (m, 6H), 5.76 (br d, 1H), 6.21 (br d, 1H), 6.77 (br d, 3H), 7.09–7.31 (m, 9H), 7.66 (m, 2H), 8.52 (dd, 2H). Mass spectrum: (M+H)$^+$=767.

EXAMPLE 155

(2S,3S,5S)-2,5-Bis-(N-(N-((2-pyridinyl)methoxycarbonyl)valinyl)amino)-1,6-diphenyl-3-(trichloroacetoxy)hexane Using the procedure of Example 35 but replacing trifluoroacetic anhydride with trichloroacetic anhydride provided, after silica gel chromatography using 5% methanol in dichloromethane, 102.8 mg (86%).of the desired compound as a white solid. $^1$H NMR (CDCl$_3$) δ 0.71 (d, 3H), 0.74 (d, 3H), 0.82 (d, 3H), 0.85 (d, 3H), 1.69 (m, 1H), 1.93 (m, 1H), 2.07 (m, 2H), 2.72 (m, 2H), 2.86 (m, 2H), 3.81 (br t, 1H), 3.89 (br t, 1H), 4.53 (br, 1H), 4.93 (m, 2H), 5.16–5.25 (m, 6H), 5.92 (br, 1H), 6.03 (br d, 1H), 7.12–7.24 (m, 12H), 7.36 (br t, 2H), 7.73 (br t, 2H), 8.61 (-br d, 2H). Mass spectrum: (M+H)$^+$=897.

EXAMPLE 156

(2S,3S,5S)-2,5-Bis-(N-(N-((2-pyridinyl)methoxycarbonyl)valinyl)amino)-1,6-diphenyl-3-(propanoxy)hexane Using the procedure of Example 35 but replacing trifluoroacetic anhydride with propanoic anhydride provided 106.1 mg (99%) of the desired compound as a colorless crystal. $^1$H NMR (CDCl$_3$) δ 0.77 (d, 6H), 0.85 (two d, 6H), 1.15 (t, 3H), 1.56 (m, 1H), 1.67 (m, 1H), 2.03 (m, 2H), 2.32 (q, 2H), 2.73 (m, 4H), 3.85 (m, 2H), 4.28 (m, 1H), 4.56 (m, 1H), 4.89 (m, 1H), 5.23 (s, 4H), 5.35 (br, 2H), 6.00 (br, 2H), 7.06–7.36 (m, 14H), 7.72 (br t, 2H), 8.59 (br s, 2H). Mass spectrum: $(M+H)^+=809$.

EXAMPLE 157

(2S,3S,5S)-2,5-Bis-(N-(N-((2-pyridinyl)methoxy-carbonyl)valinyl)amino)-1,6-diphenyl-3-(methoxyacetoxy)hexane A suspension of 100 mg (0.13 mmol) of the resultant compound of Example 2E and 24.3 mg (0.20 mmol) of 4-dimethylaminopyridine in 10 ml of dichloromethane was treated with 0.017 ml (0.20 mmol) of methoxyacetyl chloride. The resulting mixture was stirred at ambient temperature for 1 h and then quenched with pH 6 buffer. The aqueous layer was extracted with dichloromethane. The combined organic layers was dried over $MgSO_4$, and concentrated in vacuo to provide 107.0 mg (98%) of the desired compound as a white solid. $^1H$ NMR ($CDCl_3$) δ 0.74 (d, 3H), 0.77 (d, 3H), 0.83 (d, 3H), 0.86 (d, 3H), 1.66 (m, 2H), 2.04 (m, 2H), 2.73 (m, 4H), 3.45 (s, 3H), 3.86 (m, 2H), 4.01 (m, 2H), 4.32 (m, 1H), 4.63 (m, 1H), 4.98 (m, 1H), 5.22 (br s, 5H), 5.30 (br d, 1H), 5.92 (br d, 1H), 6.11 (br d, 1H), 7.07 (br d, 2H), 7.15–7.24 (m, 10H), 7.36 (br t, 2H), 7.71(tt, 2H), 8.59 (br t, 2H). Mass spectrum: $(M+H)^+=825$.

EXAMPLE 158

(2S,3S,5S)-2,5-Bis-(N-(N-((2-pyridinyl)methoxy-carbonyl)valinyl)amino)-1,6-diphenyl-3-(formoxy) hexane Using the procedure of Example 35 but replacing trifluoroacetic anhydride with acetic formic anhydride provided 106.3 mg (100%) of the desired compound as a white solid, m.p. 206°–207° C. $^1H$ NMR ($CDCl_3$) δ 0.73 (two d, 6H), 0.84 (two d, 6H), 1.68 (m, 2H), 2.06 (m, 2H), 2.65–2.79 (m, 4H), 3.85 (m, 2H), 4.36 (br, 1H), 4.68 (br q, 1H), 5.00 (br t, 1H), 5.14–5.28 (m, 6H), 5.87 (br, 1H), 6.04 (br d, 1H), 7.07 (br d, 2H), 7.13–7.23 (m, 10H), 7.34 (br d, 2H), 7.69 (td, 2H), 8.04 (br, 1H), 8.58 (br t, 2H). Mass spectrum: $(M+H)^+=781$.

Anal. Calcd for $C_{43}H_{52}N_6O_8 \cdot 0.5H_2O$: C, 65.38; H, 6.76; N, 10.64; Found: C, 65.69; H, 6.75; N, 10.60.

EXAMPLE 159

(2S,3S,5S)-2,5-Bis-(N-(N-((N-methyl-N-((2-pyridinyl)methyl)amino)carbonyl)valinyl)amino)-1,6-diphenyl-3-((N,N-dimethylamino)acetoxy)hexane A. (2S,3S,5S)-2,5-Bis-(N-(N-((N-methyl-N-((2-pyridinyl)methyl)amino)carbonyl)valinyl)amino)-1,6-diphenyl-3-(bromoacetoxy)hexane A suspension of 100 mg (0.13 mmol) of the resultant compound of Example 3G and 23.5 mg (0.19 mmol) of 4-dimethylaminopyridine in 2 ml of dichloromethane was treated with 0.022 ml (0.26 mmol) of bromoacetyl bromide. The resulting mixture was stirred at ambient temperature for 5 h and then quenched with pH 6 buffer. The organic layer was diluted with dichloromethane, separated, dried over $Na_2SO_4$, and concentrated in vacuo to provide, after silica gel chromatography using 10%-methanol in dichloro-methane, 97.8 mg (85%) of the desired compound as a white solid. Mass spectrum: $(M+H)^+=899$.

B. (2S,3S,5S)-2,5-Bis-(N-(N-((N-methyl-N-((2-pyridinyl)methyl)amino)carbonyl)valinyl)amino)-1,6-diphenyl-3-((N,N-dimethylamino)acetoxy)hexane A solution of 115.5 mg (0.13 mmol) of the resultant compound of Example 159A in 5 ml of dichloromethane was treated with 0.020 ml (0.26 mmol) of dimethylamino (1.3M in diethyl ether). After being stirred at ambient temperature for 0.5 h, the solution was diluted with dichloromethane, washed with water, dried over $Na_2SO_4$, and concentrated in vacuo. Silica gel chromatography of the residue using 5% methanol in dichloromethane provided 81.7 mg (73%) of the desired compound as a white solid, m.p. 109°–111° C. $^1H$ NMR ($CDCl_3$) δ 0.79–0.88 (four d, 12H), 1.12 (m, 1H), 1.19 (m, 1H), 2.13 (m, 2H), 2.37 (s, 6H), 2.61–2.84 (m, 4H), 2.98 (s, 6H), 3.13 (br s, 2H), 4.04 (m, 2H), 4.30 (m, 1H), 4.43–4.58 (m, 5H), 5.02 (br t, 1H), 6.01 (br, 1H), 6.12 (br, 1H), 6.20 (br, 2H), 6.52 (br d, 1H), 7.06–7.27 (m, 14H), 7.69 (m, 2H), 8.53 (m, 2H). Mass spectrum: $(M+H)^+=864$.

Anal. Calcd for $C_{48}H_{65}N_9O_6$: C, 66.72; H, 7.58; N, 14.59; Found: C, 66.35; H, 7.55; N, 14.69.

EXAMPLE 160

(2S,3S,5S)-2,5-Bis-(N-(N-((N-methyl-N-((2-pyridinyl)methyl)amino)carbonyl)valinyl)amino)-1,6-diphenyl-3-(1-(2-propoxy)ethoxy)hexane A solution of 80 mg (0.10 mmol) of the resultant compound of Example 3G and 40 mg (0.16 mmol) of pyridium p-toluenesulfonate in 4 ml of acetonitrile was treated with 4 ml of isopropyl vinyl ether. The resulting mixture was stirred at ambient temperature under $N_2$ for 20 h and then quenched with pH 6 buffer. The aqueous layer was extracted with dichloromethane. The combined organic layers were dried over $Na_2SO_4$ and concentrated in vacuo. Silica gel chromatography of the residue using 10% methanol in dichloromethane provided 86.1 mg (97%) of the desired compound as a white solid. $^1H$ NMR ($CDCl_3$) δ 0.73 (d, 3H), 0.77 (d, 3H), 0.86 (two d, 6H), 1.08 (m, 6H), 1.24 (dd, 3H), 1.61–1.75 (m, 3H), 2.12 (m, 1H), 2.21 (m, 1H), 2.64–2.92 (m, 4H), 2.96 (two d, 6H), 3.53–3.75 (m, 2H), 4.00–4.14 (m, 2H), 4.33–4.64 (m, 6H), 5.94–6.47 (m, 4H), 7.10–7.24 (m, 14H), 7.22 (td, 2H), 8.54 (m, 2H). Mass spectrum: $(M+H)^+=864$.

Anal. Calcd for $C_{49}H_{68}N_8O_6$: C, 68.03; H, 7.92; N, 12.95; Found: C, 67.67; H, 7.90; N, 12.95.

EXAMPLE 161

(2S,3S,5S)-2,5-Bis-(N-(N-((N-methyl-N-((2-pyridinyl)methyl)amino)carbonyl)valinyl)amino)-1,6-diphenyl-3-(((N-(2-hydroxyethyl)-N-methyl)amino)acetoxy)hexane A solution of 100 mg (0.11 mmol) of the resultant compound of Example 159A in 5 ml of dichloromethane was treated with 0.018 ml (0.22 mmol) of 2-(methylamino)-ethanol. After being stirred at ambient temperature for 1 h, the solution was diluted with dichloromethane, washed with water, dried over $Na_2SO_4$, and concentrated in vacuo. Silica gel chromatography of the residue using 10% methanol in dichloromethane provided 27.9 mg (28%) of the desired compound as a white solid. $^1H$ NMR ($CDCl_3$) δ 0.79 (d, 6H), 0.84 (t, 6H), 1.73 (br, 2H), 2.08 (m, 1H), 2.17 (m, 1H), 2.48 (s, 3H), 2.64–2.84 (m, 6H), 2.96 (s, 3H), 3.00 (s, 3H), 3.43 (br, 1H), 3.72 (br, 2H), 4.04 (m, 2H), 4.38 (m, 1H), 4.42–4.57 (m, 6H), 5.07 (td, 1H), 6.09 (br, 2H), 6.97 (br d, 2H), 7.08–7.26 (m, 14H), 7.69 (td, 2H), 8.52 (m, 2H). Mass spectrum: (M+H)⁺=894.

Anal. Calcd for $C_{49}H_{67}N_9O_7 \cdot CH_3OH$: C, 64.84; H, 7.73; N, 13.61; Found: C, 65.08; H, 7.52; N, 13.41.

EXAMPLE 162

(2S,3S,5S)-2,5-Bis-(N-(N-((N-methyl-N-((2-pyridinyl)methyl)amino)carbonyl)valinyl)amino)-1,6-diphenyl-3-(((N-(2-acetoxyethyl)-N-methyl)amino)acetoxy)hexane A solution of 20.6 mg (0.023 mmol) of the resultant compound of Example 161 and 5.6 mg (0.046 mmol) of 4-dimethylaminopyridine in 2 ml of dichloromethane was treated with 3.3 µl (0.035 mmol) of acetic anhydride. The resulting mixture was stirred at ambient temperature for 1.5 h and then quenched with pH 6 buffer. The organic layer was diluted with dichloromethane, separated, dried over $Na_2SO_4$, and concentrated in vacuo. Silica gel chromatography of the residue using 10% methanol in dichloromethane provided 19.3 mg (92%) of the desired compound as a white solid. ¹H NMR (CDCl₃) δ 0.80 (d, 6H), 0.86 (d, 6H), 1.60 (m, 1H), 1.71 (m, 1H), 2.08 (s, 3H), 2.13 (m, 2H), 2.45 (s, 3H), 2.49–2.79 (m, 4H), 2.84 (t, 2H), 2.97 (s, 6H), 3.29 (q, 2H), 4.04 (q, 2H), 4.17 (t, 2H), 4.31 (m, 1H), 4.48 (br t, 4H), 4.56 (m, 1H), 5.01 (br t, 1H), 6.01 (br, 1H), 6.12 (br, 1H), 6.21 (br d, 1H), 6.48 (br d, 1H), 7.07–7.25 (m, 14H), 7.68 (m, 2H), 8.53 (br t, 2H). Mass spectrum: (M+H)⁺=936.

Anal. Calcd for $C_{51}H_{69}N_9O_8$: C, 65.43; H, 7.43; N, 3.47; Found: C, 65.18; H, 7.10; N, 13.42.

EXAMPLE 163

(2S,3S,5S)-2,5-Bis-(N-(N-((N-methyl-N-((2-pyridinyl)methyl)amino)carbonyl)valinyl)amino)-1,6-diphenyl-3-(acetoxymethoxy)hexane

A. (2S,3S,5S)-2,5-Bis-(N-(benzylidene)amino)-1,6-diphenyl-3-hydroxyhexane

A solution of 150 mg (0.53 mmol) of the resultant compound of Example 1E in 6 ml of tetrahydrofuran was treated with 0.11 ml of benzaldehyde. After being stirred at ambient temperature under N₂ atmosphere for 3 h, concentrated in vacuo, and left on oil pump for 1 day to provide the crude desired compound. Mass spectrum: (M+H)⁺=461.

B. (2S,3S,5S)-2,5-Bis-(N-(benzylidene)amino)-1,6-diphenyl-3-(2-methyl-2-propenoxy)hexane A solution of the crude resultant compound of Example 163A in 6 ml of tetrahydrofuran was treated with 0.58 ml of 1M solution of sodium bis (trimethylsilyl)amide in tetrahydrofuran at 0° C. under N₂ atmosphere. The resulting mixture was stirred for 40 min and then treated with 3-iodo-2-methylpropene. Stirring was continued at 0° C. for 1 h and at ambient temperature for 5 h. Evaporating of the solvent provided the crude desired compound. ¹H NMR (CDCl₃) δ 1.71 (s, 3H), 2.07 (m, 1H), 2.33 (m, 1H), 2.82–3.11 (m, 4H), 3.52 (m, 2H), 3.68 (m, 1H), 3.94 (s, 2H), 4.80 (s, 1H), 4.92 (q, 1H), 7.02–7.37 (m, 16H), 7.54–7.58 (m, 4H), 7.72 (s, 1H), 7.88 (s, 1H). Mass spectrum: (M+H)⁺=515.

C. (2S,3S,5S)-2,5-Diamino-1,6-diphenyl-3-(2-methyl-2-propenoxy)hexane

A solution of the crude resultant compound of Example 163B in 6 ml of tetrahydrofuran was treated with 6 ml of 1M aqueous HCl and stirred at ambient temperature for 1.5 h. The reaction mixture was extracted with three 10 ml portions of hexane. The aqueous layer was neutralized with sodium bicarbonate and then extracted with five 10 ml portions of dichloromethane. The combined organic layers was dried over $Na_2SO_4$, and concentrated in vacuo. Silica gel chromatography of the residue using 2% isopropylamino and 5% methanol in dichloromethane provided 114.0 mg (64%, 3 steps) of the desired compound as a oil. Mass spectrum: (M+H)⁺=339.

D. (2S,3S,5S)-2,5-Bis-(N-(N-((N-methyl-N-((2-pyridinyl)methyl)amino)carbonyl)valinyl)amino)-1,6-diphenyl-3-(2-methyl-2-propenoxy)hexane Using the procedure of Example 6G but replacing the resultant compound of Example 6F with the resultant compound of Example 163C and replacing N-Cbz-valine p-nitrophenyl ester with the resultant compound of Example 3F provided 228.4 mg (93%) of the desired compound as a white solid. Mass spectrum: (M+H)⁺=833.

E. (2S,3S,5S)-2,5-Bis-(N-(N-((N-methyl-N-((2-pyridinyl)methyl)amino)carbonyl)valinyl)amino)-1,6-diphenyl-3-(acetoxymethoxy)hexane A stream of ozone was passed through a solution of 150 mg (0.18 mmol) of the resultant compound of Example 163D in 9 mL of 5:1 $CH_2Cl_2$/MeOH at −78° C. until the faint blue color of ozone persisted. The mixture was then purged with N₂ for 10 min and then concentrated in vacuo. The residue and 11.1 mg (0.09 mmol) of 4-dimethylaminopyridine were dissolved in 6 ml of dichloromethane, 35.1 µl (0.27 mmol) of triethylamino and 20.4 µl (0.22 mmol) of acetic anhydride were added. The resulting mixture was stirred at 40° C. for 2 h and then quenched with pH 6 buffer. The organic layer was diluted with dichloromethane, separated, dried over $Na_2SO_4$, and concentrated in vacuo to provide, after silica gel chromatography using 10% 2-propanol in dichloromethane, 90.7 mg (59%) of the desired compound as a white solid. ¹H NMR (CDCl₃) δ 0.72 (d, 3H), 0.78 (d, 3H), 0.84 (d, 6H), 1.54 (m, 1H), 1.73 (m, 1H), 1.99 (s, 3H), 2.14 (m, 2H), 2.63–2.87 (m, 4H), 2.96 (s, 3H), 2.98 (s, 3H), 3.66 (dd, 1H), 4.00–4.11 (m, 2H), 4.33 (m, 1H), 4.40–4.53 (m, 4H), 4.62 (m, 1H), 5.18 (dd, 2H), 6.08 (br, 2H), 6.22 (br d, 1H), 6.28 (br d, 1H), 7.08–7.23 (m, 14H), 7.71 (m, 2H), 8.54 (m, 2H). Mass spectrum: (M+H)⁺=851.

Anal. Calcd for $C_{47}H_{62}N_8O_7 \cdot 1i$-PrOH: 65.91; H, 7.74; N, 12.30; Found: C, 66.14; H, 7.64; N, 12.21.

EXAMPLE 164

(2S,3S,5S)-2,5-Bis-(N-(3-(3-pyridinyl)propanoyl)amino)-1,6-diphenyl-3-hydroxyhexane Using the procedure of Example 6I but replacing the resultant compound of Example 6H with the resultant compound of Example 1E and replacing trans-3-(pyridinyl)-acrylic acid with 3-(3-pyridinyl)propanoic acid provided 42.1 mg (47%) of the desired compound as a white solid. ¹H NMR (DMSO-d6) δ 1.33 (m, 2H), 2.24 (t, 2H), 2.33 (t, 2H), 2.57–2.72 (m, 8H), 3.59 (m, 1H), 4.07 (m, 2H), 4.76 (d, 1H), 7.02 (d, 2H), 7.10–7.27 (m, 10H), 7.52 (m, 3H), 7.58 (br d, 1H), 8.37 (m, 4H). Mass spectrum: (M+H)⁺=551.

EXAMPLE 165

(2S,3S,5S)-2,5-Bis-(N-(N-(3-pyridinyl)glycinyl)amino)-1,6-diphenyl-3-hydroxyhexane Using the procedure of Example 6I but replacing the resultant compound of Example 6H with the resultant compound of Example 1E and replacing trans-3-(pyridinyl)-acrylic acid with N-(3-pyridinyl)glycine provided 29.1 mg (44%) of the desired compound as a white solid. $^1$H NMR (DMSO-d6) δ 1.39 (m, 2H), 2.55 (m, 2H), 2. 67 (d, 2H), 3.43–3.58 (m, 5H), 4.14 (m, 2H), 4.87 (d, 1H), 6.07 (br t, 1H), 6.16 (br t, 1H), 6.65 (m, 2H), 7.01 (m, 4H), 7.11–7.24 (m, 8H), 7.53 (br d, 1H), 7.65 (br d, 1H), 7.78 (d, 2H ), 7.93 (t, 2H). Mass spectrum: (M+H)$^+$=553.

EXAMPLE 166

(2S,3S,5S)-2,5-Bis-(N-((3-pyrazinyl)methoxy-carbonyl)-amino)-1,6-diphenyl-3-hydroxyhexane A. Phenyl ((2-pyrazinyl)methoxy)formate Using the procedure of Example 176 but replacing 2-(hydroxymethyl)pyridine with 2-(hydroxymethyl)pyrazine provided 188.9 mg (70%) of the desired compound as a yellow oil.

B. (2S,3S,5S)-2,5-Bis-(N-((3-pyrazinyl)methoxy-carbonyl)amino)-1,6-diphenyl-3-hydroxyhexane Using the procedure of Example 176 but replacing the resultant compound of Example 176A with the resultant compound of Example 166A provided 21.2 mg (36%) of the desired compound as a white solid. $^1$H NMR (CDCl$_3$) δ 1.70 (t, 2H), 2.78 (d, 2H), 2.88 (d, 2H), 3.12 (d, 1H), 3.72 (br, 1H), 3.83 (m, 1H), 4.00 (m, 1H), 4.99 (br d, 1H), 5.22 (m, 5H), 7.09–7.27 (m, 10H), 8.54 (m, 6H). Mass spectrum: (M+H)$^+$=557.

EXAMPLE 167

(2S,3S,5S)-2,5-Bis-(N-((5-pyrimidinyl)methoxycarbonyl)amino)-1,6-diphenyl-3-hydroxyhexane A. p-Nitrophenyl ((5-pyrimidinyl)methoxy)formate Using the procedure of Example 15 but replacing 4-(hydroxymethyl)pyridine with 5-(hydroxymethyl)pyrimidine provided 433.4 mg (77.5%) of the desired compound as a white solid.

B. (2S,3S,5S)-2,5-Bis-(N-((3-pyrimidinyl)methoxycarbonyl)amino)-1,6-diphenyl-3-hydroxyhexane Using the procedure of Example 175 but replacing the resultant compound of Example 175A with the resultant compound of Example 167A provided 45.8 mg (78%) of the desired compound as a white solid. $^1$H NMR (CDCl$_3$) δ 1.66 (m, 2H), 2.76 (d, 2H), 2.85 (d, 2H), 2.88 (m, 1H), 3.67 (br, 1H), 3.81 (m, 1H), 3.95 (m, 1H), 4.87–5.14 (m, 6H), 7.04–7.28 (m, 10H), 8.70 (d, 4H), 9.19 (s, 2H). Mass spectrum: (M+H)$^+$=557.

EXAMPLE 168

(2S,3S,5S)-2,5-Bis-(N-((3,5-dimethyl-4-isoxazolyl) methoxy-carbonyl)amino)-1,6-diphenyl-3-hydroxyhexane A. Phenyl ((3,5-dimethyl-4-isoxazolyl)methoxy)formate Using the procedure of Example 175 but replacing (hydroxymethyl) pyridine with 3,5-dimethyl-4-(hydroxymethyl)isoxazole provided 0.79 g (69%) of the desired compound as a pale yellow oil.

B. (2S,3S,5S)-2,5-Bis-(N-((3,5-dimethyl-4-isoxazolyl)methoxy-carbonyl)amino)-1,6-diphenyl-3-hydroxyhexane Using the procedure of Example 175 but replacing the resultant compound of Example 175A with the resultant compound of Example 168A provided 57.1 mg (92%) of the desired compound as a white solid. $^1$H NMR (DMSO-d6) δ 1.44 (br t, 2H), 2.11 (s, 6H), 2.28 (s, 3H), 2.30 (s, 3H), 2.64 (m, 4H), 3.53 (m, 1H), 3.82 (m, 2H), 4.65 (d, 1H), 4.72 (m, 4H), 6.80 (br d, 1H), 7.02 (br d, 1H), 7.06–7.21 (m, 10H). Mass spectrum: (M+H)$^+$=591.

EXAMPLE 169

(2S,3S,5S)-2-(N-(N-((N-methyl-N-((2-pyridinyl)methyl)amino)carbonyl)isoleucinyl)amino)-5-(N-((-3pyridinyl)methoxy-carbonyl)amino)-1,6-diphenyl-3-hydroxyhexane A mixture of 40 mg (0.095 mmol) of (2S,3S,5S)-2-amino-5-(N-((3-pyridinyl)methoxy-carbonyl)amino)-1,6-diphenyl-3-hydroxyhexane from Example 37B and 57.3 mg (0.14 mmol) of the resultant compound of Example 16C in 1 ml of dry tetrahydrofuran was stirred at ambient temperature for 16 h. The solvent was then removed in vacuo, and the residue was purified by silica gel chromatography using 5% methanol in dichloromethane provided 62.1 mg (96%) of the desired compound as a white foamy solid. $^1$H NMR (CDCl$_3$) δ 0.82 (t, 3H), 0.88 (d, 3H), 1.03 (m, 1H), 1.2 3 (m, 1H), 1.65 (t, 2H), 1.97 (m, 1H), 2.72 (dd, 2H), 2.82 (dd, 2H), 2.94 (s, 3H), 3.65 (br, 1H), 3.96 (br q, 1H), 4.09 (m, 2H), 4.44 (s, 2H), 5.03 (dd, 2H), 5.32 (br d, 1H), 6.49 (br d, 2H), 7.08–7.26 (m 14H), 7.59 (br d, 1H), 7.71 (td, 1H),8.49 (dt, 1H), 8.54 (dd, 2H). Mass spectrum: (M+H)$^+$=681.

Anal. Calcd for C$_{39}$H$_{48}$N$_6$O$_5$.0.5H$_2$O: C, 67.90; H, 7.16; N, 12.18; Found: C, 67.71; H, 7.03; N, 12.13.

EXAMPLE 170

(2S,3S,5S)-2-(N-(N-((2-pyridinyl)methoxy-carbonyl)isoleucinyl)amino)-5-(N-((3-pyridinyl)methoxy-carbonyl)-amino)-1,6-diphenyl-3-hydroxyhexane Using the procedure of Example 169 but replacing the resultant compound of Example 16C with the resultant compound of Example 25C provided 37.4 mg (77%) of the desired compound as a white solid. $^1$H NMR (CDCl$_3$) δ 0.82 (t, 3H), 0.84 (d, 3H), 0.97 (m, 1H), 1.25 (m, 1H), I. 64 (m, 2H), 1.86 (m, 1H), 2.75 (br d, 2H), 2.84 (d, 2H), 3.68 (m, 1H), 3.96 (br t, 2H), 4.10 (m, 1H), 5.03 (dd, 2H), 5.13–5.32 (m, 4H), 6.28 (br d, 1H), 7.07 (d, 2H), 7.17–7.27 (m, 11H), 7.32 (d, 1H), 7.58 (dr, 1H), 7.70 (td, 1H), 8.56 (m, 3H). Mass spectrum: (M+H)$^+$=668.

99

Anal. Calcd for $C_{38}H_{45}N_5O_6 \cdot 0.75H_2O$: C, 66.99; H, 6.88; N, 10.28; Found: C, 66.87; H, 6.66; N, 10.18.

EXAMPLE 171

(2S,3S,5S)-5-(N-(N-((N-methyl-N-((2-pyridinyl)methyl)amino)carbonyl)isoleucinyl)amino)-2-(N-((-3-pyridinyl)methoxy-carbonyl)amino)-1,6-diphenyl-3-hydroxyhexane Using the procedure of Example 169 but replacing (2S, 3S,5S)-2-amino-5-(N-((3-pyridinyl)methoxy-carbonyl)amino)-1,6-diphenyl-3-hydroxyhexane with (2S,3S,5S)-5-amino-2-(N-((3-pyridinyl)methoxy-carbonyl)amino)-1,6-diphenyl-3-hydroxyhexane from Example 37B provided 62.1 mg (96%) of the desired compound as a white foamy solid. $^1$H NMR (CDCl$_3$) δ 0.82 (t, 3H), 0.86 (d, 3H), 1.02 (m, 1H), 1.18 (m, 1H), 1.62 (m, 2H), 2.03 (m, 1H), 2.73 (br t, 2H), 2.84 (dd, 2H), 2.99 (s, 3H), 3.75 (br q, 1H), 4.06 (dd, 1H), 4.19 (m, 2H), 4.43 (m, 2H), 5.04 (dd, 2H), 5.18 (br d, 2H), 6.48 (br d, 1H), 6.57 (br, 1H), 7.07–7.27 (m, 14H), 7.60 (dr, 1H), 7.73 (td, 1H), 8.47 (br d, 1H), 8.28 (br d, 2H). Mass spectrum: (M+H)$^+$=681.

Anal. Calcd for $C_{39}H_{48}N_6O_5 \cdot 0.5H_2O$: C, 67 90; H, 7.16; N, 12.18; Found: C, 67,54; H, 7.01; N, 12,10.

EXAMPLE 172

(2S,3S,5S)-5-(N-(N-((2-pyridinyl)methoxy-carbonyl)isoleucinyl)amino)-2-(N-((3-pyridinyl)methoxy-carbonyl)-amino)-1,6-diphenyl-3-hydroxyhexane Using the procedure of Example 171 but replacing the resultant compound of Example 16C with the resultant compound of Example 25C provided 25.9 mg (56%) of the desired compound as a white solid. $^1$H NMR (CDCl$_3$) δ 0.80 (t, 3H), 0.84 (d, 3H), 1.22 (m, 2H), 1.63 (m, 2H), 1.92 (m, 1H), 2.75 (br t, 2H), 2.86 (br d, 2H), 3.67 (m, 1H), 3.80 (m, 1H), 3.94 (br t, 1H), 4.16 (m, 1H), 5.04 (dd, 2H), 5.13–5.30 (m, 4H), 6.40 (br, 1H); 7.09–7.34 (m 14H), 7.59 (br d, 7.62 (br d, 1H), 8.58 (m, 3H), Mass spectrum: (M+H)$^+$=668.

Anal. Calcd for $C_{38}H_{45}N_5O_6 \cdot 0.5H_2O$: C, 67 44; H, 6.85; N, 10.35; Found: C, 67.71; H, 6.72; N, 10.30.

EXAMPLE 173

(2S,3R,4R,5S)-2,4-Di-{N-[N-methyl-N-(2-pyridylmethyl)amino-carbonyl]-L-Valyl}amino-3,4-dihydroxy-1,6-di-(4-hydroxyphenyl)hexane

A. (2S,3R,4R,5S)-2,5-Di(toluenesulfonylamino)-1,6-di-(4-methoxymethyoxyphenyl)-3,4-O-isopropylidene Hexane To a solution of 1-iodo-4-methoxymethoxybenzene (2.112 mg, 8.0 mmol) dissolved in anhydrous ether (25 mL) and cooled in a dry ice/acetone bath was added 1.7M butyl lithium (5.2 mL, 8.8 mmol). After 2 hours, the mixture was cannulated into a mixture of copper(I) bromide dimethylsulfide (820 mg, 4.0 mmol) in ether (10 mL) cooled to –30° C. After 30 minutes, 1,2-di(1-tosylaziridin-2-yl)-1-O,2-O-isopropylidine ethane (492 mg, 1.0 mmol) in ether was added. The reaction mixture was allowed to warm gradually to 0° C. and was stirred for 2 hours before quenching with ammonium hydroxide/ammonium chloride. After 30 minutes, the mixture was filtered and the filtrate diluted with ethyl acetate, dried over magnesium sulfate and concentrated under reduced pressure. The residue obtained was chromatographed on silica gel eluting with 30% ethyl acetate in hexane to give the title compound (132 mg).

B. (2S,3R,4R,5S)-2,5-Diamino-3,4-O-isopropylidene-1,6-di-(4-methoxymethoxyphenyl)hexane The compound resulting from Example 173A (387 mg, 0.564 mmol) dissolved in ether (10 mL) was added to liquid ammonia (125 mL) cooled in a dry ice/acetone bath Small pieces of sodium metal were added until the blue color remained; the color was maintained by adding small pieces of sodium over the next 30 minutes. The reaction was quenched using solid ammonium chloride, the cooling bath was removed and the ammonia allowed to evaporate. The residue was dissolved in methylene chloride, washed with 1N sodium hydroxide, dried over magnesium sulfate, and concentrated under reduced pressure to give crude title compound (211 mg).

C. (2S,3R,4R,5S)-2,5-Di-{N-[N-methyl-N-(2-pyridylmethyl)amino-carbonyl]-L-Valyl}amino-3,4-O-isopropylidene-1,6-di(4-hydroxyphenyl)hexane The compound resulting from Example 173B (210 mg, 0.456 mmol) was treated with N-(N-methyl-N-(2-pyridylmethyl)amino-carbonyl)-L-Valine 4-nitrophenyl ester (610 mg, 1.5 mmol) in tetrahydrofuran (2 mL) and dimethylformamide (1 mL). The reaction mixture was stirred overnight at room temperature and then concentrated under reduced pressure. Chromatography on silica gel eluting with 5% methanol in methylene chloride afforded the title compound (381 mg, 87%).

D. (2S,3R,4R,5S)-2,5-Di-{N-[N-methyl-N-(2-pyridylmethyl)amino-carbonyl]-L-Valyl}amino-3,4-dihydroxy-1,6-di(4-hydroxyphenyl) Hexane The compound resulting from Example 173C (233 mg, 0.244 mmol) was dissolved in 90% trifluoroacetic acid in water (4 mL) and kept in a freezer overnight. The reaction mixture was diluted with methylene chloride and washed with sodium bicarbonate and sodium chloride solutions. The separatory funnel was extracted with chloroform/methanol/isopropyl alcohol and the combined organic extracts were dried over magnesium sulfate and concentrated under reduced pressure. Chromatography on silica gel eluting with 10% methanol in methylene chloride afforded the title product. $^1$H NMR (CD$_3$OD, 300 MHz) δ 0.77 (d, 6H), 0.80 (d, 6H), 1.90 (m, 2H), 2.74 (d, 4H), 3.94 (d, 2H), 4.50 (m, 2H), 4.59 (d of d, 4H), 6.61 (m, 4H), 7.05 (m, 4H), 7.31 (m, 4H), 7.83 (m, 2H), 8.50 (m, 2H). MS (FAB) m/e 827 (M+H)$^+$.

EXAMPLE 174

(2S,3S,5S)-2,5-Di{N-[3-pyridylmethyl)oxy-carbonyl]amino}-3-hydroxy-1,6-diphenyl Hexane To the compound resulting from Example 1E (2.205 g, 7.866 mmol) dissolved in anhydrous dimethylformamide (10 mL) was added ((3-pyridinyl)methyl)-(4-nitrophenyl) carbonate (6.385 g, 0.0233 mmol). After 5.5 hours, the solvent was removed under reduced pressure and the residue dissolved in methylene chloride, washed with sodium bicarbonate and brine, dried over magnesium sulfate and concentrated under reduced pressure. The residue obtained was chromatographed on silica gel eluting with a gradient of methanol in methylene chloride (2%, 5%, 10%) to afford the title compound (2215 g, 52%). $^1$H NMR (DMSO-d$_6$, 300

MHz) δ 1.50 (m, 2H), 2.50–2.75 (m, 4H), 3.55 (m, 1H), 3.87 (m, 2H), 4.98 (d, 4H), 6.95 (d, 1H), 7.00–7.27 (m, 12H), 7.33 (m, 2H), 7.60 (m, 2H), 8.50 (m, 3H). Anal calcd for $C_{32}H_{34}N_4O_5 \cdot 0.33\ H_2O$: C, 68.64; H, 5.97; N, 9.89. Found: C, 68.57; H, 6.19; N, 10.00. MS (DCI/NH$_3$) m/e 555 (M+H)$^+$.

EXAMPLE 175

(2S,3S,5S)-2,5-Di{N-[(4-pyridylmethyl)oxy-carbonyl]amino}-3-hydroxy-1,6-diphenyl Hexane

A. ((4-pyridinyl)methyl)-(4-nitrophenyl)carbonate

To a solution of 4-pyridylcarbinol (169 mg, 1.0 mmol) and 4-methylmorpholine (NMM) (165 μL, 1.5 mmol) dissolved in methylene chloride (1.0 mL) and cooled in an ice bath was added (4-nitrophenyl)chloroformate (300 mg, 1.5 mmol). After 1.33 hours, additional methylene chloride (1 mL) was added. After 2.5 hours, the reaction mixture was treated with methylene chloride and water and filtered. The filtrate was washed with water, saturated sodium bicarbonate solution and brine, dried over magnesium sulfate and concentrated under reduced pressure. The residue obtained was chromatographed on silica gel eluting with methylene chloride and 1% going to 2% methanol in methylene chloride to afford the title compound (83 mg).

B. (2S,3S,5S)-2,5-Di{N-[4-pyridylmethyl)oxy-carbonyl]amino}-3-hydroxy-1,6-diphenyl Hexane The compound resulting from Example 175A (213 mg, 0.777 mmol) and the compound resulting from Example 1E (70 mg, 0.246 mmol) were dissolved in dimethylformamide (0.8 mL) and stirred at room temperature for 3 days. The solvent was removed under reduced pressure and the residue obtained dissolved in chloroform, filtered, and the filtrate washed with saturated sodium bicarbonate solution and brine, dried over magnesium sulfate, and concentrated under reduced pressure. Chromatography on silica gel eluting with 5% methanol in methylene chloride afforded the title compound. $^1$H NMR (DMSO-d$_6$, 300 MHz) δ 1.50 (m, 2H), 2.50–2.75 (m, 4H), 3.55 (m, 1H), 3.87 (m, 2H), 4.98 (d, 4H), 6.95 (d, 1H), 7.00–7.27 (m, 12H), 7.33 (m, 2H), 8.50 (m, 3H). MS (DCI/NH$_3$) m/e 555 (M+H)$^+$.

EXAMPLE 176

(2S,3S,5S)-2,5-Di{N-[2-pyridylmethyl)oxycarbonyl]amino}-3-hydroxy-1,6-diphenyl Hexane

A. (2-Pyridylmethyl)phenylcarbonate

To a solution of 2-pyridine carbinol (109 mg, 1.0 mmol) dissolved in methylene chloride (3 mL) and NMM (165 μL, 1.5 mmol) and cooled in an ice bath was added phenyl chloroformate (188 μL, 1.5 mmol) dissolved in methylene chloride (1.0 mL) dropwise. The reaction mixture was stirred at 0° C. for 1 hour, diluted with methylene chloride, washed with saturated sodium bicarbonate and brine, dried over magnesium sulfate, and concentrated under reduced pressure. The residue obtained was chromatographed on silica gel eluting with 40% ethyl acetate in hexane to afford the title compound (176 mg).

B. (2S,3S,5S)-2,5-Di{N-[2-pyridylmethyl)oxy-carbonyl]amino}-3-hydroxy-1,6-diphenyl Hexane The compound resulting from Example 1E (92.5 mg, 0.326 mmol) and the compound resulting from Example 176A (310 mg, 1.35 mmol) were dissolved in dimethylformamide (1 mL) and warmed at 60° C. for 6.5 hours, allowed to stand overnight at room temperature, and then heated at 80° C. for 4 hours. The reaction mixture was concentrated under reduced pressure and the residue obtained chromatographed on silica gel eluting with 5% methanol in methylene chloride to afford the title compound (104 mg). $^1$H NMR (DMSO-d$_6$, 300 MHz) δ 1.56 (m, 2H), 2.54–2.75 (m, 4H), 3.63 (m, 1H), 3.90 (m, 2H), 4.73 (m, 1H), 4.80–5.06 (m, 4H), 7.04–7.30 (m, 17H), 7.72 (m, 2H), 8.49 (m, 2H). MS (DCI/NH$_3$) m/e 555 (M+H)$^+$.

EXAMPLE 177

(2S,3S,5S)-2,5-Di{N-[Benzylamino-carbonyl]amino}-3-hydroxy-1,6-diphenyl Hexane

To a solution of the compound resulting from Example 1E (72.6 mg, 0.256 mmol) dissolved in dimethylformamide (1 mL) was added benzyl isocyanate (95 μL, 0.768 mmol). The reaction mixture was stirred overnight at room temperature and then concentrated under reduced pressure. The residue obtained was chromatographed on silica gel eluting with a gradient of methanol in methylene chloride (2%,5%) to afford the title compound. $^1$H NMR (DMSO-d$_6$, 300 MHz) δ 1.40 (m, 2H), 2.54–2.80 (m, 4H), 3.62 (m 1H), 3.90 (m, 1H), 4.01 (m, 1H), 4.98 (d, 1H), 5.71 (d, 1H), 5.83 (d, 1H), 6.16 (m, 1H), 6.39 (m, 1H), 7.04 (m, 2H), 7.11–7.32 (m, 19H). MS (DCI/NH$_3$) m/e 551 (M+H)$^+$.

EXAMPLE 178

(2S,3S,5S)-2,5-Di[N-{[1-(3-pyridyl)ethyl]oxycarbonyl}amino]-3-hydroxy-1,6-diphenyl Hexane The compound resulting from Example 1E (70 mg, 0.246 mmol) and [1-(3-pyridyl)ethyl]-(4-nitrophenyl)carbonate (220 mg, 0.764 mmol) were dissolved in dimethylformamide (1.0 mL) and stirred at room temperature for 2.5 days. The reaction mixture was concentrated under reduced pressure and the residue obtained chromatographed on silica gel eluting with a gradient of methanol in methylene chloride (2%,5%,10%,20%) containing 0.5% ammonium hydroxide to afford the title compound (80.6 mg). $^1$H NMR (DMSO-d$_6$, 300 MHz) δ 1.30–1.56 (m, 8H), 2.36–2.78 (m, 4H), 3.37–3.93 (m, 5H), 5.57 (m, 2H), 6.78–7.56 (m, 16H), 7.72 (m, 1H), 8.40–8.60 (m, 4H). MS (DCI/NH$_3$) m/e 583 (M+H)$^+$.

EXAMPLE 179

(2S,3S,5S)-2-[(tert-Butyloxycarbonyl)amino]-5-[N-{(3-pyridyl)methyloxy-carbonyl)amino]-3-hydroxy-1,6-diphenyl

A. (2S,3S,5S)-2-Amino-5-[N-{(3-pyridyl)methyloxycarbonyl}amino]-3-hydroxy-1,6-diphenyl Hexane The compound resulting from Example 1E (820 mg, 2.89 mmol) and (3-pyridylmethyl) phenyl carbonate (728 mg, 3.179 mmol) were dissolved in dimethylformamide and warmed at 50° C. for 15.5 hours. The solvent was removed under reduced pressure and the residue obtained chromatographed on silica gel eluting with a gradient of methanol in methylene chloride (2%,5%,10%) to afford a mixture of compounds (919 mg). This material was re-chromatographed on silica gel eluting with 2% methanol in methylene chloride containing 1% isopropylamino to afford the title compound (424 mg, 35%). Also isolated was the regioisomer in which substitution occurred at the 2-amino group instead of the 4-amino group.

B. (2S,3S,5S)-2-[(tert-Butyloxycarbonyl)amino]-5-[N-{(3-pyridyl)methyloxycarbonyl}amino]-3-hydroxy-1,6-diphenyl Hexane To the product of Example 179A (92.5 mg, 0.215 mmol) dissolved in methylene chloride was added di-t-butyl-dicarbonate (90 mg). After 2 hours, additional di-t-butyl-dicarbonate (33 mg) was added. After an additional hour, the reaction mixture was concentrated under reduced pressure. The residue obtained was chromatographed on silica gel eluting with methanol in methylene chloride (2%,5%) to afford the title compound (194 mg, 79%). $^1$H NMR (DMSO-$d_6$, 300 MHz) δ 1.30 (s, 9H), 1.50 (m, 2H), 2.53–2.74 (m, 4H), 3.52 (m, 1H), 3.72–3.97 (m, 3H), 4.58 (d, 1H), 4.82–5.00 (m, 2H), 6.31 (bd, 1H), 7.10–7.27 (m, 15H), 7.34 (m, 1H), 7.58 (m, 1H), 8.50 (m, 2H). MS (DCI/NH$_3$) m/e 520 (M+H)$^+$.

EXAMPLE 180

(2S,3S,5S)-2-[(Benzyloxycarbonyl)amino]-5-[N-{(3-pyridyl)methyloxycarbonyl}amino]-3-hydroxy-1,6-diphenyl Hexane To the product of Example 179A (76 mg, 0.1814 mmol) dissolved in methylene chloride (2 mL) was added N-[benzyloxycarbonyl)oxy]succinimide (68 mg, 0.272 mmol). The reaction mixture was stirred overnight at room temperature and then concentrated under reduced pressure. The residue obtained was chromatographed on silica gel eluting with methanol in methylene chloride (0%, 2%, 5%) to afford the title compound. $^1$H NMR (DMSO-$d_6$, 300 MHz) δ 1.51 (m, 2H), 2.54–2.75 (m, 4H), 3.57 (m, 1H), 3.87 (m, 2H), 4.68 (m, 1H), 4.72–4.90 (m, 1H), 4.96 (m, 4H), 6.90 (d, 1H), 7.00–7.38 (m, 18H), 7.60 m, 1H), 8.50 (m, 2H). MS (DCI/NH$_3$) m/e 554 (M+H)$^+$.

EXAMPLE 181

(2S,3S,5S)-5-[(tert-Butyloxycarbonyl)amino]-2-[N-{(3-pyridyl)methyloxycarbonyl}amino]-3-hydroxy-1,6-diphenyl Hexane The compound resulting from isolation of the regioisomer in Example 179A (80 mg, 0.191 mmol) was reacted by the procedure described in Example 179B to give crude material. Chromatography on silica gel eluting with methanol in methylene chloride (0%, 2%, 5%) afforded the title compound (87 mg, 88%). $^1$H NMR (DMSO-$d_6$, 300 MHz) δ 1.30 (s, 9H), 1.46 (m, 2H), 2.53–2.78 (m, 4H), 3.56 (m, 1H), 3.86 (m, 2H), 4.63 (bd, 1H), 4.83–5.03 (m, 3H), 6.63 (bd, 1H), 6.90 (bd, 1H), 7.00–7.27 (m, 14H), 7.34 (m, 2H), 7.59 (m, 1H), 8.49 (m, 2H). MS (DCI/NH$_3$) m/e 520 (M+H)$^+$.

EXAMPLE 182

(2S,3S,5S)-5-[(Benzyloxycarbonyl)amino]-2-[N-{(3-pyridyl)methyloxycarbonyl}amino]-3-hydroxy-1,6-diphenyl Hexane The compound resulting from isolation of the regioisomer in Example 179A (80 mg, 0.191 mmol) was reacted with N-[benzyloxycarbonyl)oxy]succinimide (71 mg, 0.286 mmol) by the procedure described in Example 180 to give, after column chromatography on silica gel, the title compound (89.3 mg, 85%). $^1$H NMR (DMSO-$d_6$, 300 MHz) δ 1.50 (m, 2H), 2.53–2.74 (m, 6H), 3.57 (m, 1H), 3.87 (m, 2H), 4.68 (m, 1H), 4.87 (m, 5H), 6.94 (bd, 1H), 7.00–7.37 (m, 18H), 7.60 (m, 1H), 8.50 (m, 2H). MS (DCI/NH$_3$) m/e 554 (M+H)$^+$.

EXAMPLE 183

(2S,3S,5S)-2,5-Di[N-{[(2-methylpyridin-5-yl)methyl]oxycarbonyl}amino]-3-hydroxy-1,6-diphenyl Hexane 2-Methylpyridine-5-carbinol (246 mg, 2.0 mmol) was converted to the 4-nitrophenyl carbonate by the procedure described in Example 175A. The crude material was chromatographed on a silica gel column eluting with a gradient of ethyl acetate in hexane (50%,90%) to give the carbonate. The 300 MHz $^1$H NMR spectrum was found to be consistent with the proposed structure.

The compound resulting from Example 1E (93 mg, 0.327 mmol) was reacted with the above carbonate (282 mg, 0.981 mmol) in dimethylformamide (0.60 mL) overnight at room temperature. The reaction mixture was concentrated under reduced pressure and the residue obtained chromatographed on silica gel eluting with a gradient of methanol in methylene chloride (2%,5%) to afford the title compound (103 mg, 54%). $^1$H NMR (DMSO-$d_6$, 300 MHz) δ 1.47 (m, 2H), 2.43 (bd, 6H), 2.53–2.74 (m, 4H), 3.52–3.60 (m, 2H), 3.87 (m, 2H), 4.67 (bd, 1H), 4.68–4.83 (m, 1H), 4.91 (bd, 4H), 6.89 (bd, 1H), 7.00–7.38 (m, 14H), 7.49 (d of d, 2H), 8.35 (m, 2H). MS (DCI/NH$_3$) m/e 583 (M+H)$^+$.

EXAMPLE 184

(2S,3S,5S)-2,5-Di[N-{[2-(3-pyridyl)propan-2-yl]oxycarbonyl}amino]-3-hydroxy-1,6-diphenyl Hexane 3-(2-Hydroxypropan-2-yl)pyridine (57 mg, 0.416 mmol) was converted to the 4-nitrophenyl carbonate by the procedure described in Example 175A. The crude residue was chromatographed on silica gel eluting with 50% ethyl acetate in hexane to afford the carbonate. The 300 MHz $^1$H NMR spectrum was found to be consistent with the proposed structure.

The compound resulting from Example 1E (88 mg, 0.31 mmol) was reacted with the above carbonate (281 mg, 0.93 mmol) in dimethylformamide (0.60 mL) overnight at room temperature. The reaction mixture was concentrated under reduced pressure and the residue obtained chromatographed on silica gel eluting with a gradient of methanol in methylene chloride (2%,5%,10%) to afford the title compound (109 mg). $^1$H NMR (DMSO-$d_6$, 300 MHz) δ 1.34–1.69 (m, 8H), 2.43–2.85 (m, 4H), 3.49 (m, 2H), 3.71 (m, 3H), 4.57 (d, 1H), 6.72 (bd, 1H), 6.86–7.32 (m, 14H), 7.49 (m, 2H), 8.36 (m, 2H), 8.51 (m, 2H). MS (DCI/NH$_3$) m/e 611 (M+H)$^+$.

EXAMPLE 185

(2S,3R,4R,5S)-1,6-Di(propylamino)-2,5-di[N-(N-Cbz-Valyl)amino]-3,4-dihydroxy Hexane

A. (2S,3R,4R,5S)-2,5-Di[N-(N-Cbz-Valyl)amino]-1,6-di(propylamino)-3,4-O-isopropylidene Hexane To the compound resulting from Example 186A (580 mg, 0.892 mmol) cooled in an ice bath was added n-propylamino (0.80 mL, 9.0 mmol). The reaction mixture was allowed to gradually warm to room temperature and then concentrated under reduced pressure. The crude product was chromatographed on silica gel eluting with a gradient of methanol in methylene chloride (5%,10%) to afford the title compound (316 mg, 46%).

B. (2S,3R,4R,5S)-1,6-Di(propylamino)-2,5-di[N-(N-Cbz-Valyl)amino]-3,4-dihydroxy Hexane The compound resulting from Example 185A (100 mg) was treated with 90% trifluoroacetic acid in water (3 mL) for 2.5 days at room temperature. The reaction mixture was concentrated under reduced pressure and the residue obtained treated with concentrated ammonium hydroxide and extracted with methylene chloride. The combined organic extracts were washed with brine, dried over magnesium sulfate and concentrated under reduced pressure. The residue obtained was chromatographed on silica gel eluting with a gradient of methanol in methylene chloride (5%,10%,20%) containing 0.5% ammonium hydroxide to afford the title compound (30 mg). $^1$H NMR (CD$_3$OD, 300 MHz) δ 0.91 (t, 6H), 0.99 (d, 12H), 1.50 (m, 6H), 2.06 (m, 3H), 2.50–2.84 (m, 8H), 2.97 (m, 3H), 3.85 (bd, 2H), 4.49 (m, 2H), 7.34 (m, 10H). MS (DCI/NH3) m/e 729 (M+H)$^+$.

EXAMPLE 186

(2S,3R,4R,5S)-1,6-Di(morpholin-1-yl)-2,5-di[N-(N-Cbz-Valyl)amino]-3,4-dihydroxy Hexane

A. 1,2-Di[N-(N-Cbz-Valyl)aziridin-2-yl]-1,2-O-isopropylidene Ethane

To 1,2-di(aziridin-2-yl)-1,2-isopropylidine ethane (2.5 g) and Z-Valine (3.51 g, 0.014 mmol) dissolved in tetrahydrofuran (30 mL) and cooled in an ice bath was added 1-ethyl-3-(3'-dimethylamino)-propylcarbodiimide (EDAC) (2.684 g, 0.014 mmol) followed by triethylamino (1.95 mL). The reaction mixture was allowed to warm to room temperature and stirred overnight. The mixture was diluted with ethyl acetate and washed with saturated sodium bicarbonate solution until the washes were colorless. The organic phase was dried over magnesium sulfate and concentrated under reduced pressure. The residue obtained was chromatographed on silica gel eluting with 40% ethyl acetate in hexane to afford the title compound (1.324 g).

B. (2S,3R,4R,5S)-2,5-Di[N-(N-Cbz-Valyl)amino]-3,4-O-isopropylidene-1,6-di(morpholin-1-yl Hexane The compound resulting from Example 186A (750 mg, 1.154 mmol) was treated with morpholine (2.0 mL) in an ice bath. The reaction mixture was allowed to gradually warm to room temperature and stirred overnight. The excess amino was removed under reduced pressure and the residue obtained was chromatographed on silica gel eluting with 2% methanol in methylene chloride to afford the title compound (677 mg).

C. (2S,3R,4R,5S)-1,6-Di(morpholin-1-yl)-2,5-di[N-(N-Cbz-Valyl)amino]-3,4-dihydroxy Hexane The compound resulting from Example 186B (160 mg) was treated with 90% trifluoroacetic acid in water (3 mL) at room temperature for 2 days and then concentrated under reduced pressure. Unreacted starting material remained, so 90% trifluoroacetic acid in water (4 mL) was added and the reaction mixture was warmed at 35° C. overnight. The reaction mixture was then concentrated under reduced pressure and the residue obtained dissolved in methylene chloride, treated with ammonium chloride, washed with saturated sodium bicarbonate solution and brine, dried over magnesium sulfate, and concentrated under reduced pressure. The residue obtained was chromatographed on silica gel eluting with 10% methanol in methylene chloride containing 0.5% ammonium hydroxide to afford the title compound (67 mg). $^1$H NMR (CD$_3$OD, 300 MHz) δ 0.97 (m, 12H), 2.13 (m, 2H), 2.38 (m, 6H), 2.52 (m, 6H), 3.60 (m, 8H), 3.96 (bd, 2H), 4.41 (m, 2H), 7.33 (m, 10H). MS (DCI/NH3) m/e 785 (M+H)$^+$.

EXAMPLE 187

(2S,3R,4R,5S)-1,6-Di(imidazol-1-yl)-2,5-di[N-(N-Cbz-Valyl)amino]-3,4-dihydroxy Hexane The compound resulting from Example 186A (330 mg, 0.508 mmol) was treated with imidazole (2.761 g, 0.0406 mmol) in dimethyformamide (4 mL) at 100° C. for 3.5 hours. The solution was cooled to room temperature and diluted with methylene chloride, washed with water, dried over magnesium sulfate, and concentrated under reduced pressure. The residue obtained was chromatographed on silica gel eluting with a gradient of methanol in methylene chloride (5%,10%) containing 0.5% ammonium hydroxide. The compound obtained was heated at 60° C. under vacuum to remove any residual imidazole to afford the title compound (258 mg, 65%).

The above compound (250 mg, 0.318 mmol) was warmed in 2N hydrochloric acid (8 mL) at 80° C. for 2 hours. The reaction mixture was concentrated under reduced pressure and chased with methanol and ethanol. The residue obtained was dissolved in chloroform, treated with ammonium hydroxide (2 mL), and the organic phase separated. The organic phase was washed with brine, dried over magnesium sulfate, and concentrated under reduced pressure to afford crude material. Chromatography on silica gel eluting with a gradient of methanol in methylene chloride (5%,10%) containing 0.5% ammmonium hydroxide afforded the title compound (101.5 mg). $^1$H NMR (DMSO-d$_6$, 300 MHz) δ 0.73 (m, 12H), 1.87 (m, 2H), 3.84 (m, 2H), 3.87–4.08 (m, 4H), 4.56 (m, 2H), 5.06 (q, 4H), 5.11 (m, 2H), 6.80 (bs, 2H), 7.05 (m, 2H), 7.14 (bd, 2H), 7.33 (m, 2H), 7.39 (m, 8H), 7.53 (m, 2H), 7.66 (bd, 2H). MS (FAB) m/e 747 (M+H)$^+$.

EXAMPLE 188

(2S,3R,4R,5S)-1,6-Diphenylamino-2,5-di[N-(N-Cbz-Valyl)amino]-3,4-dihydroxy Hexane The compound resulting from Example 186A (514 mg, 0.791 mmol) and aniline (3.725 g, 40 mmol) were heated in methylformamide (10 mL) in a 100° C. oil bath for 22 hours. The solvent was removed under reduced pressure and the residue obtained chromatographed on silica gel eluting with methylene chloride followed by a gradient of methanol in methylene chloride (1%,2%) to afford a residue which was rechromatographed on silica gel eluting with 30% ethyl acetate in methylene chloride to afford 1,6-diphenyl-2,5-di [N-(N-Cbz-Valyl)amino]-3-O,4-O-isopropylidene hexane (300 mg).

This compound (239 mg, 0.256 mmol) was treated with 2N hydrochloric acid (10 mL) in methanol (5 mL) at 50° C. for 2.5 hours. The solvent was removed under reduced pressure and the residue obtained dissolved in chloroform, treated with concentrated ammonium hydroxide, washed with water and brine, dried over magnesium sulfate, and concentrated under reduced pressure. The residue obtained was chromatographed on silica gel eluting with a gradient of methanol in methylene chloride. (2%,5%) to afford the title compound (142 mg). $^1$H NMR (DMSO-d$_6$, 300 MHz) δ 0.84 (d of d, 12H), 1.98 (m, 2H), 3.01 (m, 2H), 3.14 (m, 2H), 3.47 (bs, 2H), 3.91 (m, 2H), 4.27 (m, 2H), 4.89 (bs, 1H), 5.06 (d of d, 6H), 6.53 (m, 7H), 7.04 (m, 4H), 7.36 (m, 12H), 7.66 (bd, 2H). MS (DCI/NH$_3$) m/e 797 (M+H)$^+$.

EXAMPLE 189

2(S),5(S)-diamino-1,6-diphenyl-3,3-difluoro-4(R)-hydroxyhexane

A. Ethyl 4(S)-((t-butyloxycarbonyl)amino-5-phenyl-2,2-difluoro-3(R)-hydroxypentanoate To a solution of 9.6 gm of Boc-L phenylalaninal in 100 ml of THF was added 10 gm of zinc dust. To this sonicated mixture was added over 1.5 hours a total of 10 ml of ethyl bromidifluoroacetate. The reaction mixture was filtered through celite and concentrated. The residual oil was dissolved in ethyl acetate and washed with 10% KHSO$_4$. The combined organic layer was washed with brine, dried and concentrated. The mixture of 3(R) and 3(S) isomers were purified by HPLC using 10% EtOAc in hexane as eluting solvent to provide 4.1 gm of pure 3 (R) isomer. m.p. 137°–139° C.

B. 2-Oxazolidinone Derivative of Ethyl 4(S)-Amino-5-phenyl-2,2-difluoro-3(R)-hydroxypentanoate To 26.7 mmole of the resultant product from 189A was added 30 ml of 4N HCl in dioxane. The solution was stirred at RT for 1 hour. The solvent was removed in vacuo and the hydrochloride was dried on high vacuum for 18 hours. To this hydrochloride was added at 0° C. 300 ml of dichloromethane and 4.1 ml of triethylamino, then 2.84 gm of triphosgene. After 1 hour at 0° C., 8.2 ml of TEA and 0.41 gm of triphosgene were added. After 1.5 hours at 0° C. and 0.5 hours at RT, the reaction mixture was washed with 1N HCl and extracted with dochloromethane. The combined organic layer was washed with brine and dried and concentrated.. Silica gel column chromotography (5% EtOAc in CH$_2$CL$_2$) provided 6.1 gm (76%) of the desired product.

C. 2-Oxazolidinone Derivative of N,O-dimethylhydroxy-amide of 4(S)-amino-5-phenyl-2,2-difluoro-3(R)-hydroxypententanoic Acid To a solution of 10.86 gm of the resultant compound from Example 189B in 200 ml of dioxane and 100 ml of water was added 2.28 gm of lithium hydroxide. The solution was stirred at RT for 0.5 hr and the solvent was removed in vacuo. The residual oil was dissolved in EtOAc and acidified with 1N HCl; the aqueous phase was extracted with EtOAc. The EtOAc solution was washed with brine, dried and concentrated to give 9.54 gm of carboxylic acid. To 5.93 gm of this acid in 110 ml of dry DMF was added 6.42 gm of EDAC, 2.72 gm of N,O-dimethyl hydroxylamino hydrochloride and 9.1 ml of TEA. The reaction mixture was stirred at RT overnight, filtered and concentrated in vacuo. The residue was dissolved in EtOAc and acidified with 1N HCl. The aqueous phase was extracted with EtOAc; the combined organic layer was dried concentrated. The crude product was purified by silica gel column chromotography to give 6.34 gm of desired product (94%).

D. 4(S)-Benzyl-5(R)-(3'(3',3'-difluoro-2'-oxo-1'-phenyl))propyl-2-oxazolidinone To a solution of 6.45 gm of the resultant compound from Example 189C in 200 ml of dry THF at −78° C. was added 30.8 ml of a 2M solution of benzylmagnesium chloride. The reaction mixture was stirred for 1 hour at −78° C., 1 hour at −20° C., finally 1 hour at 0° C. The reaction was quenched with satd. NH$_4$Cl solution, concentrated and extracted with EtOAc. The crude product was purified by silica gel column chromatography (5% EtOAc in CH$_2$Cl$_2$) to give 6.59 gm of desired product (93%).

E. Oxime Derivative of 4(S)-Benzyl-5(R)-(3')3',3'-difluoro-2'-oxo-1'-phenyl))-propyl-2-oxazolidinone To a solution of 0.6 gm of the resultant product from Example 189D in 15 ml of ethanol was added 0.24 gm of hydroxylamino hydrochloride and 0.42 ml of pyridine. The solution was refluxed for 1 hour, cooled to RT and concentrated. The residue was taken up in EtOAc and washed with 1N HCl and then satd. brine, dried and concentrated. Purification by silica gel column chromatography (20% EtOAc in CH$_2$Cl$_2$) provided 0.64 gm of desired product (98%).

F. 4(S)-Benzyl-5(R)-(3'(3',3'-difluoro-2'(S)-amino-1'-phenyl))-propyl-2-ozaxolidinone To a solution of 2 gm of oxime from Example 189E in 100 ml each of EtOAc/EtOH was added 25 gm of Raney Nickel Catalyst. The mixture was shaken in a bomb at 1500 psi of hydrogen for 2 days. Filtration and concentration in vacuo provided a mixture of 2'(S)- and 2'(R)-amino which was separated by silica gel column chromatography (1:1 EtOAc/CH$_2$Cl$_2$) to provide 0.59 gm of 2'(S)-amino and 0.83 gm of 2'(R)-amino. The X-ray crystallography of a single crystal of the 2'(R)-amino establish the absolute stereochemistry.

G. 2(S),5(S)-diamino-1,6-diphenyl-3,3-difluoro-4(R)-hydroxyhexane

To a solution of 1.03 gm of the resultant compound from Example 189F in 60 ml of dioxane and 60 ml of water was added 2.5 gm of barium hydroxide. The reaction mixture was heated to reflux for 4 hours, cooled to RT, filtered and concentrated. The aqueous solution was extracted with ethyl acetate (3×100 ml). dried with anhydrous Na$_2$SO$_4$ and concentrated to give 930 mg of the desired product. $^1$H NMR (CDCl$_3$): δ 1.3–1.5 (brm, 4H), 2.50 (m, 1H), 2.70 (m, 1H), 2.90 (m, 1H), 3.15 (m, 1H), 3.45 (m, 1H), 3.72 (m, 1H). Mass spectrum: (M+H)$^+$=321.

EXAMPLE 190

2(S),5(S)-Bis-(Cbz-Valinyl)amino-1,6-diphenyl-3,3-difluoro-4-oxo-hexane

Using the resultant product from Example 189G, and coupling to Cbz-Valine using the carbodiimide procedure, followed by oxidation using sodium dichromate in acetic acid (Synthesis, 466, (1989)) provided the desired product. $^1$H NMR (DMSO-d$_6$): δ 0.62 (d, 3H), 0.65 (d, 3H), 0.70 (d, 3H), 0.72 (d, 3H), 0.78 (d, 3H), 1.80 (m, 2H), 3.80 (m, 2H), 5.0 (s, 4H), 7.10–7.40 (m, 20H). Mass spectrum: (M+H)= 785.

EXAMPLE 191

2(S),5(S)-Bis-(2-pyridyl-methoxy-carbonyl-valinyl)amino-1,6-diphenyl-3,3-difluoro-4-oxo-hexane Using the resultant compound from Example 189G and coupling to 2-pyridyl-methoxy-carbonyl-valine using the carbodiimide procedure, followed by oxidation with sodium dichromate in acetic acid provided the desired product. $^1$H NMR (DMSO-d$_6$): δ 0.70 (d, 3H), 0.78 (d, 3H), 0.80 (d, 6H), 5.08 (s, 4H), 7.10–7.30 (m, 14H), 7.70 (m, 1H), 8.20 (m, 1H), 8.50 (m, 1H), 8.60 (m, 1H). Mass spectrum: (M+H)$^+$=787.

EXAMPLE 192

2(S),5(S)-Bis(N-(N-methyl-N((2-pyridyl)methyl)amino)carbonyl)-valinyl-amino)-1,6-diphenyl-3,3-difluoro-4(R)-hydroxyhexane Using the resultant compound from Example 189G and coupling to (N-(N-methyl-N-((2-pyridyl)methyl)amino)carbonyl-valine using the carbodiimide procedure provided the desired product in 68% yield. $^1$H NMR (DMSO-d$_6$): δ 0.68 (d, 3H), 0.70 (m, 9H), 1.80 (m, 1H), 1.96 (m, 1H), 2.88 (s, 3H), 2.90 (s, 3H), 5.90 (d, 1H), 6.02 (d, 1H), 7.20–7.30 (m, 14H), 7.50 (d, 1H), 7.76 (m, 2H), 7.90 (d, 1H), 8.50 (m, 2H). Mass spectrum: (M+H)$^+$=815.

EXAMPLE 193

2(S),5(S)-Bis-(N-(N-Methyl-N-((2-pyridyl)methyl)amino)carbonyl)-valinyl-amino)-1,6-diphenyl-3,3-difluoro-4-oxo-hexane Oxidation of the resultant product from Example 192 using sodium dichromate in acetic acid provided the desired product in 60% yield. $^1$H NMR (DMSO-d$_6$): δ 0.63 (d, 3H), 0.70 (d, 3H), 0.75 (d, 3H), 0.77 (d, 3H), 2.88 (s, 3H), 2.90 (s, 3H), 6.0 (d, 1H), 6.20 (d, 1H), 7.15–7.30 (m, 14H), 7.70 (m, 2H), 8.20 (d, 1H), 8.50 (m, 2H), 8.60 (d, 1H). Mass spectrum: (M+H)$^+$=813.

EXAMPLE 194

2(S),5(S)-Bis-(N-(3-(2-pyridyl)propenyl)-valinyl-amino)-1,6-diphenyl-3,3-difluoro-4(R)-hydroxyhexane Using the resultant product from Example 189G and coupling to (N-(3-(2-pyridyl)propenoyl)-valine using the carbodiimide procedure provided the desired product in 80% yield. $^1$H NMR (DMSO-d$_6$): δ 0.70–0.80 (m, 12H), 1.85 (m, 1H), 2.00 (m, 1H), 2.60–2.95 (m, 4H), 3.85 (m, 1H), 4.30 (m, 1H), 4.60 (m, 1H), 4.80 (m, 1H), 7.10–7.60 (m, 18H), 7.80 (m, 2H), 8.05–8.20 (m, 3H), 8.62 (m, 2H). Mass spectrum: (M+H)$^+$=781.

EXAMPLE 195

2(S),5(S)-Bis-(N-(3-(2-pyridyl)propanoyl)-valinyl-amino)-1,6-diphenyl-3,3-difluoro-4(R)-hydroxyhexane Hydrogenation of the resultant product from Example 194 using 10% Pd/c as catalyst and methanol as solvent provided the desired product in quantitative yield. $^1$H NMR (DMSO-d$_6$): δ 0.62–0.70 (m, 12H), 1.75 (m, 1H), 1.95 (m, 1H), 2.80–2.95 (m, 12H), 3.80 (m, 1H), 4.10 (m, 1H), 4.60 (m, 1H), 4.80 (m, 1H), 6.02 (d, 1H), 7.18–7.22 (m, 14H), 7.46 (d, 1H), 7.65 (m, 2H), 7.75 (d, 1H), 8.00 (d, 1H), 8.45 (m, 1H). Mass spectrum: (M+H)$^+$=785.

EXAMPLE 196

2(S),5(S)-Bis-(N-(3-(2-pyridyl)propanoyl)-valinyl-amino)-1,6-diphenyl-3,3-difluoro-4-oxo-hexane Oxidation of the resultant product from Example 195 using sodium dichromate in acetic acid provided the desired product in 40% yield. $^1$H NMR (DMSO-d$_6$): δ 0.70–0.80 (m, 12H), 7.15–7.30 (m, 12H), 7.60 (m, 2H), 7.80 (d, 1H), 8.30 (d, 1H), 8.45 (m, 2H), 8.60 (d, 1H). Mass spectrum: (M+H)$^+$=783.

EXAMPLE 197

N-(2-(4-Pyridyl)ethanesulfonyl)valine

To 1 gm of valine benzyl ester p-toluene-sulfonic acid salt in 40 ml of CH$_2$Cl$_2$ at 0° C. was added 1.12 gm of 4-pyridylsulfonyl chloride (U.S. Pat. No. 431,504 (1982)) and 1.9 ml of triethylamino. After 1 hour, the solution was washed with water and extracted with CH$_2$Cl$_2$ (2×100 ml), dried and concentrated. Silica gel column chromotography provided 4-pyridyl-ethanesulfonyl-valine benzyl ester which was treated with 10% Pd/C in methanol under hydrogen atmosphere to provide the desired product in 85% overall yeild.

EXAMPLE 198

N-(2-(2-Pyridyl)ethanesulfonyl)valine

Using the procedure of Example 197, but replacing 4-pyridylethanesulfonyl chloride with 2-pyridylethanesulfonyl chloride provided the desired product in 82% overall yield.

EXAMPLE 199

2(S),5(S)-Bis-(N-(4-pyridylethanesulfonyl-valine)-amino)-1,6-diphenyl-3,3-difluoro-4(R)-hydroxyhexane Using the resultant product from Example 189G, and coupling to 4-pyridylethanesulfonyl-valine using the carbodiimide procedure provided the desired product in 70% yield. $^1$H NMR (DMSO-d$_6$): δ 0.80 (m, 12H), 1.90–2.10 (m, 2H), 2.30–3.00 (m, 12H), 3.60 (m, 1H), 3.70 (m, 1H), 3.98 (m, 1H), 4.80 (m, 1H), 8.00 (m, 1H), 6.10 (d, 1H), 6.80–7.20 (m, 14H), 7.40 (d, 1H), 7.90 (d, 1H), 8.20 (d, 1H), 8.45 (m, 4H). Mass spectrum: (M+H)$^+$=857.

EXAMPLE 200

2(S),5(S)-Bis-(N-(4-pyridylethanesulfonyl-valine)-amino)-1,6-diphenyl-3,3-difluoro-4-oxo-hexane Oxidation of the resultant product from Example 199 using the sodium dichromate in acetic acid provided the desired product in 60% yield. $^1$H NMR (DMSO-$d_6$): δ 0.90 (m, 12H), 2.00 (m, 1H), 2.20 (m, 1H), 6.80–7.30 (m, 14H), 7.80 (d, 1H), 7.70 (d, 1H), 8.38–8.52 (m, 4H), 8.40 (d, 1H). Mass spectrum: (M+H)=855.

EXAMPLE 201

2(S),5(S)-Bis-(N-(2-pyridylethanesulfonyl-valine)-amino)-1,6-diphenyl-3,3-difluoro-4 (R)-hydroxyhexane Using the resultant product from Example 189G, and coupling to 4-pyridylethanesulfonyl-valine provided the desired product in 75% yield. $^1$H NMR (DMSO-$d_6$): δ 0.80 (m, 12H), 1.90–2.00 (m, 1H), 2.45–3.10 (m, 12H), 3.60 (m, 1H), 3.70 (m, 1H), 3.80 (m, 1H), 4.70 (m, 1H), 4.90 (m, 1H), 6.12 (d, 1H), 6.90–7.30 (m, 14H), 7.70 (m, 2H), 7.88 (d, 1H), 8.40–8.50 (m, 2H). Mass spectrum: (M+H)$^+$=857.

EXAMPLE 202

2(S),5(S)-Bis(N-(2-pyridylethanesulfonyl-valine)-amino)-1,6-diphenyl-3,3-difluoro-4-oxo-hexane Oxidation of the resultant product from Example 201 using sodium dichromate in acetic acid provided the desired product provided the desired product in 53% yield. $^1$H NMR (DMSO-$d_6$): δ 0.84 (m, 12H), 1.90 (m, 2H), 2.40–3.10 (m, 12H), 3.65 (m, 2H), 4.95–5.10 (m, 3H), 6.90–7.25 (m, 15H), 7.55 (d, 1H), 7.75 (m, 2H), 8.46 (m, 2H), 8.40 (d, 1H). Mass spectrum: (M+H)$^+$=855.

EXAMPLE 203

2(S),5(S)-Bis-(N-(4-pyridylethanesulfonyl-valinyl)-amino)-1,6-diphenyl-3(R),4(R)-dihydroxy-hexane Coupling of 4-pyridylethanesulfonyl-valine to the resultant product from Example 4A provided the desired product in 51% yield. $^1$H NMR (DMSO-$d_6$): δ 0.84 (m, 12H), 1.96 (m, 2H), 2.25 (m, 2H), 2.80–3.00 (m, 12H), 3.70 (m, 2H), 4.80 (m, 2H), 6.80–7.20 (m, 14H), 7.80 (d, 2H), 8.45 (m, 4H). Mass spectrum: (M+H)$^+$=837.

EXAMPLE 204

2(S),5(S)-Bis-(N-(4-pyridylethanesulfonyl-valinyl)-amino)-1,6-diphenyl-3(S)-hydroxyhexane Coupling of 4-pyridylethanesulfonyl-valine to the resultant product from Example 1E provided the desired product in 78% yield. $^1$H NMR (DMSO-$d_6$): δ 0.88 (m, 12H), 4.30 (m, 2H), 4.95 (d, 1H), 6.90–7.20 (m, 14H), 7.25 (d, 1H), 7.32 (d, 1H), 7.30 (d, 1H), 7.90 (d, 1H), 8.46 (m, 2H). Mass spectrum: (M+H)$^+$=821.

EXAMPLE 205

2(S),5(S)-Bis-(N-(2-pyridylethanesulfonyl-valinyll)-amino)-1,6-diphenyl-3(S)-hydroxy-hexane Coupling of 2-pyridylethanesulfonyl-valine to the resultant product from Example 1E with the carbodiimide procedure provided the desired product in 88% yield. $^1$H NMR (DMSO-$d_6$): δ 0.82 (m, 12H), 1.85 (m, 2H), 2.60–3.10 (m, 12H), 3.50 (m, 1H), 3.60 (m, 1H), 4.15–4.30 (m, 2H), 4.92 (d, 1H), 6.90–7.25 (m, 14H), 7.70 (m, 1H), 7.75 (d, 1H), 7.80 (d, 1H), 8.45 (m, 2H). Mass spectrum: (M+H)$^+$=821.

EXAMPLE 206

2(S),5(S)-Bis-(N-(2-pyridylethanesulfonyl-valinyl)-amino)-1,6-diphenyl-3(R),4(R)-dihydroxyhexane Coupling of 2-pyridylethanesulfonyl-valine to the resultant product from Example 4A using the carbodiimide procedure provided the desired product in 70% yield. $^1$H NMR (DMSO-$d_6$): δ 0.75 (d, 6H), 0.80 (d, 6H), 1.88 (m, 2H), 2.55–3.10 (m, 12H), 3.60 (m, 2H), 4.65–4.80 (m, 4H), 6.90–7.35 (m, 14H), 7.70 (m, 4H), 8.45 (m, 2H). Mass spectrum: (M+H)$^+$=837.

EXAMPLE 207

2(S),5(S)-Bis-(N-(4-pyridylethanesulfonyl-valine)-amino)-1,6-diphenyl-3(R),4(S)-dihydroxyhexane Coupling of 4 -pyridylethanesulfonyl-valine to the resultant product from Example 13D using the carbodiimide procedure provided the desired product in 65% yield. $^1$H NMR (DMSO-$d_6$): δ 0.80 (m, 12H), 1.90 (m, 1H), 2.10 (m, 1H), 2.30–3.00 (m, 12H), 3.60 (m, 1H), 3.70 (m, 1H), 4.30 (m, 1H), 4.50 (m, 1H), 4.72 (d, 1H), 5.50 (d, 1H), 6.85–7.20 (m, 14H), 7.40 (d, 1H), 7.90 (d, 1H), 8.20 (d, 1H), 8.45 (m, 4H). Mass spectrum: (M+H)$^+$=837.

EXAMPLE 208

2(S),5(S)-Bis-(N-(4-pyridylethanesulfonyl-valinyl)-amino)-1,6-diphenyl-3(S),4(S)-dihydrozyhexane Coupling of 4-pyridylethanesulfonyl-valine to the resultant product from Example 11C using the carbodiimide procedure provided the desired product in 70% yield. $^1$H NMR (DMSO-$d_6$): δ 0.83 (d, 6H), 0.90 (d, 6H), 1.95 (m, 2H), 2.40–3.00 (m, 12H), 3.45 (m, 2H), 3.65 (m, 2H), 4.20 (m, 2H), 4.90 (d, 2H), 6.90–7.20 (m, 14H), 7.40 (d, 2H), 8.20 (d, 2H), 8.40 (m, 4H). Mass spectrum: (M+H)$^+$=837.

EXAMPLE 209

2(S),5(S)-Bis-(N-(2-pyridylethanesulfonyl-valinyl)-amino)-1,6-diphenyl-3(R),4(S)-dihydroxyhexane Coupling of 2-pyridylethanesulfonyl-valine to the resultant product from Example 13D using the carbodiimide procedure provided the desired product in 60% yield. $^1$H NMR (DMSO-$d_6$): δ 0.73 (d, 3H), 0.80 (d, 6H), 0.85 (d, 3H), 1.85 (m, 2H), 2.55–3.05 (m, 12H), 3.88 (d, 3H), 3.70 (m, 1H), 4.35 (m, 1H), 4.45 (m, 1H), 4.80 (d, 1H), 5.37 (d, 1H), 6.85–7.30 (m, 14H), 7.70 (m, 2H), 7.80 (d, 1H), 8.10 (d, 1H), 8.45 (m, 1H), 8.50 (m, 1H). Mass spectrum: (M+H)$^+$=837.

EXAMPLE 210

2(S),5(S)-Bis-(N-(2-pyridylethanesulfonyl-valinyl)-amino)-1,6-diphenyl-3(S),4(S)-dihydroxyhexane Coupling of 2-pyridylethanesulfonyl-valine to the resultant product from 11C using the carbodiimide procedure provided the desired product in 82% yield. $^1$H NMR (DMSO-$d_6$): δ 0.80 (m, 12H), 1.88 (m, 2H), 2.60–3.05 (m, 12H), 3.50–3.60 (m, 4H), 4.20 (m, 2H), 5.0 (d, 2H), 6.90–7.30 (m, 16H), 7.65 (m, 2H), 8.10 (d, 2H), 8.50 (m, 2H). Mass spectrum: $(M+H)^+$=837.

EXAMPLE 211

2(S),5(S)-Bis-(N-2-pyridylethanesulfonyl)-amino-1,6-diphenyl-3(S)-hydroxyhexane To a solution Of 100 mg of the resultant product from Example 1E in 3 ml of dichloromethane was added 0.108 ml of triethylamino and 0.186 gm of 2-pyridylethanesulfonyl chloride. After 0.5 hour at RT, the product was purified by silica gel column chromotography to provide the desired product in 35% yield. $^1$H NMR (CDCl$_3$): δ 1.70–2.00 (m, 4H), 2.70–3.20 (m, 10H), 3.65–3.95 (m, 3H), 5.00 (d, 1H), 5.18 (d, 1H), 7.00–7.28 (m, 14H), 7.60 (m, 2H), 8.50 (m, 2 H). Mass spectrum: $(M+H)^+$=623.

EXAMPLE 212

2(S),5(S)-Bis-(N-2-pyridylethanesulfonyl)amino-1,6-diphenyl-3,3-difluoro-4(R)-hydroxyhexane To a solution of 150 mg of the resultant product from Example 189G in 5 ml of dichloromethane was added 0.32 gm of triethylamino and 0.25 gm of 2-pyridylethanesulfonyl chloride. After workup and purification by silica gel column chromotography, 0.13 gm of desired product was obtained. $^1$H NMR (CDCl$_3$): δ 1.90 (m, 4H), 2.50–2.70 (m, 4H), 2.90–3.10 (m, 4H), 3.30 (m, 1H), 4.20–4.50 (m, 3H), 5.10 (d, 1H), 5.50 (d, 1H), 7.00–7.30 (m, 14H), 7.60 (m, 2H), 8.50 (m, 2H). Mass spectrum: $(M+H)^+$=659.

EXAMPLE 213

2(S),5(S)-Bis(N-2-pyridylethanesulfonyl)amino-1,6-diphenyl-3,3-difluoro-4-oxo-hexane Oxidation of the resultant product from Example 212 using sodium dichromate in acetic acid provided the desired product in 70% yield. $^1$H NMR (CDCl$_3$): δ 2.60–3.40 (m, 12H), 4.40–4.60 (m, 2H), 5 (m, 2H), 6.95–7.30 (m, 14H), 7.60 (m, 2H), 8.45–8.60 (m, 2H). Mass spectrum: $(M+H)^+$=657.

EXAMPLE 214

2(S),5(S)-Bis-(N-benzyloxycarbonyl)amino-1,6-diphenyl-3,3-difluoro-4(R)-hydroxyhexane To a solution of 30 mg of the resultant product from Example 189G in 1 ml of DMF was added 0.1 gm of Cbz-NOS. The solution was stirred at RT for 48 hours, concentrated in vacuo and purification by silica gel column chromotography provided 29 mg of desired product. $^1$H NMR (CDCl$_3$): δ 2.65 (m, 1H), 2.90 (m, 1H), 3.00 (m, 1H), 3.12 (m, 1H), 3.47 (m, 1H), 3.88 (m, 1H), 4.38 (m, 1H), 4.68 (m, 1H), 4.90 (m, 1H), 5.00 (s, 1H), 7.10–7.35 (m, 20H). Mass spectrum: $(M+H)^+$=589.

EXAMPLE 215

2(S),5(S)-Bis-(N-benzyloxycarbonyl)amino-1,6-diphenyl-3,3-difluoro-4(R)-hydroxyhexane Oxidation of the resultant product from Example 214 using sodium dichromate in acetic acid provided the desired compound in 80% yield. $^1$H NMR (CDCl$_3$): δ 2.70 (m, 1H), 2.90 (m, 1H), 3.15 (m, 1H), 3.28 (m, 1H), 4.70–5.15 (m, 8H), 7.10–7.40 (m, 20H). Mass spectrum: $(M+H)^+$=587.

EXAMPLE 216

2(S),5(S)-Bis-(N-3-pyridyl-methoxy-carbonyl)amino-1,6-diphenyl-3,3-difluoro-4(R)-hydroxyhexane To a solution of 150 mg of the resultant product from Example 189G in 1 ml of DMF was added 515 mg of the resultant product from Example 37A. After 48 hours at RT, solvent was removed in vacuo and purification by silica gel column chromotography provided the desired compound in 81% yield. $^1$H NMR (CDCl$_3$): δ 2.62 (m, 1H), 2.85–3.15 (m, 3H), 3.53 (m, 1H), 3.90 (m, 1H), 4.40 (m, 1H), 4.70–5.20 (m, 6H), 7.10–7.60 (m, 14H), 8.45–8.55 (m, 4H). Mass spectrum: $(M+H)^+$=591.

EXAMPLE 217

2(S),5(S)-Bis-(N-3-pyridyl-methoxy-carbonyl)amino-1,6-diphenyl-3,3-difluoro-4-oxo-hexane Oxidation of the resultant compound from Example 216 using sodium dichromate in acetic acid provided the desired product in 68% yield. $^1$H NMR (CDCl$_3$): δ 2.70 (m, 1H), 2.90 (m, 1H), 3.15 (m, 1H), 3.30 (m, 1H), 4.90–5.15 (m, 8H), 7.10–7.60 (m, 14H), 8.40–8.55 (m, 4H). Mass spectrum: $(M+H)^+$=588.

EXAMPLE 218

2(S),5(S)-Bis-(N-(p-nitrophenoxycarbonyl)-amino)-1,6-diphenyl-3(S)-trimethylsiloxy-hexane To a solution of 200 mg of the resultant product from Example 1E in 5 ml of dichloromethane was added at 0° C. 0.112 ml of TEA and 0.098 ml of trimethylsilyl chloride. After 30 minutes at 0° C., 0.215 ml of TEA and 0.3 gm of p-nitrophenylchloroformate was added. After 1 hour at 0° C., the solvent was removed in vacuo and the crude product purified by silica gel column chromatography provided 0.3 gm of desired product. $^1$H NMR (CDCl$_3$): δ 0.20 (s, 9H), 1.70 (m, 1H), 1.90 (m, 1H), 2.85 (m, 4H), 3.90 (m, 1H), 4.00 (m, 1H), 4.20 (m, 1H), 4.90 (d, 1H), 5.30 (d, 1H), 7.10–7.30 (m, 14H), 8.20 (m, 4H).

EXAMPLE 219

2(S),5(S)-Bis-(N-(3-pyridylmethylamino-carbonyl)-amino)-1,6-diphenyl-3(S)-hydroxyhexane To a solution of 87 mg of the resultant compound from Example 218 in 1 ml of DMF was added 0.028 ml of 3-aminomethylpyridine. After 18 hours, the solvent was removed in vacuo and the residue was dissolved in 1 ml of methanol and 0.05 ml of chlorotrimethylsilane was added. After 0.5 hour, the solvent was removed in vacuo, neutralized with sodium bicarbonate solution and extraction with ethyl acetate (2×25 ml). The organic solution was dried and concentrated. Purification by silica gel column chromotography provided 35 mg of desired product. 1H NMR (CD$_3$OD): δ 1.60 (t, 2H), 2.60–2.80 (m, 4H), 3.70 (m, 1H), 4.00 (m, 1H), 4.10 (m, 1H), 4.25–4.35 (m, 4H), 7.10–7.25 (m, 10H), 7.35 (m, 2H), 7.60 (m, 2H), 8.40 (m, 4H). Mass spectrum: (M+H)$^+$=553.

EXAMPLE 220

2(S),5(S)-Bis-(N-(N-methyl-N-3-pyridylmethyl)carbonyl-amino)-1,6-diphenyl-3(S)-hydroxyhexane Using the procedure described in Example 219, but replacing 3-aminomethylpyridine with N-methyl-3-aminomethylpyridine provided the desired product in 50% yield. $^1$H NMR (CDCl$_3$): δ 1.65 (m, 2H), 2.70 (s, 3H), 2.74 (s, 3H), 2.80–3.00 (m, 4H), 3.70 (m, 1H), 3.82 (m, 1H), 4.02 (m, 1H), 4.38–4.55 (m, 4H), 4.80 (d, 1H), 4.88 (d, 1H), 5.15 (d, 1H), 7.10–7.30 (m, 12H), 7.48 (m, 2H), 8.45 (m, 2H), 8.50 (m, 2H). Mass spectrum: (M+H)$^+$=581.

EXAMPLE 221

2(S)-Amino-5(S)-(N-(N-methyl-N-((2-pyridyl)methyl)amino)carbonyl)-valinyl-amino)-1,6-diphenyl-3,3-difluoro-4(R)-hydroxyhexane To a solution of 250 mg of the resultant compound from Example 189 in 5 ml of dry THF was added 440 mg of the resultant compound from Example 3F. After 3 hours at RT, the solvent was evaporated in vacuo and purification by silica gel column chromatography provided the desired coumpound in 70% yield. $^1$H NMR (CDCl$_3$): δ 0.90 (d, 3H), 0.96 (d, 3H), 2.20 (m, 1H), 2.60 (m, 1H), 2.85–3.05 (m, 2H), 3.00 (s, 3H), 3.20 (m, 2H), 3.80–3.90 (m, 1H), 4.20 (m, 1H), 4.46–4.05 (m, 3H), 6.05 (m, 1H), 6.76 (d, 1H), 7.10–7.30 (m, 12H), 7.70 (m, 1H), 8.52 (m, 1H). Mass spectrum: (M+H)$^+$=568.

EXAMPLE 222

2(S)-(N-(3-pyridylmethoxycarbonyl)amino-5(S)-(N-(N-methyl-N-((2-pyridyl)methyl)amino)carbonyl-valinyl-amino)-1,6-diphenyl-3,3-difluoro-4(R)-hydroxyhexane To a solution of 240 mg of the resultant compound from Example 221 in 2 ml of DMF was added 230 mg of the resultant compound from Example D-37A. After 72 hours, the solvent was removed in vacuo. Purification by silica gel column chromotography provided the desired compound in 90% yield. $^1$H NMR (CDCl$_3$): δ 0.86 (d, 3H), 0.95 (d, 3H), 2.22 (m, 1H), 2.60 (m, 1H), 2.95–3.20 (m, 3H), 2.96 (s, 3H), 3.90 (m, 1H), 4.05 (m, 1H), 4.40 (m, 1H), 4.46 (s, 2H), 4.65 (m, 1H), 4.83 (d, 1H), 5.00 (d, 1H), 6.85 (d, 1H), 7.10–7.30 (m, 14H), 7.40 (m, 1H), 7.70 (m, 1H), 8.45–8.55 (m, 3H). Mass spectrum: (M+H)$^+$=703.

EXAMPLE 223

2(S)-(N-(3-pyridylmethoxycarbonyl)amino-5(S)-(N-(N-methyl-N-((2-pyridyl)methyl)amino)carbonyl-valinyl-amino)-1, 6-diphenyl-3,3-difluoro-4-oxo-hexane Oxidation of the resultant compound from Example 222 using sodium dichromate in acetic acid provided the desired compound in 40% yield. $^1$H NMR (CDCl$_3$): δ 0.85 (d, 3H), 0.90 (d, 3H), 2.20 (m, 1H), 2.70–3.25 (m, 4H), 2.95 (s, 3H), 4.10 (m, 1H) 4.40 (s 2H) 4.80–5.00 (m, 2H), 5.20–5.30 (m, 2H), 6.80 (d, 1H), 7.10–7.25 (m, 13H), 7.45 (m, 1H), 7.70 (m, 1H) 8.45–8.50 (m, 3H). Mass spectrum: (M+H)$^+$=701.

EXAMPLE 224

2(S)-(Acetyl-amino-5(S)-(N-(N-methyl-N-(2-pyridyl)menhyl)amino)carbonyl-valinyl-amino)-1,6-diphenyl-3,3-difluoro-4(R)-hydroxyhexane To a solution of 100 mg of the reslultant compound from Example 221 in 2 ml of dry THF was added at 0° C. 0.037 ml of TEA and 0.014 ml of acetyl chloride. After 0.5 hour, solvent was evaporated in vacuo. Purification by silica gel column chromotography provided 87 mg of desired compound. $^1$H NMR (CDCl$_3$): δ 0.90 (d, 3H), 0.95 (d, 3H), 1.70 (s, 3H), 2.20 (m, 1H), 2.65 (m, 1H), 2.95–3.15 (m, 4H), 3.00 (s, 3H), 3.80 (m, 1H), 4.10 (m, 1H), 4.40 (m, 1H), 4.50 (s, 2H), 4.70 (m, 1H), 5.40 (d, 1H), 5.48 (d, 1H), 6.30 (m, 1H), 6.95 (d, 1H), 7.10–7.30 (m, 12H), 7.70 (m, 1H), 8.50 (m, 1H). Mass spectrum: (M+H)$^+$=610.

EXAMPLE 225

2(S)-(Acetyl-amino)-5(S)-(N-(N-methyl-N-(2-pyridyl)methyl)amino)carbonyl-valinyl-amino)-1,6-diphenyl-3,3-difluoro-4-oxo-hexane Oxidation of the resultant compound from Example 224 using sodium dichromate in acetic acid provided the desired compound in 40% yield. $^1$H NMR (CDCl$_3$): δ 0.86 (d, 3H), 0.90 (d, 3H), 1.80 (s, 3H), 2.20 (m, 1H), 2.70–3.30 (m, 4H), 2.98 (s, 3H), 4.10 (m, 1H), 4.40 (s, 2H), 5.05 (m, 1H), 5.23 (m, 1H), 5.70 (d, 1H), 6.40 (m, 1H), 6.80 (d, 1H), 7.10–7.30 (m, 12H), 7.70 (m, 1H), 8.46 (m, 1H) . Mass spectrum: (M+H)$^+$=608.

EXAMPLE 226

2(S)-(N-Methoxycarbonyl-amino)-5(S)-(N-(N-methyl-N-(2-methyl)amino)carbonyl-valinyl-amino)-1, 6-diphenyl-3,3-difluoro-4(R)-hydroxyhexane To a solution of 100 mg of the resultant compound from Example 221 in 2 ml of dry THF was added 0.043 ml of TEA and 0.030 ml of methylchloroformate. After 24 hours at RT, the solvent was removed in vacuo. Purification by silica gel column chromotography provided 52 mg of desired compound. $^1$H NMR (CDCl$_3$): δ 0.88 (d, 3H), 0.95 (d, 3H), 2.20 (m, 1H), 2.65–3.15 (m, 4H), 3.00 (s, 3H), 3.50 (s, 3H), 3.90 (m, 1H), 4.05 (m, 1H), 4.40 (m, 1H), 4.48 (s, 2H), 4.55 (m, 1H), 4.70 (m, 1H), 5.25 (d, 1H), 6.85 (m, 1H), 7.10–7.30 (m, 12H), 7.70 (m, 1H), 8.52 (m, 1H). Mass spectrum: (M+H)$^+$=626.

EXAMPLE 227

2(S)-(N-Methoxycarbonyl-amino)-5(S)-(N-(N-methyl-N-(2-methyl)amino)carbonyl-valinyl-amino)-1, 6-diphenyl-3,3-difluoro-4-oxo-hexane Oxidation of the resultant compound from Example 226 using sodium dichromate in acetic acid provided the desired compound in 50% yield. $^1$H NMR (CDCl$_3$): δ 0.86 (d, 3H), 0.90 (d, 3H), 2.20 (m, 1H), 2.70–3.30 (m, 4H), 3.00 (s, 3H), 3.50 (s, 3H), 4.10 (m, 1H), 4.42 (s, 2H), 4.70 (m, 1H), 5.05 9m, 1H), 5.30 (m, 1H), 6.40 (m, 1H), 6.75 (d, 1H), 7.10–7.30 (m, 2H), 7.70 (m, 1H), 8.50 (m, 1H). Mass spectrum: (M+H)$^+$=624.

EXAMPLE 228

3(S),6(S)-Diamino-4,4-difluoro-5(R)-hydroxy-2-methyl-7-cyclohexylheptane

Using the procedure described in detail in Examples 189A to 189G, except replacing Boc-L-phenylalaninal with Boc-L-cyclohexyl-alaninal and replacing benzyl magnesium chloride with isopropyl magnesium chloride provided the desired compound. Mass spectrum: $(M+H)^+=279$.

EXAMPLE 229

3(S),6(S)-Bis-(2-pyridyl-methoxycarbonyl-valinyl)amino-4,4-difluoro-5(R)-hydroxy-2-methyl-7-cyclohexylheptane Using the resultant compound from Example 228 and coupling to 2-pyridylmethoxyycarbonyl-valine using the carbodiimide procedure provided the desired product in 75% yield. $^1$H NMR (CDCl$_3$): δ 0.80–1.20 (m, 22H), 1.60 (m, 6H), 2.15 (m, 3H), 3.70 (m, 1H), 4.00 (m, 1H), 4.30–4.50 (m, 2H), 5.20 (m, 4H), 7.15 (m, 2H), 7.30 (m, 2H), 7.70 (m, 2H), 8.55 (m, 2H). Mass spectrum: $(M+H)^+=747$.

EXAMPLE 230

3(S),6(S)-Bis-(2-pyridylmethoxycarbonyl-valinyl)amino-4,4-difluoro-5-oxo-2-methyl-7-cyclohexylheptane Oxidation of the resultant compound from Example 229 using sodium dichromate in acetic acid provided the desired compound in 60% yield. $^1$H NMR (CDCl$_3$): δ 0.90–1.80 (m, 21H), 2.00 (m, 1H), 2.15 (m, 1H), 3.95 (m, 1H), 4.05 (m, 1H), 4.60 (m, 1H), 5.10 (m, 1H), 5.25 (m, 4H), 5.60 (m, 1H), 6.30 (m, 1H), 7.20 (m, 2H), 7.40 (d, 2H), 7.70 (m, 2H), 8.60 (m, 2H). Mass spectrum: $(M+H)^+=745$.

EXAMPLE 231

3(S),6(S)-Bis-(N-(N-methyl-N((2-pyridyl)methyl)amino)carbonyl-valinyl-amino)-4,4-difluoro-5(R)-hydroxy-2-methyl-7-cyclohexylheptane Using the resultant compound from Example 228 and coupling to (N-(N-methyl-N-((2-pyridyl)methyl)amino)carbonylvaline using the carbodiimide procedure provided the desired compound in 68% yield. $^1$H NMR (CDCl$_3$): δ 0.85 (d, 3H), 0.88 (d, 3H), 0.90 (d, 3H), 0.95 (d, 3H), 1.00 (d, 3H), 1.03 (d, 3H), 1.10–1.60 (m, 13H), 2.20 (m, 2H), 2.35 (m, 1H), 3.00 (s, 3H), 3.02 (s, 3H), 3.70 (m, 1H), 4.10 (m, 1h), 4.20 (m, 1H), 4.40 (m, 1H), 4.48 (s, 2H), 4.53 (s, 2H), 4.78 (d, 1H), 6.20 (m, 1H), 6.50 (m, 2H), 7.20–7.30 (m, 4H), 7.70 (m, 2H), 8.50 (m, 2H). Mass spectrum: $(M+H)^+=773$.

EXAMPLE 232

3(S),6(S)-Bis-(N-(N-methyl-N((2-pyridyl)methyl)amino)carbonyl-valinyl-amino)-4,4-difluoro-5-oxo-2-methyl-7-cyclohexylheptane Oxidation of the resultant compound from Example 231 using sodium dichromate in acetic acid provided the desired compound in 55% yield. $^1$H NMR (CDCl$_3$): δ 0.85 (d, 6H), 0.88 (d, 6H), 0.96 (m, 12H), 1.10–1.80 (m, 13H), 2.00 (m, 1H), 2.25 (m, 2H), 3.00 (s, 3H), 3.02 (s, 3H), 4.00 (t, 1H), 4.10 (m, 1H), 4.50 (m, 4H), 5.05 (m, 1H), 6.60 (d, 1H), 7.10–7.30 (m, 4H), 7.70 (m, 2H), 8.55 (m, 2H) . Mass spectrum: $(M+H)^+=771$.

EXAMPLE 233

4(S),7(S)-Diamino-2,9-dimethyl-5,5-difluoro-6(R)-hydroxy-decane

Using the procedure described in detail in Examples 189A to 189G, except replacing Boc-L-phenylalaninal with Boc-L-leucinal and replacing benzyl magnesium chloride with isobutyl magnesium chloride provided the desired compound. $^1$H NMR (CDCl$_3$): δ 0.95 (m, 12H), 1.25–1.45 (m, 4H), 1.65 (m, 1H), 1.85 (m, 1H), 3.20–3.35 (m, 2H), 3.40 (t, 1H), 3.50–3.60 (m, 1H) . Mass spectrum: $(M+H)^+=253$.

EXAMPLE 234

4(S),7(S)-(N-Benzyloxycarbonyl-valinyl)-amino-2,9-dimethyl-5,5-difluoro-6(R)-hydroxy-decane Using the resultant compound from Example 233 and coupling to benzyloxycarbonyl-valine using the carbodiimide procedure provided the desired compound in 65% yield. $^1$H NMR (CDCl$_3$): δ 0.90 (m, 24H), 1.45–1.60 (m, 2H), 2.15 (m, 12H), 3.90 (m, 2H), 4.25 (m, 2H), 4.60 (m, 1H), 5.10 (m, 4H), 5.40 (m, 2H), 6.00 (d, 1H), 6.30 (d, 1H), 7.35 (m, 10H). Mass spectrum: $(M+H)^+=719$.

EXAMPLE 235

4(S),7(S)-Bis-(N-(N-methyl-N-((2-pyridyl)methyl)amino)carbonyl-valinyl-amino)-2,9-dimethyl-5,5-difluoro-6(R)-hydroxydecane Using the resultant compound from Example 233 and coupling to (N-(-methyl-N-((2-pyriyl)methyl)amino) carbonylvaline using the carbodiimide procedure provided the desired compoundin 76% yield. $^1$H NMR (CDCl$_3$): δ 0.85 (d, 12H), 0.90 (d, 3H), 0.95 (d, 3H), 0.97 (d, 3H), 1.00 (d, 3H), 1.25–1.60 (m, 6H), 2.20 (m, 1H), 2.30 (m, 1H), 2.97 (s, 3H), 3.02 (s, 3H), 3.80 (m, 1H), 4.10 (m, 1H), 4.20 (m, 1H), 4.50 (m, 4H), 4.85 (d, 1H), 6.10 (m, 1H), 6.30 (d, 1H), 6.50 (d, 1H), 7.15–7.30 (m, 4H), 7.70 (m, 2H), 8.52 (m, 2H). Mass spectrum: $(M+H)^+=747$.

EXAMPLE 236

4(S),7(S)-Bis-(N-(N-methyl)-N-((2-pyridyl)methyl)amino)carbonyl-valinyl-amino)-2,9-dimethyl-5,5-difluoro-6-oxo-decane Oxidation of the resultant compound from Example 235 using sodium dichromate in acetic acid provided the desired compound in 50% yield. $^1$H NMR (CDCl$_3$): δ 0.82 (d, 3H), 0.85 (d, 3H), 0.87 (d, 3H), 0.90 (d, 3H), 0.93 (d, 6H), 0.96 (d, 6H), 1.20–1.60 (m, 6H), 2.20 (m, 2H), 3.00 (s, 3H), 3.02 (s, 3H), 4.00 (m, 1H), 4.12 (m, 1H), 4.52 (m, 4H), 4.70–4.75 (m, 1H), 4.95 (m, 1H), 6.30 (m, 1H), 6.42 (m, 1H), 6.65 (d, 1H), 6.78 (d, 1H), 7.20–7.25 (m, 4H), 7.70 (m, 2H), 8.55 (d, 2H). Mass spectrum: $(M+H)^+=745$.

EXAMPLE 237

(2S,4S)-2,4-Di-[{N-[N-(2-pyridylmethyl)oxy-carbonyl]-L-tert-Leucyl}amino]-3-hydroxy-1,5-diphenyl pentane A. L-tert-Leucine Methyl ester Hydrochloride To anhydrous methanol (15 mL) at −20° C. under nitrogen was added thionyl chloride (4 mL) dropwise. The solution was allowed to warm to room temperature and then tert- Leucine (4.00 g) was added. The reaction mixture was warmed at 50° C. for 5 hours, re-cooled to −20° C. and then additional thionyl chloride (3 mL) was added dropwise. The reaction mixture was heated an additional 2.5 hours at 50° C. and then concentrated under reduced pressure and chased twice with methanol (15 mL) to afford an amorphous solid. The solid was triturated with ether to afford the title compound in 92% yield. The 300 MHz $^1$H NMR spectrum was found to be consistent with the proposed structure. MS (DCI/NH$_3$) m/e 146 (M+H)$^+$.

B. N-[N-(2-Pyridylmethyl)oxy-carbonyl]-L-tert-Leucine Methyl ester

To the compound resulting from Example 237A (3.03 g, 16.6 mmol) dissolved in toluene (30 mL) under nitrogen was added triphosgene (5.4 g, 1.1 equiv). The reaction mixture was heated at 100° C. for 3 hours, and then the solvent was removed under reduced pressure. The residue was chased twice with toluene (2×15 mL) and dried under vacuum for 1 hour.

To the above isocyanate (2.89 g, 16.88 mmol) dissolved in methylene chloride (20 mL) at room temperature was added 2-pyridylcarbinol (1.79 mL, 1.1 equiv). The reaction mixture was stirred at room temperature overnight and then concentrated under reduced pressure. The residue obtained was chromatographed on silica gel eluting with 1:1 ethyl acetate/hexane. The product was re-chromatographed eluting with 2% methanol in methylene chloride to give the title compound. The 300 MHz $^1$H NMR spectrum was found to be consistent with the proposed structure. MS (DCI/NH$_3$) m/e 281 (M+H)$^+$.

C. N-[N-(2-Pyridylmethyl)oxy-carbonyl]-L-tert-Leucine

To the compound resulting from Example 237B (1.00 g, 3.57 mmol) dissolved in tetrahydrofuran (15 mL) was added 0.5M lithium hydroxide (14.2 mL, 2 equiv). After 5 hours, the reaction mixture was poured into methylene chloride (25 mL) and water (25 mL). The aqueous phase was separated, acidified to pH 4–5 with 1N hydrochloric acid, and extracted with methylene chloride. The combined organic extracts were dried over sodium sulfate and concentrated under reduced pressure to afford the title compound as a white solid (60%). The 300 MHz $^1$H NMR spectrum was found to be consistent with the proposed structure. MS (DCI/NH$_3$) m/e 267 (M+H)$^+$.

D. N-[N-(2-Pyridyimethyl)oxy-carbonyl]-L-tert-Leucine 4-Nitrophenyl ester

To the compound resulting from Example 237C (410 mg, 1.54 mmol) dissolved in 1:1 tetrahydrofuran/dimethylformamide was added 4-nitrophenol (256 mg, 1.2 equiv) followed by 1-ethyl-3-(3'-dimethylamino)-propylcarbodiimide (EDAC) (354 mg, 1.9 equiv). The reaction mixture was stirred overnight at room temperature and then diluted with methylene chloride (50 mL). The solution was washed with water (35 mL), dried over sodium sulfate, and concentrated under reduced pressure. The residue obtained was chromatographed on silica gel eluting with 3:2 hexane/ethyl acetate to afford the title compound in 73%. The 300 MHz $^1$H NMR spectrum was found to be consistent with the proposed structure. MS (DCI/NH$_3$) m/e 388 (M+H)$^+$.

E. (2S,4S)-2,4-Di-[{N-[N-(2-pyridylmethyl)oxy-carbonyl]-L-tert-Leucyl}amino]-3-hydroxy-1,5-diphenyl pentane To the compound resulting from Example 237D (269 mg, 3 equiv) dissolved in tetrahydrofuran (10 mL) containing triethylamine (0.4 mL, 4 equiv) was added the compound resulting from Example 6F (65 mg). The reaction mixture was heated in an 80° C. oil bath for 6 hours, cooled to room temperature, stirred with 3N sodium hydroxide (2 mL) for 1 hour and then extracted with methylene chloride. The organic phase was washed with water (35 mL), dried over sodium sulfate and concentrated under reduced pressure to afford crude material. Chromatography on silica gel eluting with 10% methanol in methylene chloride afforded the title compound (37%). $^1$H NMR (CDCl$_3$, 300 MHz) δ 0.92 (s, 18H), 2.57–3.44 (m, 14H), 3.80 (m, 3H), 4.26 (m, 2H), 4.53 (m, 1H), 5.10 (bd, 1H), 5.22 (m, 4H), 5.41 (bd, 2H), 5.54 (bd, 1H), 6.35 (bd, 1H), 6.90 (bd, 1H), 7.10–7.35 (m, 18H), 7.69 (m, 2H), 8.59 (m, 2H). MS (DCI/NH$_3$) m/e 767 (M+H)$^+$.

EXAMPLE 238

(2S,4S)-2,4-Di-[{N-[N-(2-pyridylmethyl)oxy-carbonyl]-L-Norvalyl}amino]-3-hydroxy-1,5-diphenyl pentane In analogy to the procedure described in Example 237 N-[N-(2-Pyridylmethyl)oxy-carbonyl]-L-Norvaline was prepared from Norvaline. To this compound (84 mg, 0.353 mmol) dissolved in anhydrous dimethylformamide (5 mL) and cooled to 0° C. was added the compound resulting from Example 6F (75 mg, 0.277 mmol) followed by 1-hydroxybenzotriazole (HOBT) (131 mg, 3.5 equiv), 1-ethyl-3-(3'-dimethylamino)-propylcarbodiimide (EDAC) (160 mg, 3 equiv) and triethylamine (0.1 mL, 3 equiv). The reaction mixture was allowed to warm to room temperature, stirred for 2 days and diluted with methylene chloride (50 mL). The solution was washed with water (50 mL), dried over sodium sulfate, and concentrated under reduced pressure. The residue obtained was chromatographed on silica gel eluting with 10% methanol in methylene chloride to afford the title compound in 40% yield. $^1$H NMR (CDCl$_3$, 300 MHz) δ 0.79 (t, 3H), 0.90 (t, 3H), 1.00–1.70 (m, 8H), 2.94 (m, 2H), 3.18 (m, 2H), 3.70 (m, 1H), 3.88 (m, 2H), 4.16 (m, 1H), 5.00 (m, 2H), 5.21 (m, 2H), 5.69 (bd, 1H), 6.35 (bd, 1H), 7.05–7.40 (m, 16H), 7.67 (m, 2H), 8.48 (bd, 1H), 8.54 (bd, 1H). MS (DCI/NH$_3$) m/e 739 (M+H)$^+$.

EXAMPLE 239

(2S,4S)-2,4-Di-[N-{2-(N-Benzyloxycarbonyl)amino-2-cyclobutylacetyl}amino]-3-hydroxy-1,5-diphenyl pentane A. Cyclobutylacetonitrile To a solution of cyclobutanemethanol (1.2 g, 0.0139 mol) dissolved in pyridine (5 mL) and cooled to 0° C. was added a catalytic amount of dimethylaminopyridine (DMAP) and tosyl chloride (2.92 g, 1.1 equiv). The reaction mixture was allowed to warm to room temperature and stirred for 4 hours. The reaction mixture was taken up in methylene chloride (50 mL), washed with water (50 mL), dried over sodium sulfate, and concentrated under reduced pressure to afford the rosylate (92%).

To the tosylate (14.3 g, 59.5 mmol) dissolved in dimethyl sulfoxide (20 mL) was added sodium cyanide (3.2 g, 1.1 equiv). The reaction mixture was heated at 90° C. for 2 hours, cooled to room temperature, diluted with ethyl acetate (300 mL), washed with H$_2$O (3×100 mL), dried over sodium sulfate, and concentrated under reduced pressure to afford a yellow liquid. Vacuum distillation afforded the title compound (60%). b.p. 62° C.

B. Cyclobutylacetic acid

The compound resulting from Example 239A (0.8 g, 8.41 mmol) was dissolved in 50% aqueous sodium hydroxide (4 mL) and warmed at reflux for 4 hours. After cooling to room temperature, the reaction mixture was acidified to pH 2–3 with 1N hydrochloric acid and extracted with ethyl acetate (100 mL). The organic phase was washed with water (3×100 mL), dried over sodium sulfate and concentrated under reduced pressure.

C. N-Cyclobutylacetyl-4-benzyl-2-oxazolidinone

To the compound resulting from Example 239B (0.95 g, 8.32 mmol) dissolved in anhydrous tetrahydrofuran (8 mL) and cooled at –78° C. was added triethylamine (1.5 mL, 1.3 equiv) followed by pivaloyl chloride (1.12 mL, 1.1 equiv). The reation mixture was stirred at –78° C. for 15 minutes and room temperature for 1 hour and then cooled to –78° C. again.

To (S)(–)-4-benzyl-2-oxazolidinone (2.65 g, 1.8 equiv) dissolved in tetrahydrofuran (25 mL) at –78° C. was added 2.5M butyl lithium (5.98 mL, 1.8 equiv). After 5 minutes, this solution was cannulated into the above solution. The reaction mixture was allowed to come to room temperature and stirred for 2 hours. The reaction mixture was diluted with Chloroform (150 mL), washed with 10% sodium bisulfite (100 mL), dried over sodium sulfate, and concentrated under reduced pressure. The residue obtained was chromatographed on silica gel eluting with 3:2 hexane/ethyl acetate to afford the title compound in 58% yield.

D. N-[Cyclobutyl-2-azidoacetyl]-4-benzyl-2-oxazolidinone

To the compound re.suiting from Example 239C (287 mg, 1.05 mmol) dissolved in anhydrous tetrahydrofuran (10 mL) and cooled to –78° C. under nitrogen was added potassium hexamethyldisilazide (0.5M in toluene, 2.1 mL, 1 equiv). After 15 minutes at –78° C. 2 4 6-triisopropylbenzenesulfonyl azide (Trisylazide) (389 mg, 1.2 equiv) in tetrahydrofuran (5 mL) at –78° C. was cannulated into the reaction mixture. After 2 minutes at –78° C. glacial acetic acid (0.18 mL, 3 equiv) was added and the temperature was allowed to rise to 30° C. with the use of a water bath. After 1.5 hours, methylene chloride (100 mL) was added; the solution was washed with water (3×50 mL), dried over sodium sulfate, and concentrated under reduced pressure. The residue obtained was chromatographed on silica gel eluting with 3:2 hexane/ethyl acetate to afford the title compound in 77% yield.

E. N-[Cyclobutyl-2-(Cbz-amino)acetyl]-4-benzyl-2-oxazolidinone

To the compound resulting from Example 239D (0.44 g, 1.4 mmol) dissolved in 10:8:1 methanol, tetrahydrofuran and trifluoroacetic acid was added 10% palladium on carbon (100 mg). The reaction mixture was placed under hydrogen for three hours. The catalyst was removed by filtration through Celite, washed with methanol (10 mL), and the filtrate concentrated under reduced pressure. Methylene chloride (10 mL) was added to the residue obtained and the mixture was cooled to 0° C. Benzylchloroformate (0.38 mL, 2 equiv) was added followed by triethylamine (0.3 mL, 3 equiv). The reaction mixture was allowed to warm to room temperature and stirred overnight. Sodium bisulfite was added and the reaction mixture was extracted with methylene chloride (100 mL). The combined organic extracts were washed with water (3×20 mL), dried over sodium sulfate, and concentrated under reduced pressure. The residue obtained was chromatographed on silica gel eluting with 1:3 ethyl acetate/hexane to afford the title compound in 53% yield.

F. 2-Cyclobutyl-2- (Cbz-amino) acetic acid

To the compound resulting from Example 239E (170 mg, 0.402 mmol) dissolved in 1:3 water/tetrahydrofuran (4 mL) cooled to 0° C. was added lithium hydroxide (34 mg, 2 equiv). After 40 minutes, the reaction mixture was added to aqueous sodium chloride (20 mL) and then washed with methylene chloride (3×30 mL). The aqueous phase was acidified to pH 2 with 1N hydrochloric acid and then ex. tracted with ethyl acetate (4×30 mL). The combined organic extracts were dried over sodium sulfate and concentrated under reduced pressure to afford the title compound as a white solid (71%).

G. (2S,4S)-2,4-Di-[N-{2-(N-Benzyloxycarbonyl)amino-2-cyclobutylacetyl}amino]-3-hydroxy-1,5-diphenyl pentane The compound resulting from Example 239F (80 mg, 0.34 mmol) was coupled with the compound resulting from Example 6F (68 mg, 0.252 mmol) by the procedure described in Example 238 to give crude material. Chromatography on silica gel eluting with 3% methanol in methylene chloride afforded the title compound (70 mg). $^1$H NMR (CDCl$_3$, 300 MHz) δ 1.46 (m, 14H), 2.32 (m, 1H), 2.60–3.30 (m, 6H), 3.42 (bs, 1H), 3.70 (bs, 2H), 4.07 (m, 1H), 4.72 (m, 1H), 4.83–5.05 (m, 4H), 5.20 (bs, 1H), 5.52 (bs, 1H), 6.15 (bs, 1H), 7.10–7.38 (m, 20H). MS (DCI/NH$_3$) m/e 761 (M+H)$^+$, 778 (M+H+NH$_3$)$^+$.

EXAMPLE 240

(2S,4S)-2,4-Di-[N-{2-(N-Benzyloxycarbonyl)amino-2-cyclopentylacetyl}amino]-3-hydroxy-1,5-diphenyl pentane 2-Cyclopentyl-2-(Cbz-amino)acetic acid was prepared in analogy to the procedure described in Example 239 starting from cyclopentylacetic acid. This compound (135 mg) was coupled with the compound resulting from Example 6F (107 mg) by the procedure described in Example 238 to afford crude product. Chromatography on silica gel eluting with 3% methanol in methylene chloride afforded the title compound (110 mg). $^1$H NMR (DMSO-d$_6$, 300 MHz) δ 1.02–1.66 (m, 18H), 1.96 (m, 2H), 2.76 (m, 3H), 2.96 (m, 1H), 3.52 (m, 1H), 3.77 (m, 4H), 4.09 (m, 1H), 5.01 (d, 4H), 5.34 (bd, 1H), 7.00–7.47 (m, 22H). MS (DCI/NH$_3$) m/e 789 (M+H)$^+$.

EXAMPLE 241

(2S,4S)-2,4-Di-[N-{2-(N-Benzyloxycarbonyl)amino-2-cyclopropylacetyl}amino]-3-hydroxy-1,5-diphenyl pentane 2-Cyclopropyl-2-(Cbz-amino)acetic acid was prepared in analogy to the procedure described in Example 239 starting from cyclopropylacetic acid. This compound (230 mg, 0.923 mmol) was coupled with the compound resulting from Example 6F (208 mg) by the procedure described in Example 238 to afford crude product. Chromatography on silica gel eluting with 5% methanol in methylene chloride afforded the title compound (220 mg) as a white solid. $^1$H NMR (CDCl$_3$, 300 MHz) δ 0.10–0.66 (m, 10H), 0.91 (m, 1H), 1.13 (m, 1H), 2.90–3.30 (m, 8H), 3.57 (bs, 2H), 3.95 (bs, 1H), 4.40–4.93 (m, 4H), 5.30 (m, 2H), 5.55 (bd, 1H), 6.49 (m, 1H), 7.10–7.37 (m, 20H). MS (DCI/NH$_3$) m/e 733 (M+H)$^+$.

EXAMPLE 242

(2S,4S)-2,4-Di-[N-{N-Boc-(Thiazol-2-yl)Alanyl}amino]-3-hydroxy-1,5-diphenyl pentane N-Boc-(Thiazol-2-yl)Alanine (264 mg) was coupled with the compound resulting from Example 6F by the procedure described in Example 238 to afford crude material. Chromatography on silica gel eluting with 7% methanol in methylene chloride afforded the title compound as a white solid (58%). $^1$H NMR (CDCl$_3$, 300 MHz) δ 1.22 (s, 9H), 1.40 (s, 9H), 2.80–3.50 (m, 11H), 3.64 (bs, 1H), 3.77 (bs, 1H), 4.21 (bs, 1H), 4.64 (bs, 1H), 5.68 (m, 1H), 5.97 (m, 1H), 6.07 (bs, 1H), 6.89–7.33 (m, 14H), 7.48 (m, 1H), 7.77 (bs, 1H), 8.61 (bs, 1H). MS (DCI/NH$_3$) m/e 779 (M+H)$^+$.

EXAMPLE 243

(2S,5R)-N-[2-(N-Cbz-Valyl)amino-3-phenyl-1-propyl]-N-hydroxy-Phenylalanyl-Valyl N-(2-Hydroxyethyl)amide A. N-Boc-Phenylalaninal To dimethyl sulfoxide (2.82 mL, 39.8 mmol) dissolved in anhydrous methylene chloride (5 mL) and cooled to −78° C. was added dropwise oxalyl chloride (2.6 mL, 1.5 equiv). After 10 minutes at −78° C., N-Boc-Phenylalaninol (5.00 g, 19.9 mmol) dissolved in anhydrous methylene chloride (75 mL) was cannulated into the reaction mixture. After 15 minutes at −78° C., the reaction was stirred for 2 minutes at 0° C. and then cooled again to −78° C. Triethylamine (11.9 mL, 4.3 equiv) was added dropwise. After 25 minutes, the reaction was quenched with cooled 10% citric acid (15 mL) and then diluted with additional 10% citric acid (75 mL). Ether (300 mL) was added and the solution was washed with water (5×100 mL), brine, water (5×100 mL), and brine, dried over sodium sulfate, and concentrated under reduced pressure to afford the title compound (4.22 g).

B. (2S,5R)-N-[2-(N-Boc-amino)-3-phenyl-1-propyl]-Phenylalanyl Methyl ester

To the compound resulting from Example 243A (4.22 g, 16.9 mmol) dissolved in isopropyl alcohol (60 mL) at 0° C. was added phenylalanine methyl ester hydrochloride (3.94 g, 1.08 equiv) followed by sodium acetate (2.91 g, 2.1 equiv). After stirring 30 minutes at 0° C., the reaction mixture was cooled to −35° C. and treated with sodium cyanoborohydride (1.33 g, 1.25 equiv). The reaction mixture was allowed to warm to room temperature and stirred overnight. The solvent was removed under reduced pressure and the solid obtained dissolved in ethyl acetate (300 mL). The solution was washed with saturated sodium bicarbonate (2×100 mL), water (100 mL), and brine (100 mL), dried over sodium sulfate, and concentrated under reduced pressure. The crude product was chromatographed on silica gel eluting with 1:4 ethyl acetate/methylene chloride to afford the title product. The 300 MHz $^1$H NMR spectrum was found to be consistent with the proposed structure. MS (DCI/NH$_3$) m/e 413 (M+H)$^+$.

C. (2S,5R)-N-[2-(N-Boc-amino)-3-phenyl-1-propyl]-N-hydroxy-Phenylalanyl Methyl ester To the compound resulting from Example 243B (325 mg, 0.788 mmol) dissolved in acetone (3 mL) at −40° C. was added dropwise 0.09M dimethyldioxirane (3 equiv). After 1 hour at 40° C., the reaction was warmed to 0° C. and stirred for 1 hour. The reaction was warmed to room temperature and additional 0.09M dimethyldioxirane (2 equiv) was added. After 1 hour, the solvent was removed under reduced pressure. The residue obtained was chromatographed on silica gel eluting with 1:9 ethyl acetate in methylene chloride to afford the title compound as a white solid (53%). $^1$H NMR (CDCl$_3$, 300 MHz) δ 1.43 (s, 9H), 2.50 (m, 1H), 2.79 (m, 2H), 2.98 (d of d, 1H), 3.10 (d, 2H), 3.49 (t, 1H), 3.64 (s, 3H), 4.12 (m, 1H), 4.74 (bd, 1H), 6.61 (bs, 1H), 7.04 (bd, 1H), 7.24 (m, 10H). MS (DCI/NH$_3$) m/e 429 (M+H)$^+$.

D. (2S,5R)-N-[2-(N-Boc-amino)-3-phenyl-1-propyl]-Phenylalanine

To the compound resulting from Example 243B (335 mg, 8.12 mmol) dissolved in 2:1 tetrahydrofuran/water (15 mL) was added lithium hydroxide monohydrate (1.5 equiv). After 1.74 hours, 1N hydrochloric acid (1.5 equiv) was added and the solvent removed under reduced pressure to afford the title compound as a white solid (73%). MS (DCI/NH$_3$) m/e 399 (M+H)$^+$.

E. (2S,5R)-N-[2-(N-Boc-amino)-3-phenyl-1-propyl]-Phenylalanyl-Valyl Benzyl ester The compound resulting from Example 243D (223 mg, 0.819 mmol) was coupled with Valine benzyl ester methanesulfonate salt (257 mg, 0.6766 mmol) by the procedure described in Example 238 to afford crude material. Chromatography on silica gel eluting with 2% methanol in methylene chloride afforded the title compound as a white solid (166 mg, 35%).

F. (2S,5R)-N-[2-(N-Boc-amino)-3-phenyl-1-propyl]-N-hydroxy-Phenylalanyl-Valyl Benzyl ester The compound resulting from Example 243F (166 mg) was reacted with dimethyldioxirane by the procedure described in Example 243C to give crude material. Chromatography on silica gel eluting with 2% methanol in methylene chloride afforded the title compound as a white solid (63%). $^1$H NMR (CDCl$_3$, 300 MHz) δ 0.85 (m, 6H), 0.95 (m, 1H), 1.40 (s, 9H), 2.19 (m, 1H), 2.46 (m, 1H), 2.62–2.90 (m, 3H), 3.10 (m, 4H), 3.49 (m, 1H), 4.20 (bs, 1H), 4.54 (m, 2H), 5.15 (m, 3H), 7.09 (bd, 1H), 7.10–7.46 (m, 15H). MS (DCI/NH$_3$) m/e 604 (M+H)$^+$.

G. (2S,5R)-N-[2-Amino-3-phenyl-1-propyl]-Phenylalanyl-Valyl Benzyl ester

To the compound resulting from Example 243E (528 mg, 0.99 mmol) dissolved in dioxane (20 mL) and cooled to 0° C. was added dropwise 4.4M hydrochloric acid in dioxane (0.56 mL). The reaction mixture was allowed to warm to room temperature and then additional 4.4M hydrochloric acid in dioxane (10 mL) was added. After 30 minutes, the reaction was worked up to afford the title compound in 72% yield.

H. (2S,5R)-N-[2-(N-Cbz-Valyl)amino-3-phenyl-1-propyl]-Phenylalanyl-Valyl Benzyl ester The compound resulting from Example 243G (100 mg, 0.2046 mmol) was coupled with N-Cbz-L-Valine (62 mg, 1.2 equiv) by the procedure described in Example 238 to give crude material. Chromatography on silica gel eluting with 2% methanol in methylene chloride afforded the title compound in 53% yield.

I. (2S,5R)-N-[2-(N-Cbz-Valyl)amino-3-phenyl-1-propyl]-N-hydroxy-Phenylalanyl-Valyl Benzyl ester The compound resulting from Example 243H (50 mg, 0.07 mmol) was reacted with dimethyldioxirane by the procedure described in Example 243C to afford crude material. Chromatography on silica gel eluting with 5% methanol in methylene chloride afforded the title compound (74%). $^1$H NMR (CDCl$_3$, 300 MHz) δ 0.65 (m, 8H), 2.10 (m, 1H), 2.21 (m, 1H), 2.42 (m, 1H), 2.60 (m, 1H), 2.80 (m, 1H), 3.05 (m, 2H), 3.40 (m, 1H), 3.72 (m, 1H), 4.40 (m, 1H), 4.55 (m, 1H), 4.95 (m, 1H), 5.00–5.24 (m, 3H), 6.13 (m, 1H), 7.05 (m, 1H), 7.14–7.49 (m, 15H). MS (DCI/NH$_3$) m/e 737 (M)$^+$.

J. (2S,5R)-N-[2-(N-Cbz-Valyl)amino-3-phenyl-1-propyl]-Phenylalanyl-Valyl N-(2-Hydroxyethyl)amide The compound resulting from Example 243H (232 mg, 0.3213 mmol) was hydrolyzed by the procedure described in Example 239F and triturated with acetonitrile to give the carboxylic acid as a white solid (88%).

The above carboxylic acid (203 mg, 0.3213 mmol) was coupled with ethanolamine (15.9 mg, 0.2678 mmol) by the procedure described in Example 238 to give crude material. Chromatography on silica gel eluting with 8% methanol in methylene chloride afforded the title compound as a white solid (51%). $^1$H NMR (CDCl$_3$, 300 MHz) δ 0.70–0.97 (m, 12H), 2.60–2.94 (m, 4H), 3.64 (m, 2H), 4.00 (m, 2H), 5.10 (m, 2H), 5.52 (bd, 1H), 6.78 (bd, 1H), 7.00 (m, 1H), 7.10–7.40 (m, 15H), 7.96 (bd, 1H). MS (DCI/NH$_3$) m/e 674 (M+H)$^+$.

K. (2S,5R)-N-[2-(N-Cbz-Valyl)amino-3-phenyl-1-propyl]-N-hydroxy-Phenylalanyl-Valyl N-(2-Hydroxyethyl)amide The compound resulting from Example 243J (110 mg, 0.163 mmol) was reacted with dimethyldioxirane by the procedure described in Example 243C to give crude material. Chromatography on silica gel eluting with 8% methanol in methylene chloride afforded the title compound as a white solid (50%). This compound was re-chromatographed on silica gel eluting with 6% methanol in methylene chloride. $^1$H NMR (CDCl$_3$, 300 MHz) δ 0.70–1.00 (m, 12H), 2.11 (m, 2H), 2.31 (m, 1H), 2.55–3.19 (m, 6H), 3.29 (m, 2H), 3.64 (m, 4H), 3.84 (m, 1H), 4.26 (m, 1H), 4.41 (m, 1H), 5.10 (m, 2H), 6.21 (m, 1H), 6.48 (m, 1H), 6.82 (m, 1H), 6.90–7.40 (m, 15H). MS (DCI/NH$_3$) m/e 690 (M+H)$^+$.

EXAMPLE 244

(2S,3R,4S)-2,4-Di-{N-[(2-pyridylmethyl)oxycarbonyl]-L-Valyl}amino-3-hydroxy-1-phenyl-5-(4-methylphenyl) pentane A. 2-Boc-Amino-1-phenyl-5-(4-methylphenyl) pent-3-ene To a solution of anhydrous copper(I) cyanide (0.29 g, 3.2 mmol) dissolved in anhydrous tetrahydrofuran (100 mL) under nitrogen and cooled in a dry ice/acetone bath was added a solution of p-tolylmagnesium bromide (1M solution in ether) (33 mL, 33 mmol) via syringe. The dry ice/acetone bath was removed and replaced with a cold water bath. When the internal temperature reached –1° C., the mixture was cooled in a dry ice/acetone bath and a solution of 2-Boc-amino-3-methanesulfonyloxy-1-phenyl-pent-4-ene (3.58 g, 10.5 mmol) dissolved in tetrahydrofuran (20 mL) was added via syringe. The mixture was stirred at –70° C. for 15 minutes. The bath was removed, and the solution was immediately treated with saturated ammonium chloride solution (20 mL) followed by ether (60 mL). As the mixture warmed, 1N ammonium hydroxide (20 mL) was added. The mixture was stirred at room temperature overnight and then extracted with ether (100 mL). The organic phase washed with saturated sodium chloride solution, dried over magnesium sulfate, and concentrated under reduced pressure to afford the crude compound as a semi-solid residue (3.77 g). Chromatography on silica gel eluting with hexane and 5% ethyl acetate in hexane afforded the title product as a white solid (1.6607 g, 45%). m.p. 92°–93° C.

B. 2-Boc-Amino-3,4-epoxy-1-phenyl-5-(4-methylphenyl) pentane

To a suspension of the product resulting from Example 244A (1.63 g, 4.64 mmol) and sodium bicarbonate (2.0 g, 23.8 mmol) in methylene chloride (26.7 mL) and cooled in an ice bath was added m-chloroperbenzoic acid (50%, 3.20 g, 9.27 mmol). When the reaction mixture became a thick mass, additional methylene chloride (7 mL) was added and stirring was continued at ice bath temperature for 7 hours and then the reaction mixture was placed in the refrigerator for two days. The reaction mixture was stirred in ether (40 mL) and 10% aqueous sodium thiosulfate pentahydrate (53 mL) for 2.5 hours. The layers were separated and the organic layer washed with 2N sodium hydroxide (27 mL); additional ether (75 mL) was added. The organic layer was washed with water (27 mL) and brine (27 mL). The combined aqueous layers were back-extracted with ether (3×50 mL) and these combined ether extracted were washed with water (50 mL) and brine (50 mL). The combined organic extracts were dried over magnesium sulfate and concentrated under reduced. pressure to afford crude material. Chromatography on silica gel eluting with 1:5 ethyl acetate/hexane afforded an oil which solidified on standing to give the title product (1.158 g, 68%).

C. 2-Boc-Amino-4-azido-3-hydroxy-1-phenyl-5-(4-methylphenyl)

A solution of the product resulting from Example 244B (1.1464 g, 3.12 mmol), lithium azide (844.9 mg, 17.25 mmol), and ammonium chloride (208.8 mg, 3.90 mmol) in dimethylformamide (10 mL) and water (1.0 mL) was stirred and warmed at 70° C. under nitrogen for 32 hours and let stand for two days at room temperature. The reaction mixture was partitioned between 1:1 ethyl acetate/hexane (120 mL) and water (96 mL). The aqueous layer was back-extracted with 1:1 ether/hexane (2×60 mL). The combined organic extracts were washed with water (50 mL) and brine (25 mL), dried over magnesium sulfate, and concentrated under reduced pressure. The residue obtained was chromatographed on silica gel eluting with a gradient of ethyl acetate/hexane of 1:9 going to 1:5 to afford the title compound (1.0674 g, 83%). m.p. 110° C.

D. 2-Boc-Amino-4-amino-3-hydroxy-1-phenyl-5-(4-methylphenyl)

To a suspension of 10% palladium on carbon (206 mg) in methanol (5.8 mL) was added ammonium formate (1.14 g, 18.1 mmol) with stirring under nitrogen. After 10 minutes, the compound resulting from Example 244C (1.05 g, 2.56 mmol) dissolved in methanol (9.2 mL plus 1.0 mL wash) was added. After 2.25 hours, the reaction mixture was filtered through a Millipore filter (EH type). The filtrate was concentrated under reduced pressure to approximately 6 mL, sodium chloride was added, and the mixture was extracted with chloroform (3×25 mL). The combined organic extracts were dried over magnesium sulfate and concentrated under reduced pressure to afford crude material (942 mg). Chromatography on silica gel eluting with 1:20 methanol/hexane afforded the title compound (698 mg).

E. 2,4-Diamino-3-hydroxy-1-phenyl-5-(4-methylphenyl) pentane

A solution of the compound resulting from Example 244D (691 mg, 1.797 mmol) in 4M hydrochloric acid in dioxane (10 mL) was stirred at room temperature for 2 hours and then concentrated under reduced pressure. The residue obtained was taken up in a mixture consisting of chloroform (100 mL), methanol (3.32 mL), 5% sodium bicarbonate solution (6.65 mL), and 3.0M sodium hydroxide solution (6.65 mL). The aqueous layer was extracted with chloroform (50 mL). The combined organic extracts were dried over magnesium sulfate and concentrated under reduced pressure to afford the title compound as a white solid (467 mg, 91%). m.p. 126°–128° C.

F. (2S,3R,4S)-2,4-Di-{N-[(2-pyridylmethyl)oxycarbonyl]-L-Valyl}amino-3-hydroxy-1-phenyl-5-(4-methylphenyl) pentane Triethylamine (0.15 mL, 1.052 mmol) was added to a stirred solution of the compound resulting from Example 244E (74.8 mg, 0.263 mmol) and N-[(2-pyridylmethyl)oxycarbonyl]Valine 4-nitrophenyl ester (294.5 mg, 0.789 mmol) dissolved in anhydrous tetrahydrofuran (7.5 mL). The reaction mixture was stirred at reflux under nitrogen for 5 hours

EXAMPLE 245

(2S,3R,4S)-2,4-Di-{N-[(2-pyridylmethyl)oxycarbonyl]-L-Valyl}amino-3-hydroxy-1-phenyl-5-(2-methylphenyl) pentane 2,4-Diamino-3-hydroxy-1-phenyl-5-(2-methylphenyl) pentane was prepared in analogy to Example 244E using the ortho- rather than para-substituted Grignard reagent. This compound (149.6 mg) was coupled with N-[(2-pyridylmethyl)oxycarbonyl]-Valine 4-nitrophenyl ester (589 mg) by the procedure described in Example 244F to give the title compound (172 mg). $^1$H NMR (CDCl$_3$, 300 MHz) δ 0.57–1.02 (M, 12H), 1.98 (M, 1H), 2.25 (M, 2H), 2.29 (S, 3H), 2.77 (M, 1H), 3.10 (BD, 2H), 3.35 (M, 1H), 3.70 (M, 3H), 4.02 (M, 2H), 5.10 (M, 6H), 5.72 (BD, 1H), 6.30 (BD, 1H), 7.00–7.30 (M, 18H), 7.66 (M, 2H), 8.55 (M, 2H). MS (FAB) m/e 753 (M+H)$^+$.

EXAMPLE 246

(2S,3R,4S)-2,4-Di-{N-[(2-pyridylmethyl)oxycarbonyl]-L-Valyl}amino-3-hydroxy-1-phenyl-5-(3-methylphenyl) pentane 2,4-Diamino-3-hydroxy-1-phenyl-5-(3-methylphenyl) pentane was prepared in analogy to Example 244E using the meta- rather than para-substituted Grignard reagent. This compound (149.6 mg) was coupled with N-[(2-pyridylmethyl)oxycarbonyl]-Valine 4-nitrophenyl ester (589 mg) by the procedure described in Example 244F to give the title compound (136 mg). $^1$H NMR (CDCl$_3$, 300 MHz) δ 0.68 (d, 3H), 0.77 (d, 3H), 0.90 (m, 6H), 2.01 (m, 1H), 2.25 (s, 3H), 2.29 (m, 2H), 2.95 (m, 3H), 3.15 (m, 2H), 3.68 (m, 2H), 3.85 (m, 3H), 4.10 (m, 1H), 5.14 (m, 5H), 5.33 (m, 1H), 5.87 (bs, 1H), 6.40 (bs, 1H), 6.90–7.40 (m, 18H), 7.74 (m, 2H), 8.57 (m, 2H). MS (FAB) m/e 753 (M+H)$^+$.

EXAMPLE 247

(2S,3R,4S)-2,4-Di-{N-[(3-pyridylmethyl)oxycarbonyl]-L-Valyl}amino-3-hydroxy-1-phenyl-5-(4-fluorophenyl) pentane 2,4-Diamino-3-hydroxy-1-phenyl-5-(4-fluorophenyl) pentane was prepared in an alogy to Example 244E using the para-fluoro rather than para-methyl substituted Grignard reagent. This compound (152.8 mg) was coupled with N-[(2-pyridylmethyl)oxycarbonyl]-Valine 4-nitrophenyl ester (589 mg) by the procedure described in Example 244F to give the title compound (186 mg). $^1$H NMR (CDCl$_3$, 300 MHz) δ 0.67 (d, 3H), 0.75 (d, 3H), 0.89 (m, 6H), 2.00 (m, 1H), 2.26 (m, 1H), 2.85 (m, 1H), 3.10 (m, 4H), 3.55–4.10 (m, 6H), 5.04–5.37 (m, 6H), 5.66 (bd, 1H), 6.27 (bd, 1H), 6.90 (m, 2H), 7.05–7.35 (m, 16H), 7.67 (m, 2H), 8.54 (m, 2H). MS (DCI/NH$_3$)m/e 757 (M+H)$^+$.

and then at room temperature overnight. A solution of 3M sodium hydroxide (1.5 mL) was added, and the reaction mixture was stirred at room temperature for 2 hours, diluted with chloroform (100 mL), washed with 0.5M sodium hydroxide (4×15 mL) and brine (15 mL), dried over magnesium sulfate, and concentrated under reduced pressure to afford crude material. Chromatography on silica gel eluting with 1:30 methanol in methylene chloride afforded the title compound (106 mg, 54%). m.p. 195°–198° C. MS (DCI/NH$_3$) m/e 753 (M+H)$^+$.

EXAMPLE 248

(2S,3R,4S)-2,4-Di-{N-[N-methyl-N-(2-pyridylmethyl)amino(thiocarbonyl)]-L-Valyl}amino-3-hydroxy-1,5-diphenyl pentane A. (1-Carbomethoxisobutyl)isothiocyanate To a stirred suspension of Valine methyl ester hydrochloride (1.0 g, 5.96 mmol) in chloroform (10 mL) cooled to −20° C. was added thiophosgene (0.48 mL, 6.26 mmol) followed by the dropwise addion of triethylamine (2.49 mL, 17.88 mmol) in chloroform (10 mL). The reaction mixture was stirred at −20° C. for 15 minutes and then 0.1M hydrochloric acid (10 mL) was added. The organic layer was washed with water (4×5 mL), dried over magnesium sulfate, and concentrated under reduced pressure to afford the title compound (1.01 g).

B. N-[N-Methyl-N-(2-pyridylmethyl)amino-(thiocarbonyl)] Valine Methyl ester

To a suspension of N-methyl-N-(2-pyridylmethyl) amine dihydrochloride (809.9 mg, 4.15 mmol) in methylene chloride (40 mL) was added 4-methylmorpholine (1.14 mL, 10.37 mmol) followed by a solution of the compound resulting from Example 248A (1.01 g) in methylene chloride (10 mL). The reaction mixture was stirred at room temperature overnight. The reaction mixture was washed with water (3×15 mL), dried over magnesium sulfate, and concentrated under reduced pressure to afford crude material (1.54 g). Chromatography on silica gel eluting with 1:7 ethyl acetate in methylene chloride afforded the title compound (1.2275 g, 100%).

C. N-[N-Methyl-N-(2-pyridylmethyl)amino-(thiocarbonyl)] Valine

To a solution of the compound resulting from Example 248B (1.22 g, 4.13 mmol) dissolved in tetrahydrofuran (15 mL) and cooled in an ice bath was added 0.5M lithium hydroxide (16.5 mL, 2 equiv). The reaction mixture was stirred in the ice bath for 1.5 hours and then at room temperature for 3 hours. Water (25 mL) was added and the mixture was washed with methylene chloride (25 mL). The aqueous layer was separated, acidified to pH 3–4 with 1N hydrochloric acid (8.25 mL), and extracted with ethyl acetate (5×25 mL). The combined organic extracts were dried over magnesium sulfate and concentrated under reduced pressure to afford the title compound (929 mg).

D. (2S,4S)-2,4-Di-{N-[N-methyl-N-(2-pyridylmethyl)amino(thiocarbonyl)]-L-Valyl}amino-3-hydroxy-1,5-diphenyl pentane To a stirred solution of the resultant compound of Example 6F (54 mg, 0.2 mmol), the compound resulting from Example 248C (135.1 mg, 0.48 mmol), 1-ethyl-3-(3'-dimethylamino)-propylcarbodiimide (EDAC) (191.7 mg, 1 mmol) and 1-hydroxybenzotriazole hydrate (HOBT) (189.2 mg, 1.4 mmol) in anhydrous dimethylformamide (2.5 mL) under nitrogen and cooled in an ice bath was added via syringe triethylamine (0.14 mL, 1 mmol). The mixture was stirred in the ice bath allowing the temperature to gradually rise to room temperature over 2 hours. After 24 hours, the mixture was concentrated under reduced pressure and the residue obtained triturated with water (20 mL) and extracted with ethyl acetate (4×20 mL). The combined organic extracts were dried over magnesium sulfate and concentrated under reduced pressure to afford crude material (250 mg). Chromatography on silica gel eluting wtih 1:40 methanol in methylene chloride afforded the title compound (49.7 mg, 31%) as an amorphous solid. $^1$H NMR (CDCl$_3$, 300 MHz) δ 0.69–1.10 (m, 12H), 1.67 (m, 2H), 2.07 (m, 1H), 2.40 (m, 1H), 3.07 (m, 1H), 3.23 (m, 2H), 3.37 (s, 3H), 3.60–3.94 (m, 2H), 4.06 (m, 1H), 4.37–4.56 (m, 2H), 4.80 (m, 2H), 4.98 (m, 1H), 7.00 (bd, 1H), 7.08–7.48 (m, 15H), 7.56–7.83 (m, 3H), 8.15 (m, 1H), 8.30 (m, 1H), 8.54 (m, 2H). MS (FAB) m/e 797 molecular ion.

EXAMPLE 249

(2S,3R,4R,5S)-2,4-Di-{N-[N-methyl-N-(2-pyridylmethyl)amino(thiocarbonyl)]-L-Valyl}amino-3,4-dihydroxy-1,6-diphenyl hexane A. N-[N-Methyl-N-(2-pyridylmethyl)amino-(thiocarbonyl)]-Valine 4-Nitrophenyl ester To a solution of the compound resulting from Example 248C (281.3 mg, 1 mmol) and 4-nitrophenol (153 mg, 1.1 mmol) dissolved in anhydrous methylene chloride (14 mL) and cooled in an ice bath was added dicyclohexylcarbodiimide (DCC) (227 mg, 1.1 mmol). The reaction mixture was stirred in the ice bath for 2 hours and then at room temperature for 3 hours. The by-product was removed by filtration and the filtrate concentrated under reduced pressure to afford the title compound.

B. (2S,3R,4R,5S)-2,4-Di-{N-[N-methyl-N-(2-pyridylmethyl)amino-(thiocarbonyl)]-L-Valyl}amino-3,4-dihydroxy-1,6-diphenyl hexane The compound resulting from Example 249A (0.8 mmol) and the compound resulting from Example 4A (132 mg, 0.4 mmol) were stirred in anhydrous dimethylformamide (4 mL) at room temperature for 16 hours. The reaction mixture was diluted with ethyl acetate (200 mL) and washed with 5% sodium bicarbonate solution (3×30 mL). The organic phase was dried over magnesium sulfate and concentrated under reduced pressure to afford crude material (683.4 mg). Chromatography on silica gel eluting with 1:30 methanol in methylene chloride afforded the title compound (77.2 mg). $^1$H NMR (CDCl$_3$, 300 MHz) δ 0.71 (d, 3H), 0.81 (d, d of d, 9H), 0.90 (d of d, 6H), 2.05 (m, 1H), 2.24 (m, 2H), 2.80–2.95 (m, 4H), 3.30–3.36 (2s, 6H), 3.58 (m, 2H), 3.75 (m, 1H), 3.87 (m, 1H), 4.31 (m, 2H), 4.58–4.85 (m, 6H), 6.39 (m, 2H), 7.05–7.35 (m, 16H), 7.64–7.80 (m, 2H), 8.47 (m, 2H). MS (FAB) m/e 827 (M+H)$^+$, 849 (M+Na)$^+$.

EXAMPLE 250

(2S,3R,4S)-2,4-Di-{N-Cbz-L-Histidyl}amino-3-hydroxy-1-phenyl-5-(4-methylphenyl) pentane To a stirred solution of the compound resulting from Example 244E (85.3 mg, 0.3 mmol), HOBT (121.6 mg, 0.9 mmol), and EDAC (172.5 mg, 0.9 mmol) dissolved in dimethylformamide (5 mL) and cooled in an ice bath was added 4-methylmorpholine (NMM) (0.099 mL, 0.9 mmol) via syringe. The mixture was stirred in the ice bath and was allowed to gradually warm to room temperature and stirred at room temperature for 24 hours. The mixture was concentrated under reduced pressure and the residue obtained triturated with water (20 mL) and extracted with ethyl acetate (4×20 mL). The combined organic extracts were dried over magnesium sulfate and concentrated under reduced pressure to afford crude material. Chromatography on silica gel eluting with 10–20% methanol in methylene chloride afforded the title compound (48 mg, 19%). $^1$H NMR (DMSO-d$_6$, 300 MHz) δ 2.50 (s, 3H), 2.55–2.92 (m, 4H), 3.00–3.87 (m, 4H), 4.00–4.25 (m, 2H), 4.97 (m, 2H), 6.84 (d, 1H), 6.90–7.45 (m, 14H), 7.50 (m, 1H), 7.79 (m, 2H). MS (FAB) m/e 827 (M+H)$^+$, 849 (M+Na)$^+$.

EXAMPLE 251

2,5-Di-{N-Bromoacetyl-(L)-Valyl}amino-3,4-dihydroxy-1,6-diphenyl hexane 2,5-Di-{(L)-Valyl}amino-3,4-dihydroxy-1,6-diphenyl hexane (1.00 g, 2 mmol) was dissolved in dimethylformamide (75 mL) with warming and then cooled to room temperature under nitrogen. Triethylamine (0.59 mL) was added followed by bromoacetic anhydride (1.043 g) in methylene chloride (1 mL). After 30 mintues, the solvents were removed in vacuo and the residue obtained triturated with ether and filtered. The solid obtained was washed with water and dried to afford the title compound (0.7 g, 47%). $^1$H NMR (CD$_3$OD, 300 MHz) δ 0.80 (m, 12H), 2.83 (m, 4H), 3.42 (s, 2H), 3.83 (d of d, 2H), 4.05 (m, 2H), 4.60 (m, 2H), 7.07–7.27 (m, 10H), 7.52 (d, 2H). MS (FAB) m/e 74 1 (M+H)$^+$.

EXAMPLE 252

2,5-Di-{N-[(1-Methylimidazol-2-yl)-thiomethylcarbonyl]-(L)-Valyl}amino-3,4-dihydroxy-1,6-diphenyl hexane To a solution of the resultant compound of Example 251 (100 mg, 0.135 mmol) dissolved in dimethylformamide containing triethylamine (40 μL) was added 2-mercapto-1-methyl imidazole (31 mg). The reaction mixture was stirred at room temperature for 30 minutes. The solvent was removed under reduced pressure and chased with 10% methanol in methylene chloride. The residue obtained was chromatographed on silica gel elutng with 10% methanol in methylene chloride to afford the title product (62 mg, 57%). $^1$H NMR (CDCl$_3$, 300 MHz) δ 0.83 (m, 12H), 2.17 (m, 2H), 2.85 (m, 4H), 3.40–3.80 (m, 10H), 4.20 (m, 2H), 4.47–4.85 (m, 2H), 6.82–7.37 (m, 14H), 8.69 (bd, 2H). MS (FAB) m/e 807 (M+H)$^+$.

EXAMPLE 253

2,5-Di-{N-[(Imidazol-2-yl)-thiomethylcarbonyl]-(L)-Valyl}amino-3,4-dihydroxy-1,6-diphenyl hexane The resultant compound of Example 251 (150 mg, 0.2 mmol) was reacted with 2-mercaptoimidazole (40.6 mg) by the procedure described in Example 252 and similarly purified to afford the title compound (74 mg, 47%). $^1$H NMR (DMSO-d$_6$, 300 MHz) δ 0.63 (m, 12H), 1.84 (m, 2H), 2.25–2.80 (m, 4H), 3.05–3.82 (m, 12H), 4.44 (m, 2H), 7.14 (m, 14H), 7.48 (bd, 2H), 8.07 (bd, 2H). MS (FAB) m/e 779 (M+H)$^+$.

EXAMPLE 254

2,5-Di-{N-[N-Methyl-N-(2-pyridylmethyl)aminocarbonyl]-(L)-Valyl}amino-3,4-dihydroxy-1,6-diphenyl hexane The resultant compound of Example 4A (199 mg, 0.66 mmol) and the resultant compound of Example 3F (766 mg) were dissolved in anhydrous dimethylformamide (3 mL) and stirred overnight at room temperature. The reaction mixture was diluted with ethyl acetate and washed with saturated sodium bicarbonate (3x) and water. The organic phase was dried over magnesium sulfate and concentrated under reduced pressure. The residue obtained was chromatographed on silica gel eluting with 5% methanol in methylene chloride to afford the title compound (303 mg, 58%). $^1$H NMR (CDCl$_3$, 300 MHz) δ 0.68 (d, 6H), 0.86 (d, 6H), 2.13 (m, 2H), 2.87 (m, 4H), 3.00 (s, 6H), 3.57 (bs, 2H), 4.00 (d of d, 2H), 4.25 (m, 4H), 4.48 (s, 4H), 6.40 (m, 4H), 7.07–7.30 (m, 14H), 7.74 (d of t, 2H), 8.54 (d, 2H). MS (FAB) m/e 795 (M+H)$^+$, 817 (M+Na)$^+$.

EXAMPLE 255

2,5-Di-{N-[N-Methyl-N-(2-pyridylmethyl)aminocarbonyl]-(L)-Valyl}amino-3,4-dihydroxy-1,6-diphenyl hexane 3-O, 4-O-Carbonate To the resultant compound of Example 254 (300 mg, 0.31 mmol) dissolved in tetrahydrofuran (15 mL) at room temperature and then cooled to 0° C. was added N-methyl morpholine (0.125 mL) followed by triphosgene (112 mg). The cooling bath was removed and the reaction mixture was stirred for 3 hours at room temperature and then concentrated under reduced pressure. The residue obtained was washed with water and extracted with methylene chloride. The organic layer was dried over magnesium sulfate and concentrated under reduced pressure. The residue obtained was chromatographed on silica gel eluting with 5% methanol in methylene chloride to afford the title compound (247 mg, 80%). m.p. 118°–119° C. $^1$H NMR (CDCl$_3$, 300 MHz) δ 0.69 (d, 6H), 0.79 (d, 6H), 2.04 (m, 2H), 2.74–3.04 (m, 4H), 3.00 (s, 6H), 3.95 (t, 2H), 4.40 (s, 4H), 4.58 (m, 4H), 6.56 (bd, 4H), 7.10–7.32 (m, 14H), 7.75 (d of t, 2H), 8.51 (m, 2H). Anal calcd for C$_{45}$H$_{56}$N$_8$O$_7$: C, 65.83; H, 6.88; N, 13.65. Found: C, 65.72; H, 7.44; N, 12.36. MS (FAB) m/e 821 (M+H)$^+$.

EXAMPLE 256

2,5-Di-{N-[(2-Pyridylmethyl)oxycarbonyl]-(L)-Isoleucyl}amino-3,4-dihydroxy-1,6-diphenyl hexane The resultant compound of Example 4A (150 mg, 0.5 mmol) and the resultant compound of Example 25C (580 mg) were stirred in dimethylformamde (3 mL) at room temperature overnight. The reaction mixture was diluted with ethyl acetate and washed with sodium bicarbonate (3x). The organic layer was dried over magnesium sulfate and concentrated under reduced pressure to afford the title compound (278 mg, 70%). m.p. 220°–221° C. $^1$H NMR (DMSO-d$_6$, 300 MHz) δ 0.58 (d, 6H), 0.73 (t, 6H), 0.97 (m, 2H), 1.22 (m, 2H), 1.59 (m, 2H), 2.54–2.73 (m, 4H), 3.82 (d of d, 2H), 4.52 (m, 2H), 4.82 (bs, 2H), 5.10 (d of d, 4H), 7.03–7.42 (m, 20H), 7.84 (d of t, 2H), 8.55 (bd, 2H). MS (FAB) m/e 797 (M+H)$^+$, 819 (M+Na)$^+$.

EXAMPLE 257

2,5-Di-{N-[(2-pyridylmethyl)oxycarbonyl]-(L)-Valyl}amino-3,4-dihydroxy-1,6-diphenyl hexane 3-O,4-O-Carbonate The resultant compound of Example 260 (300 mg, 0.39 mmol) was reacted with triphosgene (116 mg) by the procedure described in Example 255. Purification as described in Example 255 gave the title product (268 mg, 86%). m.p. 118°–120° C. $^1$H NMR (CDCl$_3$, 300 MHz) δ 0.74 (d, 6H), 0.84 (d, 6H), 1.98 (m, 2H), 2.67–2.98 (m 4H), 3.98 (m, 2H), 4.53 (m, 4H), 5.23 (m, 4H), 6.80 (bd, 4H), 7.10–7.38 (m, 14H), 7.70 (d of t, 2H), 8.60 (d, 2H). Anal calcd for C$_{43}$H$_{50}$N$_6$O$_9$.0.5 H$_2$O: C, 64.24; H, 6.39; N, 10.45. Found: C, 63.91; H, 6.33; N, 10.38. MS (FAB) m/e 795 (M+H)$^+$.

EXAMPLE 258

2,5-Di-{N-[(2-pyridylmethyl)oxycarbonyl]-(L)-Valyl}amino-3,4-dihydroxy-1,6-diphenyl hexane 3-O, 4-O-Thiocarbonate To the resultant compound of Example 260 (300 mg, 0.26 mmol) dissolved in toluene (5 mL) was added thiocarbonyldiimidazole (140 mg). The reaction mixture was warmed at reflux for 3 hours and diluted with methylene chloride and washed with 10% citric acid (2x). The organic phase was dried over magnesium sulfate and concentrated under reduced pressure to afford the title compound (177 mg, 56%). m.p. 115°–117° C. $^1$H NMR (CDCl$_3$, 300 MHz) δ 0.66 (d, 6H), 0.80 (d, 6H), 2.00 (m, 2H), 2.94 (m, 4H), 3.84 (d of d, 2H), 4.60 (m, 2H), 5.08 (bd, 2H), 5.20 (s, 4H), 6.23 (bd, 4H), 7.00–7.40 (m, 14H), 7.72 (d of t, 2H), 8.61 (bd, 2H). Anal calcd for C$_{43}$H$_{50}$N$_6$O$_8$S.0.5 H$_2$O: C, 62.98; H, 6.27; N, 10.25. Found: C, 62.69; H, 6.13; N, 10.15. MS (FAB) m/e 811 (M+H)$^+$.

EXAMPLE 259

2,5-Di-{N-[N-Methyl-N-(2-pyridylmethyl)aminocarbonyl]-(L)-Isoleucyl}amino-3,4-dihydroxy-1,6-diphenyl hexane The resultant compound of Example 4A (150 mg) and the resultant compound of Example 16C (630 mg) were stirred in anhydrous dimethylformamide (3 mL) overnight at room temperature. The reaction mixture was diluted with ethyl acetate and washed with saturated sodium bicarbonate solution (2x) and water. The organic layer was dried over magnesium sulfate and concentrated under reduced pressure. The residue obtained was chromatographed on silica gel eluting with 4% methanol in methylene chloride to afford the title compound (250 mg, 81%). m.p. 160°–161° C. $^1$H NMR (CDCl$_3$, 300 MHz) δ 0.78 (m, 12H), 0.84–1.13 (m, 4H), 1.87 (m, 2H), 2.87 (m, 4H), 2.97 (s, 6H), 3.58 (S, 2H), 4.02 (d of d, 2H), 4..27 (m, 4H), 4.45 (s, 4H), 6.35 (bs, 2H), 6.45 (bd, 2H), 7.07–7.30 (m, 14H), 7.74 (d of t, 2H), 8.03 (m, 2H). Anal calcd for C$_{46}$H$_{62}$N$_8$O$_6$: C, 67.13; H, 7.59; N, 13.62. Found: C, 67.06; H, 7.54; N, 13.55. MS (DCI/NH$_3$) m/e 823 (M+H)$^+$.

EXAMPLE 260

2,5-Di-{N-[(2-Pyridylmethyl)oxycarbonyl]-(L)-valinyl}amino-3,4-dihydroxy-1,6-diphenyl hexane The resultant compound of Example 4A (2.5 g, 8.3 mmol) was reacted with the resultant compound of Example 2D (9.00 g) by the procedure described in Example 254. Crystallization from methylene chloride and ethyl acetate afforded the title compound (2.88 g, 45%). m.p. 221° C. $^1$H NMR (DMSO-d$_6$, 300 MHz) δ 0.64 (d, 6H), 0.70 (d, 6H), 1.82 (m, 2H), 2.56–2.83 (m, 4H), 3.78 (m, 2H), 4.50 (m, 2H), 4.85 (bs, 2H), 5.10 (s, 4H), 7.05–7.42 (m, 20H), 7.84 (d of t, 2H), 8.54 (bd, 2H). Anal calcd for C$_{42}$H$_{52}$N$_6$O$_8$: C, 65.61; H, 6.82; N, 10.93. Found: C, 65.60; H, 6.85; N, 10.94. MS (FAB) m/e 769 (M+H)$^+$.

EXAMPLE 261

(2S,3S,5S)-2.5-Di- (Boc-amino)-1,6-diphenyl-3-hydroxy-hexane

To a solution of the resultant compound of Example 1E (1.00 g, 4.1 mmol) dissolved in methylene chloride (40 mL) was added di-t-butyldicarbonate (1.98 g, 2.2 equiv). The reaction mixture was stirred at room temperature for 1 hour and then concentrated in vacuo at 40° C. The residue obtained was chromatographed on silica gel eluting with 1:3 going to 1:2 ethyl acetate/hexane to afford the title compound (1.315 g, 72%). $^1$H NMR (CDCl$_3$, 300 MHz) δ 1.39 (s, 18H), 1.62 (m, 2H), 2.74 (d, 2H), 2.85 (t, 2H), 3.64 (m, 2H), 3.86 (d of d, 1H), 4.55 (bs, 1H), 4.80 (bd, 1H), 7.07–7.32 (m, 10H). Anal calcd for C$_{28}$H$_{40}$N$_2$O$_5$: C, 69.39; H, 8.32; N, 5.78. Found: C, 69.21; H, 8.38; N, 5.73. MS (DCI/NH$_3$) m/e 485 (M+H)$^+$, 502 (M+H+NH$_3$)$^+$.

EXAMPLE 262

(2S,3S,5S)-1,6-Diphenyl-2,5-di-(phenyloxycarbonyl)-3-hydroxy-hexane

To a solution of the resultant compound of Example 1E (100 mg, 0.35 mmol) and anhydrous triethylamine (0.12 mL, 2.5 equiv) dissolved in anhydrous methylene chloride (4 mL) and cooled under nitrogen to −40° C. was added phenyl chloroformate (0.09 mL, 2 equiv). After stirring at −40° C. for 1 hour, the reaction mixture was diluted with methylene chloride (50 mL) and washed with saturated sodium bicarbonate (20 mL) and saturated sodium chloride (20 mL). The organic phase was dried over magnesium sulfate and concentrated under reduced pressure. The residue obtained was chromatographed on silica gel eluting with 1:4 going to 1:2 going to 1:1 ethyl acetate/hexane to afford the title compound (64 mg, 35%). $^1$H NMR (CDCl$_3$, 300 MHz) δ 1.80 (m, 2H), 2.86 (d, 2H), 2.94 (d of d, 2H), 3.02 (bd, 1H), 3.76 (bs, 1H), 3.86 (d of d, 1H), 4.03 (d of d, 1H), 5.13 (bd, 1H), 5.35 (bd, 1H), 7.00–7.40 (m 20H) MS (DCI/NH$_3$) m/e 525 (M+H)$^+$, 542 (M+H+NH$_3$)$^+$.

EXAMPLE 263

(2S,3S,5S)-2,5-Di-(isopropyloxycarbonylamino)-1,6-diphenyl-3-hydroxy-hexane

The resultant compound of Example 1E (100 mg, 0.35 mmol) was reacted with 1M isopropyl chloroformate in toluene (0.70 mL, 2.0 equiv) by the procedure described in Example 262. Column chromatography on silica gel eluting with 1:2 going to 1:1 ethyl acetate/hexane afforded the title compound (92 mg, 57%). $^1$H NMR (CDCl$_3$, 300 MHz) δ 1.17 (m, 12H), 1.63 (m, 2H), 2.75 (d, 2H), 2.86 (m, 2H), 3.31 (bs, 1H), 3.69 (m, 2H), 3.90 (m, 1H), 4.63 (m, 1H), 4.89 (m, 3H), 7.04–7.42 (m, 10H). Anal calcd for C$_{26}$H$_{36}$N$_2$O$_5$: C, 68.40; H, 7.95; N, 6.14. Found: C, 68.10; H, 7.99; N, 6.14. MS (DCI/NH$_3$) m/e 457 (M+H)$^+$, 474 (M+H+NH$_3$)$^+$.

EXAMPLE 264

(2S,3S,5S)-2,5-Di-(3,3-dimethylacryloylamino)-1,6-diphenyl-3-hydroxy-hexane

The resultant compound of Example 1E (150 mg, 0.53 mmol) was reacted with 3,3-dimethylacryloyl chloride (0.12 mL, 2.0 equiv) by the procedure described in Example 262 except that pyridine (0.26 mL, 6 equiv) was used instead of triethylamine. Column chromatography on silica gel eluting with 1:2 going to 1:1 ethyl acetate/hexane afforded the title compound (182 mg, 77%). $^1$H NMR (CDCl$_3$, 300 MHz) δ 1.65 (m, 3H), 1.82 (m, 6H), 2.10 (m, 6H), 2.87 (m, 2H), 2.90 (m, 2H), 3.62 (m, 1H), 3.96 (m, 1H), 4.10 (m, 1H), 4.62 (bs, 1H), 5.43 (m, 1H), 5.50 (m, 1H), 5.53 (bd, 1H), 5.72 (bd, 1H), 7.05–7.30 (m, 10H). Anal calcd for C$_{28}$H$_{36}$N$_2$O$_3$: C, 74.97; H, 8.09; N, 6.24. Found: C, 74.25; H, 8.43; N, 6.12. MS (DCI/NH$_3$) m/e 449 (M+H)$^+$, 466 (M+H+NH$_3$)$^+$.

EXAMPLE 265

(2S,3S,5S)-2,5-Di-(isovalerylamino)-1,6-diphenyl-3-hydroxy-hexane

The resultant compound of Example 1E (150 mg, 0.53 mmol) was reacted with isovaleryl chloride (0.13 mL, 2.0 equiv) by the pyridine procedure described in Example 264. Column chromatography eluting with 1:2 going to 1:1 going to 2:1 ethyl acetate/hexane afforded the title compound (38 mg, 16%). $^1$H NMR (CDCl$_3$, 300 MHz) δ 0.84 (m, 12H), 1.65 (m, 3H), 1.97 (m, 6H), 2.78 (m, 2H), 2.89 (d, 2H), 3.63 (bs, 1H), 3.99 (m, 1H), 4.10 (m, 1H), 4.52 (bs, 1H), 5.60 (d, 1H), 5.80 (d, 1H), 7.07–7.30 (m, 10H). MS (DCI/NH$_3$) m/e 453 (M+H)$^+$, 470 (M+H+NH$_3$)$^+$.

EXAMPLE 266

(2S,3S,5S)-2,5-Di-(isobutyloxycarbonylamino)-1,6-diphenyl-3-hydroxy-hexane

The resultant compound of Example 1E (100 mg, 0.35 mmol) was reacted with isobutylchloroformate (0.09 mL, 2.0 equiv) by the procedure described in Example 262. Column chromatography on silica gel eluting with 1:2 ethyl acetate/hexane afforded the title compound (114 mg, 69%). $^1$H NMR (CDCl$_3$, 300 MHz) δ 0.89 (m, 12H), 1.65 (m, 2H), 1.86 (m, 2H), 2.77 (bd, 2H), 2.87 (m, 2H), 3.30 (bs, 1H), 3.60–3.97 (m, 7H), 4.70 (m, 1H), 4.97 (bd, 1H), 7.07–7.32 (m, 10H). Anal calcd for C$_{28}$H$_{40}$N$_2$O$_5$: C, 69.39; H, 8.32; N, 5.78. Found: C, 69.20; H, 8.32; N, 5.75. MS (DCI/NH$_3$) m/e 485 (M+H)$^+$, 502 (M+H+NH$_3$)$^+$.

EXAMPLE 267

(2S,3R,5S)-1,6-Diphenyl-3-hydroxy-2,5-di-(Boc-amino)-hexane

A. 1,6-Diphenyl-3-oxo-2,5-di-(Boc-amino)-hexane

To a solution of oxalyl chloride (0.09 mL, 1.03 mmol) dissolved in anhydrous methylene chloride (3 mL) and cooled to −78° C. was added dimethyl sulfoxide. (0.147 mL, 2.07 mmol) dropwise. The reaction mixture was stirred at −78° C. for 10 minutes and then a solution of the resultant compound of Example 261 (250 mg, 0.52 mmol) dissolved in anhydrous methylene chloride (5 mL) was added dropwise. After stirring at −78° C. for 1 hour, anhydrous triethylamine (0.57 mL, 4.12 mmol) was added, the cooling bath was removed, and the reaction mixture was stirred for 15 minutes. The reaction mixture was diluted with methylene chloride (50 mL) and washed with saturated sodium bicarbonate (20 mL) and saturated sodium chloride (20 mL), dried over magnesium sulfate, and concentrated in vacuo. The residue obtained was chromatographed on silica gel eluting with 1:6 going to 1:4 ethyl acetate/hexane to afford the title compound (235 mg, 94%). MS (DCI/NH$_3$) m/e 483 (M+H)$^+$, 500 (M+H+NH$_3$)$^+$.

B. (2S,3S,4R)-1,6-Diphenyl-3-hydroxy-2,5-di-(Boc-amino)-hexane

To the resultant compound of Example 267A (20 mg, 0.04 mmol) dissolved in methanol (0.4 mL) and methylene chloride (0.3 mL) and cooled to −78° C. was added sodium borohydride (1.6 mg, 1.0 equiv). The reaction mixture was allowed to slowly warm to −20° C. and maintained at that temperature for 18 hours. The reaction mixture was diluted with methylene chloride (10 mL) and washed with saturated sodium chloride solution (3 mL), dried over magnesium sulfate, and concentrated in vacuo. The residue obtained was chromatographed on silica gel eluting with 1:4 going to 1:2 ethyl acetate/hexane to afford the title compound (14.7 mg, 73%). $^1$H NMR (CDCl$_3$, 300 MHz) δ 1.35 (s, 9H), 1.40 (s, 9H) 1.42–1.73 (m, 3H), 2.80 (m, 2H), 2.87 (bd, 2H), 3.56 (bs, 1H), 3.84 (bs, 1H), 4.15 (m, 1H), 4.46 (m, 1H), 4.59 (m, 1H), 7.12–7.32 (m, 10H). MS (DCI/NH$_3$) m/e 485 (M+H)$^+$.

EXAMPLE 268

1,5-Dichloro-2,3,4-triformyl arabitol

To a solution of anhydrous dimethylformamide (146 mL, 1.9 mol) in anhydrous methylene chloride (1450 mL) at 0° C. was added dropwise oxalyl chloride (126 mL, 1.5 mol). The reaction mixture was stirred at 0° C. under nitrogen for 1 hour and then a solution of arabitol (22 g, 0.14 mmol) dissolved in dimethylformamide (350 mL) was added at such a rate that the temperature remained below 5° C. After the addition was complete, the bath was removed and the reaction mixture was stirred at room temperature under nitrogen for 1 hour and then at reflux for 7 hours. The reaction mixture was diluted with ethyl acetate (2 L) and washed with cold water (2 L). The aqueous layer was back-extracted with ethyl acetate (1 L). The combined organic extracts were washed with saturated sodium chloride (1 L), dried over magnesium sulfate and concentrated under reduced pressure to afford crude material (58.2 g). Chromatography on silica gel eluting with a gradient of 2:8 to 8:2 methylene chloride/hexane gave the title compound (21.7 g, 55%). $^1$H NMR (CDCl$_3$, 300 MHz) δ 3.61 (d, 2H), 3.66 (d of d, 2H), 3.81 (d of d, 1H), 5.35 (m, 1H), 5.50 (m, 1H), 5.71 (m, 1H), 8.08 (s, 1H), 8.10 (s, 1H), 8.19 (s, 1H). Anal calcd for C$_8$H$_{10}$Cl$_2$O$_6$: C, 35.19; H, 3.69. Found: C, 35.30; H, 3.75. MS (DCI/NH$_3$) m/e 290 (M+H+NH$_3$)$^+$. High Resolution Mass Spec calcd for C$_8$H$_{10}$Cl$_2$O$_6$: 272.9933. Found: 272.9930. IR (CDCl$_3$) 1150, 1720 cm$^{-1}$. [α]$_D$=+31.1° (c=1.12, CHCl$_3$, 22° C.).

EXAMPLE 269

1,2:4,5-Bis-epoxy-3-hydroxy-pentane

To the resultant compound of Example 268 (1.00 g, 3.7 mmol) dissolved in anhydrous tetrahydrofuran (20 mL) and cooled to 0° C. under nitrogen was added sodium methoxide (1.00 g, 6 equiv). The reaction mixture was stirred at 0° C. under nitrogen for 30 minutes and then diluted with ether (40 mL) and filtered through Celite. The filtrate was concentrated in vacuo to afford crude material (278 mg). Chromatography on silica gel eluting with 1:1 ethyl acetate/hexane afforded the title compound (102 mg, 24%). $^1$H NMR (CDCl$_3$, 300 MHz) δ 2.04 (d, 1H), 2.79–2.89 (m, 4H), 3.11–3.20 (m, 2H), 3.60 (d of d, 1H). MS (DCI/NH$_3$) m/e 134 (M+H+NH$_3$)$^+$. IR (CDCl$_3$) 3540 3060 3000 2925 cm$^{-1}$. [α]$_D$=−4.3° (c=1.07, CHCl$_3$, 22° C.).

EXAMPLE 270

1,2:4,5-Bis-epoxy-3-methanesulfonyloxy-pentane

To the resultant compound of Example 269 (4.2456 g, 36.6 mmol) dissolved in anhydrous tetrahydrofuran (200 mL) and cooled to −20° C. under nitrogen was added sodium hydride (878 mg, 1.0 equiv). The reaction mixture was stirred at 0° C. for 30 minutes and then cooled to −20° C. and treated with anhydrous triethylamine (9.2 mL, 1.9 equiv) and methanesulfonyl chloride (4.3 mL, 1.5 equiv). After stirring at −20° C. under nitrogen for 30 minutes, the reaction was diluted with chloroform (400 mL) and washed with pH 6 phosphate buffer (80 mL). The aqueous wash was back-extracted with chloroform (100 mL). The combined organic extracts were dried over magnesium sulfate and concentrated in vacuo to give crude material (9.8 g). Chromatography on silica gel eluting with 8:2 methylene chloride/hexane going to 9/1 methylene chloride/ethyl acetate gave the title compound (6.23 g, 88%). $^1$H NMR (CDCl$_3$, 300 MHz) δ 2.80–2.85 (m, 2H), 2.92 (d of d, 1H), 2.98 (d of d, 1H), 3.14 (s, 3H), 3.24–3.33 (m, 2H), 4.13 (d of d, 1H). Anal calcd for C$_6$H$_{10}$O$_5$S: C, 37.11; H, 5.19. Found: C, 36.52; H, 5.12. MS (DCI/NH$_3$) m/e 212 (M+H+NH$_3$)$^+$. IR (CDCl$_3$) 1365, 1175, 955 cm$^{-1}$. [α]$_D$=+3.9° (c=1.44, CHCl$_3$, 22° C.).

EXAMPLE 271

1,5-Dichloro-2,3,4-trihydroxy pentane

The resultant compound of Example 268 (250 mg, 0.92 mmol) was dissolved in methanol (5 mL), stirred at 50° C. for 1 hour, and then concentrated in vacuo to give crude material (192 mg). Chromatography on silica gel eluting with 1:1 ethyl acetate/hexane afforded the title compound (172 mg, 99%). $^1$H NMR (D$_2$O, 300 MHz) δ 3.67–3.71 (m, 2H), 3.76–3.79 (m, 1H), 3.86–3.89 (m, 2H), 3.96–4.02 (m, 1H), 4.06–4.11 (m, 1H). $^{13}$C NMR (D$_2$O, 300 MHz) PPM 48.278, 50.574, 72.434, 72.741, 72.951. Anal calcd for C$_5$H$_{10}$C$_{12}$O$_3$: C, 31.77; H, 5.33. Found: C, 31.67; H, 5.29. MS (DCI/NH$_3$) m/e 206 (M+H+NH$_3$)$^+$. [α]$_D$=−3.2° (c=1.21, H$_2$O, 22° C.).

EXAMPLE 272

(2S,3S,5S)-1,6-Diphenyl-2,5-di[N-(furan-2-ylmethyloxycarbonyl)amino]-3-hydroxy hexane A. (Furan-2-yl) (4-nitrophenyl)carbonate To a solution of 2-furanmethanol (413 mg, 0.261 mmol) and N-methylmorpholine (468 μL, 4.261 mmol) dissolved in methylene chloride (3 mL) and cooled in an ice bath was added a solution of 4-nitrophenylchloroformate (859 mg, 4.261 mmol) dissolved in methylene chloride (3 mL). The mixture was stirred at 0° C. for 3.5 hours and then worked up to give a residue which was chromatographed on silica gel eluting with 10% ethyl acetate in hexane followed by 10% ethyl acetate in methylene chloride to afford the title compound (113 mg) after cyrstallization from ethyl acetate and hexane.

B. (2S,3S,5S)-1,6-Diphenyl-2,5-di[N-(furan-2-ylmethyloxycarbonyl)amino]-3-hydroxy hexane To the compound resulting from Example 1E (75 mg, 0.264 mmol) dissolved in dimethylformamide (0.6 mL) was added the compound resulting from Example 272A (208 mg, 0.79 mmol). The mixture was stirred at room temperature overnight and then the solvent removed under reduced pressure. The crude product was chromatograhed on silica gel eluting with 5–10% ethyl acetate in methylene chloride to afford the title compound. $^1$H NMR (DMSO-d$_6$, 300 MHz) δ 1.46 (m, 2H), 2.53–2.79 (m, 5H), 3.57 (m, 1H), 3.89 (m, 3H), 4.64 (d, 1H), 4.79–4.95 (m, 5H), 6.41 (m, 4H), 6.89 (d, 1H), 7.08–7.29 (m, 13H), 7.63 (m, 2H). Anal calcd for C$_{30}$H$_{32}$N$_2$O$_7$: C, 67.67; H, 6.01; N, 5.26. Found: C, 67.25; H, 5.94; N, 5.22. MS (DCI/NH$_3$) m/e 533 (M+H)$^+$, 550 (M+H+NH$_3$)$^+$.

EXAMPLE 273

(2S,3S,5S)-1,6-Diphenyl-2,5-di[N-(furan-3-ylmethyloxycarbonyl)amino]-3-hydroxy hexane (Furan-3-yl) (4-nitrophenyl)carbonate was prepared in analogy to Example 272A starting from 3-furanmethanol instead of 2-furanmethanol. The compound resulting from Example 1E (70 mg, 0.249 mmol) was reacted with the above carbonate (144 mg, 0.548 mmol) by the procedure described in Example 272B to afford crude material. Column chromatography on silica gel eluting with a gradient (5%, 10%, 50%) of ethyl acetate in methylene chloride afforded the title compound. $^1$H NMR (DMSO-$d_6$, 300 MHz) δ 1.48 (m, 2H), 2.52–2.78 (m, 5H), 3.56 (m, 1H), 3.88 (m, 2H), 4.64 (d, 1H), 4.78 (d, 4H), 6.37 (s, 2H), 6.78 (d, 1H), 7.03 (d, 1H), 7.10–7.28 (m, 10H), 7.60 (m, 3H). Anal calcd for $C_{30}H_{32}N_2O_7$: C, 67.67; H, 6.01; N, 5.26. Found: C, 67.31; H, 5.99, N, 5.21. MS (DCI/NH$_3$) m/e 533 (M+H)$^+$, 550 (M+H+NH$_3$)$^+$.

EXAMPLE 274

(2S, 3S, 5S)-1,6-Diphenyl-2,5-di[N-(5-bromopyridin-3-ylmethyloxycarbonyl)amino]-3-hydroxy hexane A. (5-Bromo-pyridin-3-ylmethyl)(4-nitrophenyl)carbonate 5-Bromo-nicotinic acid (5,00 g, 24.7 mmol) was dissolved in methanol (50 mL) and saturated with hydrochloric acid gas. The reaction mixture was allowed to stand for 2.5 days and then filtered. The filtrate was concentrated under reduced pressure and methylene chloride was added. The solution was washed with saturated sodium bicarbonate solution. The aqueous wash was back-extracted with methylene chloride (2x). The combined organic extracts were dried over magnesium sulfate and concentrated in vacuo to afford 5-bromo-nicotinic acid methyl ester (4.72 g).

To the above methyl ester (4.536 g, 21 mmol) dissolved in tetrahydrofuran (15 mL) and cooled in a dry ice/acetone bath was added 1M lithium aluminum hydride (21 mL, 21 mmol) diluted with tetrahydrofuran (10 mL). The reaction mixture was stirred for 40 minutes and then water (0.80 mL) followed by 15% sodium hydroxide (0.80 mL) and water (2.4 mL) were added. The mixture was stirred for 1 hour and filtered. The filtrate was dried over magnesium sulfate and concentrated under reduced pressure. The crude product was chromatographed on silica gel eluting with 2% methanol in methylene chloride to afford 5-bromo-3-pyridinemethanol (2.472 g).

The above compound (817 mg, 4.346 mmol) was reacted with 4-nitrophenylchloroformate (1.051 g, 5.21 mmol) by the procedure described in Example 272A to give the title compound (847 mg, 55%).

B. (2S,3S,5S)-1,6-Diphenyl-2,5-di[N-(5-bromopyridin-3-ylmethyloxycarbonyl)amino]-3-hydroxy hexane The compound resulting from Example 1E (65 mg, 0.229 mmol) was reacted with the compound resulting from Example 274A (242 mg, 0.687 mmol) by the procedure described in Example 272B to give the title compound (114 mg, 70%). $^1$H NMR (DMSO-$d_6$, 300 MHz) δ 1.50 (m, 2H), 2.53–2.74 (m, 5H), 3.56 (m, 1H), 3.76 (m, 2H), 4.72 (d, 1H), 4.98 (d, 4H), 6.99–7.25 (m, 12H), 7.92 (m, 2H), 8.49 (m, 2H), 8.64 (dd, 2H). Anal calcd for $C_{32}H_{32}Br_2N_4O_5$: C, 53.93; H, 4.49; N, 7.86. Found: C, 54.46; H, 4.63; N, 7.93. MS (DCI/NH$_3$) m/e 711 (M+H)$^+$.

EXAMPLE 275

(2S,3S,5S)-1,6-Diphenyl-2,5-di[N-(5-methylpyridin-3-ylmethyloxycarbonyl)amino]-3-hydroxy hexane 5-Methylpyridine-3-methanol was prepared in analogy to the procedure described in Example 274A. It was reacted with 4-nitrophenylchloroformate by the procedure described in Example 272A to give (5-methylpyridin-3-yl) (4-nitrophenyl)carbonate (474 mg).

The compound resulting from Example 1E (36.1 mg, 0.127 mmol) was reacted with the above carbonate (110 mg, 0.38 mmol) by the procedure described in Example 272B to give crude material. Column chromatography on silica gel eluting with a gradient (2%,5%) methanol in methylene chloride afforded the title compound (64 mg). $^1$H NMR (DMSO-$d_6$, 300 MHz) δ 1.48 (m, 2H), 2.25 (d, 6H), 2.52–2.73 (m, 5H), 3.55 (m, 1H), 3.88 (m, 2H), 4.68 (d, 1H), 4.93 (d, 4H), 6.92 (d, 1H), 7.08–7.26 (m, 12H), 7.46 (s, 2H), 8.32 (m, 3H). Anal calcd for $C_{34}H_{38}N_4O_5$: C, 70.10; H, 6.53; N, 9.62. Found: C, 70.29; H, 6.62; N, 9.60. MS (DCI/NH$_3$) m/e 583 (M+H)$^+$.

EXAMPLE 276

(2S,3S,5S)-1,6-Diphenyl-2,5-di[N-(N-Boc-6-aminopyridin-3-ylmethyloxycarbonyl)amino]-3-hydroxy hexane 6-Amino-nicotinic acid (5.00 g, 36.2 mmol) was esterified by the procedure described in Example 274A to give the methyl ester. To the methyl ester (2.013 g, 9.32 mmol) dissolved in acetonitrile (80 mL) was added di-t-butyldicarbonate (2.235 g, 10.25 mmol) followed by dimethylaminopyridine (122 mg, 1.0 mmol). The reaction mixture was stirred at room temperature for 4 hours and then additional di-t-butyl-dicarbonate (450 mg) was added. The reaction mixture was stirred an additional hour at room temperature and then stored in the refrigerator overnight. The solvent was removed under reduced pressure and the crude material was chromatographed on silica gel eluting with a gradient (5%, 10%) of ethyl acetate in methylene chloride to afford the N-Boc-6-amino-nicotinic acid methyl ester (1.85 g, 79%).

The methyl ester (1.85 g, 7.34 mmol) was reduced with lithium aluminum hydride by the procedure described in Example 274A to give, after chromatography on silica gel eluting with a gradient (2%,5%) of methanol in methylene chloride, N-Boc-6-amino-pyridine-3-methanol (1.064 g). This compound (311 mg, 1.388 mmol) was reacted with 4-nitrophenylchloroformate (308 mg, 1.53 mmol) by the procedure described in Example 272A to give (N-Boc-6-amino-pyridin-3-ylmethyl) (4-nitrophenyl)carbonate (388 mg).

The compound resulting from Example 1E (87 mg, 0.301 mmol) was reacted with the above carbonate (340 mg, 0.904 mmol) by the procedure described in Example 272B to give crude material. Chromatography on silica gel eluting with a gradient (2%,5%) of methanol in methylene chloride afforded the title compound (133 mg). $^1$H NMR (DMSO-$d_6$, 300 MHz) δ 1.47 (s, 20H), 2.53–2.75 (m, 5H), 3.55 (m, 1H), 3.87 (m, 2H), 4.65 (d, 1H), 4.89 (d, 4H), 6.87 (d, 1H), 7.07–7.27 (m, 11H), 7.59 (dd, 2H), 7.75 (dd, 2H), 8.18 (m, 2H), 9.80 (d, 2H). Anal calcd for $C_{42}H_{52}N_6O_9 \cdot 0.33 H_2O$: C, 63.80; H, 6.71; N, 10.63. Found: C, 63.94; H, 6.67; N, 10.57. MS (FAB) M/E 785 (M+1).

EXAMPLE 277

(2S,3S,5S)-1,6-Diphenyl-2-[N-(furan-3-ylmethyloxycarbonyl)amino]-5-[N-(pyridin-3-ylmethyloxycarbonyl)amino]-3-hydroxy hexane 3-Pyridinemethanol was reacted with 4-nitrophenylchloroformate by the procedure described in Example 272A to give the (3-pyridylmethyl) (4-nitrophenyl) carbonate. This compound was reacted with the compound resulting from Example 1E by the procedure described in Example 272B to give a mixture of 2- and 5- substituted compounds which were separable by column chromatography. The (2S,3R,5S)-1,6-diphenyl-5-[N-(pyridin-3-ylmethyloxycarbonyl)amino]-3-hydroxy hexane compound (55 mg, 0.131 mmol) was reacted with (furan-3-yl) (4-nitrophenyl)carbonate, prepared as described in Example 273, by the procedure described in Example 272B to give, after chromatography on silica gel eluting with a gradient (2%,5%) of methanol in methylene chloride, the title compound (63.1 mg). $^1$H NMR (DMSO-$d_6$, 300 MHz) δ 1.50 (m, 2H), 2.54–2.75 (m, 5H), 3.56 (m, 1H), 3.88 (m, 2H), 4.66 (d, 1H), 4.68–4.92 (m, 1H), 4.79 (s, 2H), 4.97 (s, 2H), 6.37 (m, 1H), 6.79 (d, 1H), 6.90–7.38 (m, 12H), 7.25 (dd, 1H), 7.6 (m, 3H), 8.50 (m, 2H). Anal calcd for $C_{31}H_{33}N_3O_6 \cdot 0.33\ H_2O$: C, 67.78; H, 6.19; N, 7.65. Found: C, 67.97; H, 6.15; N, 7.69. MS (DCI/$NH_3$) m/e 544 (M+H)$^+$.

EXAMPLE 278

(2S,3S,5S)-1,6-Diphenyl-5-[N-(furan-3-ylmethyloxycarbonyl)amino]-2-[N-(pyridin-3-ylmethyloxycarbonyl)amino]-3-hydroxy hexane The other regio-isomer described in Example 277, (2S,3R,5S)-1,6-diphenyl-2-[N-(pyridin-3-ylmethyloxycarbonyl)amino]-3-hydroxy hexane, (31.7 mg, 0.0756 mmol) was reacted with (furan-3-yl) (4-nitrophenyl)carbonate (24 mg, 0.091 mmol), prepared as described in Example 273, by the procedure described in Example 272B to give, after column chromatography on silica gel eluting with a gradient (2%, 5%) methanol in methylene chloride, the title compound (22.7 mg). $^1$H NMR (DMSO-$d_6$, 300 MHz) δ 1.48 (m, 2H), 2.53–2.76 (m, 5H), 3.57 (m, 1H), 3.87 (m, 2H), 4.68 (d, 1H), 4.77 (s, 2H), 4.99 (s, 2H), 6.37 (s, 1H), 6.95 (d, 1H), 7.03 (d, 1H), 7.08–7.27 (m, 10H), 7.33 (dd, 1H), 7.60 (m, 3H), 8.50 (m, 2H). MS (DCI/$NH_3$) m/e 544 (M+H)$^+$.

EXAMPLE 279

(2S,3S,5S)-1,6-Diphenyl-2,5-[N-(thiophene-3-ylmethyloxycarbonyl)amino]-3-hydroxy hexane 3-Thiophenemethanol (285 mg, 2.5 mmol) was reacted with 4-nitrophenylchloroformate (554 mg, 2.75 mmol) by the procedure described in Example 272A to give (thiophen-3-ylmethyl) (4-nitrophenyl)carbonate (598 mg). This compound (170 mg, 0.61 mmol) was reacted with the compound resulting from Example 1E (57.8 mg, 0.203 mmol) by the procedure described in Example 272B to give, after column chromatography on silica gel eluting with a gradient (5%, 10%,20%) of ethyl acetate in methylene chloride, the title compound. $^1$H NMR (DMSO-$d_6$, 300 MHz) δ 1.50 (m, 2H), 2.54–2.78 (m, 5H), 3.58 (m, 1H), 3.90 (m, 3H), 4.67 (d, 1H), 4.85 (m, 1H), 4.91 (m, 4H), 6.84 (d, 1H), 6.95–7.33 (m, 16H), 7.49 (m, 2H). Anal calcd for $C_{30}H_{32}N_2O_5S_2$: C, 63.83; H, 5.67; N, 4.96. Found: C, 63.74; H, 5.76; N, 4.97. MS (DCI/$NH_3$) m/e 565 (M+H)$^+$, 582 (M+H+$NH_3$)$^+$.

EXAMPLE 280

(2S,3S,5S)-1,6-Diphenyl-2,5-[N-(thiophene-3-ylmethyloxycarbonyl)amino]-3-hydroxy hexane This compound was prepared in analogy to Example 279 starting from 2-thiophenemethanol instead of 3-thiophenemethanol. The crude product was chromatographed on silica gel eluting with a gradient (5%, 10%) ethyl acetate in methylene chloride to give the title compound. $^1$H NMR (DMSO-$d_6$, 300 MHz) δ 1.48 (m, 2H), 2.53–2.77 (m, 4H), 3.56 (m, 1H), 3.90 (m, 2H), 4.63 (d, 1H), 5.00–5.17 (m, 5H), 6.86 (d, 1H), 6.94–7.28 (m, 16H), 7.50 (m, 2H). Anal calcd for $C_{30}H_{32}N_2O_5S_2$: C, 63.83; H, 5.67; N, 4.96. Found: C, 63.80; H, 5.74; N, 4.89. MS (DCI/$NH_3$) m/e 565 (M+H)$^+$, 582 (M+H+$NH_3$)$^+$.

EXAMPLE 281

(2S,3S,5S)-1,6-Diphenyl-2,5-[N-(2-methyl-pyridin-3-ylmethyloxycarbonyl)amino]-3-hydroxy hexane Methyl 2-methylnicotinate (2.00 g, 12.1 mmol) was reduced to 2-methyl-3-pyridinemethanol using lithium aluminum hydride by the procedure described in Example 274A. This compound was converted to (2-methyl-pyridin-3-ylmethyl) (4-nitrophenyl)carbonate by the procedure also described in Example 274A. This carbonate (170 mg, 0.59 mmol) was reacted with the compound resulting from Example 1E (56 mg, 0.0197 mmol) by the procedure described in Example 272B to give, after column chromatography on silica gel eluting with a gradient (2%,5%) of methanol in methylene chloride, the title compound (63.6 mg). $^1$H NMR (DMSO-$d_6$, 300 MHz) δ 1.51 (m, 2H), 2.40 (s, 6H), 2.54–2.75 (m, 5H), 3.60 (m, 1H), 3.88 (m, 2H), 4.72 (d, 1H), 4.95 (m, 4H), 7.00 (d, 1H), 7.03–7.28 (m, 16H), 7.47 (m, 2H), 8.35 (m, 2H). Anal calcd for $C_{34}H_{38}N_4O_5 \cdot 0.5\ H_2O$: C, 69.04; H, 6.60; N, 9.48. Found: C, 68.98; H, 6.48; N, 9.39. MS (DCI/$NH_3$) m/e 583 (M+H)$^+$.

EXAMPLE 282

(2S,3S,5S)-1,6-Diphenyl-2,5-[N-(tetrahydrofuran-3-ylmethyloxycarbonyl)amino]-3-hydroxy hexane 3-Tetrahydrofuranmethanol (265 mg, 2.59 mmol) was reacted with 4-nitrophenylchloroformate (575 mg, 2.85 mmol) by the procedure described in Example 272A to give (tetrahydrofuran-3-ylmethyl) (4-nitrophenyl)carbonate (585 mg). This compound (155 mg, 0.581 mmol) was reacted with the compound resulting from Example 1E (55 mg, 0.194 mmol) to give, after column chromatography on silica gel eluting with a gradient (2%,5%) of methanol in methylene chloride, the tite compound (68.8 mg). $^1$H NMR (DMSO-$d_6$, 300 MHz) δ 1.48 (m, 2H), 1.85 (m, 2H), 2.35 (m, 2H), 2.54–2.77 (m, 5H), 3.52–3.88 (m, 16H), 4.64 (m, 2H), 6.70 (d, 1H), 6.98 (d, 1H), 7.10–7.28 (m, 10H). Anal calcd for $C_{30}H_{40}N_2O_7 \cdot H_2O$: C, 64.52; H, 7.53; N, 5.02. Found: C, 64.87; H, 7.22; N, 5.00. MS (DCI/$NH_3$) m/e 541 (M+H)$^+$, 558 (M+H+$NH_3$)$^+$.

EXAMPLE 283

(2R,3S,4R)-5-Cyclohexyl-2,4-bis-(N-(N-((benzyloxycarbonyl)valinyl)-amino)-3-hydroxy-1-phenylpentane A. (4S,5R)-N-Boc-5-(Cyclohexylmethyl)-4-hydroxy-2-pyrrolidinone To a solution of N-Boc-cyclohexylalanine (8.76 g, 32.3 mmole), Meldrum's acid (4.89 g, 33.9 mmole) and DMAP (9.07 g, 74.2 mmole) in anhydrous dichloromethane (160 mL) at ca. −10° C. was added isopropenyl chloroformate (3.80 g, 31.8 mmole) in anhydrous dichloromethane (7 mL) dropwise over 35 m. After 2 h at ca. −5° to 0° C. the reaction was quenched by the addition of cold 5% KHSO$_4$ solution (200 mL). The layers were separated and the organics were washed with cold 5% KHSO$_4$ solution (200 mL), then the combined aqueous portions were extracted with dichloromethane (50 mL) and the combined organics were washed with brine (100 mL) and dried (MgSO$_4$). Solvent evaporation left 12.41 g of the condensation adduct as a light yellow oil which was dissolved in ethyl acetate (350 mL) and heated to reflux for 30 m. The solution was allowed to cool and was extracted with half-saturated sodium bicarbonate solution (6×200 mL). The combined aqueous portions were carefully acidified to ca. pH 2 with powdered citric acid. The solution was extracted with ethyl acetate (3×200 mL) and the combined organics were dried (MgSO$_4$), filtered and concentrated to give 10.26 g of the (5R)-N-Boc-5-(cyclohexylmethyl)-2,4-pyrrolidindione as a thick yellow oil which was dissolved in dichloromethane (150 mL) and glacial acetic acid (20 mL) After chilling to ca. 0° C. sodium borohydride (4.69 g, 124 mmole) was added in portions over 1 h. After stirring the resulting mixture for ca. 3 h it was poured into ice water (300 mL) and stirred 10 m. The layers were separated and the aqueous portion was extracted with dichloromethane (2×100 mL). The organics were washed once with brine (300 mL) and then dried (Na$_2$SO$_4$). Evaporation left 9.0 g oil which was applied to a flash silica gel column (2"×16") and eluted with 50% ethyl acetate/hexane, yielding after solvent removal 5.58 g of the desired (4S,5R)-N-Boc-5-(cyclohexylmethyl)-4-hydroxy-2-pyrrolidinone: R$_f$=0.35 (50% EA/Hx); [α]$^{21}_D$=+40.9° (c=2.1, CHCl$_3$).

B. (3R,4S,5R)-N-Boc-3-Benzyl-5-(cyclohexylmethyl)-4-hydroxy-2-pyrrolidinone

To a solution of LDA (prepared from diisopropylamine (0.60 mL, 4.28 mmole) and n-BuLi (2.90 mL, 3.97 mmole) in THF (6.50 mL)) at −78° C. was added dropwise a solution of the resultant compound of Example 283A in THF (15.0 mL). After 2 h at −78° C., DMPU (0.98 mL, 8.10 mmole) was added and after 15 m, benzyl bromide (0.64 mL, 5.38 mmole). The reaction mixture was stirred at −78° C. for ca. 2.5 h and then was allowed to warm slowly to ca. −30° C. over 1.25 h at which point the reaction was quenched by the addition of 0.1N citric acid solution. The mixture was warmed to RT and partitioned between water and ether, the layers were separated, and the aqueous portion was extracted with ether (2x). The combined organics were washed with brine (2x) and then dried (MgSO$_4$). Flash silica gel chromatography (col. 1"×8"; hexane to 20% ethyl acetate/hexane) gave the product 0.482 g; R$_f$=0.35 (1:2 EA/Hx); [α]$^{25}_D$=+41.4° (c=3.01, CHCl$_3$).

C. (2R,3S,4R)-4-(N-Boc-amino)-2-benzyl-5-cyclohexyl-3-hydroxy-pentanoic acid acetonide To a solution of the resultant compound of Example 283B (176 mg, 0.45 mmole) in THF (5.0 mL) was added LiOH solution (1.35 mL, 1.35 mmole) and the resulting mixture was stirred 1.5 h at which point the solvents were removed in vacuo and the residue was partitioned between ethyl acetate and 1.0N citric acid solution. The aqueous phase was extracted with ethyl acetate (2x) and the combined organics were dried (NaSO$_4$). Evaporation of solvent left 256 mg residue which was dissolved in CH$_2$Cl$_2$ (6 mL) and to which was added 2-methoxypropene (0.13 mL, 1.35 mmole) and PPTS (ca. 5 mg). After stirring 2 h at RT the mixture was concentrated and residue applied to a column of flash silica gel (1"×5"; 5% to 25% ethyl acetate/hexane) to yield 191.9 mg of the desired compound; R$_f$=0.38 (1:2 EA/Hx); [α]$^{20}_D$= −10.1° (c=0.68, CHCl$_3$).

D. (2R,3S,4R)-4-(N-Boc-amino)-2-(N-Cbz-amino)-5-cyclohexyl-3-hydroxy-1-phenylpentane acetonide A solution of the resultant compound of Example 283C (176 mg, 395 μmole), triethylamine (0.11 mL, 790 μmole), and diphenylphosphoryl azide (0.13 mL, 603 μmole) in dry xylene (1.30 mL) was heated at ca. 50° C. for 1 h, the temperature was increased to ca. 85° C. and DMAP (ca. 10 mg) and benzyl alcohol (0.20 mL, 1.93 mmole) were added. The reaction was stirred 19 h then allowed to cool to RT and evaporated. The residue was subject to flash chromatography (1"×8"; 10% ethyl acetate/hexane) to give 150.6 mg of the desired compound; R$_f$=0.48 (20% EA/Hx); [α]$^{20}_D$=+2.7° (c=1.11, CHCl$_3$).

E. (2R,3S,4R)-4-(N-Boc-amino)-2-amino-5-cyclohexyl-3-hydroxy-1-phenylpentane acetonide A mixture of the resultant compound of Example 283D (133 mg, 240 μmole), 10% Pd/carbon (0.13 g) and glacial acetic acid (ca. 6 mL) were stirred together under an atmosphere of hydrogen for 21 h. After filtration, the solvent was removed from the filtrate and the residue taken up in CH$_2$Cl$_2$ and washed with 1M NaOH. The aqueous phase was extracted twice and the combined organics were washed with brine (1x) and dried (MgSO$_4$). Filtration and evaporation left 96.9 mg of the desired product; R$_f$=0.41 (1:2 EA/Hx); [α]$^{20}_D$=+3.8° (c=1.20, CHCl$_3$).

F. (2R,3S,4R)-5-cyclohexyl-2,4-diamino-3-hydroxy-1-phenylpentane

To a solution of the resultant compound of Example 283E (79 mg, 189 μmole) in MeOH (1.50 mL) at 0° C. was added 4.8M HCl/dioxane (0.40 mL, 1.9 mmole). The reaction was stirred ca. 2 h then allowed to warm slowly to RT over ca. 23 h. After flushing the solution with N$_2$ for several minutes, solid sodium carbonate was added and stirred 10 m. The mixture was diluted with CH$_2$Cl$_2$ (ca. 2x volume) and filtered though Celite. Evaporation left 80 mg yellow glass which was purified by flash silica gel chromatography (½"×4"; 1:10:89 conc. NH$_4$OH/MeOH/CH$_2$Cl$_2$) to give 41 mg desired product; R$_f$=0.05 (7% MeOH/CH$_2$Cl$_2$); [α]$^{20}_D$= −32.0° (c=0.67, CHCl$_3$); $^1$H NMR (CDCl$_3$, 300 MHz) δ 0.8–1.45(m, 8H), 1.6–1.85(m, 5H), 1.9–2.2(br s, 5H), 2.50(dd, J=10.5,13.8 Hz, 1H), 2.95(dd, J=4, 13.8 Hz, 1H), 3.1–3.2 (m, 2H), 3.25 (t, J=4.5 Hz, 1H), 7.1–7.4 (m, 5H); Mass spectrum: (M+H)$^+$=277; IR spectrum: (CDCl$_3$) 3390 cm$^{-1}$.

G. (2R,3S,4R)-5-Cyclohexyl-2,4-bis-(N-(N((benzyloxycarbonyl)-valinyl)-amino)-3-hydroxy-1-phenylpentane A solution of (2R,3S,4R)-5-cyclohexyl-2,4-diamino-3-hydroxy-1-phenylpentane (37.3 mg, 135 μmole) and N-(benzyloxycarbonyl)-valine p-nitrophenyl ester (111 mg, 298 μmole) in THF (1.3 mL) was stirred at RT for 2½ d. 1M NaOH (ca. 1 mL) was added and the mixture stirred 45 m when it was partitioned between ethyl acetate and saturated sodium bicarbonate solution. The layers were separated and the aqueous portion was saturated with NaCl and extracted with ethyl acetate (3x). The combined organics were washed with brine (1x) and dried (Na$_2$SO$_4$ and activated carbon). Filtration and evaporation left ca. 150 mg yellow oil which was subject to flash chromatography (1"×6"; 50% ethyl acetate) to give 70 mg desired compound; R$_f$=0.42 (1:2 EA/Hx); $^1$H NMR (CDCl$_3$, 300 MHz) δ 0.7–0.9 (m, 3H), 0.68 (d, J=7 Hz,3H), 0.75(d,J=7 Hz,3H), 0.96(d,J=7 Hz,3H), 1.00(d,J=7 Hz, 3H), 1.05–1.35 (m, 5H), 1.4–1.8 (m, 4H), 1.9–2.0 (m, 1H), 2.30 (dd, J=6, 13.5 Hz, 1H), 2.95 (dd, J=9, 13.8 Hz, 1H), 3.21(dd, J=3, 13.8 Hz, 1H), 3.45–3.55(m, 1H), 3.55–3.7(m, 1H), 3.7–3.75 (m, 1H), 3.8–3.9 (m, 1H), 4.02 (dd, J=6, 8 Hz, 1H), 4.78(d,J=9 Hz, 1h), 4.95–5.05(m,4H), 5.05(t,J=12 Hz, 1H), 5.58(d,J=7 Hz, 1H), 6.27(d,J=9 Hz, 1H), 6.95(d,J=7 Hz, 1H), 7.1–7.4 (m, 15H); Mass spectrum: (M+NH$_4$)$^+$=760, (M+H)$^+$=743.

EXAMPLE 284

(2R,3S,4R)-5-Cyclohexyl-2,4-bis-(N-(N-((2-pyridinyl)methoxycarbonyl)-valinyl)-amino-3-hydroxy-1-phenylpentane A solution of the resultant compound of Example 283F (20 mg, 72 μmole), the resultant compound of Example 2D (85 mg, 228 μmole) and triethylamine (33 μL, 236 μmole) in THF (0.70 mL) was stirred at RT for 2 d. The solvents were removed in vacuo and the residue subject to flash chromatography (½"×6"; 2% to 5% MeOH/CH$_2$Cl$_2$) to yield 31.5 mg desired compound; R$_f$=0.50 (10% MeOH/CH$_2$Cl$_2$); [α]$^{20}_D$=–19.5° (c=0.80, CHCl$_3$); $^1$H NMR (CDCl$_3$, 300 MHz) δ 0.7–1.3 (m, 3H), 0.68(d,J=7 Hz,3H), 0.78(d,J=7 Hz,3H), 0.98(d,J=7 Hz,3H), 1.00 (d, J=7 Hz, 3H), 1.4–1.5 (m, 1H), 1.5–1.85 (m, 9H), 2.05(dd, J=6.13 Hz,1H), 2.3–2.4(m, 1H), 2.95(dd, 9, 13.8 Hz,1H), 3.18(d,J=13.8 Hz,1H), 3.5–3.65(m,2H), 3.82(t,J=3 Hz, 1H), 3.85–3.95 (m, 1H), 4.06 (dd, J=5.4,7.5 Hz, 1H), 4.7–4.8 (m, 1H), 5.1–5.3 (m, 5H), 5.73 (d, J=7.5 Hz, 1H), 6.37 (d, J=9 Hz, 1H), 6.90 (d, J=6 Hz, 1H), 7.1–7.4 (m, 9H), 7.6–7.8 (m, 2H), 8.5–8.6 (m, 2H); Mass spectrum: (M+H)$^+$=745; Anal. Calcd for C$_{41}$H$_{56}$N$_6$O$_7$.½H$_2$O: C,65.32; H,7.62; N,11.15. Found: C, 65.32; H, 7.54; N, 11.10.

EXAMPLE 285

(2R,3S,4R)-2,4-Bis-(N-(N-((2-pyridinyl)methoxycarbonyl)-valinyl)-amino)-3-hydroxy-1-(2-napthyl)-5-phenylpentane A. (4S,5R)-N-Boc-5-Benzyl-4-hydroxy-2-pyrrolidinone Using the procedure of Example 283A but with N-Boc-phenylalanine replacing N-Boc-cyclohexylalanine the desired compound was provided.

B. (3R,4S,5R)-N-Boc-5-benzyl-4-hydroxy-3-(2-napthylmethyl)-2-pyrrolidinone

To a solution of LDA (prepared from diisopropylamine (0.68 mL, 4.85 mmole) and n-BuLi (3.45 mL, 4.66 mmole) in THF (8.0 mL)) at 0° C. was added HMPA (1.29 mL, 7.41 mmole); chilled to –78° C. and added the resultant compound of Example 285A (0.540 g, 1.85 mmole) in THE (7.0 mL). After 50 m a solution of 2-(bromomethyl)napthalene in THF (5.0 mL) was added and the reaction was stirred at –78° C. for 30 m before it was quenched by the addition of 1.0N citric acid solution. The mixture was diluted with ether(100 mL) and washed with 1.0N citric acid solution (2×50 mL). The aqueous portions were extracted with ether (1×50 mL) and discarded. The combined organics were washed with brine (3× 50 mL) and dried (MgSO$_4$). Evaporation and flash silica gel chromatography (1"×12"; hexane to 20% ethyl acetate/hexane) gave 0.28 g desired compound; R$_f$=0.39 (1:2 EA/Hx); [α]$^{25}_D$=–4.4° (c=0.59, CHCl$_3$).

C. (2R,3S,4R)-4-(N-Boc-amino)-3-hydroxy-2-(2-napthylmethyl)-5-phenylpentanoic acid acetonide Using the procedure of Example 283C but with the resultant compound of Example 285B (0.23 g, 0.53 mmole) replacing the resultant compound of Example 283B, 0.21 g of the desired compound was obtained; R$_f$=0.61 (50% EA/Hx).

D. (2R,3S,4R)-4-(N-Boc-amino)-2-(N-Cbz-amino)-3-hydroxy-1-(2-napthyl)-5-phenylpentane acetonide Using the procedure of Example 283D but with the resultant compound of Example 285C (203 mg, 414 μmole) replacing the resultant compound of Example 283C, 187 mg of the desired compound was obtained; R$_f$=0.36 (20% EA/Hx); $^1$H NMR (CDCl$_3$, 300 MHz) δ 1.36(s,3H), 1.53(s, 9H), 1.75 (s, 3H), 2.6–2.9 (m, 2H), 3.05–3.30 (m, 2H), 3.7–4.2 (m, 4H), 4.8–5.0(m, 2H), 7.0–7.3 (m, 11H), 7.4–7.5 (m, 3H), 7.65–7.8 (m, 3H); Mass spectrum: (M+NH$_4$)$^+$=612, (M+H)$^+$=595.

E. (2R,3S,4R)-2-amino-4-(N-Boc-amino)-3-hydroxy-1-(2-napthyl)-5-phenylpentane acetonide Using the procedure of Example 283E but with the resultant compound of Example 285D (180 mg, 303 μmole) replacing the resultant compound of Example 283D, 119 mg of the desired compound was obtained; R$_f$=0.06 (EA/Hx); $^1$H NMR (CDCl$_3$, 300 MHz) δ 1.33(s,3H), 1.54(s,9H), 1.6–1.7(m,2H), 1.75 (s, 3H), 2.3–2.5 (m, 1H), 2.6–2.8 (m, 1H), 2.85–2.95 (m, 1H), 3.1–3.2 (m, 1H), 3.2–3.3 (m, 1H), 3.7–3.85 (m, 1H), 4.1–4.25 (m, 1H) 7.15–7.3 (m, 6H), 7.4–7.5 (m, 2H), 7.53 (s, 1H), 7.7–7.9 (m, 3H); Mass spectrum: (M+H)$^+$=460.

F. (2R,3S,4R)-2,4-diamino-3-hydroxy-1-(2-napthyl)-5-phenylpentane

Using the procedure of Example 283F but with the resultant compound of Example 285E (114 mg, 248 μmole) replacing the resultant compound of Example 283E, 111 mg of the desired compound was obtained; R$_f$=0.28 (1:10:89 conc.NH$_4$OH/MeOH/CH$_2$Cl$_2$); Mass spectrum: (M+H)$^+$= 321.

G. (2R,3S,4R)-2,4-Bis-(N-(N-((2-pyridinyl)methoxycarbonyl)-valinyl)-amino)-3-hydroxy-1-(2-napthyl)-5-phenylpentane Using the procedure of Example 284A but with the resultant compound of Example 285F (58.5 mg, 182 μmole) replacing the resultant compound of Example 283F, 80 mg of the desired compound was obtained; R$_f$=0.50 (10% MeOH/CH$_2$Cl$_2$); $^1$H NMR (CDCl$_3$, 300 MHz) δ 0.53 (d, J=7 Hz, 3H), 0.66 (d, J=7 Hz, 3H), 0.93 (d, J=7 Hz, 6H), 1.65–2.0 (m, 4H), 2.2–2.4 (m, 1H), 3.0–3.2 (m, 3H), 3.3–3.4 (m, 1H), 3.5–3.8 (m, 3H), 4.05–4.15 (m, 1H), 5.00 (s, 1H), 5.05–5.25 (m, 4H), 5.74 (d, J=9 Hz, 1H), 6.28(d,J=7.5 Hz,1H), 7.0–7.5(m, 12H), 7.55–7.8 (m, 6H). 8.4–8.6 (m, 2H); Mass spectrum (FAB): (M+Na)$^+$=811 , (M+H)$^+$=789.

EXAMPLE 286

(2R,3S,4R)-2,4-Bis-(N-(N-((2-pyridinyl)methoxycarbonyl)-valinyl)-amino)-3-hydroxy-1-(1-napthyl)-5-phenylpentane A. (3R,4S,5R)-N-Boc-5-benzyl-4-hydroxy-3-(1-napthylmethyl)-2-pyrrolidinone Using the procedure of Example 285B with the resultant compound of Example 285A (0.694 g, 2.38 mmole) but replacing 2-(bromomethyl)napthalene with 1-(bromomethyl)napthalene, 0.440 g of the desired compound was obtained; $R_f$=0.39 (1:2 EA/Hx); $[\alpha]^{25}_D$=+36.3° (c=2.59, CHCl$_3$).

B. (2R,3S,4R)-4-(N-Boc-amino)-3-hydroxy-2-(1-napthylmethyl)-5-phenylpentanoic acid acetonide Using the procedure of Example 283C but with the resultant compound of Example 286A (0.46 g, 1.08 mmole) replacing the resultant compound of Example 283B, 319 mg of the desired compound was obtained: $R_f$=0.34 (1:2 EA/Hx); $[\alpha]^{24}_D$=−53.4° (c=2.6, CHCl$_3$).

C. (2R,3S,4R)-4-(N-Boc-amino)-2-(N-Cbz-amino)-3-hydroxy-1-(1-napthyl)-5-phenylpentane acetonide Using the procedure of Example 283D but with the resultant compound of Example 286B (131 mg, 264 µmole) replacing the resultant compound of Example 283C, 119 mg the desired compound was obtained: $R_f$=0.38 (20% EA/Hx); $[\alpha]^{24}_D$=−73.7° (c=2.6, CHCl$_3$).

D. (2R,3S,4R)-4-(N-Boc-amino)-2-amino-3-hydroxy-1-(1-napthyl)-5-phenylpentane acetonide Using the procedure of Example 283E but with the resultant compound of Example 286C (233 mg, 392 µmole) replacing the resultant compound of Example 283D, 140 mg of the desired compound was obtained: $R_f$=0.52 (1:2 EA/Hx); $[\alpha]^{24}_D$=−60.6° (c=1.04, CHCl$_3$).

E. (2R,3S,4R)-2,4-diamino-3-hydroxy-1-(1-napthyl)-5-phenylpentane

Using the procedure of Example 283F but with the resultant compound of Example 286D (116 mg, 251 µmole) replacing the resultant compound of Example 283E, 51.3 mg of the desired compound was obtained: $R_f$=0.14 (1:10:89 conc.NH$_4$OH/MeOH/CH$_2$Cl$_2$); $[\alpha]^{20}_D$=−33.5° (c=1.07, CHCl$_3$); $^1$H NMR (CDCl$_3$, 300 MHz) δ 2.1 (br s, 5H), 2.72 (dd, J=10, 14 Hz, 1H), 2.82 (dd, J=10.5, 14.8 Hz, 1H), 2.96 (dd, J=6, 14 Hz, 1H), 3.28 (ddd, J=3,6,10 Hz, 1H), 3.45 (m, 2H), 3.63 (dd, J=3,14 Hz, 1H), 7.2–7.55(m, 9H), 7.74(d,J=9 Hz,1H), 7.8–7.9(m, 1H), 8.0–8.1(m, 1H); Mass spectrum: (M+H)$^+$=321; IR spectrum: (CDCl$_3$) 3390, 3020, 1590 cm$^{-1}$.

F. (2R,3S,4R)-2,4-Bis-(N-(N-((2-pyridinyl)methoxycarbonyl)-valinyl)-amino)-3-hydroxy-1-(1-napthyl)-5-phenylpentane Using the procedure of Example 284A but with the resultant compound of Example 286E (45 mg, 140 µmole) replacing the resultant compound of Example 283E, 77.7 mg of the desired compound was obtained: $R_f$=0.32 (5% MeOH/CH$_2$Cl$_2$); $[\alpha]^{20}_D$=−54.8° (c=2.14, CHCl$_3$); $^1$H NMR (CDCl$_3$, 300 MHz) δ 0.47 (d, J=6 Hz, 3H), 0.67 (d, J=6 Hz, 3H), 0.79(d,J=6 Hz,3H), 0.86(d,J=6 Hz,3H), 1.92(dd, J=7, 12.6 Hz, 1H), 2.25(dd, J=7,12 Hz, 1H), 2.69(br s,1H), 3.12(d,J=7 Hz,2H), 3.27(dd, J=9,13.8 Hz, 1H), 3.7–3.9(m, 3H),3.95–4.15 (m, 2H), 4.85–5.3 (m, 5H), 5.64 (d, J=8 Hz, 1H), 6.37 (d, J=9 Hz, 1H), 7.1–7.35 (m, 13H), 7.4–7.5 (m, 2H), 7.55–7.7 (m, 3H), 7.75(d,J=7.5 Hz, 1H), 8.13(d,J=9 Hz, 1H), 8.53(br s,2H); Mass spectrum: (M+H)$^+$=789; IR spectrum: (CDCl$_3$) 3420, 3140, 1720, 1660, 1510 cm$^{-1}$; Anal. Calcd for C$_{45}$H$_{52}$N$_6$O$_7$.H$_2$O: C,66.98; H,6.74; N,10.41. Found: C,66.69; H, 6.51; N,10.29.

EXAMPLE 287

(2R,3S,4R)-2,4-Bis-(N-(N-((2-pyridinyl)methoxycarbonyl)-valinyl-amino)-3-hydroxy-5-(1-napthyl)-1-phenylpentane A. (4S,5R)-N-Boc-4-hydroxy-5-(1-napthylmethyl)-2-pyrrolidinone Using the procedure of Example 283A but with N-Boc-(1-napthyl)alanine replacing N-Boc-cyclohexylalanine the desired compound was provided; $R_f$=0.77 (2:3:95 HOAc/MeOH/EA) and 0.04 (1:1:2 ether/CH$_2$Cl$_2$/Hx); $[\alpha]^{24}_D$=−59.5° (c=2.6, CHCl$_3$).

B. (3R,4S,5R)-N-Boc-3-benzyl-4-hydroxy-5-(1-napthylmethyl)-2-pyrrolidinone

Using the procedure of Example 285B with the resultant compound of Example 287A (0.708 g, 2.07 mole) but replacing 2-(bromomethyl)napthalene with benzyl bromide, 0.497 g of the desired compound was obtained; $R_f$=0.25 (1:1:2 ether/CH$_2$Cl$_2$/Hx); $[\alpha]^{20}_D$=−17.4° (c=1.21, CHCl$_3$).

C. (2R,3S,4R)-4-(N-Boc-amino)-2-benzyl-3-hydroxy-5-(1-napthyl)pentanoic acid acetonide Using the procedure of Example 283C but with the resultant compound of Examp.le 287B (0.41 g, 0.95 mole) replacing the resultant compound of Example 283B, 190 mg of the desired compound was obtained; $R_f$=0.25 (1;2 EA/Hx); $[\alpha]^{20}_D$=−41.3° (c=0.15, CHCl$_3$).

D. (2R,3S,4R)-4-(N-Boc-amino)-2-(N-Cbz-amino)-3-hydroxy-5-(1-napthyl)-1-phenylpentane acetonide Using the procedure of Example 283D but with the resultant compound of Example 287C (155 mg, 317 µmole) replacing the resultant compound of Example 283C, 152 mg of the desired compound was obtained; $R_f$=0.36 (20% EA/Hx); $[\alpha]^{20}_D$=−58.4° (c=2.16, CHCl$_3$).

E. (2R,3S,4R)-2-amino-4-(N-Boc-amino)-3-hydroxy-5-(1-napthyl)-1-phenylpentane acetonide Using the procedure of Example 283E but with the resultant compound of Example 287D (140 mg, 230 µmole) replacing the resultant compound of Example 283D, 49.1 mg of the desired compound was obtained; $R_f$=0.22 (1:2 EA/Hx); $[\alpha]^{20}_D$=−62.2° (c=0.83, CHCl$_3$).

F. (2R,3S,4R)-2,4-diamino-3-hydroxy-5-(1-napthyl)-1-phenylpentane

Using the procedure of Example 283F but with the resultant compound of Example 287E (40 mg, 87 µmole) replacing the resultant compound of Example 283E, 21.2 mg of the desired compound was obtained; $R_f$=0.32 (1:15:84 conc.NH$_4$OH/MeOH/CH$_2$Cl$_2$); $[\alpha]^{20}_D$=−6.8° (c=0.56, CHCl$_3$); $^1$H NMR (CDCl$_3$, 300 MHz) δ 2.15 (br s, 5H), 2.54 (dd, J=9, 13.5 Hz, 1H), 2.94(dd, J=4,13.5 Hz, 1H), 3.13(dd, J=9,14 Hz, 1H), 3.23(ddd, J=4,5,4,9 Hz,1H), 3.42(dd, J=5.4, 14 Hz, 1H), 3.48(dd, J=2.4,5.4 Hz, 1H), 3.57(ddd, J=2.4, 5.4,9 Hz,1H), 7.1–7.6(m, 9H), 7.76(d,J=8.7 Hz, 1H), 7.85–7.9(m, 1H), 8.06(d,J=8.7 Hz, 1H); Mass spectrum: (M+H)$^+$=321; IR spectrum: (CDCl$_3$) 3380, 3320, 1595 cm$^{-1}$.

G. (2R,3S,4R)-2,4-Bis-(N-(N-((2-pyridinyl)methoxycarbonyl)-valinyl)-amino)-3-hydroxy-5-(1-napthyl)-1-phenylpentane Using the procedure of Example 284A but with the resultant compound of Example 287F (18 mg, 56 µmole) replacing the resultant compound of Example 283F, 20 mg of the desired compound was obtained; $R_f$=0.31 (5% MeOH/CH$_2$Cl$_2$); $[\alpha]^{20}_D$=−34.9° (c=0.37, CHCl$_3$); $^1$H NMR (CDCl$_3$, 300 MHz) δ 0.58 (d, J=7 Hz, 3H), 0.68 (d, J=7 Hz, 3H), 0.85 (d, J=7 Hz, 3H), 0.93 (d, J=7 Hz, 3H), 1.85–2.0 (m, 1H), 2.31(dd, 6,12 Hz,1H), 2.87(dd, J=9,13.5 Hz, 1H), 3.20 (d, J=13.5 Hz, 1H ), 3.5–3.9 (m, 6H), 3.95–4.1 (m, 1H), 4.12 (dd, J=5.4,9 Hz, 1H ), 4.7–4.9 (m, 2H), 5.0–5.2 (m, 2H), 5.15 (s, 2H), 5.68 (d, J=9 Hz, 1H ), 6.17 (d, J=8 Hz, 1H), 7.0–7.45 (m, 12H), 7.48 (t, J=7.5 Hz, 1H ), 7.55–7.7 (m, 3H), 7.75 (d, J=8 Hz, 1H), 8.04 (d, J=9 Hz, 1H), 8.45 (d, J=4 Hz, 1H), 8.55 (d, J=4 Hz, 1H); Mass spectrum: (M+H)$^+$=789; Anal. Calcd for C$_{45}$H$_{52}$N$_6$O$_7$.H$_2$O: C, 66.98; H, 6.74; N, 10.41. Found: C, 66.77; H, 6.66; N, 10.01.

EXAMPLE 288

(6-Methylpyridin-2-yl)methoxycarbonyl-Valine

To a solution of the isocyanate derived from Valine methyl ester (17.9 mmol) dissolved in toluene was added 6-methyl-pyridine-2-methanol (2.42 g, 1.1 equivalent). The solution was he ated at reflux for 2 hours. After concentration in vacuo and purifiction by silica gel column chromatography, (6-methylpyridin-2-yl)methoxycarbonyl-Valine methyl ester (2.8 g) was obtained. Hydrolysis of the methyl ester using aqueous lithium hydroxide provide the title compound upon recrystallization from hot ethyl acetate.

EXAMPLE 289

(2S,3S,5S)-2-(N-[(6-Methylpyridin-2-yl)methoxycarbonyl-Valyllamino)5-(N-[(pyridin-3-yl)methoxycarbonyl]amino)-1,6-diphenyl-3-hydroxyhexane Coupling of the resultant compound from Example 288 with (2S,3S,5S)-2-amino-5-(N-[(pyridin-3-yl)methoxycarbonyl]amino)-1,6-diphenyl-3-hydroxy hexane using standard EDAC/HOBT methodology afforded the title compound in 79% yield. m.p. 175°–176° C. $^1$H NMR (DMSO-$d_6$, 300 MHz) δ 0.73 (d, 3H), 0.78 (d, 3H), 1.50 (m, 2H), 1.90 (m, 1H), 2.45 (s, 3H), 2.60–2.70 (m, 4H), 3.55 (m, 1H), 3.85 (m, 2H), 4.95 (ABq, 2H), 5.05 (s, 2H), 7.10–7.20 (m, 12H), 7.35 (m, 2H), 7.49 (d, 1H), 7.55 (d, 1H), 7.70 (t, 1H), 8.50 (m, 2H). MS (DCI/NH$_3$) m/e 668 (M+H)$^+$.

EXAMPLE 290

(2S,3S,5S)-2-(N-[(pyridin-3-yl)methoxycarbonyl]amino)-5-(N-[(6-methylpyridin-2-yl)methoxycarbonyl-valyllamino)-1,6-diphenyl-3-hydroxyhexane Coupling of the resultant compounds from Example 288 with (2S,3S,5S)-2-(N-[(pyridin-3-yl-methoxycarbonyl]amino)-5-amino-1,6-diphenyl-3-hydroxyhexane using standard EDAC/HOBt methodology afforded the title compound in 70% yield. $^1$H NMR (DMSO-$d_6$; 300 MHz): δ 0.75 (d, 3H), 0.78 (d, 3H), 2.45 (s, 3H), 4.60 (d, 1H), 4.95 (m, 2H), 5.05 (s, 2H), 7.05–7.70 (m, 15H), 8.50 (m, 2H). Mass spectrum: (M+H)$^+$=668.

EXAMPLE 291

[(6-Methylpyridin-3-yl)methyl](4-nitrophenyl)carbonate

To a solution of 4-nitrophenylchloroformate (2.00 g) dissolved in methylene chloride (20 mL) and cooled to 0° C. was added (6-methylpyridin-3-yl)methanol (1 equivalent) and triethylamine (1 equivalent). The solution was allowed to warm to room temperature and stirred for 0.5 hours, diluted with methylene chloride, washed with saturated sodium bica4rbonate solution, dired over sodium sulfate and concentrated in vacuo. The residue obtained was column chromatographed on silica gel to afford the title compound (80%).

EXAMPLE 292

(6-Methylpyridin-3-yl]methoxycarbonyl-Valine

To a solution of the resultant compound from Example 291 (2.00 g) dissolved in dimethylformamide (20 mL) was added Valine methyl ester hydrochloride (1 equivalent) and triethylamine (2 equivalents). After stirring at room temperature for 1 hour, the solvent was removed in vacuo. The residue obtained was chromatographed on silica gel eluting with 5% methanol in methylene chloride to afford the title compound methyl ester. Hydrolysis with lithium hydroxide in aqueous dioxane afforded the title compound.

EXAMPLE 293

(2S,3S,5S)-2-(N-[(6-Methylpyridin-3-yl)methoxycarbonyl-valyllamino)-5-(N[(pyridin-3-yl)methoxycarbonyl]amino-1,6-diphenyl-3-hydroxyhexane Coupling of the resultant compound from Example 292 with (2S,3S,5S)-2-amino-5-(N-[(pyridin-3-yl)methoxycarbonyl]amino-1,6-diphenyl-3-hydroxyhexane using standard EDAC/HOBt methodology afforded the title compound. $^1$H NMT (DMSO-$d_6$; 300 MHz): δ 0.70 (d, 3H), 0.75 (d, 3H), 2.45 (s, 3H), 4.90 (m, 3H), 5.03 (s, 2H) 7.10–7.65 (m, 16H), 8.45 (m, 2H). Mass spectrum: (M+H)$^+$=668.

EXAMPLE 294

(2S,3S,5S)-2-(N-[(Pyridin-3-yl]methoxycarbonyl]amino-5-(N-[(6-methyl-pyridin-3-yl)methoxycarbonyl-Valyl]amino)-1,6-diphenyl-3-hydroxyhexane Coupling of the resultant compound from Example 292 with (2S,3S,5S)-2-(N-[(pyridin-3-yl)methoxycarbonyl]amino-5-amino-1,6-diphenyl-3-hydroxyhexane using standard EDAC/HOBt methodology afforded the title compound. $^1$H NMR (DMSO-$d_6$; 300 MHz): δ 0.73 (d, 3H), 0.75 (d, 3H), 1.80 (m, 1H), 2.45 (s, 3H), 4.67 (d, 1H), 4.96 (m, 2H), 5.05 (s, 2H), 6.90 (br d, 1H), 7.05–7.70 (m, 16H), 8.47 (m, 3H). Mass spectrum: (M+H)$^+$=668.

EXAMPLE 295

A. (2R,5R)-2,5-Diamino-1,6-diphenylhexane

A mixture of 200 mg (0.75 mmol) of the resultant compound of Example 18B and 20 mg of 10% Pd/C in 5 ml of methanol was stirred under 1 atmosphere of H$_2$ for 16 h. The resulting mixture was filtered and concentrated in vacuo to provide the desired compound.

B. (2R,5R)-2,5-Bis-(N-(N-((N-methyl-N-((2-pyridinyl)methyl)amino)carbonyl)valinyl)amino)-1,6-diphenylhexane Using the procedure of Example 85 but replacing the resultant compound of Example 4A with the resultant compound. of Example 295A and replacing the resultant compound of Example 43B with the resultant compound of Example 3F provided, after silica gel chromatography using first 2% then 3.5% methanol in chloroform, 17 mg (55%) of the desired compound (R$_f$0.34, 10% methanol in chloroform) as a white solid. Mass spectrum: (M+1)$^+$=763.

EXAMPLE 296

A. 1-Iodo-2-(iodomethyl]-2-propene

A mixture of 4 ml (3.5 mmol) of 1-chloro-2-(chloromethyl)-2-propene and 15 g of sodium iodide in 50 ml of acetone was heated at reflux for 5 h. The resulting mixture was filtered, concentrated in vacuo, taken up in dichloromethane, washed sequentially with aqueous NaHSO$_3$ and water, dried over MgSO$_4$ and concentrated in vacuo to provide 7.2 g (68%) of the crude desired compound as an oil.

B. (2R,5R,4'R,5'S)-2,5-Bis-((4-methyl-2-oxo-5-phenyloxazolidinyl)carbonyl)-1,7-diphenyl-4-methyleneheptane A solution of 1.36 ml of dry diisopropylamine (9.7 mmol) in 30 ml of anydrous tetrahydrofuran was cooled under N$_2$ to −78°, treated with 6 ml (9.7 mmol) of n-butyllithium, allowed to warm for 10 min, recooled, treated with 3.0 g (9.7 mmol) of (4R,5S)-3-dihydrocinnamoyl-4-methyl-5-phenyloxazolidin-2-one, stirred at −78° C. for 30 min, treated with 1.5 g of the resultant compound of Example 296A in 5 ml of tetrahydrofuran, and stirred at −40° C. for 16 h. The resulting solution was quenched with aqueous NH$_4$Cl, extracted with dichloromethane, dried over MgSO$_4$, and concentrated in vacuo. Silica gel chromatography of the residue using 10%–20% ethyl acetate in hexane provided 2.0 g (60%) of the desired compound.

C.  (2R,5R)-1,7-Diphenyl-4-methyleneheptane-2,5-dicarboxylic Acid

A solution of 2.0 g (3 mmol) of the resultant compound of Example 296B in 60 ml of 1:1 tetrahydrofuran:water was cooled to 0° C. and treated with a mixture of 19 ml of 0.5M LiOH and 4.5 ml of 30% hydrogen peroxide. The resulting solution was allowed to stand for 20 h, treated with aqueous NaHSO$_3$, stirred for 1 h, concentrated in vacuo, basified with 1N NaOH, washed with ethyl acetate, acidified with 6N HCl, and extracted with chloroform. The organic phase was dried over Na$_2$SO$_4$ and concentrated to provide 0.9 g (86%) of the crude desired compound.

D.  (2R,5R)-2,5-Bis-(N-(benzyloxycarbonyl)amino)-1,7-diphenyl-4-methyleneheptane A solution of 600 mg (1.7 mmol) of the resultant compound of Example 296C, 0.73 ml (3.4 mmol) of diphenylphosphorylazide, and 0.47 ml (3.4 mmol) of triethylamine in 6 ml of toluene was heated at reflux for 3 h, treated with 0.7 ml (6.8 mmol) of benzyl alcohol, and heated for an additional 2 h. The resulting solution was concentrated in vacuo, taken up in dichloromethane, washed with saturated brine, dried over MgSO$_4$, and concentrated in vacuo. Silica gel chromatography using first chloroform then 10% ethyl acetate in chloroform provided 302 mg (32%) of the desired compound.

E.  (2R,5R)-2,5-Bis-(N-(benzyloxycarbonyl)amino)-1,7-diphenylheptan-4-one

A solution of 50 mg (0.09 mmol) of the resultant compound of Example 296D in 1 ml of dioxane and 0.3 ml of water was treated with 0.0055 ml of 4% osmium tetroxide in water. After 10 min, 41 mg of sodium periodate was added, and the mixture was stirred for 1.5 h, treated with 10% aqueous NaHSO$_3$, stirred for 15 min, and extracted with ethyl acetate. The organic phase was dried over MgSO$_4$ and concentrated in vacuo to provide the crude desired compound.

F.  (2R,5R)-2,5-Bis-(N-(benzyloxycarbonyl)amino)-1,7-diphenyl-4-hydroxyheptane

The crude resultant compound of Example 296E (40 mg) was suspended in 4 ml of methanol, treated with 5.5 mg of sodium borohydride, stirred for 45 min, treated with saturated brine, stirred for 10 min, and extracted with dichloromethane. The organic phase was dried over MgSO$_4$ and concentrated in vacuo. Silica gel chromatography using 25%–30% ethyl acetate in hexane provided 14.2 mg of the desired compound. Mass spectrum: (M+H)$^+$=567.

EXAMPLE 297

(2S,3S,5S)-2-(N-(N-((N-Methyl-N-((6-methyl-2-pyridinyl)methyl)amino)carbonyl)valinyl)amino)-5-(N-((3-pyridinyl)-methoxycarbonyl)amino)-1,6-diphenyl-3-hydroxyhexane Coupling of (N-((N-methyl-N-((6-methyl-2-pyridinyl)methyl)amino)carbonyl)valine with (2S,3S,5S)-2-amino-5-(N-((3-pyridinyl)methoxycarbonyl)amino)-1,6-diphenyl-3-hydroxyhexane using standard EDAC/HOBt methodology provided the desired compound in 91% yield. $^1$H NMR (DMSO-d$_6$; 300 MHz) δ 0.72 (d, 3H), 0.77 (d, 3H), 1.92 (m, 1H), 2.43 (s, 3H), 2.88 (s, 3H), 4.43 (s, 2H), 4.92 (m, 2H), 6.37 (br d, 1H), 7.0–7.65 (m, 15H), 8.50 (m, 2H). Mass spectrum: (M+H)$^+$=681.

EXAMPLE 298

(2S,3S,5S)-2-(N-((3-Pyridinyl)-methoxycarbonyl)amino-5-(N-(N-((N-Methyl-N-((6-methyl-2-pyridinyl)methyl)amino)carbonyl)valinyl)amino)-1,6-diphenyl-3-hydroxyhexane Coupling of (N-((N-methyl-N-((6-methyl-2-pyridinyl)methyl)amino)carbonyl)valine with (2S,3S,5S)-2-(N-((3-pyridinyl)methoxy-carbonyl)amino)-5-amino-1,6-diphenyl-3-hydroxyhexane using standard EDAC/HOBt method provided the desired compound in 88% yield. $^1$H NMR (DMSO-d$_6$; 300 MHz); δ 0.74 (d, 6H), 2.45 (s, 3H), 2.88 (s, 3H), 4.42 (br s, 2H), 4.60 (d, 1H), 4.95 (m, 2H), 6.27 (br d, 1H), 6.87 (br d, 1H), 7.10–7. 70 (m, 15H), 8.50 (m, 2H). Mass spectrum: (M+H)$^+$=681.

EXAMPLE 299

(2S,3S,5S)-2-(N-((5-Methyl-3-pyridinyl)methoxycarbonyl)valinyl)amino)-5-(N-(3-pyridinyl)methoxycarbonyl)amino)-1,6-diphenyl-3-hydroxyhexane Coupling of (5-methyl-3-pyridinyl)methoxycarbonyl)valine with (2S,3S,5S)-2-amino-5-(N((3-pyridinyl)methoxycarbonyl)amino)-1,6-diphenyl-3-hydroxyhexane using standard EDAC/HOBt method provided the desired compound in 82% yield. $^1$H NMR (DMSO-d$_6$; 300 MHz): δ 0.72 (d, 3H), 0.75 (d, 3H), 1.50 (m, 2H), 1.90 (m, 1H), 2.28 (s, 3H), 4.88 (br d, 1H), 4.92 (m, 2H), 5.04 (s, 2H), 7.10–7.58 (m, 15H), 8.35 (m, 2H), 8.45 (m, 2H). Mass spectrum: (M+H)$^+$=668.

EXAMPLE 300

(2S,3S,5S)-2-(N ((3-Pyridinyl)methoxycarbonyl)amino)-5-(N((5-methyl-3-pyridinyl)methoxycarbonyl)valinyl)amino)-1,6-diphenyl-3-hydroxyhexane Coupling of (5-methyl-3-pyridinyl)methoxycarbonyl-valine with (2S,3S,5S)-2-(N-((3-pyridinyl)methoxycarbonyl)amino)-5-amino-1,6-diphenyl-3-hydroxyhexane using standard EDAC/HOBt method provided the desired compound in 80% yield. $^1$H NMR (DMSO-d$_6$; 300 MHz): δ 0.73 (d, 3H), 0.77 (d, 3H), 1.45 (m, 2H), 1.80 (m, 1H), 2.29 (s, 3H), 4.63 (br d, 1H), 4.95 (m, 2H), 5.05 (s, 2H), 6.90 (br d, 1H), 7.10–7.60 (m, 15H), 7.70 (br d, 1H), 8.37 (m, 2H), 8.50 (m, 2H). Mass spectrum: (M+H)$^+$=668.

EXAMPLE 301

(2S,3S,5S)-2-(N-(N-((N-Methyl-N((6-methyl-3-pyridinyl)methyl)amino)carbonyl)valinyl)amino)-5-(N((3-pyridinyl)-methoxycarbonyl)amino)-1,6diphenyl-3-hydroxyhexane Coupling of (N-((N-Methyl-N-((6-methyl-3-pyridinyl)methyl)amino)carbonyl)valine with (2S,3S,5S)- 2-amino-5-(N-((3-pyridinyl)methoxycarbonyl)amino)-1,6-diphenyl-3-hydroxyhexane using standard EDAC/HOBt methodology provided the desired compound in 85% yield. $^1$H NMR (DMSO-d$_6$; 300 MHz): δ 0.70 (d, 3H), 0.76 (d, 3H), 1.50 (m, 2H), 1.90 (m, 1H), 2.40 (s, 3H), 2.79 (s, 3H), 4.40 (m, 2H), 4.85 (br d, 1H), 4.92 (m, 2H), 6.0 (br d, 1H), 7.10–7.55 (m, 15H), 8.30 (d, 1H), 8.50 (m, 2H). Mass spectrum: (M+H)$^+$=681.

EXAMPLE 302

(2S,3S,5S)-2-(N((3-Pyridinyl)-methoxycarbonyl)amino)-5-(N-(N-((N-methyl-N-((6-methyl-3-pyridinyl)methyl)amino)carbonyl)valinyl)amino)-1,6-diphenyl-3-hydroxyhexane Coupling of (N-((N-Methyl-N-((6-methyl-3-pyridinyl)methyl)amino)carbonyl)valine with (2S,3S,5S)-2-(N((3-pyridinyl)methoxy-carbonyl)amino)-5-amino-1,6-diphenyl-3-hydroxyhexane using standard EDAC/HOBt method provided the desired compound in 83% yield. $^1$H NMR (DMSO-d$_6$; 300 MHz): δ 0.72 (d, 3H), 0.75 (d, 3H), 1.48 (m, 2H), 1.88 (m, 1H), 2.40 (s, 3H), 2.78 (s, 3H), 4.42 (s, 2H), 4.70 (d, 1H), 4.96 (m, 2H), 5.85 (d, 1H), 6.90 (d, 1H), 7.10–7.58 (m, 16H), 7.70 (d, 1H), 8.30 (d, 1H), 8.50 (m, 2H). Mass spectrum: (M+H)$^+$=681.

EXAMPLE 303

(2S,3S,5S)-2-(N-(N-((N-(6-methyl-2-pyridinyl)methyl)amino)carbonyl)valinyl)amino-5-(N-((3-pyridinyl)methoxycarbonyl)amino)-1,6-diphenyl-3-hydroxyhexane Coupling of (N-((6-methyl-2-pyridinyl)methyl)amino)carbonyl)valine with (2S,3S,5S)-2-amino-5-(N-((3-pyridinyl)methoxycarbonyl)amino)-1,6-diphenyl-3 -hydroxyhexane using standard EDAC/HOBt method provided the desired compound. $^1$H NMR (DMSO-d$_6$; 300 MHz): δ 0.74 (d, 3H), 0.80 (d, 3H, 1.50 (m, 2H), 1.90 (m, 1H), 2.45 (s, 3H), 4.25 (m, 2H), 4.83 (d, 1H), 4.92 (m, 2H), 6.20 (d, 1H), 6.65 (t, 1H), 7.05–7.60 (m, 15H), 8.50 (m, 2H). Mass spectrum: (M+H)$^+$=667.

EXAMPLE 304

(2S,3S,5S)-2-(N-((3-Pyridinyl)-methoxycarbonyl)amino)-5-((N-((N-6-methyl-2-pyridinyl)methyl)amino)carbonyl)valinyl)amino)-1,6-diphenyl-3-hydroxyhexane Coupling of N-((N-((6-methyl-2-pyridinyl)methyl)amino)carbonyl)valine with (2S,3S,5S)-2-(N((3-pyridinyl)methoxy-carbonyl)amino)-5-amino-1,6-diphenyl-3-hydroxyhexane provided the desired compound in 80% yield. $^1$H NMR (DMSO-d$_6$; 300 MHz): δ 0.72 (d, 3H), 0.78 (d, 3H), 1.45 (m, 2H), 1.80 (m, 1H), 2.44 (s, 3H), 4.25 (d, 2H), 4.63 (d, 1H), 4.95 (m, 2H), 6.15 (d, 1H), 6.65 (t, 1H), 6.88 (d, 1H), 7.05–7.60 (m, 15H), 7.27 (d, 1H), 8.50 (m, 2H). Mass spectrum: (M+H)$^+$=667.

EXAMPLE 305

(2S,5S)-Bis-(N((6-methyl-2-pyridinyl)methoxycarbonyl)valinyl)amino)-1,6-diphenyl-3,3-difluoro-4(R)-hydroxyhexane Coupling of N-((6-methyl-2-pyridinyl)methoxycarbonyl)valine with (2S,5S)-diamino-1,6-diphenyl-3,3-difluoro-4(R)hydroxyhexane using standard EDAC/HOBt methodology provided the desired compounds in 70% yield. $^1$H NMR (DMSO-d$_6$; 300 MHz): δ 0.62–0.73 (m, 12H), 2.47 (s, 3H), 2.48 (s, 3H), 3.80 (m, 4H), 5.03 (s, 2H), 5.04 (s, 2H), 6.10 (br d, 1H), 7.20 (m, 10H), 7.50 (br d, 2H), 7.70 (m, 2H), 8.00 (br d, 2H). Mass spectrum: (M+H)$^+$=817.

EXAMPLE 306

(2S,5S)-Bis-(N-((6-methyl-2-pyridinyl)methoxycarbonyl)valinyl)amino)-1,6-diphenyl-3,3-difluoro-4-oxo-hexane Oxidation of the resultant compound from Example 305 using sodium dichromate in acetic acid provided the desired compound in 69% yield. $^1$H NMR (DMSO-d$_6$; 300 MHz): 0.68 (d, 3H), 0.74 (d, 3H), 0.80 (d, 6H), 1.80 (m, 1H), 1.90 (m, 1H), 2.46 (s, 3H), 2.47 (s, 3H), 3.80–3.90 (m, 2H), 5.03 (s, 4H), 7.15 (m, 14H), 7.30 (br d, 1H), 7.67 (t, 2H), 8.25 (br d, 1H), 8.62 (br d, 1H). Mass spectrum: (M+H)$^+$=815.

EXAMPLE 307

(2S,3S,5S)-2-(N-((5-Methyl-2-pyrazinyl)methoxycarbonyl)valinyl)amino)5-(N-(3-pyridinyl)methoxycarbonyl)amino)-1,6-diphenyl-3-hydroxyhexane Coupling of ((5-methyl-2-pyrazinyl)methoxycarbonyl)valine with (2S,3S,5S)-2-amino-5(N((3-pyridinyl)methoxycarbonyl)amino)-1,6-diphenyl-3-hydroxyhexane using standard EDAC/HOBt method provided the desired compound in 80% yield. $^1$H NMR (DMSO-d$_6$; 300 MHz): 0.72 (d, 3H), 0.77 (d, 3H), 1.50 (m, 2H), 1.85 (m, 1H), 2.48 (s, 3H), 2.60–270 (m, 4H), 3.80 (m, 2H), 4.10 (m, 1H), 4.88 (br d, 1H), 4.92 (m, 2H), 5.10 (s, 2H), 7.10–7.30 (m, 14H), 7.45 (br d, 1H), 7.50 (br d, 1H), 8.50 (m, 4H). Mass spectrum: (M+H)$^+$=669.

EXAMPLE 308

(2S,3S,5S)-2-(N((3-Pyridinyl)methoxycarbonyl)amino)-5-(N((5-methyl-2-pyrazinyl)methoxycarbonyl)valinyl)amino)-1,6-diphenyl-3-hydroxyhexane Coupling of ((5-methyl-2-pyrazinyl)methoxycarbonyl)valine with (2S,3S,5S)-2-(N-((3-pyridinyl)methoxycarbonyl)amino)-5-amino-1,6-diphenyl-3-hydroxyhexane using standard EDAC/HOBt method provided the desired compound in 80% yield. $^1$H NMR (DMSO-d$_6$; 300 MHz): 0.70 (d, 3H), 0.73 (d, 3H), 1.40 (m, 2H), 1.80 (m, 1H), 2.45 (s, 3H), 2.60 (m, 4H), 3.70 (m, 2H), 4.05 (m, 1H), 4.60 (d, 1H), 4.90 (m, 2H), 5.08 (s, 2H), 6.85 (br d, H), 7.05–7.30 (m, 12H), 7.50 (br d, 1H), 7.70 (br d, 1H), 8.45 (m, 4H). Mass spectrum: (M+H)$^+$=669.

EXAMPLE 309

(2S,3S,5S)-2-(N-((6-Methoxy-3-pyridinyl)methoxycarbonyl)valinyl)amino)5-(N-(3-pyridinyl)methoxycarbonyl)amino)-1,6-diphenyl-3-hydroxyhexane Coupling of ((6-methoxy-3-pyridinyl)methoxycarbonyl)valine with (2S,3S,5S)-2-amino-5-(N((3-pyridinyl)methoxycarbonyl)amino)-1,6-diphenyl-3-hydroxyhexane using standard EDAC/HOBt method provided the desired compound in 90% yield. $^1$H NMR (DMSO-d$_6$; 300 MHz): 0.70 (d, 3H), 0.73 (d, 3H), 1.50 (m, 2H), 1.85 (m, 1H), 2.65 (m, 4H), 3.82 (s, 3H), 4.90–4.96 (m, 5H), 6.80 (m, 1H), 7.10–7.20 (m, 12H), 7.30 (m, 1H), 7.40 (m, 1H), 7.50 (m, 1H), 7.65 (m, 1H), 8.18 (m, 1H), 8.46 (m, 2H). Mass spectrum: (M+H)$^+$=684.

EXAMPLE 310

(2S,3S,5S)-2-(N((3-pyridinyl)methoxycarbonyl)amino)-5-(N((6-methoxy-3-pyridinyl)methoxycarbonyl)valinyl)amino)-1,6-diphenyl-3-hydroxyhexane Coupling of ((5-methoxy-3-pyridinyl) methoxycarbonyl)valine with (2S,3S,5S)-2-(N-((3-pyridinyl)methoxycarbonyl)amino)-5-amino-1,6-diphenyl-3-hydroxyhexane using standard EDAC/HOBt method provided the desired compound in 79% yield. $^1$H NMR (DMSO-$d_6$; 300 MHz): δ 0.73 (m, 6H), 1.45 (m, 2H), 1.80 (m, 1H), 2.60–2.70 (m, 4H), 3.83 (s, 3H), 4.10 (m, 1H), 4.62 (m, 1H), 4.97 (m, 4H), 6.80 (br d, 1H), 6.90 (br d, 1H), 7.00–7.35 (m, 12H), 7.57 (br d, 1H), 7.70 (m, 2H), 8.18 (m, 1H), 8.50 (m, 2H). Mass spectrum: (M+H)$^+$=684.

EXAMPLE 311

(2S,3S,5S)-2-(N-(N-((N-Methyl-N-((6-methoxy-3-pyridinyl)methyl)amino)carbonyl)valinyl)amino)-5-(N-((3-pyridinyl)methoxycarbonyl)amino)-1,6-diphenyl-3-hydroxyhexane Coupling of (N-((N-methyl-N-((6-methoxy-3-pyridinyl)methyl)amino)carbonyl)valine with (2S,3S,5S)-2-amino-5-(N-((3-pyridinyl)methoxycarbonyl)amino)-1,6-diphenyl-3-hydroxyhexane using standard EDAC/HOBt method provided the desired compound in 83% yield. $^1$H NMR (DMSO-$d_6$; 300 MHz): δ 0.71 (d, 3H), 0.77 (d, 3H), 1.5 (m, 2H), 1.95 (m, 1H), 2.65–2.73 (m, 4H), 2.77 (s, 3H), 3.80 (s, 3H), 3.93 (m, 1H), 4.15 (m, 1H), 4.38 (m, 2H), 4.86 (br d, 1H), 4.93 (m, 2H), 6.00 (br d, 1H), 6.77 (d, 1H), 7.05–7.20 (m, 10H), 7.36 (m, 1H), 7.48 (br d, 1H), 7.55 (m, 1H), 8.03 (d, 1H), 8.50 (m, 2H). Mass spectrum: (M+H)$^+$=697.

EXAMPLE 312

(2S,3S,5S)-2-(N-((3-Pyridinyl)methoxycarbonyl)amino)-5-(N-(N-((N-methyl-N-((6-methoxy-3-pyridinyl)methyl)amino)carbonyl)valinyl)amino- 1,6-diphenyl-3-hydroxyhexane Coupling of (N-((N-methyl-N-((6-methoxy-3-pyridinyl)methyl)amino)carbonyl)valine with (2S,3S,5S)-2-(N-((3-pyridinyl)methoxycarbonyl)amino)-5-amino-1,6-diphenyl-3-hydroxyhexane using standard EDAC/HOBt method provided the desired compound in 90% yield. $^1$H NMR (DMSO-$d_6$; 300 MHz): δ 0.73 (d, 3H), 0.76 (d, 3H), 1.48 (m, 2H), 1.90 (m, 1H), 2.60–2.70 (m, 4H), 2.77 (s, 3H), 3.60 (m, 1H), 3.81 (s, 3H), 3.90 (m, 1H), 4.13 (m, 1H), 4.38 (m, 2H), 4.62 (d, 1H), 4.95 (m, 2H), 5.80 (br d, 1H), 6.75 (d, 1H), 6.88 (br d, 1H), 7.07–7.21 (m, 10H), 7.32 (m, 1H), 7.55 (m, 2H), 7.70 (br d, 1H), 8.03 (d, 1H), 8.50 (m, 2H). Mass spectrum: (M+H)$^+$=697.

EXAMPLE 313

(2S,3S,5S)-2-(N-(N-((N-Methyl-N-((5-methyl-3-pyridinyl)methyl)amino)carbonyl)valinyl)amino)-5-(N-((3-pyridinyl)methoxycarbonyl)amino)-1,6-diphenyl-3-hydroxyhexane Coupling of (N-((N-methyl-N-((5-methyl-3-pyridinyl)methyl)amino)carbonyl)valine with (2S,3S,5S)-2-amino-5-(N-((3-pyridinyl)methoxycarbonyl)amino)-1,6-diphenyl-3-hydroxyhexane using standard EDAC/HOBt method provided the desired compound in 82% yield. $^1$H NMR (DMSO-$d_6$; 300 MHz): 0.72 (d, 3H), 0.77 (d, 3H), 1.50 (m, 2H), 1.90 (m, 1H), 2.25 (s, 3H), 2.60–27 6 (m, 4H), 2.80 (s, 3H), 3.55 (m, 1H), 3.85–4.10 (m, 3H), 4.45 (m, 2H), 4.86 (d, 1H), 4.93 (m, 2H), 6.02 (d, 1H), 7.10–7.20 (m, 11H), 7.35 (m, 1H), 7.42 (m, 1H), 7.50 (m, 2H), 8.27 (m, 2H), 8.50 (m, 2H). Mass spectrum: (M+H)$^+$=681.

EXAMPLE 314

(2S,3S,5S)-2-(N-((3pyridinyl)methoxycarbonyl)amino-5-(N-(N-((N-methyl-N-((5-methyl-3-pyridinyl)methyl)amino)carbonyl)valinyl)amino)-1,6-diphenyl-3-hydroxyhexane Coupling of (N-((N-methyl-N-((5-methyl-3-pyridinyl)methyl)amino)carbonyl)valine with (2S,3S,5S)-2-(N-((3-pyridinyl)methoxycarbonyl)amino)-5-amino-1,6-diphenyl-3-hydroxyhexane using standard EDAC/HOBt method provided the desired compound in 80% yield. $^1$H NMR (DMSO-$d_6$; 300 MHz): δ 0.72 (d, 3H), 0.75 (d, 3H), 1.45 (m, 2H), 1.88 (m, 1H), 2.24 (s, 3H), 2.55–2.70 (m, 4H), 2.80 (s, 3H), 3.57 (m, 1H), 3.80 (m, 1H), 3.90 (m, 1H), 4.10 (m, 1H), 4.45 (s, 2H), 4.68 (d, 1H), 4.96 (m, 2H), 5.96 (br d, 1H), 6.92 (br d, 1H), 7.10–7.20 (m, 11H), 7.30 (m, 1H), 7.42 (m, 1H), 7.55 (m, 1H), 7.70 (br d, 1H), 8.28 (m, 2H), 8.50 (m, 2H). Mass spectrum: (M+H)$^+$=681.

EXAMPLE 315

(2S,5S)-Bis-(N-((6-Methoxy-3-pyridinyl)methoxycarbonyl)valinyl)amino)-1,6-diphenyl-3(S)-hydroxyhexane Coupling of ((6-methoxy-3-pyridinyl)methoxycarbonyl)valine with (2S,3S,5S)-2,5-diamino-1,6-diphenyl-3-hydroxyhexane using standard EDAC/HOBt method provided the desired product in 60% yield. $^1$H NMR (DMSO-$d_6$; 300 MHz): δ 0.70 (d, 6H), 1.45 (m, 2H), 1.80 (m, 2H), 2.60–2.70 (m, 4H), 3.82 (s, 6H), 4.05 (m, 2H), 4.90 (d, 2H), 4.98 (4H), 6.82 (d, 2H), 7.00–7.20 (m, 14H), 7.45 (br d, 1H), 7.70 (m, 3H), 8.20 (m, 2H). Mass spectrum: (M+H)$^+$=813.

EXAMPLE 316

(2S,3S,5S)-2-(N-((2-pyrazinyl)methoxycarbenyl)valinyl)amino)-5-(N-(3-pyridinyl)methoxycarbonyl)amino)-1,6-diphenyl-3-hydroxyhexane Coupling of N-((2-piprazinyl)methoxycarbonyl)valine with (2S,3S,5S)-2-amine-5-(N-(3-pyridinyl)methoxycarbonyl)amino)-1,6-diphenyl-3-hydroxyhexane provided the desired compound in 95% yield. $^1$H NMR (DMSO-$d_6$; 300 MHz): δ0.73 (d, 3H), 0.80 (d, 3H), 1.50 (m, 2H), 1.90 (m, 1H), 2.60–2.70 (m, 4H), 3.56 (m, 1H), 3.80 (m, 2H), 4.10 (m, 1H), 4.90 (m, 3H), 5.15 (s, 2H), 7.10–7.20 (m, 12H), 7.35 (m, 2H), 7.50 (m, 2H), 8.50–8.70 (m, 5H). Mass spectrum: (M+H)$^+$=655.

EXAMPLE 317

(2S,3S,5S)-2-(N-((3-pyridinyl)methoxycarbonyl)amine)-5-(N((2-pyrazinyl)methoxycarbonyl)valinyl)amino)-1,6-diphenyl-3-hydroxyhexane Coupling of N-((2-pyrazinyl)methoxycarbonyl)valine with (2S,3S,5S)-2-(N-((3-pyridinyl)methoxycarbonyl)amino-5-amino-1,6-diphenyl-3-hydroxyhexane using standard EDAC/HOBt method provided the desired compound in 60% yield. $^1$H NMR (DMSO-$d_6$; 300 MHz): δ0.77 (t, 6H), 1.46 (m, 2H), 1.85 (m, 1H), 2.60–2.70 (m, 4H), 3.58

(m, 1H), 3.77 (m, 2H), 4.12 (m, 1H), 4.64 (d, 1H), 4.96 (m, 2H), 5.17 (s, 2H), 6.90 (br d, 1H), 7.10–7.30 (m, 14H), 7.55 (m, 1H), 7.70 (br d, 1H), 8.50 (m, 2H), 8.60 (m, 2H), 8.68 (s, 1H). Mass spectrum: $(M+H)^+=655$.

EXAMPLE 318

A. (2S,3S,5S)-5-Amino-2-(N-((5-pyrimidinyl) methoxycarbonyl)amine)-1,6-diphenyl-3-hydroxyhexane and (2S,3S,5S)-2-Amino-5-(N-((5-pyrimidinyl)methoxycarbonyl)amino)-1,6-diphenyl-3-hydroxyhexane Using the procedure of Example 37B but replacing the resultant compound of Example 37A with the resultant compound of Example 167A provided 68.1 mg (13%) of (2S,3S,5S)-5-amino-2-(N-((5-pyrimidinyl)methoxycarbonyl)-amino)-1,6-diphenyl-3-hydroxyhexane and 148.1 mg (28%) of (2S,3S,5S)-2-amino-5-(N-((5-pyrimidinyl)methoxycarbonyl)-amino)-1,6-diphenyl-3-hydroxyhexane.

B. (2S,3S,5S)-2-(N-(N-((N-Methyl-N-((2-pyridinyl) methyl)amino)carbonyl)valinyl)amino)-5-(N-((5-pyrimidinyl)methoxycarbonyl)amino)-1,6-diphenyl-3-hydroxyhexane A mixture of 50 mg (0.119 mmol) of (2S,3S,5S)-2-amino-5-(N-((5-pyrimidinyl)methoxycarbonyl)amino)-1,6-diphenyl-3-hydroxyhexane and 68.9 mg (0.178 mmol) of the resultant compound of Example 3F in 1 ml of tetrahydrofuran was stirred at ambient temperature for 16 h. The solvent was then removed in vacuo, and the residue was purified by silica gel chromatography using 5% methanol in dichloromethane provided 63.5 mg (80% ) of the desired compound as a white solid. $^1$H NMR (CDCl$_3$) δ 0.78 (d, 3H), 0.92 (d, 3H), 1.65 (m, 2H), 2.26 (m, 1H), 2.74 (m, 2H), 2.83 (m, 2H), 2.97 (s, 3H), 3.63 (m, 1H), 3.95 (m, 1H), 4,05 (m, 2H), 4.45 (s, 2H), 5.02 (dd, 2H), 5.33 (br d, 1H), 6.48 (br d, 1H), 6.56 (br, 1H), 7.07–7.24 (m, 12H), 7.72 (td, 1H), 8.51 (d, 1H), 8.67 (s, 2H), 9.18 (s, 1H). Mass spectrum: $(M+H)^+=668$.

EXAMPLE 319

(2S,3S,5S)-2-(N-(N-((2-Pyridinyl)methoxycarbonyl)valinyl)amino)-5-(N-((5-pyrimidinyl)methoxycarbonyl)amino)-1,6-diphenyl-3-hydroxyhexane Using the procedure of Example 318B but replacing the resultant compound of Example 3F with the resultant compound of Example 2D provided 48.9 mg (63%) of the desired compound as a white solid. $^1$H NMR (CDCl$_3$) δ 0.76 (d, 3H), 0.89 (d, 3H), 1.64 (m, 2H), 2.13 (m, 1H), 2.75 (d, 2H), 2.85 (d, 2H), 3.68 (m, 1H), 3.93 (m, 2H), 4.08 (m, 1H), 4.96–5.33 (m, 6H), 6.34 (br, 1H), 7.04–7.22 (m, 11H), 7.33 (d, 1H), 7.70 (td, 1H), 8.57 (d, 1H), 8.68 (s, 2H), 9.18 (s, 1H). Mass spectrum: $(M+H)^+=655$.

EXAMPLE 320

(2S,3S,5S)-5-(N-(N-((N-Methyl-N-((2-pyridinyl)methyl)amino)carbonyl)valinyl)amino)-2-(N-((5-pyrimidinyl)methoxycarbonyl)amino)-1,6-diphenyl-3-hydroxyhexane Using the procedure of Example 318B but replacing (2S,3S,5S)-2-amino-5-(N-((5-pyrimidinyl)methoxycarbonyl)amino)-1,6-diphenyl-3-hydroxyhexane with (2S,3S, 5S)-5-amino-2-(N-((5-pyrimidinyl)methoxycarbonyl)-amino)-1,6-diphenyl-3-hydroxyhexane provided 60.4 mg (76%) of the desired compound as a white solid. $^1$H NMR (CDCl$_3$) δ 0.77 (d, 3H), 0.90 (d, 3H), 1.62 (m, 2H), 2.31 (m, 1H), 2.73 (m, 2H), 2.84 (m, 2H), 2.99 (s, 3H), 3.66 (m, 1H), 3.74 (m, 1H), 4.04 (m, 1H), 4.22 (m, 1H), 4.43 (dd, 2H), 5.03 (dd, 2H), 5.24 (br d, 1H), 6.52 (br d, 1H), 6.66 (br, 1H), 7.08–7.28 (m, 12H), 7.74 (td, 1H), 8.49 (dd, 1H), 8.67 (s, 2H), 9.18 (s, 1H). Mass spectrum: $(M+H)^+=668$.

EXAMPLE 321

(2S,3S,5S)-5-(N-(N-((2-Pyridinyl)methoxycarbonyl)valinyl)amino)-2-(N-((5-pyrimidinyl)methoxycarbonyl)amino)-1,6-diphenyl-3-hydroxyhexane Using the procedure of Example 318B but replacing (2S,3S,5S)-2-amino-5-(N-((5-pyrimidinyl)methoxycarbonyl)amino)-1,6-diphenyl-3-hydroxyhexane with (2S,3S, 5S)-5-amino-2-(N-((5-pyrimidinyl)methoxycarbonyl)amino)-1,6-diphenyl-3-hydroxyhexane and replacing the resultant compound of Example 3F with the resultant compound of Example 2D provided 14.6 mg (78%) of the desired compound as a white foamy solid. $^1$H NMR (CDCl$_3$) δ 0.71 (d, 3H), 0.86 (d, 3H), 1.67 (m, 2H), 2.07 (m, 1H), 2.30 (m, 4H), 3.68 (m, 1H), 3.77 (m, 1H), 3.90 (m, 1H), 4.26 (m, 1H), 5.03 (dd, 2H), 5.19 (dd, 2H), 5.22 (br, 1H), 6.45 (br, 1H), 7.09–7.23 (m, 12H), 7.34 (d, 1H), 7.73 (td, 1H), 8.57 (dd, 1H), 8.67 (s, 2H), 9.18 (s, 1H). Mass spectrum: $(M+H)^+=655$.

EXAMPLE 322

A. (2S,3S,5S)-5-Amino-2-(N-((3-furyl)methoxycarbonyl)amino)-1,6-diphenyl-3-hydroxyhexane and (2S,3S,5S)-2-Amino-5-(N-((3-furyl)methoxycarbonyl)amino)-1,6-diphenyl-3-hydroxyhexane Using the procedure of Example 37B but replacing the resultant compound of Example 37A with 3-furylmethyl 4-nitrophenyl carbonate from Example 273 provided 69.0 mg (17%) of (2S,3S,5S)-5-amino-2-(N-((3-furyl)methoxycarbonyl)amino)-1,6-diphenyl-3-hydroxyhexane and 156.4 mg (36%) of (2S,3S,5S)-2-amino-5-(N-((3-furyl)methoxycarbonyl)amino)-1,6-diphenyl-3-hydroxyhexane B. (2S,3S,5S)-2-(N-(N-(2-(6-Methylpyridinyl)methoxycarbonyl)valinyl)amino)-5-(N-((3-furyl)methoxycarbonyl)amino)-1,6-diphenyl-3-hydroxyhexane Using the procedure of Example 6I but replacing the resultant compound of Example 6H with (2S,3S,5S)-2-amino-5-(N-((3-furyl)methoxycarbonyl)amino)-1,6-diphenyl-3-hydroxyhexane and replacing trans-3-(pyridinyl)acrylic acid with the resultant compound of Example 288 provided 92.9 mg (96%) of the desired compound as a white solid. $^1$H NMR (CDCl$_3$) δ 0.73 (d, 3H), 0.87 (d, 3H), 1.64 (m, 2H), 2.13 (m, 1H), 2.50 (s, 3H), 2.76 (dd, 2H), 2.84 (d, 2H), 3.67 (m, 1H), 3.75 (m, 1H), 3.88 (m, 1H), 4.17 (m, 1H), 4.90 (s, 2H), 5.09 (br d, 1H), 5.15–5.22 (m, 3H), 6.31 (br d, 1H), 6.37 (s, 1H), 7.07–7.25 (m, 12H), 7.39 (m, 2H), 7.60 (t, 1H). Mass spectrum: $(M+H)^+=657$.

EXAMPLE 323

A. Methyl 3-(Methoxymethoxy)-5-isoxazole Carboxylate

A solution of 2.0 g (14.0 mmol) of methyl 3-hydroxy-5-isoxazole carboxylate and 29.2 ml (16.8 mmol) of N,N-diisopropylethylamine in 20 ml of tetrahydrofuran was treated with 1.27 ml of chloromethyl methyl ether. After being stirred at ambient temperature for 2 h, the solution was diluted with dichloromethane, washed with water, dried over MgSO$_4$, and concentrated in vacuo. Silica gel chromatography of the residue using 10% methanol in dichloromethane provided 129.6 mg (78%) of the desired compound as a white solid. $^1$H NMR (CDCl$_3$) δ 3.57 (s, 3H), 3.96 (s, 3H), 5.37 (s, 2H), 6.64 (s, 1H).

B. 5-(Hydroxymethyl)-3-(methoxymethoxy)isoxazole

A suspension of 0.40 g (10.7 mmol) of lithium aluminum hydride in 40 ml of tetrahydrofuran was treated with 2.0 g of the resultant compound of Example 323A in 40 ml of tetrahydrofuran. After being stirred at ambient temperature for 5 h, the solution was treated with 20 ml of saturated ammonium chloride solution, extracted with three 20 ml portions of dichloromethane. The combined organic layers were dried over MgSO$_4$, and concentrated in vacuo provided 1.25 g of the desired compound as a yellow oil. $^1$H NMR (CDCl$_3$) δ 3.55 (s, 3H), 4.66 (s, 2H), 5.31 (s, 2H), 5.97 (s, 1H). Mass spectrum: (M+H)$^+$=160.

C. p-Nitrophenyl (5-(3-(Methoxymethoxy)isoxazolyl)methoxy)formate

Using the procedure of Example 37A but replacing 3-(hydroxymethyl)pyridine with the resultant compound of Example 323B provided 2.14 g (84%) of the desired compound as a pale yellow solid. $^1$H NMR (CDCl$_3$) δ 3.57 (s, 3H), 5.28 (s, 2H), 5.35 (s, 2H), 6.17 (s, 1H), 7.42 (d, 2H), 8.30 (dt, 2H). Mass spectrum: (M+H)$^+$=325.

D. (2S,3S,5S)-2,5-Bis-(N-(5-(3-(methoxymethoxy)isoxazolyl)methoxycarbonyl)amino)-1,6-diphenyl-3-hydroxyhexane A mixture of 50 mg (0.176 mmol) of the resultant compound of Example 1E and 171.0 mg (0.527 mmol) of the resultant compound of Example 323C in 2 ml of tetrahydrofuran was stirred at ambient temperature for 20 h. The solvent was then removed in vacuo, and the residue was purified by silica gel chromatography using 5% methanol in dichloromethane provided 78.2 mg (69%) of the desired compound as a white solid. $^1$H NMR (CDCl$_3$) δ 1.64 (m, 2H), 2.76 (d, 2H), 2.85 (d, 2H), 3.54 (s, 6H), 3.66 (m, 1H), 3.81 (m, 1H), 3.96 (m, 1H), 4.95 (br, 2H), 4.99 (s, 4H), 5.19 (br d, 1H), 5.30 (s, 4H), 5.91 (d, 2H), 7.07–7.30 (m, 10H). Mass spectrum: (M+H)$^+$=655.

EXAMPLE 324

A. 4-(Hydroxymethyl)isoxazole 0.50 g (2.57 mmol) of 3,3-dimethoxy-2-(dimethoxymethyl)-1-propanol was added dropwise to a solution of 0.18 g (2.57 mmol) of hydroxyamine hydrochloride in 2 ml of water and 0.2 ml of 1N aqueous HCl. The mixture was then refluxed for 1 h. After cooling, the resulting solution was neutralized with solid NaHCO$_3$, extracted with five 5 ml portions of dichloromethane. The combined organic layers were dried over MgSO$_4$, and concentrated in vacuo provided 1.25 g of the desired compound as a yellow oil. $^1$H NMR (CDCl$_3$) δ 4.67 (s, 2H), 8.33 (s, 1H), 8.42 (s, 1H).

B. p-Nitrophenyl (4-Isoxazolyl)methoxy)formate

Using the procedure of Example 37A but replacing 3-(hydroxymethyl)pyridine with the resultant compound of Example 324A provided 134.0 mg (39%) of the desired compound as a pale yellow solid. $^1$H NMR (CDCl$_3$) δ 5.23 (s, 2H), 7.39 (dt, 2H), 8.29 (dt, 2H), 8.44 (s, 1H), 8.63 (s, 1H).

C. (2S,3S,5S)-2,5-Bis-(N-(4-isoxazolyl)methoxycarbonyl)amino)-1,6-diphenyl-3-hydroxyhexane A mixture of 50 mg (0.176 mmol) of the resultant compound of Example 1E and 116.0 mg (0.440 mmol) of the resultant compound of Example 324B in 1 ml of tetrahydrofuran was stirred at ambient temperature for 20 h. The solvent was then removed in vacuo, and the residue was purified by silica gel chromatography using 5% methanol in dichloromethane provided 68.0 mg (72%) of the desired compound as a white solid. $^1$H NMR (CDCl$_3$) δ 1.61 (m, 2H), 2.74 (d, 2H), 2.83 (d, 2H), 3.65 (m, 1H), 3.79 (m, 1H), 3.94 (m, 1H), 4.73 (br, 1H), 4.94 (dd, 4H), 4.98 (br, 1H), 7.05–7.25 (m, 10H), 8.26 (two s, 2H), 8.40 (two s, 2H). Mass spectrum: (M+H)$^+$=535.

EXAMPLE 325

(2S,3S,5S)-2,5-Bis-(N-((3-pyridazinyl)methoxycarbonyl)amino)-1,6-diphenyl-3-hydroxyhexane A. Phenyl ((3-Pyridazinyl)methoxy)formate Using the procedure of Example 176 but replacing 2-(hydroxymethyl)pyridine with 3-(hydroxymethyl)pyridazine provided 252.0 mg (60%) of the desired compound as a white solid. $^1$H NMR (CDCl$_3$) δ 5.63 (s, 2H), 7.20–7.29 (m, 3H), 7.37–7.44 (m, 2H), 7.56 (dd, 1H), 9.21 (dd, 1H). Mass spectrum: (M+H)$^+$=231.

B. (2S,3S,5S)-2,5-Bis-(N-((3-pyridazinyl)methoxycarbonyl)amino)-1,6-diphenyl-3-hydroxyhexane A mixture of 50 mg (0.176 mmol) of the resultant compound of Example 1E and 122.0 mg (0.527 mmol) of the resultant compound of Example 325A in 1 ml of dimethylformamide was stirred at 50° C. for 2 days. The solvent was then removed in vacuo, and the residue was purified by silica gel chromatography using 5% methanol in dichloromethane provided 48.2 mg (49%) of the desired compound as a white solid. $^1$H NMR (CDCl$_3$) δ 1.73 (m, 2H), 2.79 (d, 2H), 2.91 (d, 2H), 3.78 (br, 1H), 3.89 (dd, 1H), 4.04 (br, 1H), 5.33 (dd, 2H), 5.36 (dd, 2H), 5.49 (br, 1H), 5.64 (br d, 1H), 7.11–7.34 (m, 12H), 7.43 (m, 2H), 9.11 (d, 2H).

EXAMPLE 326

A. 2-(Hydroxymethyl)quinoline

A solution of 3.0 g of quinoline-2-carboxaldehyde in 100 ml of ethanol was treated with 750 mg of sodium borohydride and stirred at ambient temperature for 15 min. The resulting solution was neutralized with 1N HCl, concentrated in vacuo, and extracted three times with ethyl acetate. The combined organic layers were dried over Na$_2$SO$_4$ and concentrated to provide 2.65 g (88%) of the crude desired compound.

B. N-((2-Quinolinyl)methoxycarbonyl)valine Methyl Ester

Using the procedure of Example 2B but replacing pyridine-2-methanol with the resultant compound of Example 326A provided the desired compound (R$_f$ 0.55, 50% ethyl acetate in hexane) in 85% yield.

C. N-((2-Quinoiinyl)methoxycarbonyl)valine

Using the procedure of Example 3E but replacing the resultant compound of Example 3D with the resultant compound of Example 326B provided the desired compound.

D. (2S,3S,5S)-2-(N-(N-((2-Quinolinyl)methoxycarbonyl)valinyl)amino)-5-(N-((3-pyridinyl)methoxycarbonyl)amino)-1,6-diphenyl-3-hydroxyhexane Using the procedure of Example 81C but replacing the resultant compound of Example 81B with the resultant compound of Example 326C and replacing the resultant compound of Example 62A with (2S,3S,5S)-2-amino-5-(N-((3-pyridinyl)methoxycarbonyl)-amino)-1,6-diphenyl-3-hydroxyhexane provided, after silica gel chromatography using a gradient of 2–4% methanol in chloroform, 105 mg (60%) of the desired compound (R$_f$ 0.63, 10% methanol in chloroform) as a white solid, m.p. 159°–163° C. Mass spectrum: (M+1)⁺=704.

EXAMPLE 327

(2S,3S,5S)-5-(N-(N-((2-Quinolinyl)methoxycarbonyl)valinyl)amino)-2-(N-((3-pyridinyl)methoxycarbonyl)amino)-1,6-diphenyl-3-hydroxyhexane Using the procedure of Example 81C but replacing the resultant compound of Example 81B with the resultant compound of Example 326C and replacing the resultant compound of Example 62A with (2S,3S,5S)-5-amino-2-(N-((3-pyridinyl)methoxycarbonyl)-amino)-1,6-diphenyl-3-hydroxyhexane provided, after silica gel chromatography using a gradient of 2–4% methanol in chloroform, 101 mg (59%) of the desired compound ($R_f$ 0.61, 10% methanol in chloroform) as a white solid, m.p. 141°–143° C. Mass spectrum: (M+1)⁺=704.

EXAMPLE 328

A. (1S,2S)-2-((3-Pyridinyl)methoxycarbonyl)amino-1-cyclopentanol

Using the procedure of Example 42A but replacing (S,S)-2-aminocyclohexanol with (S,S)-2-aminocyclopentanol (Overman and Sugai, et. al., J. Org. Chem. 1985, 50, 4154), provided, after silica gel chromatography using first 20% ethyl acetate in chloroform then 5% methanol in chloroform, 324 mg (66%) of the desired compound ($R_f$ 0.33, 10% methanol in chloroform). ¹H NMR (CDCl₃) δ 1.40 (dq, J=12, 8 Hz, 1 H), 1.6–1.9 (m, 3 H), 2.02 (m, 1 H), 2.15 (m, 1 H), 3.70 (m, 1 H), 4.01 (br q, 1 H), 4.91 (br, 1 H), 5.13 (s, 2 H), 7.30 (dd, J=7, 5 Hz, 1 H), 7.71 (d, J=8 Hz, 1 H), 8.59 (dd, J=5, 1 Hz, 1 H), 8.62 (br s, 1 H). Mass spectrum: (M+1)⁺=237.

B. (1'S,2'S)-(2-((3-pyridinyl)methoxycarbonyl)amino-1-cyclopentyl)-4-nitrophenylcarbonate Using the procedure of Example 42B but replacing the resultant compound of Example 42A with the resultant compound of Example 328A, provided, after silica gel chromatography using first 20% ethyl acetate in chloroform then 4% methanol in chloroform, 495 mg (90%) of the desired compound ($R_f$ 0.63, 10% methanol in chloroform). ¹H NMR (CDCl₃) δ 1.5–1.6 (m, 1 H), 1.75–1.95 (m, 3 H), 2.1–2.3 (m, 2 H), 4.13 (m, 1 H), 4.98 (br, 1 H), 5.04 (m, 1 H), 5.14 (s, 2 H), 7.29 (dd, J=7, 5 Hz, 1 H), 7.38 (d, J=10 Hz, 2 H), 7.70 (d, J=8 Hz, 1 H), 8.27 (d, J=10 Hz, 2 H), 8.58 (br d, 1 H), 8.63 (br s, 1 H). Mass spectrum: (M+H)⁺=402.

C. (2S,3S,5S, 1'S,2'S,1"S,2"S)-2,5-Bis-(N-(2-(N-((3-pyridinyl)methoxycarbonyl)amino-1-cyclopentyl)oxycarbonyl)amino)-1,6-diphenyl-3-hydroxyhexane Using the procedure of Example 42C but replacing the resultant compound of Example 42B with the resultant compound of Example 328B, provided, after filtration, the desired compound ($R_f$ 0.27, 10% methanol in chloroform) in 65% yield, m.p. 190°–192° C. Mass spectrum: (M+1)⁺=809.

EXAMPLE 329

(2S,3S,5S,1'S,2'S)-2-(N-(2-(N-((3-Pyridinyl)methoxycarbonyl)amino-1-cyclopentyl)oxycarbonyl)amino)-5-(N-((3-pyridinyl)methoxycarbonyl)amino)-1,6-diphenyl-3-hydroxyhexane A solution of 25 mg (0.06 mmol) of the resultant compound of Example 328B and 26 mg (0.06 mmol) of (2S,3S,5S)-2-amino-5-(N-((3-pyridinyl)methoxycarbonyl)-amino)-1,6-diphenyl-3-hydroxyhexane in 5 ml of tetrahydrofuran was stirred for 16 h at ambient temperature. The resulting solution was concentrated in vacuo and purified by silica gel chromatography using first 20% ethyl acetate in chloroform then 4% methanol in chloroform to provide 35 mg (86%) of the desired compound ($R_f$ 0.21, 10% methanol in chloroform) as a white solid, m.p. 98°–100° C. Mass spectrum: (M+1)⁺=682.

EXAMPLE 330

(2S,3S,5S,1'S,2'S)-5-(N-(2-(N-((3-Pyridinyl)methoxycarbonyl)amino-1-cyclopentyl)oxycarbonyl)amino)-2-(N-((3-pyridinyl)methoxycarbonyl)amino)-1,6-diphenyl-3-hydroxyhexane Using the procedure of Example 329 but replacing (2S,3S,5S)-2-amino-5-(N-((3-pyridinyl)methoxycarbonyl)amino)-1,6-diphenyl-3-hydroxyhexane with (2S,3S,5S)-5-amino-2-(N((3-pyridinyl)methoxycarbonyl)-amino)-1,6-diphenyl-3-hydroxyhexane provided, after silica gel chromatography using a gradient of first 20% ethyl acetate in chloroform then 4% methanol in chloroform, 35 mg (85%) of the desired compound ($R_f$ 0.22, 10% methanol in chloroform) as a white solid, m.p. 125°–128° C. Mass spectrum: (M+1)⁺=682.

EXAMPLE 331

(2S,3S,5S)-2,5-Bis-(N-((3-methyloxetan-3-yl)methoxycarbonyl)amino)-1,6-diphenyl-3-hydroxyhexane

EXAMPLE 331A

3-Phenyloxycarbonyloxymethyl-3-methyloxetane

A 0.552 mL (4.42 mmol) sample of phenoxycarbonylchloride in 2 mL of methylene chloride was added to a solution of 376 mg (3.68 mmol) of 3-hydroxymethyl-3-methyloxetane and 60.7 mL (5.52 mmol) of 4-methylmorpholine in 2 mL of methylene chloride cooled in an ice bath. The mixture was stirred at 0° C. for 3.5 hours. The mixture was diluted with methylene chloride, which was washed with water, dried and concentrated. The crude product was chromatographed on silica gel, eluting with 20% ethyl acetate in hexane. The solvent was removed and the product dried to afford 0.582 g of the title compound, which was taken directly to the next step.

EXAMPLE 331B (2S,3S,5S)-2,5-Bis-(N-((3-methyloxetan-3-yl)methoxycarbonyl)amino)-1,6-diphenyl-3-hydroxyhexane A 180 mg sample of the compound from Example 331A above was added to 57 mg (0.203 mmol) of the product of Example 1E and then dissolved in DMF and heated at 50° C. overnight. The solvent was removed and the crude product chromatographed on silica gel, eluting with 2% methanol in chloroform. The solvent was removed and the product dried to afford 52.9 mg of the title compound. MS M/Z (DCI/NH₃): 541 (M+H), 558 (M+18). Anal. calc. for $C_{30}H_{40}N_2O_7 \cdot 0.5 H_2O$: C, 65.57; H, 7.47; N, 5.10; found: C, 65.80; H, 7.41; N, 5.19. Proton NMR (DMSO): δ 1.18 (m, 6H), 1.51 ((t, 2H), 2.58–2.73 (4H), 3.58 (m, 1H), 3.84 (m, 2 H), 3.95 (m, 4H), 4.15 (m, 4H), 4.30 (m, 4H), 4.67 (d, 1H), 6.78 (d, 1H), 7.05 (d, 1H), 7.11–7.27 (10H).

EXAMPLE 332

(2S,3S,5S)-2,5-Bis-(N-((2,3-dihydrofuro[2,3-b]pyridin-3-yl)oxycarbonyl)amino)-1,6-diphenyl-3-hydroxyhexane

EXAMPLE 332A 3-p-Nitrophenoxycarbonyloxy-2,3-dihydrofuro[2,3-b]pyridine

A 534 mg (2.65 mmol) sample of p-nitrophenoxycarbonylchloride in methylene chloride was added to a solution of 330 mg (2.41 mmol) of 3-hydroxy-2,3-dihydrofuro[2,3-b]pyridine (prepared as described by H.Sliwa, *Bull. Soc. Chim. Fr.* 1970 (2), 646–652) and 0.291 mL of 4-methylmorpholine in 2 mL of methylene chloride cooled in an ice bath. The mixture was stirred at 0° C. for 2.75 hours. The mixture was diluted with methylene chloride, which was washed with water, dried and concentrated. The crude product was chromatographed on silica gel, eluting with 5% ethyl acetate in methylene chloride. The solvent was removed and the product dried to afford 0.493 g of the title compound, which was taken directly to the next step.

EXAMPLE 332B (2S,3S,5S)-2,5-Bis-(N-((2,3-dihydrofuro[2,3-b]pyridin-3-yl)oxycarbonyl)amino)-1,6-diphenyl-3-hydroxyhexane A 164 mg (0,544 mmol) sample of the compound from Example 332A above was added to 51.5 mg (0.181 mmol) of the product of Example 1E in 0.5 mL of DMF and stirred for 7 hours. The solvent was removed and the crude product chromatographed on silica gel, eluting with 2% and 5% methanol in chloroform. The solvent was removed and the product dried to afford 62.8 mg of the title compound. MS M/Z (FAB): 611 (M+H). Anal. calc. for $C_{34}H_{34}N_4O_7 \cdot 2H_2O$: C, 63.15; H, 5.88; N, 9.18; found: C, 63.22; H, 5.41; N, 8.64. Proton NMR (DMSO): δ 1.50 (m, 2H), 2.50–2.75 (4H), 3.92 (bs, 2H), 4.18 (m, 1H), 4.36 (m, 1H), 4.58 (m, 2H), 4.68 (m, 2H), 6.0 (m, 2H), 6.94 (m, 3H), 7.1–7.3 (11H), 7.59 (m, 1H) 7.83 (d, 1H), 8.12 (m, 2H).

EXAMPLE 333

(2S,3S,5S,1'S)-2,5-Bis-(N-(1-(3-pyridyl)ethoxycarbonyl)amino)-1,6-diphenyl-3hydroxyhexane

EXAMPLE 333A (S)-3-(1-(p-Nitrophenoxycarbonyloxy)ethyl)pyridine

A 534 mg (2.65 mmol) sample of p-nitrophenoxycarbonylchloride in methylene chloride was added to a solution of 74 mg (0.606 mmol) of (S)-1-(3-pyridyl)ethanol and 0.080 mL of 4-methylmorpholine in 2 mL of methylene chloride cooled in an ice bath. The mixture was stirred at 0° C. for 3.5 hours. The mixture was diluted with methylene chloride, which was washed with water, dried and concentrated. The crude produce was chromatographed on silica gel, eluting with 50% and 90% ethyl acetate in hexane. The solvent was removed and the product dried to afford 0.078 g of the title compound, which was taken directly to the next step.

EXAMPLE 333B (2S,3S,5S,1'S)-2,5-Bis-(N-(1-(3-pyridyl)ethoxycarbonyl)amino)-1,6-diphenyl-3-hydroxyhexane A 68 mg (0.236 mmol) sample of the compound from Example 333A above was added to 22 mg (0.079 mmol) of the product from Example 1E in 1.0 mL of DMF and stirred for 16 hours. The solvent was removed and the crude product chromatographed on silica gel, eluting with 2%,5% and 10% methanol in methylene chloride. The solvent was removed and the product dried to afford 25.0 mg of the title compound. MS M/Z (DCI/NH$_3$): 583 (M+H). Proton NMR (DMSO): δ 1.02–1.16 (1H), 1.43 (m, 6H), 1.54 (m, 2H), 2.58–2.70 (m, 4H), 3.45 (m, 1H), 3.60 (m, 1H), 3.75–3.90 (2H), 4.70 (d, 1H), 5.62 (m, 2H), 6.93 (d, 1H), 7.09 (d, 2H), 7.14–7.22 (9H), 7.30 (m, 1H), 7.53 (m, 1H), 8.47 (br, 4H).

EXAMPLE 334

(2S,3S,5S)-2.5-Bis-(N-(isoxazol-5-ylmethoxycarbonyl)amino)-1,6-diphenyl-3-hydroxyhexane

EXAMPLE 334A 5-(p-Nitrophenoxycarbonyloxymethyl)isoxazole

A 631 mg (2.65 mmol) sample of p-nitrophenoxycarbonylchloride in 2 mL of methylene chloride was added to a solution of 310 mg (3.13 mmol) of 5-hydroxymethyisoxazole and 0.344 mL of 4-methylmorpholine in 2 mL of methylene chloride cooled in an ice bath. The solution was stirred for 4 hours. The mixture was diluted with methylene chloride, which was washed with water, dried and concentrated. The crude product was chromatographed on silica gel, eluting with 2% ethyl acetate in methylene chloride. The solvent was removed and the product dried to afford 0.473 g of the title compound, which was taken directly to the next step.

EXAMPLE 334B (2S,3S,5S)-2,5-Bis-(N-(isoxazol-5-ylmethoxycarbonyl)amino)-1,6-diphenyl-3-hydroxyhexane A 125.8 mg (0.476 mmol) sample of the compound from Example 334B above was added to 45 mg (0.159 mmol) of the product of Example 1E in 0.5 mL of DMF and stirred for 16 hours. The solvent was removed and the crude product chromatographed on silica gel, eluting with 20% ethyl acetate in methylene chloride. The solvent was removed and the product dried to afford 30.6 mg of the title compound. MS M/Z (DCI/NH$_3$): 552 (m+H$_2$O), 535 (M+H). Proton NMR (DMSO): δ 1.5 (t, 2H), 2.65–2.77 (4H), 3.57 (m, 1H), 3.86 (br, 2H), 4.71 (d, 1H), 4.95–5.12 (4H), 6.32 (m, 2H), 7.07–7.34 (12H), 8.53 (d, 2H). Anal calc. for $C_{28}H_{30}N_4O_7 \cdot \frac{1}{3} H_2O$: C, 62.22; H, 5.68; N, 10.37; found: C, 62.06; H, 5.63; N, 10.33.

EXAMPLE 335

(2S,3S,5S)-2,5-Bis-(N-(2-hydroxyethoxycarbonyl)amino)-1,6-diphenyl-3-hydroxyhexane

EXAMPLE 335A 1-(t-Butyldimethylsilyloxy)-2-(p-nitrophenoxycarbonyloxy)ethane A 604 mg (3.00 mmol) sample of p-nitrophenoxycarbonylchloride in 3 mL of methylene chloride was added to a solution of 0.528 g (3.00 mmol) of 2-(t-butyldimethylsilyloxy)ethanol and 0.330 mL of 4-methylmorpholine in 2 mL of methylene chloride cooled in an ice bath. The solution was stirred for 2 hours. The mixture was diluted with methylene chloride, which was washed with water, dried and concentrated. The crude product was chromatographed on silica gel, eluting with 10% ethyl acetate in hexane. The solvent was removed and the product dried to afford 0.453 g of the title compound, which was taken directly to the next step.

EXAMPLE 335B (2S,3S,5S)-2,5-Bis-(N-(2-(t-butyldimethylsilyloxy) ethoxycarbonyl)amino)-1,6-diphenyl-3-hydroxyhexane A 328 mg (0.961 mmol) sample of the compound from Example 335A above was added to 91 mg (0.32 mmol) of the product of Example 1E in 0.8 mL of DMF and stirred for 16 hours. The solvent was removed and the crude product chromatographed on silica gel, eluting with 50% ethyl acetate in hexane. The product was rechromatographed on silica gel, eluting with 2% and 10% ethyl acetate in methylene chloride. The solvent was removed and the product dried to afford 100 mg of the title compound. This material was taken directly to the next step.

EXAMPLE 335C (2S,3S,5S)-2,5-Bis-(N-(2-hydroxyethoxycarbonyl)amino)-1,6-diphenyl-3-hydroxyhexane In two batches, 81.4 mg (0.016 mmol) of the compound from Example 335B above was dissolved in 2 mL of methanol to which 14.9 µL of trimethylsilyl chloride was added and stirred for 2 hours. The solvent was removed and the crude product chromatographed on silica gel, eluting with 2% and 5% methanol in methylene chloride. The solvent was removed and the product dried to afford 42.6 mg of the title compound. MS M/Z (DCI/NH$_3$): 461 (M+H), 478 (M+NH$_4$). Proton NMR (DMSO): δ 1.46 (t, 2H), 2.53–2.77 (4H), 3.45 (m, 3H), 3.55 (d, 1H), 3.64–3.92 (6H), 4.64 (m, 2H), 6.65 (d, 1H), 6.94 (d, 1H), 7.07–7.27 (10H). Anal calc. for C$_{24}$H$_{32}$N$_2$O$_7$.H$_2$O: C, 60.25; H, 7.11; N, 5.86; found: C, 60.38; H, 6.56; N, 5.86.

EXAMPLE 336

(2S,3S,5S)-2,5-Bis-(N-(2,5-dihydrofuran-3-yl-methoxycarbonyl)amino)-1,6-diphenyl-3-hydroxyhexane

EXAMPLE 336A 3-((t-butyldimethylsilyloxy)methyl)-4-hydroxybut-2-eneoic acid, 1,4-lactone A 2.960 g (196 mmol) sample of t-butyldimethylsilyl chloride was added to a solution of 1.86 g (163.7 mmol) of 3-hydroxymethyl-4-hydroxybut-2-eneoic acid, 1,4-lactone and 2.783 g (40.9 mmol) of imidazole in 6 mL of DMF. The mixture was stirred for 5.5 hours. The mixture was diluted with water and extracted with ethyl acetate. The solvent was removed and the residue was chromatographed on a silica gel column, eluting with 20% ethyl acetate in hexane. The solvent was removed and the product dried to afford 3.109 g of the title product.

EXAMPLE 336B 2-((t-Butyldimethylsilyloxy)methyl)-but-2-ene-1,4-diol

A 2.210 g (9.69 mmol) sample of 3-((t-butyldimethylsilyloxy)methyl)-4-hydroxybut-2-eneoic acid, 1,4-lactone, from Example 336A, was dissolved in 6 mL of methylene chloride, cooled in a dry ice bath, and 14.2 mL (21.3 mmol) of DIBAL was added. The mixture was stirred at 78° C. for 4 hours, allowed to warm to room temperature and stirred for 16 hours. The mixture was cooled to −78° C. and quenched with 1.53 mL of methanol and 2.55 mL of water. The mixture was filtered, and the filtrate concentrated and chromatographed on silica gel, eluting with 50% and 90% ethyl acetate in hexane. The solvent was removed and the product dried to afford 1.055 g of the title product, which was taken directly to the next step.

EXAMPLE 336C 3-t-(Butyldimethylsilyloxy)methyl-2,5-dihydrofuran

To a 0.792 g sample of the compound from Example 336B above in 5 mL of methylene chloride was added a solution of 4.59 g (6.53 mmol) of Martin's Sulfurane (Aldrich) in methylene chloride. The solution was stirred for 3.25 hours, diluted, washed with 20% KOH and saturated brine, dried and concentrated. The residue was chromatographed on silica gel, eluting with 10% ethyl acetate in hexane. The solvent was removed and the product dried to afford 0.282 g of the title product, which was taken directly to the next step.

EXAMPLE 336D 3-hydroxymethyl-2,5-dihydrofuran

To a 0.270 g (1.26 mmol) sample of the compound from Example 336C above dissolved in 2 mL of methanol was added 0.160 mL (1.26 mmol) of trimethylsilyl chloride The solution was sitted for 2.25 hours, the solvent was removed, and the residue chromatographed on a silica gel column, eluting with 50% and 90% ethyl acetate in hexane. The solvent was removed and the product dried to afford 65 mg of the title compound, which was taken directly to the next step.

EXAMPLE 336E 3-p-nitrophenoxycarbonyloxymethyl-2,5-dihydrofuran

To 65 mg (0.65 mmol) of the compound from Example 336D in methylene chloride was added 0.079 mL of 4-methylmorpholine and 144 mg (0.715 mmol) of p-nitrophenoxycarbonylchloride. The mixture was stirred for 2 hours, diluted with solvent, washed with saturated brine, and the solvent removed. The residue was chromatographed on a silica gel column, eluting with 20% and 30% ethyl acetate in hexane. The solvent was removed and the product dried to afford 0.115 g of the title product.

EXAMPLE 336F (2S,3S,5S)-2,5-Bis-(N-(2,5-dihydrofuran-3-yl-methoxycarbonyl)amino)-1,6-diphenyl-3-hydroxyhexane A 0.110 g (0.415 mmol) sample of the compound from Example 336D above and 47 mg (0.166 mmol) of the product of Example 1E were stirred in 0.80 mL of DMF for 16 hours. The solvent was removed, and the residue was chromatographed on a silica gel column, eluting with 20% and 50% ethyl acetate in methylene chloride. The solvent was removed and the product dried to afford 34.8 mg of the title compound. MS M/Z (DCI/NH$_3$): 537 (M+H), 554 (M+NH$_4$). Proton NMR (DMSO): δ 1.48 (t, 2H), 2.62–2.72 (4H), 3.56 (m, 1H), 3.78–3.93 (2H), 4.36 (br, 4H), 4.47 (br, 8H), 4.68 (d, 1H), 5.67 (s, 2H), 6.82 (d, 1H), 7.05–7.25 (11H).

EXAMPLE 337

(2S,3S,5S)-2,5-Bis-(N-(3-hydroxy-1-propoxycarbonyl)amino)-1,6-diphenyl-3-hydroxyhexane

EXAMPLE 337A 1-(t-Butyldimethylsilyloxy)-3-(p-nitrophenoxycarbonyloxy)propane A 0.604 g (3.00 mmol) sample of p-nitrophenoxycarbonylchloride in 3 mL of methylene chloride was added to a solution of 0.570 g (3.00 mmol) of 3-(t-butyldimethylsilyloxy)-1-propanol and 0.329 mL of 4-methylmorpholine in 2 mL of methylene chloride cooled in an ice bath. The solution was stirred for 2 hours. The mixture was diluted with methylene chloride, which was washed with water, dried and concentrated. The crude product was chromatographed on silica gel, eluting with 10% ethyl acetate in hexane. The solvent was removed and the product dried to afford 0.831 g of the title compound, which was taken directly to the next step.

EXAMPLE 337B 2,5-Bis-(N-(3-(t-butyldimethylsilyloxy)-1-propoxycarbonyl)amino)-1,6-diphenyl-3-hydroxyhexane A 328 mg (0.961 mmol) sample of the compound from Example 337A above was added to 105 mg (0.32 mmol) of the product of Example 1E in 1.2 mL of DMF and stirred for 16 hours. The solvent was removed and the crude product chromatographed on silica gel, eluting with 50% ethyl acetate in hexane. The product was rechromatographed on silica gel, eluting with 10% and 20% ethyl acetate in methylene chloride. The solvent was removed and the product dried to afford 185 mg of the title compound. This material was taken directly to the next step.

EXAMPLE 337C (2S,3S,5S)-2,5-Bis-(N-(3-hydroxyl-propoxycarbonyl)amino)-1,6-diphenyl-3-hydroxyhexane A 0.170 g (0.237 mmol) of the compound from Example 337B above was dissolved in 2 mL of methanol to which 30 μL of trimethylsilyl chloride was added and stirred for 2.25 hours. The solvent was removed and the crude product chromatographed on silica gel, eluting with 2% and 5% methanol in methylene chloride. The solvent was removed and the product dried to afford 22.7 mg of the title compound. MS M/Z (DCI/NH$_3$): 489 (M+H), 506 (M+NH$_4$). Proton NMR (DMSO): δ 1.45 (t, 2H), 1.60 (m, 4H), 2.55–2.75 (4H), 3.40 (m, 2H), 3.55 (br, 1H), 3.74–3.96 (18H), 4.44 (t, 2H), 4.62 (d, 1H), 6.63 (d, 1H), 6.89 (d, 1H), 7.07–7.27 (10H).

Fluorogenic Assay for Screening Inhibitors of HIV Protease

The inhibitory potency of the compounds of the invention can be determined by the following method.

A compound of the invention is dissolved in DMSO and a small aliquot further diluted with DMSO to 100 times the final concentration desired for testing. The reaction is carried out in a 6×50 mm tube in a total volume of 300 microliters. The final concentrations of the components in the reaction buffer are: 125 mM sodium acetate, 1M sodium chloride, 5 mM dithiothreitol, 0.5 mg/ml bovine serum albumin, 1.3 μM fluorogenic substrate, 2% (v/v) dimethylsulfoxide, pH 4.5. After addition of inhibitor, the reaction mixture is placed in the fluorometer cell holder and incubated at 30° C. for several minutes. The reaction is initiated by the addition of a small aliquot of cold HIV protease. The fluorescence intensity (excitation 340 nM, emmision 490 nM) is recorded as a function of time. The reaction rate is determined for the first six to eight minutes. The observed rate is directly proportional to the moles of substrate cleaved per unit time. The percent inhibition is 100×(1−(rate in presence of inhibitor)/(rate in absence of inhibitor)).

Fluorogenic substrate: Dabcyl-Ser-Gln-Asn-Tyr-Pro-Ile-Val-Gln-EDANS wherein DABCYL=4-(4-dimethylaminophenyl)azobenzoic acid and EDANS=5-((2-aminoethyl)amino)naphthalene-1-sulfonic acid.

Table 1 shows the inhibitory potencies of compounds of the invention against HIV-1 protease.

TABLE 1

| Compound of Example | Percent Inhibition | Inhibitor Concentration (nanomolar) |
|---|---|---|
| 37C | 61 | 1 |
| 38 | 55 | 0.5 |
| 39 | 61 | 0.5 |
| 40 | 61 | 0.5 |
| 171 | 62 | 0.5 |
| 174 | 51 | 0.5 |
| 290 | 65 | 0.5 |
| 297 | 43 | 0.5 |
| 298 | 56 | 0.5 |
| 305 | 91 | 0.5 |
| 306 | 88 | 0.5 |
| 307 | 64 | 0.5 |
| 308 | 67 | 0.5 |
| 309 | 97 | 0.5 |
| 310 | 83 | 0.5 |
| 311 | 84 | 0.5 |
| 312 | 84 | 0.5 |
| 314 | 63 | 0.5 |
| 315 | 80 | 0.5 |
| 319 | 52 | 0.5 |
| 320 | 60 | 0.5 |
| 321 | 64 | 0.5 |
| 322B | 72 | 0.5 |
| 326 | 66 | 0.5 |
| 327 | 69 | 0.5 |
| 334B | 56 | 1.0 |

Antiviral Activity

The anti-HIV activity of the compounds of the invention can be determined in MT4 cells according to the procedure of Pauwels et. al. (J. Virol. Methods 1988, 20, 309). The IC$_{50}$ is the concentration of compound that gives 50% inhibition of the cytopathic effect of HIV. The LC$_{50}$ is the concentration of compound at which 50% of the cells remain viable.

Table 2 shows the inhibitory potencies of compounds of the invention against HIV-1$_{3B}$ in MT4 cells.

TABLE 2

| Compound of Example | IC$_{50}$ (micromolar) | LC$_{50}$ (micromolar) |
|---|---|---|
| 37C | 0.84–1.44 | >100 |
| 38 | 0.55–0.61 | >100 |
| 39 | 0.13–0.25 | >100 |
| 40 | 0.23–0.55 | 64 |
| 171 | 0.38–0.55 | >100 |
| 174 | 0.14–0.23 | >100 |
| 290 | 0.026–0.075 | >100 |
| 297 | 0.31–0.35 | 81 |
| 298 | 0.22–0.29 | 59 |
| 305 | 0.005–0.017 | >100 |
| 306 | 0.007–0.019 | >100 |
| 307 | 0.16–0.26 | >100 |
| 308 | 0.077–0.124 | 96 |
| 310 | 0.013–0.025 | 55 |
| 311 | 0.058–0.067 | 58 |
| 312 | 0.058–0.077 | 61 |
| 313 | 0.46–0.5 | >100 |
| 314 | 0.098–0.144 | >100 |
| 315 | 0.003–0.005 | >100 |
| 319 | 0.21–0.29 | >100 |
| 320 | 0.4–0.5 | >100 |
| 321 | 0.14–0.19 | >100 |
| 322B | 0.086–0.094 | >100 |
| 326 | 0.053–0.086 | 27 |
| 327 | 0.034–0.064 | 84 |
| 334B | 0.74–1.6 | 91 |

The compounds of the present invention can be used in the form of salts derived from inorganic or organic acids. These salts include but are not limited to the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemisulfate, heptanoate, hexanoate, fumarate, hydrochloride, hydrobromide, hydroiodide, 2-hydroxy-ethanesulfonate (isethionate), lactate, maleate, methanesulfonate, nicotinate, 2-naphthalenesulfonate, oxalate, pamoate, pectinate, persulfate, 3-phenylpropionate, picrate, pivalate, propionate, succinate, tartrate, thiocyanate, p-toluenesulfonate and undecanoate. Also, the basic nitrogen-containing groups can be quaternized with such agents as loweralkyl halides, such as methyl, ethyl, propyl, and butyl chloride, bromides, and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. Water or oil-soluble or dispersible products are thereby obtained.

Examples of acids which may be employed to form pharmaceutically acceptable acid addition salts include such inorganic acids as hydrochloric acid, sulphuric acid and phosphoric acid and such organic acids as oxalic acid, maleic acid, succinic acid and citric acid. Other salts include salts with alkali metals or alkaline earth metals, such as sodium, potassium, calcium or magnesium or with organic bases.

Preferred salts of the compounds of the invention include hydrochloride, methanesulfonate, sulfonate, phosphonate and isethionate.

The compounds of the present invention can also be used in the form of esters. Examples of such esters include a hydroxyl-substituted compound of formula I which has been acylated with a blocked or unblocked amino acid residue, a phosphate function, a hemisuccinate residue, an acyl residue of the formula R*C(O)- or R*C(S)- wherein R* is hydrogen, loweralkyl, haloalkyl, alkoxy, thioalkoxy, alkoxyalkyl, thioalkoxyalkyl or haloalkoxy, or an acyl residue of the formula $R_a$-C($R_b$)($R_d$)-C(O)- or $R_a$-C($R_b$)($R_d$)-C(S)- wherein $R_b$ and $R_d$ are independently selected from hydrogen or loweralkyl and $R_a$ is -N($R_e$)($R_f$), OR$_e$ or -SR$_e$ wherein $R_e$ and $R_f$ are independently selected.from hydrogen, loweralkyl and haloalkyl, or an amino-acyl residue of the formula $R_{180}$NH(CH$_2$)$_2$NHCH$_2$C(O)- or $R_{180}$NH(CH$_2$)$_2$OCH$_2$C(O)- wherein $R_{180}$ is hydrogen, loweralkyl, arylalkyl, cycloalkylalkyl, alkanoyl, benzoyl or an α-amino acyl group. The amino acid esters of particular interest are glycine and lysine; however, other amino acid residues can also be used, including those wherein the amino acyl group is -C(O)CH$_2$NR$_{200}$R$_{201}$ wherein $R_{200}$ and $R_{201}$ are independently selected from hydrogen and loweralkyl or the group -NR$_{200}$R$_{201}$ forms a nitrogen containing heterocyclic ring. These esters serve as pro-drugs of the compounds of the present invention and serve to increase the solubility of these substances in the gastrointestinal tract. These esters also serve to increase solubility for intravenous administration of the compounds. Other prodrugs include a hydroxyl-substituted compound of formula I wherein the hydroxyl group is functionalized with a substituent of the formula -CH(R$_g$)O-C(O)R$_{181}$ or -CH(R$_g$)OC(S)R$_{181}$ wherein R$_{181}$ is loweralkyl, haloalkyl, alkoxy, thioalkoxy or haloalkoxy and R$_g$ is hydrogen, loweralkyl, haloalkyl, alkoxycarbonyl, aminocarbonyl, alkylaminocarbonyl or dialkylaminocarbonyl. The prodrugs of this invention are metabolized in vivo to provide the hydroxyl-substituted compound of formula I. The preparation of the prodrug esters is carried out by reacting a hydroxyl-substituted compound of formula I with an activated amino acyl, phosphoryl, hemisuccinyl or acyl derivative as defined above. The resulting product is then deprotected to provide the desired pro-drug ester. Prodrugs of the invention can also be prepared by alkylation of the hydroxyl group with (haloalkyl)esters, transacetalization with bis-(alkanoyl)acetals or condensation of the hydroxyl group with an activated aldehyde followed by acylation of the intermediate hemiacetal.

The compounds of the invention are useful for inhibiting retroviral protease, in particular HIV protease, in vitro or in vivo. The compounds of the present invention are also useful for the treatment or prophylaxis of diseases caused by retroviruses, especially acquired immune deficiency syndrome or an HIV infection in a human or other mammal.

Total daily dose administered to a human or other mammal host in single or divided doses may be in amounts, for example, from 0.001 to 300 mg/kg body weight daily and more usually 0.1 to 10 mg. Dosage unit compositions may contain such amounts of submultiples thereof to make up the daily dose.

The amount of active ingredient that may be combined with the carrier materials to produce a single dosage form will vary depending upon the host treated and the particular mode of administration.

It will be understood, however, that the specific dose level for any particular patient will depend upon a variety of factors including the activity of the specific compound employed, the age, body weight, general health, sex, diet, time of administration, route of administration, rate of excretion, drug combination, and the severity of the particular disease undergoing therapy.

The compounds of the present invention may be administered orally, parenterally, sublingually, by inhalation spray, rectally, or topically in dosage unit formulations containing conventional nontoxic pharmaceutically acceptable carriers, adjuvants, and vehicles as desired. Topical administration may also involve the use of transdermal administration such as transdermal patches or iontophoresis devices. The term parenteral as used herein includes subcutaneous injections, intravenous, intramuscular, intrasternal injection, or infusion techniques.

Injectable preparations, for example, sterile injectable aqueous or oleagenous suspensions may be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3-propanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Suppositories for rectal administration of the drug can be prepared by mixing the drug with a suitable nonirritating excipient such as cocoa butter and polyethylene glycols which are solid at ordinary temperatures but liquid at the rectal temperature and will therefore melt in the rectum and release the drug.

Solid dosage forms for oral administration may include capsules, tablets, pills, powders, and granules. In such solid dosage forms, the active compound may be admixed with at least one inert diluent such as sucrose lactose or starch. Such dosage forms may also comprise, as is normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting agents, emulsifying and suspending agents, and sweetening, flavoring, and perfuming agents.

The compounds of the present invention can also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically aceptable and metabolizable lipid capabale of forming liposomes can be used. The present compositions in liposome form can contain, in addition to a compound of the present invention, stabilizers, preservatives, excipients, and the like. The preferred lipids are the phospholipids and phosphatidyl cholines (lecithins), both natureal and synthetic.

Methods to form liposomes are known in the art. See, for example, Prescott, Ed., *Methods in Cell Biology*, Volume XIV, Academic Press, New York, N.Y. (1976), p. 33 et seq.

While the compounds of the invention can be administered as the sole active pharmaceutical agent, they can also be used in combination with one or more immunomodulators, antiviral agents, other antiinfective agents or vaccines. Other antiviral agents to be administered in combination with a compound of the present invention include AL-721, beta interferon, polymannoacetate, reverse transcriptase inhibitors (for example, ganciclovir, dideoxycytidine (DDC), dideoxyinosine (DDI), BCH-189, AzdU, carbovir, DDA, D4C, D4T, DP-AZT, FLT (fluorothymidine), BCH-189, 5-halo-3'-thiadideoxycytidine, PMEA, zidovudine (AZT) and the like), non-nucleoside reverse transcriptase inhibitors (for example, R82193, L-697,661, BI-RG-587 (nevirapine), HEPT compounds, L,697,639, R82150, U-87201E and the like), TAT inhibitors (for example, RO-24-7429 and the like), trisodium phosphonoformate, HPA-23, eflonithine, Peptide T, Reticulose (nucleophosphoprotein), ansamycin LM 427, trimetrexate, UA001, ribavirin, alpha interferon, oxetanocin, oxetanocin-G, cylobut-G, cyclobut-A, ara-M, BW882C87, foscarnet, BW256U87, BW348U87, BV ara-U, CMV triclonal antibodies, FIAC, HOE-602, HPMPC, MSL-109, TI-23, trifluridine, vidarabine, famciclovir, penciclovir, acyclovir, castanospermine, rCD4/CD4-IgG, CD4-PE40, butyl-DNJ, hypericin, oxamyristic acid, dextran sulfate and pentosan polysulfate. Immunomodulators that can be administered in combination with a compound of the present invention include bropirimine, Ampligen, anti-human alpha interferon antibody, colony stimulting factor, CL246,738, Imreg-1, Imreg-2, diethydithiocarbamate, interleukin-2, alpha-interferon, inosine pranobex, methionine enkephalin, muramyl-tripeptide, TP-5, erythropoietin, naltrexone, tumor necrosis facator, beta interferon, gamma interferon, interleukin-4, autologous CD8+ infusion, alpha interferon immunoglobulin, anti-Leu-3A, autovaccination, biostimulation, extracorporeal photophoresis, FK-565, FK-506, G-CSF, GM-CSF, hyperthermia, isopinosine, IVIG, passisve immunotherapy and polio vaccine hyperimmunization. Other antiinfective agents that can be administered in combination with a compound of the present invention include pentamidine isethionate. Any of a variety of HIV or AIDS vaccines (for example, gp120 (recombinant), Env 2-3 (gp120), HIVAC-1e (gp120), gp160 (recombinant), VaxSyn HIV-1 (gp160), Immuno-Ag (gp160), HGP-30, HIV-Immunogen, p24 (recombinant), VaxSyn HIV-1 (p24) can be used in combination with a compound of the present invention.

Other agents that can be used in combination with the compounds of this invention are ansamycin LM 427, apurinic acid, ABPP, Al-721, carrisyn, AS-101, avarol, azimexon, colchicine, compound Q, CS-85, N-acetyl cysteine (2-oxothiazolidine-4-carboxylate), D-penicillamine, diphenylhydantoin, EL-10, erythropoieten, fusidic acid, glucan, HPA-23, human growth hormone, hydorxchloroquine, iscador, L-ofloxacin or other quinolone antibiotics, lentinan, lithium carbonate, MM-1, monolaurin, MTP-PE, naltrexone, neurotropin, ozone, PAI, panax ginseng, pentofylline, Peptide T, pine cone extract, polymannoacetate, reticulose, retrogen, ribavirin, ribozymes, RS-47, Sdc-28, silicotungstate, THA, thymic humoral factor, thymopentin, thymosin fraction 5, thymosin alpha one, thymostimulin, UA001, uridine, vitamin B12 and wobemugos.

Other agents that can be used in combination with the compounds of this invention are antifungals such as amphotericin B, clotrimazole, flucytosine, fluconazole, itraconazole, ketoconazole and nystatin and the like.

Other agents that can be used in combination with the compounds of this invention are anitbacterials such as amikacin sulfate, azithromycin, ciprofloxacin, temafloxacin, tosufloxacin, clarithromycin, clofazimine, ethambutol, isoniazid, pyrazinamide, rifabutin, rifampin, streptomycin and TLC G-65 and the like.

Other agents that can be used in combination with the compounds of this invention are anti-neoplastics such as alpha interferon, COMP (cyclophosphamide, vincristine, methotrexate and prednisone), etoposide, mBACOD (methotrexate, bleomycin, doxorubicin, cyclophosphamide, vincristine and dexamethasone), pRO-MACE/MOPP(prednisone, methotrexate (w/leucovin rescue), doxorubicin, cyclophosphamide, etoposide/mechlorethamine, vincristine, prednisone and procarbazine), vincristine, vinblastine, angioinhibins, pentosan polysulfate, platelet factor 4 and SP-PG and the like.

Other agents that can be used in combination with the compounds of this invention are drugs for treating neurological disease such as peptide T, ritalin, lithium, elavil, phenytoin, carbamazipine, mexitetine, heparin and cytosine arabinoside and the like.

Other agents that can be used in combination with the compounds of this invention are anti-protozoals such as albendazole, azithromycin, clarithromycin, clindamycin, corticosteroids, dapsone, DIMP, eflornithine, 566C$_{80}$, fansidar, furazolidone, L, 671,329, letrazuril, metronidazole, paromycin, pefloxacin, pentamidine, piritrexim, primaquine, pyrimethamine, somatostatin, spiramycin, sulfadiazine, trimethoprim, TMP/SMX, trimetrexate and WR 6026 and the like.

Among the preferred agents for treatment of HIV or AIDS in combination with the compounds of this invention are reverse transcriptase inhibitors.

It will be understood that agents which can be combined with the compounds of the present invention for the treatment or prophylaxis of AIDS or an HIV infection are not limited to those listed above, but include in principle any agents useful for the treatment or prophylaxis of AIDS or an HIV infection.

When administered as a combination, the therapeutic agents can be formulated as separate compositions which are given at the same time or different times, or the therapeutic agents can be given as a single composition.

The foregoing is merely illustrative of the invention and is not intended to limit the invention to the disclosed compounds. Variations and changes which are obvious to one skilled in the art are intended to be within the scope and nature of the invention which are defined in the appended claims.

What is claimed is:
1. A compound of the formula:

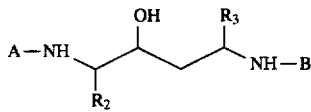

wherein $R_2$ and $R_3$ are independently selected from $C_3$-to-$C_7$-cycloalkyl-$C_1$-to-$C_6$-alkyl and ($C_6$-monocyclic or $C_9$- or $C_{10}$-bicyclic)aryl-$C_1$-to-$C_6$-alkyl; and (a) A is pyridyl-$C_1$-to-$C_6$-alkyl-$R_9$-C(O)-NH-CH($R_5$)-C(O)- or (substituted-pyridyl)-$C_1$-to-$C_6$-alkyl-$R_9$-C(O)-NH-CH($R_5$)-C(O)- wherein $R_9$ is -O-, -NH- or -N($C_1$-to-$C_6$-loweralkyl)-, $R_5$ is $C_1$-to-$C_6$-loweralkyl and substituted-pyridyl is a pyridyl ring substituted with one or two substituents independently selected from $C_1$-to-$C_6$-loweralkyl, hydroxy, halo, amino, $C_1$-to-$C_6$-alkylamino, di-$C_1$-to-$C_6$-alkylamino, $C_1$-to-$C_6$-alkoxy, halo-$C_1$-to-$C_6$-alkyl, unsubstituted -$C_3$-to-$C_7$-cycloalkyl, unsubstituted ($C_6$-monocyclic or $C_9$- or $C_{10}$-bicyclic)aryl, unsubstituted ($C_6$-monocyclic or $C_9$- or $C_{10}$-bicyclic)aryl-$C_1$-to-$C_6$-alkyl,-COOH and -SO$_3$H and B is thiazolyl-$C_1$-to-$C_6$-alkyl-O-C(O)-, thiazolyl-$C_1$-to-$C_6$-alkyl-NH-C(O)-, thiazolyl-$C_1$-to-$C_6$-alkyl-N($C_1$-to-$C_6$-loweralkyl)-C(O)-, (substituted-thiazolyl)-$C_1$-to-$C_6$-alkyl-O-C(O)-, (substituted-thiazolyl)-$C_1$-to-$C_6$-alkyl-NH-C(O)- or (substituted-thiazolyl)-$C_1$-to-$C_6$-alkyl-N($C_1$-to-$C_6$-loweralkyl)-C(O)- wherein substituted-thiazolyl is a thiazolyl ring substituted with one or two substituents independently selected from $C_1$-to-$C_6$-loweralkyl, hydroxy, halo, amino, $C_1$-to-$C_6$-alkylamino, di-$C_1$-to-$C_6$-alkylamino, $C_1$-to-$C_6$-alkoxy, halo-$C_1$-to-$C_6$-alkyl, unsubstituted -$C_3$-to-$C_7$-cycloalkyl, unsubstituted ($C_6$-monocyclic or $C_9$- or $C_{10}$-bicyclic)aryl, unsubstituted ($C_6$-monocyclic or $C_9$- or $C_{10}$-bicyclic)aryl-$C_1$-to-$C_6$-alkyl, -COOH and -SO$_3$H; or (b) A is thiazolyl-$C_1$-to-$C_6$-alkyl-$R_9$-C(O)-NH-CH($R_5$)-C(O)- or (substituted-thiazolyl)-$C_1$-to-$C_6$-alkyl-$R_9$-C(O)-NH-CH($R_5$)-C(O)- wherein $R_9$ is -O-, -NH- or -N($C_1$-to-$C_6$-loweralkyl)-, $R_5$ is $C_1$-to-$C_6$-loweralkyl and substituted-thiazolyl is a thiazolyl ring substituted with one or two substituents independently selected from $C_1$-to-$C_6$-loweralkyl, hydroxy, halo, amino, $C_1$-to-$C_6$-alkylamino, di-$C_1$-to-$C_6$-alkylamino, $C_1$-to-$C_6$-alkoxy, halo-$C_1$-to-$C_6$-alkyl, unsubstituted -$C_3$-to-$C_7$-cycloalkyl, unsubstituted ($C_6$-monocyclic or $C_9$- or $C_{10}$-bicyclic)aryl, unsubstituted ($C_6$-monocyclic or $C_9$- or $C_{10}$-bicyclic)aryl-$C_1$-to-$C_6$-alkyl, -COOH and -SO$_3$H and B is pyridyl-$C_1$-to-$C_6$-alkyl-O-C(O)-, pyridyl-$C_1$-to-$C_6$-alkyl-NH-C(O)-, pyridyl-$C_1$-to-$C_6$-alkyl-N(loweralkyl)-C(O)-, (substituted-pyridyl)-$C_1$-to-$C_6$-alkyl-O-C(O)-, (substituted-pyridyl)-$C_1$-to-$C_6$-alkyl-NH-C(O)- or (substituted-pyridyl)-$C_1$-to-$C_6$-alkyl-N($C_1$-to-$C_6$-loweralkyl)-C(O)- wherein substituted-pyridyl is a pyridyl ring substituted with one or two substituents independently selected from $C_1$-to-$C_6$-loweralkyl, hydroxy, halo, amino, $C_1$-to-$C_6$-alkylamino, di-$C_1$-to-$C_6$-alkylamino, $C_1$-to-$C_6$-alkoxy, halo-$C_1$-to-$C_6$-alkyl, unsubstituted -$C_3$-to-$C_7$-cycloalkyl, unsubstituted ($C_6$-monocyclic or $C_9$- or $C_{10}$-bicyclic)aryl, unsubstituted ($C_6$-monocyclic or $C_9$- or $C_{10}$-bicyclic)aryl-$C_1$-to-$C_6$-alkyl, -COOH and -SO$_3$H; or (c) A is thiazolyl-$C_1$-to-$C_6$-alkyl-O-C(O)-, thiazolyl-$C_1$-to-$C_6$-alkyl-NH-C(O)-, thiazolyl-$C_1$-to-$C_6$-alkyl-N($C_1$-to-$C_6$-loweralkyl)-C(O)-, (substituted-thiazolyl)-$C_1$-to-$C_6$-alkyl-O-C(O)-, (substituted-thiazolyl)-$C_1$-to-$C_6$-alkyl-NH-C(O)- or (substituted-thiazolyl)-$C_1$-to-$C_6$-alkyl-N($C_1$-to-$C_6$-loweralkyl)-C(O)- wherein substituted-thiazolyl is a thiazolyl ring substituted with one or two substituents independently selected from $C_1$-to-$C_6$-loweralkyl, hydroxy, halo, amino, $C_1$-to-$C_6$-alkylamino, di-$C_1$-to-$C_6$-alkylamino, $C_1$-to-$C_6$-alkoxy, halo-$C_1$-to-$C_6$-alkyl, unsubstituted -$C_3$-to-$C_7$-cycloalkyl, unsubstituted ($C_6$-monocyclic or $C_9$- or $C_{10}$-bicyclic)aryl, unsubstituted ($C_6$-monocyclic or $C_9$- or $C_{10}$-bicyclic)aryl-$C_1$-to-$C_6$-alkyl, -COOH and -SO$_3$H and B is pyridyl-$C_1$-to-$C_6$-alkyl-$R_9$-C(O)-NH-CH($R_5$)-C(O)- or (substituted-pyridyl)-$C_1$-to-$C_6$-alkyl-$R_9$-C(O)-NH-CH($R_5$)-C(O)- wherein $R_9$ is -O-, -NH- or -N($C_1$-to-$C_6$-loweralkyl)-, $R_5$ is $C_1$-to-$C_6$-loweralkyl and substituted-pyridyl is a pyridyl ring substituted with one or two substituents independently selected from $C_1$-to-$C_6$-loweralkyl, hydroxy, halo, amino, $C_1$-to-$C_6$-alkylamino, di-$C_1$-to-$C_6$-alkylamino, $C_1$-to-$C_6$-alkoxy, halo-$C_1$-to-$C_6$-alkyl, unsubstituted -$C_3$-to-$C_7$-cycloalkyl, unsubstituted ($C_6$-monocyclic or $C_9$- or $C_{10}$-bicyclic)aryl, unsubstituted ($C_6$-monocyclic or $C_9$- or $C_{10}$-bicyclic)aryl-$C_1$-to-$C_6$-alkyl, -COOH and -SO$_3$H; or (d) A is pyridyl-$C_1$-to-$C_6$-alkyl-O-C(O)-, pyridyl-$C_1$-to-$C_6$-alkyl-NH-C(O)-, pyridyl-$C_1$-to-$C_6$-alkyl-N($C_1$-to-$C_6$-loweralkyl)-C(O)-, (substituted-pyridyl)-$C_1$-to-$C_6$-alkyl-O-C(O)-, (substituted-pyridyl)-$C_1$-to-$C_6$-alkyl- NH-C(O)- or (substituted-pyridyl)-$C_1$-to-$C_6$-alkyl-N($C_1$-to-$C_6$-loweralkyl)-C(O)- wherein substituted-pyridyl is a pyridyl ring substituted with one or two substituents independently selected from $C_1$-to-$C_6$-loweralkyl, hydroxy, halo, amino, $C_1$-to-$C_6$-alkylamino, di-$C_1$-to-$C_6$-alkylamino, $C_1$-to-$C_6$-alkoxy, halo-$C_1$-to-$C_6$-alkyl, unsubstituted -$C_3$-to-$C_7$-cycloalkyl, unsubstituted ($C_6$-monocyclic or $C_9$- or $C_{10}$-bicyclic)aryl, unsubstituted ($C_6$-monocyclic or $C_9$- or $C_{10}$-bicyclic)aryl-$C_1$-to-$C_6$-alkyl, -COOH and -$SO_3H$ and B is thiazolyl-$C_1$-to-$C_6$-alkyl-$R_9$-C(O)-NH-CH($R_5$)-C(O)- or (substituted-thiazolyl)-$C_1$-to-$C_6$-alkyl-$R_9$-C(O)-NH-CH($R_5$)-C(O)- wherein $R_9$ is -O-, -NH- or -N($C_1$-to-$C_6$-loweralkyl)-, $R_5$ is -$C_1$-to-$C_6$-loweralkyl and substituted-thiazolyl is a thiazolyl ring substituted with one or two substituents independently selected from $C_1$-to-$C_6$-loweralkyl, hydroxy, halo, amino, $C_1$-to-$C_6$-alkylamino, di-$C_1$-to-$C_6$-alkylamino, $C_1$-to-$C_6$-alkoxy, halo-$C_1$-to-$C_6$-alkyl, unsubstituted -$C_3$-to-$C_7$-cycloalkyl, unsubstituted ($C_6$-monocyclic or $C_9$- or $C_{10}$-bicyclic)aryl, unsubstituted ($C_6$-monocyclic or $C_9$- or $C_{10}$-bicyclic)aryl-$C_1$-to-$C_6$-alkyl, -COOH and -$SO_3H$; or a pharmaceutically acceptable salt thereof.

2. The compound of claim 1 wherein A is pyddyl-$C_1$-to-$C_6$-alkyl-$R_9$-C(O)-NH-CH($R_5$)-C(O)- or (substituted-pyridyl)-$C_1$-to-$C_6$-alkyl-$R_9$-C(O)-NH-CH($R_5$)-C(O)- wherein $R_9$ is -O-, -NH- or -N($C_1$-to-$C_6$-loweralkyl)-, $R_5$ is $C_1$-to-$C_6$-loweralkyl and substituted-pyridyl is a pyridyl ring substituted with one or two substituents independently selected from $C_1$-to-$C_6$-loweralkyl, hydroxy, halo, amino, $C_1$-to-$C_6$-alkylamino, di-$C_1$-to-$C_6$-alkylamino, $C_1$-to-$C_6$-alkoxy, halo -$C_1$-to-$C_6$-alkyl, unsubstituted -$C_3$-to-$C_7$-cycloalkyl, unsubstituted ($C_6$-monocyclic or $C_9$- or $C_{10}$-bicyclic)aryl, unsubstituted ($C_6$-monocyclic or $C_9$- or $C_{10}$-bicyclic)aryl-$C_1$-to-$C_6$-alkyl, -COOH and -$SO_3H$ and B is thiazolyl-$C_1$-to-$C_6$-alkyl-O-C(O)-, thiazolyl-$C_1$-to-$C_6$-alkyl-NH-C(O)-, thiazolyl-$C_1$-to-$C_6$-alkyl-N($C_1$-to-$C_6$-loweralkyl)-C(O)-, (substituted-thiazolyl)-$C_1$-to-$C_6$-alkyl-O-C(O)-, (substituted-thiazolyl)-$C_1$-to-$C_6$-alkyl-NH-C(O)- or (substituted-thiazolyl)-$C_1$-to-$C_6$-alkyl-N($C_1$-to-$C_6$-loweralkyl)-C(O)- wherein substituted-thiazolyl is a thiazolyl ring substituted with one or two substituents independently selected from $C_1$-to-$C_6$-loweralkyl, hydroxy, halo, amino, $C_1$-to-$C_6$-alkylamino, di-$C_1$-to-$C_6$-alkylamino, $C_1$-to-$C_6$-alkoxy, halo-$C_1$-to-$C_6$-alkyl, unsubstituted-$C_3$-to-$C_7$-cycloalkyl, unsubstituted ($C_6$-monocyclic or $C_9$- or $C_{10}$-bicyclic)aryl, unsubstituted ($C_6$-monocyclic or $C_9$- or $C_{10}$-bicyclic)aryl-$C_1$-to-$C_6$-alkyl, -COOH and -$SO_3H$.

3. The compound of claim 2 wherein $R_2$ and $R_3$ are benzyl, A is pyridyl-$C_1$-to-$C_6$-alkyl-$R_9$-C(O)-NH-CH($R_5$)-C(O)- wherein $R_9$ is -O- or -N($CH_3$)- and $R_5$ is isoproply or 2-butyl and B is thiazolyl-$C_1$-to-$C_6$-alkyl-O-C(O)-or (substituted-thiazolyl)-$C_1$-to-$C_6$-alkyl-O-C(O)- wherein substituted-thiazolyl is a thiazolyl ring substituted with $C_1$-to-$C_6$-loweralkyl or amino.

4. The compound of claim 1 wherein A is thiazolyl-$C_1$-to-$C_6$-alkyl-$R_9$-C(O)-NH-CH($R_5$)-C(O)- or (substituted-thiazolyl)-$C_1$-to-$C_6$-alkyl-$R_9$-C(O)-NH-CH($R_5$)-C(O)- wherein $R_9$ is -O-, -NH- or -N($C_1$-to-$C_6$-loweralkyl)-, $R_5$ is $C_1$-to-$C_6$-loweralkyl and substituted-thiazolyl is a thiazolyl ring substituted with one or two substituents independently selected from $C_1$-to-$C_6$-loweralkyl, hydroxy, halo, amino, $C_1$-to-$C_6$-alkylamino, di-$C_1$-to-$C_6$-alkylamino, $C_1$-to-$C_6$-alkoxy, halo-$C_1$-to-$C_6$-alkyl, unsubstituted-$C_3$-to-$C_7$-cycloalkyl, unsubstituted ($C_6$-monocyclic or $C_9$- or $C_{10}$-bicyclic)aryl, unsubstituted ($C_6$-monocyclic or $C_9$- or $C_{10}$-bicyclic)aryl-$C_1$-to-$C_6$-alkyl, -COOH and -$SO_3H$ and B is pyridyl-$C_1$-to-$C_6$-alkyl-O-C(O)-, pyridyl-$C_1$-to-$C_6$-alkyl-NH-C(O)-, pyridyl-$C_1$-to-$C_6$-alkyl-N(loweralkyl)-C(O)-, (substituted-pyridyl)-$C_1$-to-$C_6$-alkyl-O-C(O)-, (substituted-pyridyl)-$C_1$-to-$C_6$-alkyl-NH-C(O)- or (substituted-pyridyl)-$C_1$-to-$C_6$-alkyl-N($C_1$-to-$C_6$-loweralkyl)-C(O)- wherein substituted-pyridyl is a pyridyl ring substituted with one or two substituents independently selected from $C_1$-to-$C_6$-loweralkyl, hydroxy, halo, amino, $C_1$-to-$C_6$-alkylamino, di-$C_1$-to-$C_6$-alkylamino, $C_1$-to-$C_6$-alkoxy, halo-$C_1$-to-$C_6$-alkyl, unsubstituted -$C_3$-to-$C_7$-cycloalkyl, unsubstituted ($C_6$-monocyclic or $C_9$- or $C_{10}$-bicyclic)aryl, unsubstituted ($C_6$-monocyclic or $C_9$- or $C_{10}$-bicyclic)aryl-$C_1$-to-$C_6$-alkyl, -COOH and -$SO_3H$.

5. The compound of claim 4 wherein $R_2$ and $R_3$ are benzyl, A is thiazolyl-$C_1$-to-$C_6$-alkyl-$R_9$-C(O)-NH-CH($R_5$)-C(O)- or (substituted-thiazolyl)-$C_1$-to-$C_6$-alkyl-$R_9$-C(O)-NH-CH($R_5$)-C(O)- wherein $R_9$ is -O- or -N($CH_3$)-, $R_5$ is isopropyl or 2-butyl and substituted-thiazolyl is a thiazolyl ring substituted with $C_1$-to-$C_6$-loweralkyl or amino and B is pyridyl-$C_1$-to-$C_6$-alkyl-O-C(O)-.

6. The compound of claim 1 wherein A is thiazolyl-$C_1$-to-$C_6$-alkyl-O-C(O)-, thiazolyl-$C_1$-to-$C_6$-alkyl-NH-C(O)-, thiazolyl-$C_1$-to-$C_6$-alkyl-N($C_1$-to-$C_6$-loweralkyl)-C(O)-, (substituted-thiazolyl)-$C_1$-to-$C_6$-alkyl-O-C(O)-, (substituted-thiazolyl)-$C_1$-to-$C_6$-alkyl-NH-C(O)- or (substituted-thiazolyl)-$C_1$-to-$C_6$-alkyl-N($C_1$-to-$C_6$-loweralkyl)-C(O)- wherein substituted-thiazolyl is a thiazolyl ring substituted with one or two substituents independently selected from $C_1$-to-$C_6$-loweralkyl, hydroxy, halo, amino, $C_1$-to-$C_6$-alkylamino, di-$C_1$-to-$C_6$-alkylamino, $C_1$-to-$C_6$-alkoxy, halo-$C_1$-to-$C_6$-alkyl, unsubstituted -$C_3$-to-$C_7$-cycloalkyl, unsubstituted ($C_6$-monocyclic or $C_9$- or $C_{10}$-bicyclic)aryl, unsubstituted ($C_6$-monocyclic or $C_9$- or $C_{10}$-bicyclic)aryl-$C_1$-to-$C_6$-alkyl, -COOH and -$SO_3H$ and B is pyridyl-$C_1$-to-$C_6$-alkyl-$R_9$-C(O)-NH-CH($R_5$)-C(O)- or (substituted-pyridyl)-$C_1$-to-$C_6$-alkyl-$R_9$-C(O)-NH-CH($R_5$)-C(O)- wherein $R_9$ is -O-, -NH- or -N($C_1$-to-$C_6$-loweralkyl)-, $R_5$ is $C_1$-to-$C_6$-loweralkyl and substituted-pyridyl is a pyridyl ring substituted with one or two substituents independently selected from $C_1$-to-$C_6$-loweralkyl, hydroxy, halo, amino, $C_1$-to-$C_6$-alkylamino, di-$C_1$-to-$C_6$-alkylamino, $C_1$-to-$C_6$-alkoxy, halo-$C_1$-to-$C_6$-alkyl, unsubstituted -$C_3$-to-$C_7$-cycloalkyl, unsubstituted ($C_6$-monocyclic or $C_9$- or $C_{10}$-bicyclic)aryl, unsubstituted ($C_6$-monocyclic or $C_9$- or $C_{10}$-bicyclic)aryl-$C_1$-to-$C_6$-alkyl, -COOH and -$SO_3H$.

7. The compound of claim 6 wherein $R_2$ and $R_3$ are benzyl, A is thiazolyl-$C_1$-to-$C_6$-alkyl-O-C(O)- or (substituted-thiazolyl)-$C_1$-to-$C_6$-alkyl-O-C(O)- wherein substituted-thiazolyl is a thiazolyl ring substituted with $C_1$-to-$C_6$-loweralkyl or amino and B is pyridyl-$C_1$-to-$C_6$-alkyl-$R_9$-C(O)-NH-CH($R_5$)-C(O)- wherein $R_9$ is -O- or -N($CH_3$)- and $R_5$ is isopropyl or 2-butyl.

8. The compound of claim 1 wherein A is pyridyl-$C_1$-to-$C_6$-alkyl-O-C(O)-, pyridyl-$C_1$-to-$C_6$-alkyl-NH-C(O)-pyridyl-$C_1$-to-$C_6$-alkyl-N($C_1$-to-$C_6$-loweralkyl)-C(O)-, (substituted-pyridyl)-$C_1$-to-$C_6$-alkyl-O-C(O)-, (substituted-pyridyl)-$C_1$-to-$C_6$-alkyl-NH-C(O)- or (substituted-pyridyl)-$C_1$-to-$C_6$-alkyl-N($C_1$-to-$C_6$-loweralkyl)-C(O)- wherein substituted-pyridyl is a pyridyl ring substituted with one or two substituents independently selected from $C_1$-to-$C_6$-loweralkyl, hydroxy, halo, amino, $C_1$-to-$C_6$-alkylamino, di-$C_1$-to-$C_6$-alkylamino, $C_1$-to-$C_6$-alkoxy-halo-$C_1$-to-$C_6$-alkyl, unsubstituted -$C_3$-to-$C_7$-cycloalkyl, unsubstituted ($C_6$-monocyclic or $C_9$- or $C_{10}$-bicyclic)aryl, unsubstituted ($C_6$-monocyclic or $C_9$- or $C_{10}$-bicyclic)aryl-$C_1$-to-$C_6$-alkyl, -COOH and -$SO_3H$ and B is thiazolyl-$C_1$-to-$C_6$-alkyl-$R_9$-C(O)-NH-CH($R_5$)-C(O)- or (substituted-thiazolyl)-$C_1$-to- $C_6$-alkyl-$R_9$-C(O)-NH-CH($R_5$)-C(O)- wherein $R_9$ is -O-, -NH- or -N($C_1$-to-$C_6$-loweralkyl)-, $R_5$ is -$C_1$-to-$C_6$-loweralkyl and substituted-thiazolyl is a thiazolyl ring substituted with one or two substituents independently selected from $C_1$-to-$C_6$-loweralkyl, hydroxy, halo, amino, $C_1$-to-$C_6$-alkylamino, di-$C_1$-to-$C_6$-alkylamino, $C_1$-to-$C_6$-alkoxy-halo-$C_1$-to-$C_6$-alkyl, unsubstituted -$C_3$-to-$C_7$-cycloalkyl, unsubstituted ($C_6$-monocyclic or $C_9$- or $C_{10}$-bicyclic)aryl, unsubstituted ($C_6$-monocyclic or $C_9$- or $C_{10}$-bicyclic)aryl-$C_1$-to-$C_6$-alkyl, -COOH and -$SO_3$H.

9. The compound of claim 8 wherein $R_2$ and $R_3$ are benzyl, A is pyridyl-$C_1$-to-$C_6$-alkyl-O-C(O)- and B is thiazolyl-$C_1$-to-$C_6$-alkyl-$R_9$-C(O)-NH-CH($R_5$)-C(O)- or (substituted-thiazolyl)-$C_1$-to-$C_6$-alkyl-$R_9$-C(O)-NH-CH($R_5$)-C(O)- wherein $R_9$ is -O- or -N($CH_3$)-, $R_5$ is isopropyl or 2-butyl and substituted-thiazolyl is a thiazolyl ring substituted with $C_1$-to-$C_6$-loweralkyl or amino.

10. A compound selected from the group consisting of
   (2S,3S,5S)-2-(N-(N-((N-Methy-N-((2-thiazolyl)-methyl)amino)carbonyl)valinyl)amino)-5-(N-((3-pyridinyl)methoxycarbonyl)amino)-1,6-diphenyl-3-hydroxyhexane;
   (2S,3S,5S)-2-(N-(N-((N-Methyl-N-((4-thiazolyl)-methyl)amino)carbonyl)valinyl)amino)-5-(N-((3-pyridinyl)methoxycarbonyl)amino)-1,6-diphenyl-3-hydroxyhexane;
   (2S,3S,5S)-5-(N-(N-((N-Methyl-N-((4-thiazolyl)-methyl)amino)carbonyl)valinyl)amino)-2-(N-((3-pyridinyl)methoxycarbonyl)amino)-1,6-diphenyl-3-hydroxyhexane;
   (2S,3S,5S)-5-(N-(N-((2-Thiazolyl)methoxycarbonyl)valinyl)amino)-2-(N-((3-pyridinyl)methoxycarbonyl)amino)-1,6-diphenyl-3-hydroxyhexane;
   (2S,3S,5S)-2-(N-(N-((2-Thiazolyl)methoxycarbonyl)valinyl)amino)-5-(N-((3-pyridinyl)methoxycarbonyl)amino)-1,6-diphenyl-3-hydroxyhexane;
   (2S,3S,5S)-2-(N-(N-((N-Methyl-N-((2-methyl-4-thiazolyl)methyl)amino)carbonyl)valinyl)amino)-5-(N-((3-pyridinyl)methoxycarbonyl)amino)-1,6-diphenyl-3-hydroxyhexane;
   (2S,3S,5S)-2-(N-(N-((N-Methyl-N-((2-amino-4-thiazolyl)methyl)amino)carbonyl)valinyl)amino)-5-(N-((3-pyridinyl)methoxycarbonyl)amino)-1,6-diphenyl-3-hydroxyhexane;
   (2S,3S,5S)-5-(N-(N-((N-Methyl-N-((2-amino-4-thiazolyl)methyl)amino)carbonyl)valinyl)amino)-2-(N-((3-pyridinyl)methoxycarbonyl)amino)-1,6-diphenyl-3-hydroxyhexane;
   (2S,3S,5S)-5-(N-(N-((N-Methyl-N-((2-methyl-4-thiazolyl)methyl)amino)carbonyl)valinyl)amino)-2-(N-((3-pyridinyl)methoxycarbonyl)amino)-1,6-diphenyl-3-hydroxyhexane;
   (2S,3S,5S)-2-(N-(N-((2-Pyridinyl)methoxycarbonyl)valinyl)amino)-5-(N-((5-thiazolyl)methoxycarbonyl)amino)-1,6-diphenyl-3-hydroxyhexane;
   (2S,3S,5S)-5-(N-(N-((2-Pyridinyl)methoxycarbonyl)valinyl)amino)-2-(N-((5-thiazolyl)methoxycarbonyl)amino)-1,6-diphenyl-3-hydroxyhexane;
   (2S,3S,5S)-2-(N-(N-((N-Methyl-N-((2-pyridinyl)methyl)-amino)carbonyl)isoleucinyl)amino)-5-(N-((5-thiazolyl)-methoxycarbonyl)amino)-1,6-diphenyl-3-hydroxyhexane; and
   (2S,3S,5S)-5-(N-(N-((N-Methyl-N-((2-pyridinyl)methyl)-amino)carbonyl)isoleucinyl)amino)-2-(N-((5-thiazolyl)-methoxycarbonyl)amino)-1,6-diphenyl-3-hydroxyhexane;
or a pharmaceutically acceptable salt thereof.

* * * * *

UNITED STATES PATENT AND TRADEMARK OFFICE
CERTIFICATE OF CORRECTION

PATENT NO. : 5,616,714
DATED : April 1, 1997
INVENTOR(S) : Kempf, et. al.

It is certified that error appears in the above-indentified patent and that said Letters Patent is hereby corrected as shown below:

Column 173, line 24, change "pyddyl" to --pyridyl--.

Column 173, line 51, change "isoproply" to --isopropyl--.

Column 175, line 6, change "alkoxy-halo" to --alkoxy, halo--.

Column 175, line 19, change "Methy" to --Methyl--.

Signed and Sealed this

Twenty-second Day of July, 1997

Attest:

Attesting Officer

BRUCE LEHMAN

Commissioner of Patents and Trademarks